US008980580B2

(12) United States Patent
Watanabe et al.

(10) Patent No.: US 8,980,580 B2
(45) Date of Patent: Mar. 17, 2015

(54) HETEROLOGOUS EXPRESSION OF FUNGAL POLYKETIDE SYNTHETIC GENE IN YEAST AND A METHOD OF PREPARING A COMPOUND PRODUCED BY A PROTEAN ENCODED BY THE POLYKETIDE SYNTHETIC GENE BY THE HETEROLOGOUS EXPRESSION

(75) Inventors: Kenji Watanabe, Shizuoka (JP); Hisao Moriya, Okayama (JP)

(73) Assignees: Shizuoka Prefecture Public University Corporation, Shizukoa (JP); National University Corporation Okayama University, Okayama (JP)

( * ) Notice: Subject to any disclaimer, the term of this patent is extended or adjusted under 35 U.S.C. 154(b) by 0 days.

(21) Appl. No.: 13/816,826

(22) PCT Filed: Aug. 11, 2011

(86) PCT No.: PCT/JP2011/004566
§ 371 (c)(1),
(2), (4) Date: Feb. 13, 2013

(87) PCT Pub. No.: WO2012/020574
PCT Pub. Date: Feb. 16, 2012

(65) Prior Publication Data
US 2013/0171698 A1 Jul. 4, 2013

(30) Foreign Application Priority Data

Aug. 13, 2010 (JP) ................................ 2010-181279
Jan. 17, 2011 (JP) ................................ 2011-007312

(51) Int. Cl.
*C12Q 1/68* (2006.01)
*C12P 19/34* (2006.01)

(52) U.S. Cl.
USPC ........................................ 435/69.1; 435/91.2

(58) Field of Classification Search
USPC .............................................. 435/69.1, 91.2
See application file for complete search history.

(56) References Cited

U.S. PATENT DOCUMENTS

| 3,947,517 | A | * | 3/1976 | Muxfeldt et al. | ............. | 552/206 |
|---|---|---|---|---|---|---|
| 5,958,405 | A | * | 9/1999 | Goli | ............. | 424/94.6 |
| 7,868,228 | B2 | * | 1/2011 | Valentin et al. | ............. | 800/298 |
| 2002/0151058 | A1 | | 10/2002 | Perkins et al. | | |
| 2005/0239088 | A1 | * | 10/2005 | Shepard et al. | ............. | 435/6 |

FOREIGN PATENT DOCUMENTS

WO WO 99/66035 A2 12/1999

OTHER PUBLICATIONS

NCBI, "*Chaetomium globosum* CBS 148.51 hypothetical protein (CHGG_10128) partial mRNA," NCBI, Oct. 27, 2011.

Ayako Chino et al., "Plasmid Construction Using Recombination Activity in the Fission Yeast *Schizosaccharomyces pombe*," PLoS One, PLoS One, (vol. 5), (Issue. 3), (Mar. 2010).
Yuzy Matsuo et al., "Simple and Effective Gap-Repair Cloning Using Short Tracts of Flanking Homology in Fission Yeast," Biosci, Biotechnol, Biochem, (vol. 74), (Issue. 3), (p. 685-689), (2010).
B. Birren et al., "Hypothetical protein CHGG_10128 [*Chaetomium globosum* CBS 148.51]," NCBI, NCBI, (Feb. 4, 2010).
S. M. Samson et al., "Isolation, sequence determination and expression in *Escherichia coli* of the isopenicillin N synthetase gene from *Cephalosporium acremonium*," Nature, 6043 ed., (vol. 318), (p. 191-194), (Nov. 14, 1985).
Jesus Cortes, et al., "An unusually large multifunctional polypeptide in the erythromycin-producing polyketide synthase of *Saccharopolyspora erythraea*," Nature, (vol. 348), (p. 176-178), (Nov. 8, 1990).
Stefano Donadio et al., "Modular Organization of Genes Required for Complex Polyketide Biosynthesis," Science, Science, p. 675-679, (May 3, 1991).
Xiaoping An et al. "Rapid Assembly of Multiple-Exon cDNA Directly from Genomic DNA", PLOS ONE, Nov. 14, 2007, pp. e1179.
Robert M. Horton et al. "Engineering hybrid genes without the use of restriction enzymes: gene splicing by overlap extension", Elsevier, Amsterdam, NL, Apr. 15, 1989, pp. 61-68.
Kevin R. Oldenburg et al. "Recombination-mediated PCR-directed plasmid construction in vivo in yeast", Oxford University Press, GB, Jan. 15, 1997, pp. 451-452.
China Patent Office, "Office Action", issued on Nov. 4, 2014 for corresponding Chinese patent application No. 201180041800.2.
Richard Linsk et al., "Structure and Function of Three Novel MHC Class I Antigens Derived from a C3H Ultraviolet-Induced Fibrosarcoma," J.Exp. Med., vol. 164 1986, pp. 794-813.
E. Weiss et al., "The DNA sequence of the H-2Kb gene: evidence for gene conversion as a mechanism for the generation of polymorphism in histocompatibility antigens", The EMBO Journal, vol. 2, No. 3, 1983, pp. 453-462.
Takayoshi Saruwatari et al., Symposium on Biocatalyst Chemistry Japan Koen Yoshishu, Sep. 2010, vol. 14, pp. 26-27.
Noriyasu Ishikawa et al., Abstracts of Annual Meeting of Pharmaceutical Society of Japan, Mar. 2011, vol. 131, No. 2, p. 74 [29F-ppm13].

* cited by examiner

*Primary Examiner* — Ardin Marschel
(74) *Attorney, Agent, or Firm* — Hammer & Associates, P.C.

(57) ABSTRACT

The present invention relates to a method of removing an intron contained in a gene from a eukaryotic gene, and linking only the exon sequences to prepare an expression vector comprising the linked sequences. Specifically, the invention relates to a method of preparing an expression vector containing linked exon sequences comprising amplifying exon sequences by PCR as one or more fragments from a giant fungal gene containing an intron, and linking the fragments together with a restriction enzyme-treated vector using the gap repair cloning method; a method of preparing an expression vector containing a full-length cDNA sequence by synthesizing and linking cDNA fragments from a fungal giant gene; a transformant having introduced therein an expression vector prepared by the method; a protein produced by the transformant; and a method of preparing a compound produced by the protein using the expression vector.

4 Claims, 16 Drawing Sheets

Fig. 1

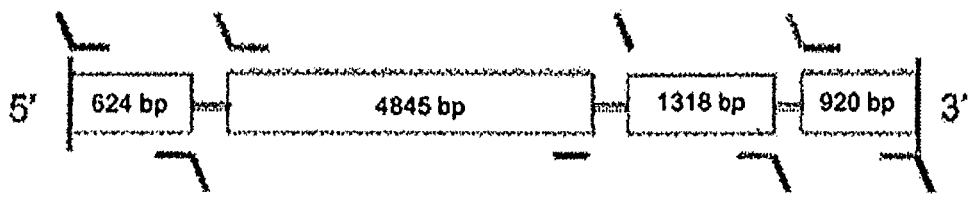

EXON 1 FORWARD PRIMER

5'-TCTTCTGGTCTGGTGCCACGCGGTTCTGGTATGGCATCACCTTCACTTTTAGTCTTTGGG-3'

EXON 1 REVERSE PRIMER

3'-CAAAGCGATAGAGGAACATGCTGAGgcatacgtttctgtcaactccgat-5'

EXON 2 FORWARD PRIMER

5'- AAAGCGATAGAGGAACATGCTGAGgcatacgtttctgtcaactccgatg -3'

EXON 2 REVERSE PRIMER

3'-CCGACCTGCACTTTTGCTGACCTGgccctgcagcggaaaaggacctcc -5'

EXON 3 FORWARD PRIMER

5'-TCCGACCTGCACTTTTGCTGACCTGgccctgcagcggaaaaggacctc-3'

EXON 3 REVERSE PRIMER

3'-GACGGCACCGCCAAGCGCCCCATCGCTCTCATGATCCACGGCGGCGGAC-5'

EXON 4 FORWARD PRIMER

5'-GACGGCACCGCCAAGCGCCCCATCGCTCTCATGATCCACGGCGGCGGAC- 3'

EXON 4 REVERSE PRIMER

3'-gtatgagttcttgttcaagcagattggcgtcGGAGCCGTTGCTTTAATCGTCGCACACCAC-5'

PKS MOLECULAR WEIGHT        279 kDa
Tag PEPTIDE                   8 kDa
PREDICTED MOLECULAR WEIGHT  287 kDa

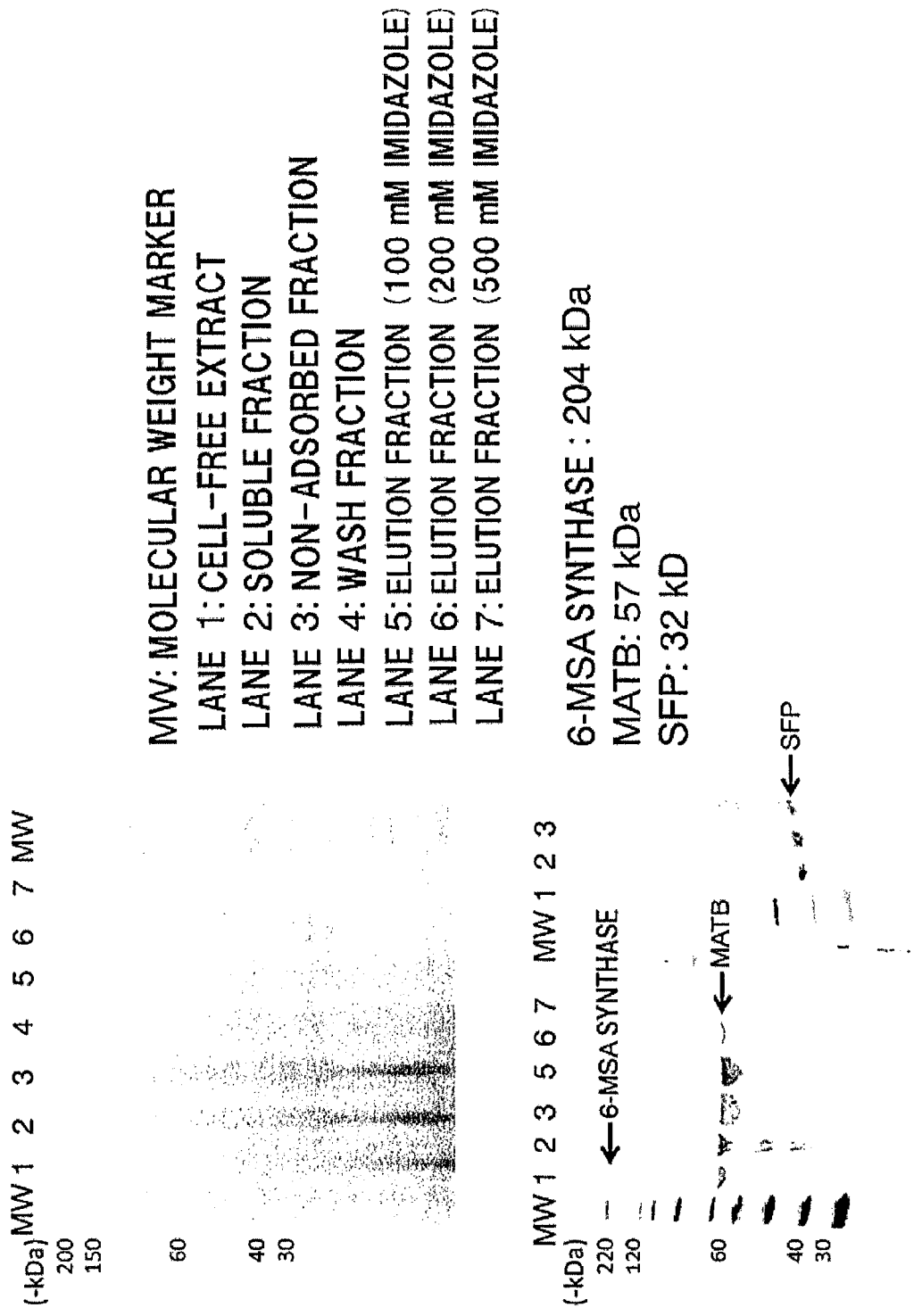

Fig. 11

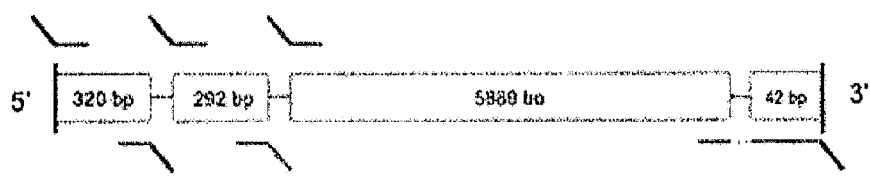

EXON 1 FORWARD PRIMER

5'-TCTTCTGGTCTGGTGCCACGCGGTTCTGGTATGGAGGAGGCCATGCTCGACGAAAGCTGG-3'

EXON 1 REVERSE PRIMER

3'-ATCGCAAATTGCGCACTACCTCGA*tcacgctgaaaagaactgtggcgat*-5'

EXON 2 FORWARD PRIMER

5'-TATCGCAAATTGCGCACTACCTCGA*tcacgctgaaaagaactgtggcga*-3'

EXON 2 REVERSE PRIMER

3'-*GTTGGACGCTTTTCACGATACCTCG*aaccttcctcctgctagccgcgcg-5'

EXON 3 FORWARD PRIMER

5'-*GTTGGACGCTTTTCACGATACCTCG*aaccttcctcctgctagccgcgcg-3'

EXON 3·4 REVERSE PRIMER

3'-CTTCTCCATGATCCATGGCGATCAGGCCAAAATTCTTGAAGGTTTTTTGCGGGAGGCTCTTCTGGATGGAGCCGTTGCTTTAATCGTCGCACACCACC-5'

94°C, 2 MINITES
94°C, 15 SECONDS
55°C, 30 SECONDS
68°C, *1 MINUTE/KILOBASE
} REPEAT THIS CYCLE 30 TIMES

· PCR RESULTS

* EXON 1: 30 SECONDS
  EXON 2: 30 SECONDS
  EXON 3·4: 6 MINUTES

Fig. 14
PKS MOLECULAR WEIGHT  239kDa
Tag PEPTIDE  8 kDa
PREDICTED MOLECULAR WEIGHT  247 kDa
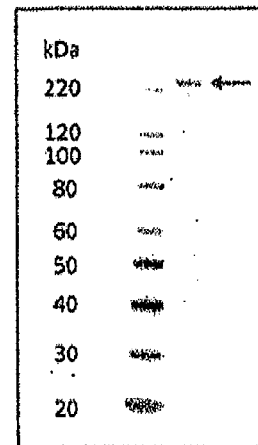
Fig. 15
ANALYSIS OF YEAST EXTRACT BY LC/MS
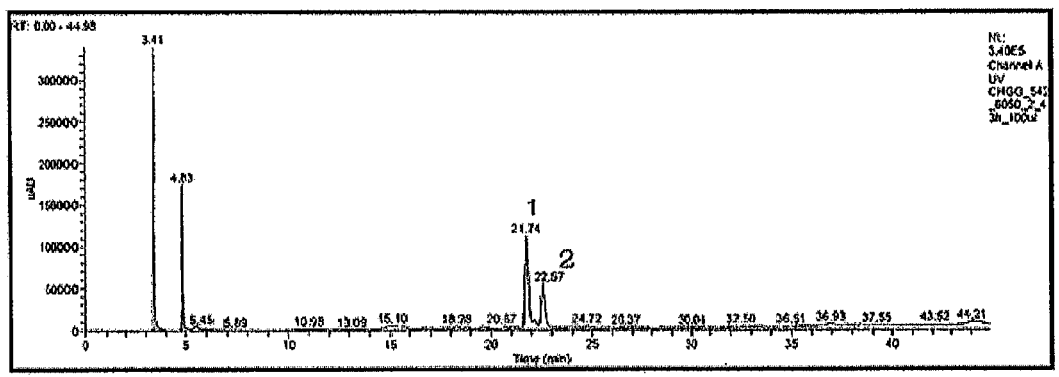
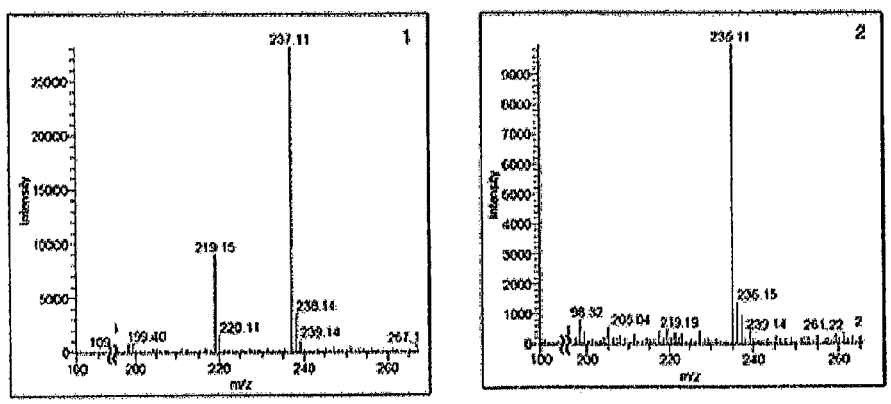

Fig. 16
CHGG_542-1
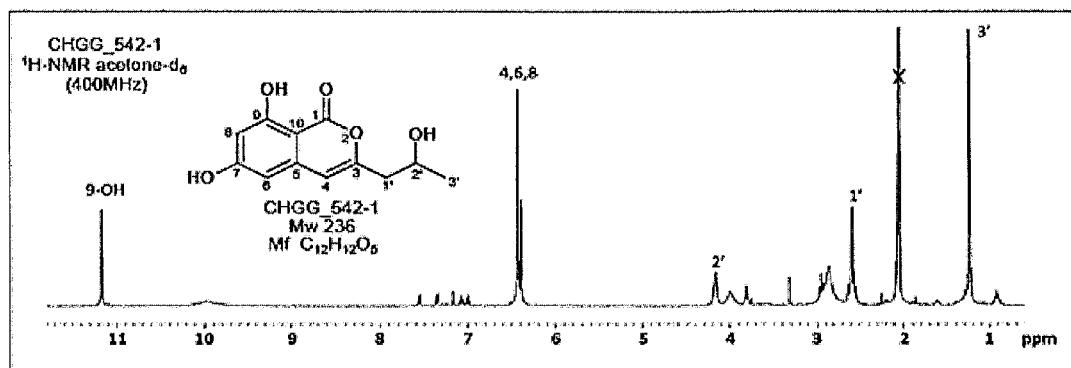
CHGG_542-2
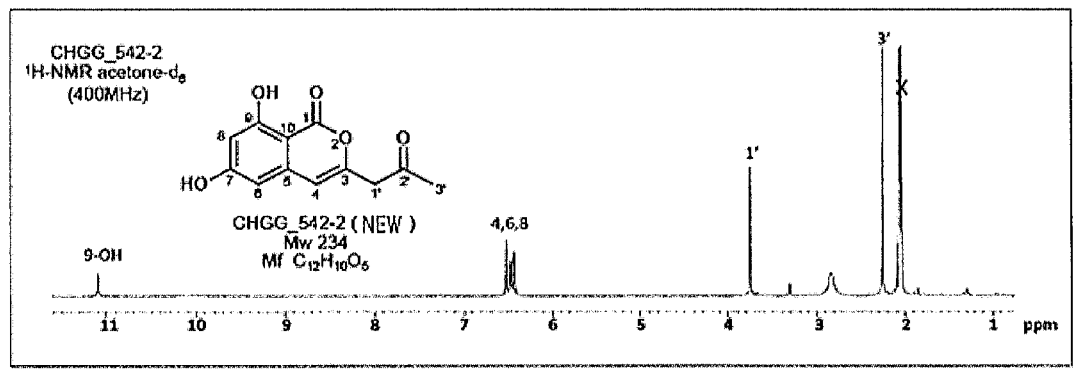

SEQUENCE LISTING

```
<160> NUMBER OF SEQ ID NOS: 47

<210> SEQ ID NO 1
<211> LENGTH: 7968
<212> TYPE: DNA
<213> ORGANISM: Chatomium globosum

<400> SEQUENCE: 1
atggcatcac ctttcacttt agtctttggg ccgcagtcga gcctgctgtc ggaagactgg      60
ctcgtgcaac tgcggtcgac tttgctggga aaccgtaaac ttgagggcct agttaccgca     120
```

```
ataactcagc ttgaatccat ctggaacgat cttgctctcg ccgacccatc tttcaaaggc    180
atccctggcc aggaacattt ccgggccctt tccaactgga tcagcagccc tggcaactcg    240
gacccgccag cggagctttc ccgactcaac ctgctcctca cccccttac cgtcatcgct     300 cacctagtcg aatacttcaa ctacttggag gtgtccggcc tttcccatga acaactcctc    360
aatagcactt ccatcaatgg cggcggattc caaggcttct gtaccggatt gctggccgca    420
gtgacgttgt cattggccaa ggatgaagga gaggcggtaa aactctcaac atcggtattg    480
gggcttgccg tggctctcgg cgcatatgtc gacttggatg gatgttttgc gaatccaccg    540
agggaatttt cctgtctctc ggttcgctgg aagagcagtg aagagagcct atcggttttc    600
aaagcgatag aggaacatgc tgaggtatgc actgcctgaa gctttcccca acaataccttt   660 atccctgagt gaagttgcat ttgtattaac acagtaacag gcatacgttt ctgtcaactc    720
cgatgtattg agtgccaccg tcacccttcc caagcaaacg caagacgagc tcgttgcaaa    780
actcactgat ctcggggtca ccgctcgtcc gtacccactc tcgggccgct ttcactcctc    840
catccacgag gaacatgtgg agaagatcgt ctctctcggg aactccaaca ccaagttccg    900
attcccggtg gcttgtgggt tgcctaatct cgtcagggac ggcacggggt cccccattgg    960
caacagcact ccccttcatg aggtgattgc gaggtctatg ttggttcagc ggtcagaatg   1020
gagcagcaca attcggtctg ccctgccgga acctgcttct actggcacgg aggctgtcgt   1080
gtttggactt gtggactgca tacctcgatc cctggtcact gaaggtggcc ttaccgtcac   1140
tcgacctggc ttccagaaga cgggggcata cgtctaccct gaagacgcgg tagccgtcgt   1200
cggactggcc tgccgatttc ccggcgcgga ttcgctcgaa gagtattggc agctacttct   1260
gtctaaagct tccatgctcg gcaagctccc aaccgaacgg ttcccaacaa agggggttgcg  1320 ccggacacca aaggacgaca ttcccttcat cggaaacttc ctccgtgatg gctacgcctt   1380
tgacaacaag tttttcaacc gatctccgcg cgaggcctcg gccatggatc cgcagcacaa   1440
attaattctg caggtcgcgt acgaagctct cgagacggcg ggatatttca gccatggctc   1500
gtcacctagc gacgtcggct gttacgtcgg tgtagcggcg tctgactacg aggacaatgt   1560
cgcgtcccat ctcccgacag ccttctccgt cctcggcatg gtccgcgcgt ttgtgagcgg   1620
caagatcagc catttctta acttgagtgg cccgtctatg gtattcgaca cggcttgttc    1680
ttcctctgct gtggccatcc acactcgcat gccaggctct caggaatggg gagtgctctc    1740
atggccctcg gctggcggag tcaacgttat tacaagccca gtcctgcatc agaacctcgc    1800
ggcagcaaat tttctaagcc ctacaggcga atccaaggcc ttcgatgcgc gtgctgacgg    1860
gtactgccgc ggggagggcg cgggaatggt cgtcctgaag aagtactcta cagcgcttgc    1920
cgacggcgat cacatttacg gaatcatcgc agggtctgcg gtcaaccaga atgacaactg    1980
tgcggccatt accgtccctg tatcaaagtc gcagaccgcg ctgtacaagc gagtgctcaa    2040
gatgggacga atggaccctg agaaggtttc gtatgtcgag gcacacgaaa ccggcacccc    2100
gaaaggagac ccaatcgaat gtgcaagcat ccgagaggta ttcggaaacc agccctcgcg    2160
caagctgcac tttggctccg tcaaagcaag catcggccat acggaagccg cgtctggcgt    2220
ggcaggcctc atcaaggtct tgctcatgat gcaccatcgg acgatcccgc cgcaggccag    2280
cttccagaca ctcaacccta atatcccacc cctgggtccg tccaatatgg aaattgctct    2340
gacacccagg gactggaatg gcgaattcct cgccgcatgc gtcaataact acggcgcggc    2400
cggcagcaat gccgccatgc ttatttgcca gcctccacgt ctcaccacga cgccgaaggc    2460
```

```
ccgccgtgga agggacagcc ttcccatgaa atacccgtc atgctaagag ccaagtccgc    2520
agccagcctt caagcctact gcaatgcgtt gacgcaattc ttggacaagg cgtctgctca    2580
taccagcgat gaccaactcc tggctgacgt tgcctatggg ctcgccaccc accagaacat    2640
cagcttgccc tactctctcg gcaccaccgt cgattctctt gctcgcctgc gccaggaact    2700
gagcgcctgc gcttccgcca cactgcccga agagcaaacg gcaaaagcca atcccggcc     2760
tgtcatcatg gtcttctccg gcaaacggg caacaccgtc aacctatccg aagaagcata    2820
ccggtcctcc ctgcttctcc agagccacct gaaccgctgc gaccgcattc tccgatcgct    2880
gggccacccg agcatcttcc ccgccatctt ctccaagcag cccatctccg acaccctggt    2940
gctccactgc gccgtgtttg cgctgcagta ctcctgcgct tgggcctgga tcgacgcggg    3000
ggtccagatc gatgccatga tcggccatag ctttggccag ctgaccgcgc tctgcgtggc    3060
cggtgccatg tccctcgagg atgggctgaa gctgattgct ggccgagcta tccttgttcg    3120
ggaccagtgg ggtccggaaa gggggctat gatctctgtc ggcgcgggcg agcaacagac     3180
gcaggagctg gtggcgagcg ctcatcaagc tggcatcgag gttgagattg cttgcttcaa    3240
cgccaaggat aaccatgtcg tggttggttc tgcgtcttcc attgccgcct ttgaggacct    3300
ggttgcaggc cagggcagtg aggtccgttt gaagcggctg gaggtcactc acgggtttca    3360
ttccgtgttt gtcgatggga ttatgccgga gtacaaggcg ctgctggata gcatttcctt    3420
ttcccagccc aagatccatg ttgagacttg ctcgccgggc tcagcttgga acacggtcaa    3480
ctcggagctt gttgcccaac agtctcgcga tgccgtccac tttagtgctg ccatttcccg    3540
catccagaag aagttcagtg attgcgtgtg gctggaagcc ggttcgggca cggcggccat    3600
cccccttgct cgccgagccc tgcaggcgga acaggtcgac atcgcgaagc atgctttcca    3660
cgcagtcaaa ctcggagcgc cggacgccat ggagttgctg gcgcagacga cgcttgattt    3720
gtggaacagc gggaccaagg ccatgttctg gcccttccat cgctcccaaa agcaccagta    3780
caatgtcctg cagcttcctc cgtaccagtt cgagaagcgg caccactggc tggagtatgt    3840
ggatcgccac ggcagtgatg cccctgtccc cgtggcggcg atcgaggcaa agccggccga    3900
catggtatct ttctcccagt atgccgacga cacggggaac ctcgcgatct tcaacatcaa    3960
ccaggagacc agcgagttcc aagcagccat gaaggccac cgcgtcctcg gccatccgct     4020
ctgtcccgtc tccttgtaca tcgaagttgc gacacgggcg gcggctctgc tccaccccaa    4080
cttctcgact gagacgcatg catcgggcgt tgatgcgctg gaaatcttca cgcctcttgg    4140
tcttgacacg gcacggcaag cccaggttac gcttctcagc attggcgagg acgagtggga    4200
gttcaccgtc catagctttc gcttggcga cacggcgtcg agaaagacca ggcacgccac     4260
ggccagaatt cgcatcacgt ccctgcttga caagagcacc gcggccatgt ttgcgcgctt    4320
ccagcgtctg gccaagtacg aggaatgcga agctctcttt gccgacggag ccgccgcagg    4380
catccagggg ccgttggtgt acaagatgtt cgacaaggtc gtcaattact cggggatcta    4440
ccgtggcgtg ctgaagattg cgtccaagaa ccagaaagtg agcggtctcg ttcagctacc    4500
agacgctacg gcgaagggag cagacatgga gaagtcggcc tgcaatccac tggccattga    4560
caacttcacc caagttgccg gcctccacgt caacgggctt gatgagtgcg aaacgacga    4620
agtgtacatc tgctcgcagg tcgatgagat tcgcgccctt cagagcctca agagacctga    4680
tggtggcagt gctggcccgt ggcggtgca tgccaacttt agcaggcaag gggacagaga     4740
gctcctgaac gatatcttcg tcttcgatac gtcagctaag actctagtca tgaccatcct    4800
gggggtccga tttaccaaga ccaacgtgaa tatgctgcag aaggtactgg ctcgtgcaaa    4860
```

```
cacagcgcac tctcatcaag cccaggcaaa ggttgaacct ccccgtaccg ctgcggcgca    4920
gatcaagtcc gccatcagca cccagctcat ccgcactgcc aatgctccgg agcgtagccg    4980
gaaccgcaag agggctctcg aagacaaggt caacagcaac attagaattg gcctcaagca    5040
actactgcaa gaggtagcgg acgtgtctcc cgagcagatc catgacagca ctctcctcgt    5100
cgatgtcggc atcgactccc tgatggccac cgaggtgcag acggccatcg cgacaggtt    5160 tggcgtcctc ctcacaactg ctgagttcca atccattgag gactttggat ccttgtgcgc    5220
agcagtgcag ccggcccaga gcagtgctcg gagctcctcc gaggacgacc tgtctgacga    5280
taacgagctc ctagcctcct ctcactcggc cacgcctgca tccagtgtcg agtacgagtt    5340
tcaaaacgac gagctcgtgg ccaaactgca gaagttggtg gcaggccatc ttgatgtctc    5400
agaggctatt gcgccagacc ttttgctagc agacgccggc gtggactcct tgttgggaat    5460
cgagctgggg gcagatattg aaaaggagtt tggacggacc atcgacatga tgcagctcag    5520
tccgacctgc acttttgctg acctggtaaa gatggtgatc cccgaggaca gccacaacac    5580
caacatcgat gtggcccggg ctgcatccat gtctggtgga aagcccctaa cccccagctt    5640
cgcagctaag ggacaggccc ctgcagcgga aaaggacctc ctcgcacacg cggccgagga    5700
cttccgcgcg atccgttcgg attaccttcg cttcgcaaag gaaaccggct gggcaggatt    5760
ccgacagaat gcgtaccccca agcagaggca actggtgctg agctacgtcc tcgaggcttt    5820
cgcccagttg ggctgtgaca ttgcccgtgt tgaggggggc gatgtcctcc ccaatgtccc    5880
gcatatgccg aagcatgcca agtcgtagg ccagttctac aaggttctcc aagaggctag    5940
ccttgtccgc aaacaggggg acaagctggt caggtcccaa accccgtgcc caagaccga    6000 tgcggaagaa ctagtccagc agatgatcgt cgcctatccc cagcacgcct ccgagctcaa    6060
gctgctacga tccacgggct ccaagctggc agacgtcctg tcgggcaagg tcgatcccct    6120
ccagatcatc ttccgcacaa aggccgacag agatctgctc gaggatgtct ataccaactc    6180
gccaatgttc tcgaccggaa ccaaggtgct agccaacttc ttcaccaaag cactcgaaat    6240
ccaccgcggc ggcgagcaag tacgcatcct cgagcttggt gccggcacgg gcggtacgac    6300
caagacgatc ctcgagacgc tctcgtcgat gggagtcaac ttttcgtaca ccttcaccga    6360
cctgtcgtcg tcgctcgtgg cggcggccaa gaggaagttt gccaagtacg ggacgccgt    6420 caacttctcc gtcctcgacg tcgaaaagcc accgccgcag cacctcgttg gaactacca    6480 catcgccctc gcgtccaact gcgtccatgc caccaagagc ctgctggttt cgtcgaccaa    6540
tacctgcaag atgcttcgtc aagacggtat gctctgcctg ctggagctga cgagaaacct    6600
gtactggctg gactgtgtct ttggtctgct cgagggctgg tggctctttg aggatggccg    6660
ggaacatgtc cttgcggatg agttcctctg gaaggatacc ctgctgagag ccgggttcaa    6720
gcacgttgac tggagcgatg acgacagcga ggagtcggat cagttccgtc tggtggtggg    6780
attcaagtct gcgccggacc acctaatctc cgcggttgag aagctacagc tcgcggcagc    6840
ggcggccaaa aaggcggccg ccaagctggt gaccaaagaa accgtcgagt accaccgcgt    6900
cggagatgtc tccctccaag ccgacatcta ctaccccgac cagcccgacg acggcaccgc    6960
caagcgcccc atcggtaagc ctagcaccta gcccgccaca atatacccccc ccagccaacc    7020 aactctaacc accccactcc ccaattagct ctcatgatcc acggcggcgg acacatcatg    7080
ctctcgcgca aagacatccg cccgcggcaa acccgcctcc tcctctcacg gggtctcctc    7140
cccatcagca tcgactaccg gctctgcccc gaagtgaccc tccccgccgg ccccatgacc    7200
```

-continued

```
gacgtcggca cagctctaca ctgggcgcgc accacgctcc cctctctcct acctaacgcc    7260
acccggccgg acatccgcgc ggacggcagc cgggtcgtgg tcattggctg gtcgacgggc    7320
ggcaccctct ccatgacgct gccgttcacg gcgccggcgc ggggcattgc gccgcccgag    7380
gcggtgctgg cgttttattg cccgacggat tatcaggatg ggttttggag ggagccgaat    7440
tttcccgagg agacgacgga gagagaggcc ggggtggagt atgatttgct agaggggta    7500
agggacggcg cgattaccgc gtataatgtg ccggcgcgc agcgggcgac gggagggtgg     7560
atgtcgttgg aggatccgcg gtcgaggatc gcgctgcata tgaattggaa ggggcaggcg    7620
ttgccggttt tgttgggggg gttgccgagt aagggcaagg cgggtgaggg ggtggattgg    7680
aagaatcggc cgcagccgag tgatgaggag gtggcggcgg tgagtccgta tgcgcaggtg    7740
gtggcgggga gttataggac gccaacgttc ttgattcatg gcacgaggga tgatttgatc    7800
ccgtggcagc atacggagag gattaaggat gcgttggtgg agaggggcgt gccggcgggg    7860
gcggcgattg tgcaggatgc ggttcatttg tttgatttgt atgggagtga gggctgggag    7920
gcggtcttgg aggggtatga gttcttgttc aagcagattg gcgtctag                 7968
```

```
<210> SEQ ID NO 2
<211> LENGTH: 60
<212> TYPE: DNA
<213> ORGANISM: Artificial Sequence
<220> FEATURE:
<223> OTHER INFORMATION: primer

<400> SEQUENCE: 2
tcttctggtc tggtgccacg cggttctggt atggcatcac cttcactttt agtctttggg    60

<210> SEQ ID NO 3
<211> LENGTH: 49
<212> TYPE: DNA
<213> ORGANISM: Artificial Sequence
<220> FEATURE:
<223> OTHER INFORMATION: primer

<400> SEQUENCE: 3
caaagcgata gaggaacatg ctgaggcata cgtttctgtc aactccgat                 49

<210> SEQ ID NO 4
<211> LENGTH: 49
<212> TYPE: DNA
<213> ORGANISM: Artificial Sequence
<220> FEATURE:
<223> OTHER INFORMATION: primer

<400> SEQUENCE: 4
aaagcgatag aggaacatgc tgaggcatac gtttctgtca actccgatg                 49

<210> SEQ ID NO 5
<211> LENGTH: 49
<212> TYPE: DNA
<213> ORGANISM: Artificial Sequence
<220> FEATURE:
<223> OTHER INFORMATION: primer

<400> SEQUENCE: 5
ccgacctgca cttttgctga cctggcccct gcagcggaaa aggacctcc                 49

<210> SEQ ID NO 6
<211> LENGTH: 49
<212> TYPE: DNA
<213> ORGANISM: Artificial Sequence
```

```
<220> FEATURE:
<223> OTHER INFORMATION: primer

<400> SEQUENCE: 6
tccgacctgc acttttgctg acctggcccc tgcagcggaa aaggacctc          49

<210> SEQ ID NO 7
<211> LENGTH: 49
<212> TYPE: DNA
<213> ORGANISM: Artificial Sequence
<220> FEATURE:
<223> OTHER INFORMATION: primer

<400> SEQUENCE: 7
gacggcaccg ccaagcgccc catcgctctc atgatccacg gcggcggac           49

<210> SEQ ID NO 8
<211> LENGTH: 49
<212> TYPE: DNA
<213> ORGANISM: Artificial Sequence
<220> FEATURE:
<223> OTHER INFORMATION: primer

<400> SEQUENCE: 8
gacggcaccg ccaagcgccc catcgctctc atgatccacg gcggcggac           49

<210> SEQ ID NO 9
<211> LENGTH: 61
<212> TYPE: DNA
<213> ORGANISM: Artificial Sequence
<220> FEATURE:
<223> OTHER INFORMATION: primer

<400> SEQUENCE: 9
gtatgagttc ttgttcaagc agattggcgt cggagccgtt gctttaatcg tcgcacacca    60
c                                                                    61

<210> SEQ ID NO 10
<211> LENGTH: 624
<212> TYPE: DNA
<213> ORGANISM: Chatomium globosum

<400> SEQUENCE: 10
atggcatcac cttcactttt agtctttggg ccgcagtcga gcctgctgtc ggaagactgg    60
ctcgtgcaac tgcggtcgac tttgctggga aaccgtaaac ttgagggcct agttaccgca   120
ataactcagc ttgaatccat ctggaacgat cttgctctcg ccgacccatc tttcaaaggc   180
atccctggcc aggaacattt ccgggccctt tccaactgga tcagcagccc tggcaactcg   240
gacccgccag cggagctttc ccgactcaac ctgctcctca caccccttac cgtcatcgct   300
cacctagtcg aatacttcaa ctacttggag gtgtccggcc tttcccatga caactcctc    360 aatagcactt ccatcaatgg cggcggattc caaggcttct gtaccggatt gctgccgca    420 gtgacgttgt cattggccaa ggatgaagga gaggcggtaa aactctcaac atcggtattg   480
gggcttgccg tggctctcgg cgcatatgtc gacttggatg gatgttttgc gaatccaccg   540
agggaatttt cctgtctctc ggttcgctgg aagagcagtg aagagagcct atcggttttc   600
aaagcgatag aggaacatgc tgag                                          624

<210> SEQ ID NO 11
<211> LENGTH: 4845
<212> TYPE: DNA
```

<213> ORGANISM: Chatomium globosum

<400> SEQUENCE: 11

```
gcatacgttt ctgtcaactc cgatgtattg agtgccaccg tcacccttcc caagcaaacg      60
caagacgagc tcgttgcaaa actcactgat ctcggggtca ccgctcgtcc gtacccactc     120
tcgggccgct ttcactcctc catccacgag gaacatgtgg agaagatcgt ctctctcggg     180
aactccaaca ccaagttccg attcccggtg gcttgtgggt tgcctaatct cgtcagggac     240
ggcacggggt cccccattgg caacagcact cccttcatg aggtgattgc gaggtctatg      300
ttggttcagc ggtcagaatg gagcagcaca attcggtctg ccctgccgga acctgcttct     360
actggcacgg aggctgtcgt gtttggactt gtggactgca tacctcgatc cctggtcact     420
gaaggtggcc ttaccgtcac tcgacctggc ttccagaaga cggggcata cgtctaccct      480
gaagacgcgg tagccgtcgt cggactggcc tgccgatttc ccggcgcgga ttcgctcgaa     540
gagtattggc agctacttct gtctaaagct tccatgctcg gcaagctccc aaccgaacgg     600
ttcccaacaa aagggttgcg ccggacacca aggacgaca ttcccttcat cggaaacttc      660
ctccgtgatg gctacgcctt tgacaacaag ttttcaacc gatctccgcg cgaggcctcg      720
gccatggatc cgcagcacaa attaattctg caggtcgcgt acgaagctct cgagacggcg     780
ggatatttca gccatggctc gtcacctagc gacgtcggct gttacgtcgg tgtagcggcg     840
tctgactacg aggacaatgt cgcgtcccat ctcccgacag ccttctccgt cctcggcatg     900
gtccgcgcgt ttgtgagcgg caagatcagc catttcttta acttgagtgg cccgtctatg     960
gtattcgaca cggcttgttc ttcctctgct gtggccatcc acactcgcat gccaggctct    1020
caggaatggg gagtgctctc atggccctcg gctggcggag tcaacgttat tacaagccca    1080
gtcctgcatc agaacctcgc ggcagcaaat tttctaagcc ctacaggcga atccaaggcc    1140
ttcgatgcgc gtgctgacgg gtactgccgc ggggagggcg cgggaatggt cgtcctgaag    1200
aagtactcta cagcgcttgc cgacggcgat cacatttacg gaatcatcgc agggtctgcg    1260
gtcaaccaga atgacaactg tgcggccatt accgtccctg tatcaaagtc gcagaccgcg    1320
ctgtacaagc gagtgctcaa gatgggacgg atggaccctg agaaggtttc gtatgtcgag    1380
gcacacggaa ccggcacccc gaaaggagac ccaatcgaat gtgcaagcat ccgagaggta    1440
ttcggaaacc agccctcgcg caagctgcac tttggctccg tcaaagcaag catcggccat    1500
acggaagccg cgtctggcgt ggcaggcctc atcaaggtct tgctcatgat gcaccatcgg    1560
acgatcccgc cgcaggccag cttccagaca ctcaacccta atatcccacc cctgggtccg    1620
tccaatatgg aaattgctct gacacccagg gactggaatg cgaattcct cgccgcatgc     1680
gtcaataact acggcgcggc cggcagcaat gccgccatgc ttatttgcca gcctccacgt    1740
ctcaccacga cgccgaaggc ccgccgtgga agggacagcc ttcccatgaa ataccccgtc    1800
atgctaagag ccaagtccgc agccagcctt caagcctact gcaatgcgtt gacgcaattc    1860
ttggacaagg cgtctgctca taccagcgat gaccaactcc tggctgacgt tgcctatggg    1920
ctcgccaccc accagaacat cagcttgccc tactctctcg gcaccaccgt cgattctctt    1980
gctcgcctgc gccaggaact gagcgcctgc gcttccgcca cactgcccga agagcaaacg    2040
gcaaaagcca atcccggcc tgtcatcatg gtcttctccg ggcaaacggg caacaccgtc    2100
aacctatccg aagaagcata ccggtcctcc ctgcttctcc agagccacct gaaccgctgc    2160
gaccgcattc tccgatcgct gggccacccg agcatcttcc ccgccatctt ctccaagcag    2220
cccatctccg acaccctggt gctccactgc gccgtgtttg cgctgcagta ctcctgcgct    2280
```

```
tgggcctgga tcgacgcggg ggtccagatc gatgccatga tcggccatag ctttggccag   2340
ctgaccgcgc tctgcgtggc cggtgccatg tccctcgagg atgggctgaa gctgattgct   2400
ggccgagcta tccttgttcg ggaccagtgg ggtccggaaa ggggggctat gatctctgtc   2460
ggcgcgggcg agcaacagac gcaggagctg gtggcgagcg ctcatcaagc tggcatcgag   2520
gttgagattg cttgcttcaa cgccaaggat aaccatgtcg tggttggttc tgcgtcttcc   2580
attgccgcct ttgaggacct ggttgcaggc cagggcagtg aggtccgttt gaagcggctg   2640
gaggtcactc acgggtttca ttccgtgttt gtcgatggga ttatgccgga gtacaaggcg   2700
ctgctggata gcatttcctt ttcccagccc aagatccatg ttgagacttg ctcgccgggc   2760
tcagcttgga acacggtcaa ctcggagctt gttgcccaac agtctcgcga tgccgtccac   2820
tttagtgctg ccatttcccg catccagaag aagttcagtg attgcgtgtg gctggaagcc   2880
ggttcgggca cggcggccat ccccctttgct cgccgagccc tgcaggcgga acaggtcgac   2940
atcgcgaagc atgcttttcca cgcagtcaaa ctcggagcgc cggacgccat ggagttgctg   3000
gcgcagacga cgcttgattt gtggaacagc gggaccaagg ccatgttctg gcccttccat   3060
cgctcccaaa agcaccagta caatgtcctg cagcttcctc cgtaccagtt cgagaagcgg   3120
caccactggc tggagtatgt ggatcgccac ggcagtgatg cccctgtccc cgtggcggcg   3180
atcgaggcaa agccggccga catggtatcc ttctcccagt atgccgacga cacggggaac   3240
ctcgcgatct tcaacatcaa ccaggagacc agcgagttcc aagcagccat tgaaggccac   3300
cgcgtcctcg gccatccgct ctgtcccgtc tccttgtaca tcgaagttgc gacacgggcg   3360
gcggctctgc tccaccccaa cttctcgact gagacgcatg catcgggcgt tgatgcgctg   3420
gaaatcttca cgcctcttgg tcttgacacg gcacggcaag cccaggttac gcttctcagc   3480
attggcgagg acgagtggga gttcaccgtc catagctttc cgcttggcga cacggcgtcg   3540
agaaagacca ggcacgccac ggccagaatt cgcatcacgt ccctgcttga caagagcacc   3600
gcggccatgt ttgcgcgctt ccagcgtctg gccaagtacg aggaatgcga agctctcttt   3660
gccgacggag ccgccgcagg catccagggg ccgttggtgt acaagatgtt cgacaaggtc   3720
gtcaattact cggggatcta ccgtggcgtg ctgaagattg cgtccaagaa ccagaaagtg   3780
agcggtctcg ttcagctacc agacgctacg gcgaagggag cagacatgga gaagtcggcc   3840
tgcaatccac tggccattga caacttcacc caagttgccg gcctccacgt caacgggctt   3900
gatgagtgcg gaaacgacga agtgtacatc tgctcgcagg tcgatgagat tcgcgccctt   3960
cagagcctca gagacctga tggtggcagt gctggcccgt ggctggtgca tgccaacttt   4020
agcaggcaag gggacagaga gctcctgaac gatatcttcg tcttcgatac gtcagctaag   4080
actctagtca tgaccatcct gggggtccga tttaccaaga ccaacgtgaa tatgctgcag   4140
aaggtactgg ctcgtgcaaa cacagcgcac tctcatcaag cccaggcaaa ggttgaacct   4200
ccccgtaccg ctgcggcgca gatcaagtcc gccatcagca cccagctcat ccgcactgcc   4260
aatgctccgg agcgtagccg gaaccgcaag agggctctcg aagacaaggt caacagcaac   4320
attagaattg gcctcaagca actactgcaa gaggtagcgg acgtgtctcc cgagcagatc   4380
catgacagca ctctcctcgt cgatgtcggc atcgactccc tgatggccac cgaggtgcag   4440
acggccatcg gcgacaggtt tggcgtcctc ctcacaactg ctgagttcca atccattgag   4500
gactttggat ccttgtgcgc agcagtgcag ccggcccaga gcagtgctcg gagctcctcc   4560
gaggacgacc tgtctgacga taacgagctc ctagcctcct ctcactcggc cacgcctgca   4620
```

```
tccagtgtcg agtacgagtt tcaaaacgac gagctcgtgg ccaaactgca gaagttggtg    4680
gcaggccatc ttgatgtctc agaggctatt gcgccagacc ttttgctagc agacgccggc    4740
gtggactcct tgttgggaat cgagctgggg gcagatattg aaaaggagtt tggacggacc    4800
atcgacatga tgcagctcag tccgacctgc acttttgctg acctg                    4845
```

<210> SEQ ID NO 12
<211> LENGTH: 1318
<212> TYPE: DNA
<213> ORGANISM: Chatomium globosum

<400> SEQUENCE: 12

```
gcccctgcag cggaaaagga cctcctcgca cacgcggccg aggacttccg cgcgatccgt      60
tcggattacc ttcgcttcgc aaaggaaacc ggctgggcag gattccgaca gaatgcgtac     120
cccaagcaga ggcaactggt gctgagctac gtcctcgagg ctttcgccca gttgggctgt     180
gacattgccc gtgttgaggg gggcgatgtc ctccccaatg tcccgcatat gccgaagcat     240
gccaaagtcg taggccagtt ctacaaggtt ctccaagagg ctagccttgt ccgcaaacag     300
ggggacaagc tggtcaggtc ccaaaccccg tgcccaagaa ccgatgcgga agaactagtc     360
cagcagatga tcgtcgccta tccccagcac gcctccgagc tcaagctgct acgatccacg     420
ggctccaagc tggcagacgt cctgtcgggc aaggtcgatc ccctccagat catcttccgc     480
acaaaggccg acagagatct gctcgaggat gtctatacca actcgccaat gttctcgacc     540
ggaaccaagg tgctagccaa cttcttcacc aaagcactcg aaatccaccg cggcggcgag     600
caagtacgca tcctcgagct tggtgccggc acgggcggta cgaccaagac gatcctcgag     660
acgctctcgt cgatgggagt caacttttcg tacaccttca ccgacctgtc gtcgtcgctc     720
gtggcggcgg ccaagaggaa gtttgccaag tacgggacg ccgtcaactt ctccgtcctc     780
gacgtcgaaa agccaccgcc gcagcacctc gttgggaact accacatcgc cctcgcgtcc     840
aactgcgtcc atgccaccaa gagcctgctg gtttcgtcga ccaatacctg caagatgctt     900
cgtcaagacg gtatgctctg cctgctggag ctgacgagaa acctgtactg gctggactgt     960
gtctttggtc tgctcgaggg ctggtggctc tttgaggatg ccggggaaca tgtccttgcg    1020
gatgagttcc tctggaagga taccctgctg agagccgggt tcaagcacgt tgactggagc    1080
gatgacgaca gcgaggagtc ggatcagttc cgtctggtgg tgggattcaa gtctgcgccg    1140
gaccacctaa tctccgcggt tgagaagcta cagctcgcgg cagcggcggc caaaaaggcg    1200
gccgccaagc tggtgaccaa agaaaccgtc gagtaccacc gcgtcggaga tgtctcccctc    1260 caagccgaca tctactaccc cgaccagccc gacgacggca ccgccaagcg ccccatcg     1318
```

<210> SEQ ID NO 13
<211> LENGTH: 920
<212> TYPE: DNA
<213> ORGANISM: Chatomium globosum

<400> SEQUENCE: 13

```
ctctcatgat ccacggcggc ggacacatca tgctctcgcg caaagacatc cgcccgcggc      60
aaacccgcct cctcctctca cggggtctcc tccccatcag catcgactac cggctctgcc     120
ccgaagtgac cctccccgcc ggccccatga ccgacgtcgg cacagctcta cactgggcgc     180
gcaccacgct cccctctctc ctacctaacg ccaccggcc ggacatccgc gcggacggca     240
gccgggtcgt ggtcattggc tggtcgacgg gcggcaccct ctccatgacg ctgccgttca     300
cggcgccggc gcggggcatt gcgccgcccg aggcggtgct ggcgttttat tgcccgacgg     360
```

```
attatcagga tgggttttgg agggagccga attttcccga ggagacgacg gagagagagg    420
ccggggtgga gtatgatttg ctagaggggg taagggacgg cgcgattacc gcgtataatg    480
tgccggcggc gcagcgggcg acgggagggt ggatgtcgtt ggaggatccg cggtcgagga    540
tcgcgctgca tatgaattgg aaggggcagg cgttgccggt tttgttgggg gggttgccga    600
gtaagggcaa ggcgggtgag ggggtggatt ggaagaatcg gccgcagccg agtgatgagg    660
aggtggcggc ggtgagtccg tatgcgcagg tggtggcggg gagttatagg acgccaacgt    720
tcttgattca tggcacgagg gatgatttga tcccgtggca gcatacggag aggattaagg    780
atgcgttggt ggagaggggc gtgccggcg gggcggcgat tgtgcaggat gcggttcatt    840
tgtttgattt gtatgggagt gagggctggg aggcggtctt ggaggggtat gagttcttgt    900
tcaagcagat tggcgtctag                                                920

<210> SEQ ID NO 14
<211> LENGTH: 16401
<212> TYPE: DNA
<213> ORGANISM: Artificial Sequence
<220> FEATURE:
<223> OTHER INFORMATION: vector

<400> SEQUENCE: 14
tcgcgcgttt cggtgatgac ggtgaaaacc tctgacacat gcagctcccg gagacggtca     60
cagcttgtct gtaagcggat gccggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga gggaactttc    240
accattatgg gaaatgcttc aagaaggtat tgacttaaac tccatcaaat ggtcaggtca    300
ttgagtgttt tttatttgtt gtattttttt tttttagag aaaatcctcc aatatcaaat    360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tccttttttct ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggatttttctt aacttcttcg gcgacagcat caccgacttc ggtggtactg    720
ttggaaccac ctaaatcacc agttctgata cctgcatcca aaccttttt aactgcatct    780 tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140
acagtttttc tccataatct tgaagaggcc aaaagattag ctttatccaa ggaccaaata   1200
ggcaatggtg ctcatgttg tagggccatg aaagcggcca ttcttgtgat tctttgcact   1260
tctggaacgg tgtattgttc actatcccaa gcgacaccat caccatcgtc ttccttttctc   1320 ttaccaaagt aaatacctcc cactaattct ctgacaacaa cgaagtcagt acctttagca   1380
aattgtggct tgattggaga taagtctaaa agagagtcgg atgcaaagtt acatggtctt   1440
```

```
aagttggcgt acaattgaag ttctttacgg attttttagta aaccttgttc aggtctaaca    1500
ctaccggtac cccatttagg accagccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa aacgacgatc    1740
ttcttagggg cagacatagg ggcagacatt agaatggtat atccttgaaa tatatatata    1800
tattgctgaa atgtaaaagg taagaaaagt tagaaagtaa gacgattgct aaccaccttat   1860
tggaaaaaac aataggtcct taaataatat tgtcaacttc aagtattgtg atgcaagcat    1920
ttagtcatga acgcttctct attctatatg aaaagccggt tccggcctct cacctttcct    1980
ttttctccca atttttcagt tgaaaaaggt atatgcgtca ggcgacctct gaaattaaca    2040
aaaaatttcc agtcatcgaa tttgattctg tgcgatagcg cccctgtgtg ttctcgttat    2100
gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca tttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttttgt   2520
taaatcagct cattttttaa ccaataggcc gaaatcggca aaatccctta taaatcaaaa    2580
gaatagaccg atatagggtt gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag ttttttgggg tcgaggtgcc gtaaagcact aaatcggaac    2760
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacccgc cgcgcttaat gcgccgctac agggcgcgtc gcgccattcg      2940
ccattcaggc tgcgcaactg ttgggaaggg cgatcggtgc gggcctcttc gctattacgc    3000
cagctggcga aaggggggatg tgctgcaagg cgattaagtt gggtaacgcc agggttttcc    3060
cagtcacgac gttgtaaaac gacggccagt gagcgcgcgt aatacgactc actatagtat    3120
attaccctgt tatccctagc ggatctgccg gtagaggtgg ggtcaataag agcgacctca    3180
tactatacct gagaaagcaa cctgacctac aggaaagagt tactcaagaa taagaatttt    3240
cgttttaaaa cctaagagtc actttaaaat ttgtatacac ttatttttt tataacttat     3300
ttaataataa aaatcataaa tcataagaaa ttcgcttatt tagaagtggc gcgccgaatt    3360
cactagtgat tgattaattt ttgttcaccg ttcaagtctt cctcggagat tagcttttgt    3420
tcaccgttca aatcttcttc agaaatcaac ttttgttcac cgtcgagtcc gttcaagtct    3480
tcttctgaga ttaattttttg ttcaccgttc aagtcttcct cggagattag cttttgttca    3540
ccgttcaaat cttcttcaga aatcaacttt tgttcaccgt cgagtccgtt caagtcttct    3600
tctgagatta attttttgttc accgttcaag tcttcctcgg agattagctt tgttcaccg    3660
ttcaaatctt cttcagaaat caacttttgt tcaccgtcga gtccgttcaa gtcttcttct    3720
gagattaatt tttgttcacc gttcaagtct tcctcggaga ttagcttttg ttcaccgttc    3780
aaatcttctt cagaaatcaa cttttgttca ccgtcgagtc cgttcaagtc ttcttctgag    3840
```

```
attaattttt gttcaccgtt caagtcttcc tcggagatta gcttttgttc accgttaatt    3900
aacccggggg cgaattgggt accgggcccc ccctcgaggt cgacggtatc gataagttat    3960
attgaatttt caaaaattct tactttttt ttggatggac gcaaagaagt ttaataatca     4020
tattacatgg cattaccacc atatacatat ccatatctaa tcttacttat atgttgtgga    4080
aatgtaaaga gccccattat cttagcctaa aaaaaccttc tctttggaac tttcagtaat    4140
acgcttaact gctcattgct atattgaagt acggattaga agccgccgag cgggcgacag    4200
ccctccgacg gaagactctc ctccgtgcgt cctcgtcttc accggtcgcg ttcctgaaac    4260
gcagatgtgc ctcgcgccgc actgctccga acaataaaga ttctacaata ctagctttta    4320
tggttatgaa gaggaaaaat tggcagtaac ctggccccac aaaccttcaa attaacgaat    4380
caaattaaca accataggat gataatgcga ttagtttttt agccttattt ctggggtaat    4440
taatcagcga agcgatgatt tttgatctat taacagatat ataaatggaa aagctgcata    4500
accactttaa ctaatacttt caacattttc agtttgtatt acttcttatt caaatgtcat    4560
aaaagtatca acaaaaaatt gttaatatac ctctatactt taacgtcaag gagaaaaaac    4620
tataatgcac catcaccatc accatcatca tcatcattct tctggtctgg tgccacgcgg    4680
ttctggtatg gcatcacctt cacttttagt ctttgggccg cagtcgagcc tgctgtcgga    4740
agactggctc gtgcaactgc ggtcgacttt gctgggaaac cgtaaacttg agggcctagt    4800
taccgcaata actcagcttg aatccatctg gaacgatctt gctctcgccg acccatcttt    4860
caaaggcatc cctggccagg aacatttccg ggccctttcc aactggatca gcagccctgg    4920
caactcggac ccgccagcgg agctttcccg actcaacctg ctcctcacac cccttaccgt    4980
catcgctcac ctagtcgaat acttcaacta cttggaggtg tccggccttt ccatgaaca    5040
actcctcaat agcacttcca tcaatggcgg cggattccaa ggcttctgta ccggattgct    5100
ggccgcagtg acgttgtcat tggccaagga tgaaggagag gcggtaaaac tctcaacatc    5160
ggtattgggg cttccgtgg ctctcggcgc atatgtcgac ttggatggat gttttgcgaa     5220
tccaccgagg gaattttcct gtctctcggt tcgctggaag agcagtgaag agagcctatc    5280
ggttttcaaa gcgatagagg aacatgctga ggcatacgtt tctgtcaact ccgatgtatt    5340
gagtgccacc gtcaccccttc ccaagcaaac gcaagacgag ctcgttgcaa aactcactga   5400
tctcggggtc accgctcgtc cgtacccact ctcgggccgc tttcactcct ccatccacga    5460
ggaacatgtg gagaagatcg tctctctcgg gaactccaac accaagttcc gattcccggt    5520
ggcttgtggg ttgcctaatc tcgtcaggga cggcacgggg tcccccattg gcaacagcac    5580
tccccttcat gaggtgattg cgaggtctat gttggttcag cggtcagaat ggagcagcac    5640
aattcggtct gccctgccgg aacctgcttc tactggcacg gaggctgtcg tgtttggact    5700
tgtggactgc ataccctcgat ccctggtcac tgaaggtggc cttaccgtca ctcgacctgg    5760
cttccagaag acggggcat acgtctaccc tgaagacgcg gtagccgtcg tcggactggc    5820
ctgccgattt cccggcgcgg attcgctcga agagtattgg cagctacttc tgtctaaagc    5880
ttccatgctc ggcaagctcc caaccgaacg gttcccaaca aaagggttgc gccggacacc    5940
aaaggacgac attcccttca tcggaaactt cctccgtgat ggctacgcct ttgacaacaa    6000
gttttttcaac cgatctccgc gcgaggcctc ggccatggat ccgcagcaca aattaattct    6060
gcaggtcgcg tacagaagctc tcgagacggc gggatatttc agccatggct cgtcacctag    6120
cgacgtcggc tgttacgtcg gtgtagcggc gtctgactac gaggacaatg tcgcgtccca    6180
```

```
tctcccgaca gccttctccg tcctcggcat ggtccgcgcg tttgtgagcg gcaagatcag   6240
ccatttcttt aacttgagtg gcccgtctat ggtattcgac acggcttgtt cttcctctgc   6300
tgtggccatc cacactcgca tgccaggctc tcaggaatgg ggagtgctct catggccctc   6360
ggctggcgga gtcaacgtta ttacaagccc agtcctgcat cagaacctcg cggcagcaaa   6420
ttttctaagc cctacaggcg aatccaaggc cttcgatgcg cgtgctgacg ggtactgccg   6480
cggggagggc gcgggaatgg tcgtcctgaa gaagtactct acagcgcttg ccgacgcgca   6540
tcacatttac ggaatcatcg cagggtctgc ggtcaaccag aatgacaact gtgcggccat   6600
taccgtccct gtatcaaagt cgcagaccgc gctgtacaag cgagtgctca agatgggacg   6660
gatggaccct gagaaggttt cgtatgtcga ggcacacgga accggcaccc cgaaaggaga   6720
cccaatcgaa tgtgcaagca tccgagaggt attcggaaac cagccctcgc gcaagctgca   6780 cttggctcc gtcaaagcaa gcatcggcca tacgaagcc gcgtctggcg tggcaggcct   6840
catcaaggtc ttgctcatga tgcaccatcg gacgatcccg ccgcaggcca gcttccagac   6900
actcaaccct aatatcccac ccctgggtcc gtccaatatg gaaattgctc tgacacccag   6960
ggactggaat ggcgaattcc tcgccgcatg cgtcaataac tacggcgcgg ccggcagcaa   7020
tgccgccatg cttatttgcc agcctccacg tctcaccacg acgccgaagg cccgccgtgg   7080
aagggacagc cttcccatga aatacccggt catgctaaga gccaagtccg cagccagcct   7140
tcaagcctac tgcaatgcgt tgacgcaatt cttggacaag gcgtctgctc ataccagcga   7200
tgaccaactc ctggctgacg ttgcctatgg gctcgccacc caccagaaca tcagcttgcc   7260
ctactctctc ggcaccaccg tcgattctct tgctcgcctg cgccaggaac tgagcgcctg   7320
cgcttccgcc acactgcccg aagagcaaac ggcaaaagcc aaatcccggc ctgtcatcat   7380
ggtcttctcc gggcaaacgg gcaacaccgt caacctatcc gaagaagcat accggtcctc   7440
cctgcttctc cagagccacc tgaaccgctg cgaccgcatt ctccgatcgc tgggccaccc   7500
gagcatcttc cccgccatct tctccaagca gcccatctcc gacaccctgg tgctccactg   7560
cgccgtgttt gcgctgcagt actcctgcgc ttgggcctgg atcgacgcgg gggtccagat   7620
cgatgccatg atcggccata gctttggcca gctgaccgcg ctctgcgtgg ccggtgccat   7680
gtccctcgag gatgggctga agctgattgc tggccgagct atccttgttc gggaccagtg   7740
gggtccggaa aggggggcta tgatctctgt cggcgcgggc gagcaacaga cgcaggagct   7800
ggtggcgagc gctcatcaag ctggcatcga ggttgagatt gcttgcttca acgccaagga   7860
taaccatgtc gtggttggtt ctgcgtcttc cattgccgcc tttgaggacc tggttgcagg   7920
ccagggcagt gaggtccgtt tgaagcggct ggaggtcact cacgggtttc attccgtgtt   7980
tgtcgatggg attatgccgg agtacaaggc gctgctggat agcatttcct tttcccagcc   8040
caagatccat gttgagactt gctcgccggg ctcagcttgg aacacggtca actcggagct   8100
tgttgcccaa cagtctcgcg atgccgtcca ctttagtgct gccatttccc gcatccagaa   8160
gaagttcagt gattgcgtgt ggctggaagc cggttcgggc acggcggcca tccccttgc   8220 tcgccgagcc ctgcaggcgg aacaggtcga catcgcgaag catgctttcc acgcagtcaa   8280
actcggagcg ccgacgcca tggagttgct ggcgcagacg acgcttgatt gtgaacag   8340 cgggaccaag gccatgttct ggcccttcca tcgctcccaa aagcaccagt acaatgtcct   8400
gcagcttcct ccgtaccagt tcgagaagcg gcaccactgg ctggagtatg tggatcgcca   8460
cggcagtgat gcccctgtcc ccgtggcggc gatcgaggca aagccggccg acatggtatc   8520
cttctcccag tatgccgacg acacggggaa cctcgcgatc ttcaacatca accaggagac   8580
```

```
cagcgagttc caagcagcca ttgaaggcca ccgcgtcctc ggccatccgc tctgtcccgt   8640
ctccttgtac atcgaagttg cgacacgggc ggcggctctg ctccacccca acttctcgac   8700
tgagacgcat gcatcgggcg ttgatgcgct ggaaatcttc acgcctcttg gtcttgacac   8760
ggcacggcaa gcccaggtta cgcttctcag cattggcgag gacgagtggg agttcaccgt   8820
ccatagcttt ccgcttggcg acacggcgtc gagaaagacc aggcacgcca cggccagaat   8880
tcgcatcacg tccctgcttg acaagagcac cgcggccatg tttgcgcgct tccagcgtct   8940
ggccaagtac gaggaatgcg aagctctctt tgccgacgga gccgccgcag gcatccaggg   9000
gccgttggtg tacaagatgt tcgacaaggt cgtcaattac tcggggatct accgtggcgt   9060
gctgaagatt gcgtccaaga accagaaagt gagcggtctc gttcagctac cagacgctac   9120
ggcgaaggga gcagacatgg agaagtcggc ctgcaatcca ctggccattg caacttcac    9180 ccaagttgcc ggcctccacg tcaacgggct tgatgagtgc ggaaacgacg aagtgtacat   9240
ctgctcgcag gtcgatgaga ttcgcgccct cagagcctc aagagacctg atggtggcag    9300
tgctggcccg tggctggtgc atgccaactt tagcaggcaa ggggacagag agctcctgaa   9360
cgatatcttc gtcttcgata cgtcagctaa gactctagtc atgaccatcc tgggggtccg   9420
atttaccaag accaacgtga atatgctgca gaaggtactg gctcgtgcaa acacagcgca   9480
ctctcatcaa gcccaggcaa aggttgaacc tccccgtacc gctgcggcgc agatcaagtc   9540
cgccatcagc acccagctca tccgcactgc caatgctccg gagcgtagcc ggaaccgcaa   9600
gagggctctc gaagacaagg tcaacagcaa cattagaatt ggcctcaagc aactactgca   9660
agaggtagcg gacgtgtctc ccgagcagat ccatgacagc actctcctcg tcgatgtcgg   9720
catcgactcc ctgatggcca ccgaggtgca cacggccatc ggcgacaggt ttggcgtcct   9780
cctcacaact gctgagttcc aatccattga ggactttgga tccttgtgcg cagcagtgca   9840
gccggcccag agcagtgctc ggagctcctc cgaggacgac ctgtctgacg ataacgagct   9900
cctagcctcc tctcactcgg ccacgcctgc atccagtgtc gagtacgagt ttcaaaacga   9960
cgagctcgtg gccaaactgc agaagttggt ggcaggccat cttgatgtct cagaggctat  10020
tgcgccagac ctttttgctag cagacgccgg cgtggactcc ttgttgggaa tcgagctggg  10080
ggcagatatt gaaaaggagt ttggacggac catcgacatg atgcagctca gtccgacctg  10140
cacttttgct gacctggccc ctgcagcgga aaaggacctc ctcgcacacg cggccgagga  10200
cttccgcgcg atccgttcgg attaccttcg cttcgcaaag gaaaccggct gggcaggatt  10260
ccgacagaat gcgtacccca agcagaggca actggtgctg agctacgtcc tcgaggcttt  10320
cgcccagttg ggctgtgaca ttgcccgtgt tgaggggggc gatgtcctcc ccaatgtccc  10380
gcatatgccg aagcatgcca aagtcgtagg ccagttctac aaggttctcc aagaggctag  10440
ccttgtccgc aaacaggggg acaagctggt caggtcccaa accccgtgcc ccaagaccga  10500
tgcggaagaa ctagtccagc agatgatcgt cgcctatccc cagcacgcct ccgagctcaa  10560
gctgctacga tccacgggct ccaagctggc agacgtcctg tcgggcaagg tcgatcccct  10620
ccagatcatc ttccgcacaa aggccgacag agatctgctc gaggatgtct ataccaactc  10680
gccaatgttc tcgaccggaa ccaaggtgct agccaacttc ttcaccaaag cactcgaaat  10740
ccaccgcggc ggcgagcaag tacgcatcct cgagcttggt gccggcacgg gcggtacgac  10800
caagacgatc ctcgagacgc tctcgtcgat gggagtcaac ttttcgtaca ccttcaccga  10860
cctgtcgtcg tcgctcgtgg cggcggccaa gaggaagttt gccaagtacg gggacgccgt  10920
```

```
caacttctcc gtcctcgacg tcgaaaagcc accgccgcag cacctcgttg ggaactacca   10980
catcgccctc gcgtccaact gcgtccatgc caccaagagc ctgctggttt cgtcgaccaa   11040
tacctgcaag atgcttcgtc aagacggtat gctctgcctg ctggagctga cgagaaacct   11100
gtactggctg gactgtgtct ttggtctgct cgagggctgg tggctctttg aggatggccg   11160
ggaacatgtc cttgcggatg agttcctctg aaggatacc ctgctgagag ccgggttcaa   11220
gcacgttgac tggagcgatg acgacagcga ggagtcggat cagttccgtc tggtggtggg   11280
attcaagtct gcgccggacc acctaatctc cgcggttgag aagctacagc tcgcggcagc   11340
ggcggccaaa aaggcggccg ccaagctggt gaccaaagaa accgtcgagt accaccgcgt   11400
cggagatgtc tccctccaag ccgacatcta ctaccccgac cagcccgacg acggcaccgc   11460
caagcgcccc atcgctctca tgatccacgc cggcggacac atcatgctct cgcgcaaaga   11520
catccgcccg cggcaaaccc gcctcctcct ctcacggggt ctcctcccca tcagcatcga   11580
ctaccggctc tgccccgaag tgaccctccc cgccggcccc atgaccgacg tcggcacagc   11640
tctacactgg gcgcgcacca cgctcccctc tctcctacct aacgccaccc ggccggacat   11700
ccgcgcggac ggcagccggg tcgtggtcat tggctggtcg acgggcggca ccctctccat   11760
gacgctgccg ttcacggcgc cggcgcgggg cattgcgccg cccgaggcgg tgctggcgtt   11820
ttattgcccg acggattatc aggatgggtt ttggagggag ccgaattttc ccgaggagac   11880
gacggagaga gaggccgggg tggagtatga tttgctagag ggggtaaggg acggcgcgat   11940
taccgcgtat aatgtgccgg cggcgcagcg ggcgacggga gggtggatgt cgttggagga   12000
tccgcggtcg aggatcgcgc tgcatatgaa ttggaagggg caggcgttgc cggttttgtt   12060
gggggggttg ccgagtaagg gcaaggcggg tgaggggtg gattggaaga atcggccgca   12120
gccgagtgat gaggaggtgg cggcggtgag tccgtatgcg caggtggtgg cggggagtta   12180
taggacgcca acgttcttga ttcatggcac gagggatgat ttgatcccgt ggcagcatac   12240
ggagaggatt aaggatgcgt tggtggagag gggcgtgccg gcggggggcgg cgattgtgca   12300 ggatgcggtt catttgtttg atttgtatgg gagtgagggc tgggaggcgg tcttggaggg   12360
gtatgagttc ttgttcaagc agattggcgt cggagccgtt gctttaatcg tcgcacacca   12420
ccaccaccac cacccccgggt taattaacat cttttacccca tacgatgttc ctgactatgc   12480
gggctatccg tatgacgtcc cggactatgc aggatcctat ccatatgacg ttccagatta   12540
cgctgctcag tgctgaggcg cgccacttct aaataagcga atttcttatg atttatgatt   12600
tttattatta aataagttat aaaaaaaata agtgtataca aattttaaag tgactcttag   12660
gttttaaaac gaaaattctt attcttgagt aactctttcc tgtaggtcag gttgctttct   12720
caggtatagt atgaggtcgc tcttattgac cacacctcta ccggcagatc cgctagggat   12780
aacagggtaa tatagttccc tttagtgagg gttaattgcg cgcttggcgt aatcatggtc   12840
atagctgttt cctgtgtgaa attgttatcc gctcacaatt ccacacaaca taggagccgg   12900
aagcataaag tgtaaagcct ggggtgccta atgagtgagg taactcacat taattgcgtt   12960
gcgctcactg cccgctttcc agtcgggaaa cctgtcgtgc cagctgcatt aatgaatcgg   13020
ccaacgcgcg gggagaggcg gtttgcgtat gggcgctct ccgcttcct cgctcactga   13080 ctcgctgcgc tcggtcgttc ggctgcggcg agcggtatca gctcactcaa aggcggtaat   13140
acggttatcc acagaatcag gggataacgc aggaaagaac atgtgagcaa aaggccagca   13200
aaaggccagg aaccgtaaaa aggccgcgtt gctggcgttt ttccataggc tccgccccc   13260 tgacgagcat cacaaaaatc gacgctcaag tcagaggtgg cgaaacccga caggactata   13320
```

```
aagataccag gcgtttcccc ctggaagctc cctcgtgcgc tctcctgttc cgaccctgcc   13380
gcttaccgga tacctgtccg cctttctccc ttcgggaagc gtggcgcttt ctcatagctc   13440
acgctgtagg tatctcagtt cggtgtaggt cgttcgctcc aagctgggct gtgtgcacga   13500
accccccgtt cagcccgacc gctgcgcctt atccggtaac tatcgtcttg agtccaaccc   13560
ggtaagacac gacttatcgc cactggcagc agccactggt aacaggatta gcagagcgag   13620
gtatgtaggc ggtgctacag agttcttgaa gtggtggcct aactacggct acactagaag   13680
gacagtattt ggtatctgcg ctctgctgaa gccagttacc ttcggaaaaa gagttggtag   13740
ctcttgatcc ggcaaacaaa ccaccgctgg tagcggtggt ttttttgttt gcaagcagca   13800
gattacgcgc agaaaaaaag gatctcaaga agatcctttg atcttttcta cggggtctga   13860
cgctcagtgg aacgaaaact cacgttaagg gattttggtc atgagattat caaaaaggat   13920
cttcacctag atccttttaa attaaaaatg aagttttaaa tcaatctaaa gtatatatga   13980
gtaaacttgg tctgacagtt accaatgctt aatcagtgag gcacctatct cagcgatctg   14040
tctatttcgt tcatccatag ttgcctgact ccccgtcgtg tagataacta cgatacggga   14100
gggcttacca tctggcccca gtgctgcaat gataccgcga gacccacgct caccggctcc   14160
agatttatca gcaataaacc agccagccgg aagggccgag cgcagaagtg gtcctgcaac   14220
tttatccgcc tccatccagt ctattaattg ttgccgggaa gctagagtaa gtagttcgcc   14280
agttaatagt ttgcgcaacg ttgttgccat tgctacaggc atcgtggtgt cacgctcgtc   14340
gtttggtatg gcttcattca gctccggttc ccaacgatca aggcgagtta catgatcccc   14400
catgttgtgc aaaaaagcgg ttagctcctt cggtcctccg atcgttgtca gaagtaagtt   14460
ggccgcagtg ttatcactca tggttatggc agcactgcat aattctctta ctgtcatgcc   14520
atccgtaaga tgcttttctg tgactggtga gtactcaacc aagtcattct gagaatagtg   14580
tatgcggcga ccgagttgct cttgcccggc gtcaatacgg gataataccg cgccacatag   14640
cagaacttta aaagtgctca tcattggaaa acgttcttcg gggcgaaaac tctcaaggat   14700
cttaccgctg ttgagatcca gttcgatgta acccactcgt gcacccaact gatcttcagc   14760
atcttttact ttcaccagcg tttctgggtg agcaaaaaca ggaaggcaaa atgccgcaaa   14820
aaagggaata agggcgacac ggaaatgttg aatactcata ctcttccttt ttcaatatta   14880
ttgaagcatt tatcagggtt attgtctcat gagcggatac atatttgaat gtatttagaa   14940
aaataaacaa ataggggttc cgcgcacatt tccccgaaaa gtgccacctg aacgaagcat   15000
ctgtgcttca ttttgtagaa caaaaatgca acgcgagagc gctaattttt caaacaaaga   15060
atctgagctg cattttttaca gaacagaaat gcaacgcgaa agcgctattt taccaacgaa   15120
gaatctgtgc ttcattttg taaaacaaaa atgcaacgcg agagcgctaa ttttcaaac   15180 aaagaatctg agctgcattt ttacagaaca gaaatgcaac gcgagagcgc tattttacca   15240
acaaagaatc tatacttctt ttttgttcta caaaaatgca tcccgagagc gctattttc   15300 taacaaagca tcttagatta ctttttttct cctttgtgcg ctctataatg cagtctcttg   15360
ataacttttt gcactgtagg tccgttaagg ttagaagaag gctactttgg tgtctatttt   15420
ctcttccata aaaaaagcct gactccactt cccgcgttta ctgattacta gcgaagctgc   15480
gggtgcattt tttcaagata aaggcatccc cgattatatt ctataccgat gtggattgcg   15540
catactttgt gaacagaaag tgatagcgtt gatgattctt cattggtcag aaaattatga   15600
acggtttctt ctatttttgtc tctatatact acgtatagga aatgtttaca ttttcgtatt   15660
```

```
gttttcgatt cactctatga atagttctta ctacaatttt tttgtctaaa gagtaatact   15720
agagataaac ataaaaaatg tagaggtcga gtttagatgc aagttcaagg agcgaaaggt   15780
ggatgggtag gttatatagg gatatagcac agagatatat agcaaagaga tacttttgag   15840
caatgtttgt ggaagcggta ttcgcaatat tttagtagct cgttacagtc cggtgcgttt   15900
ttggtttttt gaaagtgcgt cttcagagcg cttttggttt tcaaaagcgc tctgaagttc   15960
ctatactttc tagagaatag gaacttcgga ataggaactt caaagcgttt ccgaaaacga   16020
gcgcttccga aaatgcaacg cgagctgcgc acatacagct cactgttcac gtcgcaccta   16080
tatctgcgtg ttgcctgtat atatatatac atgagaagaa cggcatagtg cgtgtttatg   16140
cttaaatgcg tacttatatg cgtctatttta tgtaggatga aaggtagtct agtacctcct   16200
gtgatattat cccattccat gcggggtatc gtatgcttcc ttcagcacta cccctttagct   16260 gttctatatg ctgccactcc tcaattggat tagtctcatc cttcaatgct atcatttcct   16320
ttgatattgg atcatactaa gaaaccatta ttatcatgac attaacctat aaaaataggc   16380
gtatcacgag gcccttcgt c                                              16401

<210> SEQ ID NO 15
<211> LENGTH: 7636
<212> TYPE: DNA
<213> ORGANISM: Chatomium globosum

<400> SEQUENCE: 15
atggttacgc cggcagccag ccaagaccct cctgccattc cagccaggca gaatgccagt     60
gcgactgctg ccatggcagt gaatgccaaa gacactgtgg agcaagagcg taacgttgtc    120
cttctatttg gctgccaatg gctcacgttc actgcatccg acttccgcca gctccgaaaa    180
gctgtcctcg ataatcctga gcttcactgg atgctcgatg ttctaagcga attgccaggc    240
tattaccgcg ctgctgccgg aactagttgt gtcccatcct tgcgggcgat caggggagaa    300
gaggaccttc gggagttgga agatggttc cgatgcgatg atctatccac agccaaattt    360
ccactgtgct atacacagct cgcaccgttg ctcatgatga cccattttgt gcagtattca    420
cagtggctga agatgcagcc aaatggaagg aaccccgtgg ttgaaattgt cggattttgt    480
attggactcc tgagcagtat tgcagtctct gcgacgagga tgggcagcct gaagatgtac    540
ggctctgttg caatgcgttt agctatgtta ttaggggcaa tgggagattt acagcaagct    600
ggggaagagt atacgtctct agcaattggg tggaagcgtc ctgaattaga ggacgaggtg    660
gaaggcttgc tcgaaaaata tccggggtta tgtatggcct tcatagttgc cggctgaacg    720
agcactgacg gaacagtcat atattaccgt tcaatatgac gagaacagag caacaatcat    780
ggctcctcgg cgaagtgttg ctgccctgca acaaactctc cagtctgctg gattttcagc    840
caacgcggtt gaatacaatg gccgatatca ctggccaggc cacgaaaaga gcctgacccc    900
attgattcat ctctgcaata tcattccgg tcttcaacta cctgacgcat cagagctgct    960
ccaccctccg cgtgcaaaca gcactgcaga accggttcgt tcgggctgcc tccacgagct   1020
ggtcctccgc gctgtccttg ctcaacagtg tctgtggcac aagactttct ctgccgtata   1080
ccgagaacat ctcaccacac ccagctctat agtcgtcgag ttcgggccgg aacgatgcgt   1140
gcccccgaca ctgtttcgcc gtcttccaca acgcatcgtc cacttcgctg atgtagagct   1200
tccggccacc ataagccgcg accatgagct agccacgagg ccccggcag aaaccgacat    1260 agccatagtc ggtatggcct gccgtgttgc gggcgctgat gaccttgacg aattctggga   1320
tcttttgtgt tctggccagt cacagcaccg cgagatgcca cgagaaagat acgcaaacta   1380
```

```
cgagactcct tggcgccctg aggcgagtca tcgctcatgg ctcggtaatt ttgtccgcga    1440
tattgatgcc tttgaccaca agttcttcag gaaatcaccg cgggaagcga tgtcacagga    1500
tccccagcaa cggctcatgc ttcaagtcgc ctatcaagcg ctggagtcag caggctactt    1560
ttcccaacca tccccaggaa aagatatagg atgctttatt gcaacctgta cagtggacta    1620
cgaacacaac gtgaattgcc atccagcttc cgcctatgca gcgacagggc tgttgagaag    1680
cttcctagcc ggaaaactct cacatcactt tgggtggcgg ggcccctcac tatgtgtgga    1740
tacagcgtgt tctggctctg ctgtagcatt gcatcatgca tgtcgggcaa tactgagcgg    1800
cgattgcacg gccgccctgg tgggcggcgc caatgccatc accagtcctc tcgcatatga    1860
taatctcgca ggggcatcat ttctttcgcc tacaggtccg tgtaagccat ttgacgcgaa    1920
ggctgacggt tattgtcgcg gtgaaggctt cgcagcgatc tatatcaaaa agttatcaca    1980
cgcaattgca gatggagatc aggtcctggc aactattgca agtacagctg tggaacagaa    2040
tgacaactgt acacctattg ttgtgccgga cactgcttcg ttggctggtc tgtttaagaa    2100
ggtaacgcag cgtgcgcatc ttcactcaag ggacatcagt atcgtcgaag ctcatggaac    2160
aggcactcaa gctggggatc cagccgagta tgagagcgtg cgggacgtgc taggtggtcc    2220
aaggagggta gggaatttag ctttaggctc tgtaaaaggc ctggtcgggc acactgaggg    2280
tgtatccgga attattgccc tgtgcaaggt cgtcctgatg atcctgaacg gacagatccc    2340
tcctcaaccc gggttccatt ctctgaatcc acatatcagg gccatgccag acgaccatat    2400
cgagatagga acaagagtca aaccttggga agttggattt cgcgcagcgc tgataaacaa    2460
ttatggagct tgtgggtcta atgcatcaat ggtcatcaca cagggaccgc aaaaggatga    2520
agttcaagaa cggggtattc acgcagaaaa tgttgcgctg ccgtttcgcg tgtgcggttt    2580
agacaaggcc cgtctgcagg catatgcggc acgtttgcgg aggttcctct ctcgctcaga    2640
gcgaggcata tcttttgcta atatcgcgtt caatctcacg cgaaaatcga acccggccct    2700
ggagtgccag tgcgtcttcc aaacccgatc agagtcggag cttaaagaca tcctgactgg    2760
tctggaggaa gggacaata aatatataat tcaagtgaag aaacccaaac gcccactggt    2820
gttgtgtttt ggaggacagg tagggagaag tattggactc gaccgcacgt tctataacgc    2880
atttccttg ttcaaacatc atctcgactc ctgtgatgat attcttaaag cgaatgggga    2940
ttcaagcatc taccctggta tatttgcaac ggccccgta ctggatattg tgcagctcca    3000
tacgcagctt tttgcattgc agtatgcttg cgctcgcagc tggatggatt gtggagtgga    3060
ggtcacagcg gttataggcc acagcttcgg cgagctaaca gcattgtgta tatctggcgc    3120
gctgtctcta ccagacgcct tgactcttat cgtgcgccgt gctgttctga tccgtgacaa    3180
atggggtgct gacccgggtg ctatgctcgc cgtagaagga gacaggtcta ccttggagaa    3240
acaccttgaa tcgtcctccg caaacatagc atgctttaat ggccctcgaa gttttaccgt    3300
cgcagggcct accgcagtta ttgacttcct tcaggaagaa ctgggggctg attccgcatt    3360
tcgactgaag cgccttgagg tcacaaatgc tttccattcc accctggtgg acccgttgct    3420
tcctgcactc gcaagtgcca tagatggttt agctcttaac accgcaacta ttccgatcga    3480
gcgtgctact gaacaccaag cagcagatac aataccgttg agcatcgtgg cagaccatct    3540
ccgtcagcct gtttatttca ataatgctgt acagcgcctc gctgcacgtc atggccctgc    3600
tatctggctt gaggcaggct ccaactccac gattacctcg ctagcacgga gagcgcttgg    3660
tttgggcgtc tctggcaaca ctttccattc ggtgaatgta acatccacgt cggcattgat    3720
```

```
gaacctcact gatgtcacgg tcgggctctg gagcgataat gtgccttgca cattctgggg   3780
ttatcacgct cgccaaacca gagaatatgc tcccctttg  ctaccacctt accagtttga   3840
aagaacgcga cactggatgg aaaataagcc ccttcccttg aaatataacc aggcgcaagc   3900
ggttatggaa ggtaagatgg aagagcctct tttttcattt atcggttacg aagaccatgc   3960
ccgtctgttg agtaaatacc tcatccatac ggaccatcca aactatattg cagcagtctc   4020
cgggcataca gccgcgaaga ccgcccaat  cgcacccgca actctgctgc ttgattatgc   4080
aatcgagctg ctcagatctc ttcccaacaa ccaaaggaaa atacccagag tgtttgatgt   4140
cgggagtgat gcgccactac tgctagattc aaaccgcgag gtgtggatcg aggtttccgc   4200
tgaagatgat aaaaggactt gggccttaag gtttcagagt cagacgaaag ggggtcaatc   4260
tgactcccgg cttctacatt gcacagcaca tatatcgatg catgacgtcc gatgctctag   4320
gttacaaacc gagttcacac agtacgcaag gctagtcagc cacgccaggt gtgccgacct   4380
cctaacagac ccagaagttg atgatatcct gcagggccga aatgtgtatc ggtcattcgc   4440
agaaatagtg gagtattctg agcagtatca gggtgtgaaa aggctagttg ggaaaggtag   4500
agaaagcgcc ggtcgagttg tcaaatcata ttctgggaaa acatgggcag atcccttttt   4560
gtgtgactcc ttcagccagt gtgctgggtt ttgggtgaat gcatgaccg  acagagctga   4620 agacgaagtt tatgtcgcga gtggaattga gcagtggatg cgcacgccat tatacgcgga   4680
tatggcgact gctaggccgg ataccctgca tgtatgggct cgtcaccagc aatctgaggg   4740
attatataca agcgacgtct ttgtgttcac acctgatgga gagctggtgg agatgtttct   4800
cggcttgcgg tattcgcgcg tagcaaaaag cctgtttacc cgcctacttc gtggctccac   4860
gctgaaagtt gactgcagga caaaagatac tgctaaccag gaaaataact caataaagga   4920
tctggtcagt cgtgttaagg ctgttgtggc cgagatctgc gcggtgaagc ccagcgagat   4980
acaggatgat agtcatctag ccgatgcggg cgttgattcg ctgatggcaa tggagcttgc   5040
ccgcgaatta gaggttgcct tcaaatgcac gatagctttg gaggcgctcg ttgaggcaga   5100
gacatttcat gatcttgtgc aagcggttca aagtgcactg ggagagacgt atgaagactc   5160 cagcgttgc  agtggcaacc agtgcagcac aactgacgag gccaccgaat tccctagcac   5220
tagctggtca attacaagtg tatccgatac ggcagacttg gtactaccgc ttgatggcgt   5280
actggatgct ctggatgaaa ccaaaggact gaccgatcag ttcctagcgg acaataaatg   5340
cagtggtcgt cttctcaact tcactccttt gatggttgaa atgtgcattg tattgacact   5400
ggaagcattg gaggaattgg ggagcaacat ccgatctgct cgtgcaaacg accgcctccc   5460
gcgcattgaa tttgatacgc agcacggccc actagttgag tacctatacg ggcggctatt   5520
ggaggcggga ttgataaaac tagacggatc gacagtcatt cgcacggaga tctgcgctcc   5580
aacagaatcg agcagtacac ttctccacaa gatcgaacgc gagtacccag aatatggcgg   5640
tgcaagtaaa ctcaccttct acactggcag tagacttgcc tcggttctgc gcggggagca   5700
ggacgggctg cagctcatct tcggcacagc ggagggccag cggcttgtat cgtggatgta   5760
tggcgatgag ccgcataatg tggcgggtta caagctaatg ggagagttta tccggcgact   5820
tgtcgacaag ctacctccag ccgcagccag agaaggatg  accttgagaa ttctcgaaat   5880
gggtgcaggc acaggtggtg gcacgaagtg gatgcttcct ctgctggcag cgcttccagt   5940
tccggtagaa tataccttta gcgacatatc ccccgcattt ctagctcagg cgcgacgcaa   6000
atttcgcgac tatcaatttg tccggtattg cgtgcatgat atcgaaaaac cgccatcaga   6060
ggacctagga aaataccata tcatcatggc gagcaatgcg gtccatgcga cctcaaatct   6120
```

```
gcaggtgtcc acgggtaata tgcgacaggc cctgcgaccg gatggcgtgt tgatgttgct    6180
agagatgact aggccggttt ttgcgataga cctggtattc gggttatttc gtggctggtg    6240
ggttttcaac gatggacgga cgcatgcaat taccaacgag caacggtgga aagacgacct    6300
gcaagcagta ggatacggtc acgtcgattg gacggacggc gaatccaacg aggtcggcgt    6360
ccagcgtgta attttgcta ctgccggagg agagcaatat cacccggtct cgccccaaga    6420
ggatgccgca agactgcgga cagtggtgga gtatgtttac caacacaccg caggctttac    6480
aatgccagca ttgccgccac ggatcagagc tccagctaac catgcatgca ttttagtcac    6540
tggggccaca ggtagccttg gtagccattt ggttgcgcgc ctcgtacagc tttcgaatgt    6600
tcaagctgtt atctgcctga accgggtaag ccgaatgggg ccgcgggttc gacaaaagga    6660
agcagtggcg gcgcggggcc tatctcttga gtcaaaagaa gagaccaaac taatggttat    6720
tgagactgac actgcaaacg accgtatggg actatccgtt gagcagtgca ggtaccttca    6780
agaaaacgta actcacataa ttcacaatgc ttggcccatg aacggtgccg caccgctgtc    6840
gaagttcgag ggacagttcc gtgcgctgcg aaatttgatc gatctggcta gatgcattgc    6900
cactgctcaa cgacacccag tccgattcca gttcatatct tcgattggta cggtcaatgg    6960
aggtggagcg ctggaagaac gtacgcggat tgaacaggtg atgagcaacg ggtataacga    7020
ggcgaagttc gtctgcgagc gaatgattca cgagacgctg cagcggtatc cggcagtatt    7080 ccagcaaca attgtacggc caggacagat ttctggatcc gaggaaacag ggtactggaa    7140 cacgccgag cattttccgg ccatggtgaa atcgtcccag agccttggtg ctttcccttc    7200 actgcgggg cggttgggat ggacgccagt agatgtagca gctcgtatta cgccgaact    7260 gctactggac gagggaatcc ccgaggaaat ctatcacgtc gaccatccta caggtcagaa    7320
ctggaccact gtcgtagacg tgctcgccga ggagctggaa gccaccgagg tgccgttcaa    7380
ggattggatt cagcgagtta gaaaccgtgg tggcagcagg gagaatccag cagggtttat    7440
ggcagactgg ctggagacga atttcgaaag gatgtcgtgt cagggaccgc tagacacaag    7500
ggtggcaaga agacattcca aaacgttgag agagatgggg ggaggggag gggatgaaca    7560 cgtgaggcgg gttgtccgca gttggaagga gtgcggtttc ttaacacaag cacagaccag    7620
acagggcatt ccatga                                                    7636
```

<210> SEQ ID NO 16
<211> LENGTH: 7883
<212> TYPE: DNA
<213> ORGANISM: Chatomium globosum

<400> SEQUENCE: 16

```
atgcttggtc atcgggactt cactacattg cctctttcac ggcgtgagtt tctcctcttt     60
ggccctctgg ccctgtcgtt tgaccaggct gcctttgagc atcttcgcaa aacgattgtc    120
aacagcgaag agcaccgttg ggctctagag gtactcggca gccttcccca atactatgcg    180
accattgtca acgctttcc tggaatcaat ggtaggaatg aggttcaact cgaagatctc    240
aaaggtgccc ttcacagtgg aaagcctctc gcgaccagct tcccactgcc caacacccttt   300 cttattcctc tggtaatggt cctccacttg accgaatact ccagattcct tcaggagatc    360
agtgaggaac ttgaatctgg tattgatctc ttcgatgcgt cccgtcacaa taaggagact    420
gttggtttct gcactggtct cctcagtgcc atggcagttt ccagcgccgg cagccgggaa    480
gattttcgca aatatgcggc tgttgccgtg cgacttggcc tgctcgttgg tgtggtggtg    540
```

```
gattctcatg atatatcatc cgcgcaaggg cccagcaagt ctatcagtgc gtcttggaat    600
tctgcgcaaa agcgtgaaga cgcacggcgt atcatggatg aatttcccca ggtattataa    660
cttgctgggc atatctttac cgtgaaattt gttcatatgg ctaattcacg gtgcaggcgt    720
acatctctgt ctattatgac gaagaccgtg ctactatcac agccccagca tccgagattt    780
ctgatctgca tcggcgtttg cgagcttctg gcattgtaac agccgagatc ggcctgaatg    840
gatgtttcca tgctgattgt tatcttgatc aactggatcc aattatccag ttttgcgact    900
ctcagcccga cttccagctt ccggatgcat ccaaggttgt tattcctacc cgatccaatg    960
ctactggaga gttaatccgc gacggtgctt gcaccagca cgccctgcgg tctatcctgg   1020
tcgaaccccc tcagtggttc gagagcttca ctgcagtgcg tgacgcttgc gcagaggatg   1080
aaggggccat tatattctcc ttcggtcccg agcggtgcgt tcctccgtct ctcctccggg   1140
tgttgagcca gaaagtggtg accgtggaag atctcgacgt ttttaaagaga taccagtact   1200
cctactccga gaacgatatt gctgttgtcg ggatgtcctg caaggtggct ggtgccaaca   1260
atcttgaaga attctgggac cttctttgta ccggaaagtc ccaacatagg gaagttccga   1320
aggaacgatt cagctttgag acagtcttcc gagatgtcga ttctaagagg aagtggtttg   1380
gcaattttat tgacggccat gatcagttcg atcacaaatt cttcaaaaag agcccccgcg   1440
agagcgctac aatggatcct cagcagcgtc atttgctcca gattgcctac caggctgttg   1500
agcaatctgg atactttcat tcggccaatc agacagaca gattggttgc tacatgggtg   1560
tgtgtgcctg cgactatgag aataatattg cctgccatgc tcccaatgcg ttctcagcta   1620
cgggaaacct gcaaggtttc atcgccggca aagtcagtca tttctttgga tggactggac   1680
ctggactcac aattgacact gcctgctcat cctccgccgt tgcagtacac caagcatgca   1740
aggccatcat taccggagag tgcactgctg ccctggccgg cggcacacat gttatgacga   1800
acccgctatg gttccagaac cttgctggag cgtcatttct cagcaccact gggcagtgca   1860
agcccttga cgccaaagca gatggctact gtagaggtga gggtattgca actgttttc   1920
tgaagaaact ctctgctgcc gttgccgacg gggatcagat tcttggggtt atcacggcca   1980
ctgctgtgca gcagaaccag aattgcaccc ctatcttcgt ccccaacgtg ccatcacttt   2040
ccgacctgtt tcgtgtcgtg gtgaagcaat ctcgactaca accatcggac gtgactgtgg   2100
ttgaggcgca cggcaccgga actgctgttg gagaccggc tgagtacgac agcattcgat   2160
cagtgctagg tggctcgagc cgggagaaaa cgcttgctct cagctccgtc aagggcctag   2220
ttggtcacat tgagtgcacc tccggcattg tctcgctcat caaagtactc ttaatgctgc   2280
agaagcggat gatcccaccc caggcaagct tcactaccat taacccggcc attaaggcta   2340
ctcctgcaga caaaatcaac ataccgacca ctgtcaagac ttgggacgcc gaattctgcg   2400
cagctttgat taataactac ggtgcctcgg gctccaacgc atccattgtc gtcactcaac   2460
cgcctgttgg tacagttaag ccaagtgcag aaacctcagg tcttaaatac cccttccgat   2520
tctgcggcat ggatgaacaa agtctgcgcc ggtactccaa aatctttcgg cagtttctca   2580
accgaaaaag ctactctgcg caggatctct cgttgcggaa tatctccttc aatgtaaatc   2640
gacaaagcaa ccgtcagcta gatcgaactc tactcttcag cgtcaagaca ctagaggaac   2700
tcgaacagaa gctcgtcact ttcgagaatg ataatgacag tattacatct ctcgcactgc   2760
ccaagtccaa gccagtcgtc ctctgctttg gaggtcaagt ctcaacattt gtcgggctgg   2820
atcgcactgt atacgagcgc gtggctattt tacggaagca tctccatact gtcgatgcag   2880
tagctcgctc gatcggactg aagagcatct tccccaggat cttttgagact acacccgtta   2940
```

```
gtgacactgt ccatttgcag atcatgctat ttgcatctca gtacgcctgc gcacgcagct    3000
ggatcgactc tggcatccag cctgttgctg tagttggtca tagcttcggt gaactcacta    3060
gcctttgcgt ctcgcagtca ttgtctttag aagacgccgt caagatgatc gcagctcgtg    3120
cgaccctaat cagggacgct tggggcccag agaaaggcgc catgcttgca gtggaagcgg    3180
atctggaaga cgtccagaaa ttactcgctg agtcgagtgc tggatgtcaa gatgtacaac    3240
cagccacgat tgcctgctat aacgaccca ggagctttac acttgctggt gcggttgcag    3300
cgattgacgc cgttgctgag gccctcgcca cacctgcgtt ctcctccatg aagaacaagc    3360
gccttaacgt gacgaatgca ttccattgtg ctctagtaga tccctccctt gatcgactcg    3420
aggagagtgc ccgggaactg actttccgtg cgcctgtgat tcccgtccag agagcaaccg    3480
agtatcagac agaggagctt cctacctcca gatttgtcgc tgatcatatt cgttctccgg    3540 tcttttttcaa ccacgcaatt cacagactgg cggataagta tccttcttgt gtcttcttag    3600
aagcaggctc caactcgacc gtcaccaaca tggccagtcg tgcacttggc aatcccagca    3660
gctcccactt ccaggcaatc aacatcacga gccataacgg atggaataac cttgtagatg    3720
caactatgaa tatgtggaaa tcggggctag gtgtccattt ctgggctcat cagcccagcc    3780
agaccaagga atacgctctt ctcctgctac caccgtatca gttcgagcct tctcgccact    3840
ggatagaatt gaagaatccg ccaaagctga cagccgcacc agcaattgag gaagttaaaa    3900
aagaagaggc taaggtaccg aatactttat tgacatttgt ggggtaccaa gacagtgaga    3960
ggcagcaggc aagattccga gtcaatacta tgatccccaa atacgacaag ctcatccgag    4020
gccatatcat tgcacaaacc gctcccatct gcccagcaac cgtacagctt gacctggtca    4080
tcgagtctat ccggagtatc cgtccggagc ttgcaagcac tgaacacgag cctcagatcc    4140
atgccgtaga gaatctggcg ccaatatgcg tgaatccact gagagctgtg tgggtggagg    4200
tcacagccga cgacgtcgct caaggaacct cctggaattt ccaggtatac agcgacgatc    4260
tacagaacgg tttctccaaa accatccata caaccggtcg agttatcttc cggtccatta    4320
gtgatgtgtc cctaaagtat gagttttgccc ggtttgagcg gcacttcagg caccaaaacgt    4380 gtgtcgaact aatgcgcggc ggtgaagtcg atgaagtatt acagaacaga aatatctaca    4440
agatgttcgc cgagattgtc gattatggcg aggactaccg tgggctccag aagcttgtga    4500
gcaagggcaa tcagtccgct ggatatgtgg tgaagaaata caaccctgag tcctggcttg    4560
atgggcatct agccgacagt ttctgtcaag tgggaggcat ttacgtcaac tgtatgacgg    4620
atcgtgttcc aaatgatatg ttcatcgcca acggcatcga gcagtggatg cgttcaccca    4680
aaatgcgtca acaggaccct cgacccgagt cgtaccatgt gctggcaacg caccatcggc    4740
cctctgataa ggcatttctg actgatgtgt tcgctttcga ctcgactact ggtgtcttaa    4800
tcgaagttat tctgggtatc agctacgtca agattcccaa agcctcgatg agcaagttac    4860
tctctcgcct tacagtgaat gatagtgcta gttgtcctac caacatgcct ctgctttcaa    4920
aatcagccag tgtgaacctg tttgatgctc cagagaacct cagcactcca tcactgtctg    4980
ttgctcctac ccagcagtct gctcccgccc tcagcctctc caaagtaaaa aaggtcaaga    5040
acgatgggcc agacaagggg cagctcacgc aacgaatcaa gtccatcctg gcggaacttt    5100
ccggtctcga aattgcagag ataaaggacg atagcgagct tgccgacctc ggaatcgatt    5160
ctctcatggg tatggaaatg gcacatgaga tagagaaggc tttcacaatt tcgctgcctg    5220
agagtgacct catggaggtc gtagacgtgc cgagcctaat taaatgcgta cggaaagcta    5280
```

```
tgagcggcga tgctgattcc gctgaataca ccaccgagca gagtacatcc gaagcggcgg    5340
acagcgacga taaatccacg aattatacca ctcctagcac tccaggcgag gaagctctcg    5400
acatggacaa gtctatgcgc gagttTctag ggaaagaggg cacggagtta aatctcccct    5460
ttgagacggt catgaaggca ttcaatgaga ccaagaacat gacggacgac aggattgcag    5520
agtaccagca aactcggtac gtcgaaagcg ttcttccaat gcagagccag atgtgtgtgt    5580
ctctcgtgtt ggaggcattt gatcaactca acatgaggat tcgcaccgct cctgcagggg    5640
agaaattcac gcgtatctct catccgaagg aacatactcg gctagtcgac tacctataca    5700
agatgctaga ggacgcaagc cttatcaaca ttgacggaga ggtcatcacc cgaacggcca    5760
tccaggttcc acggcctagc aaagagattt tcgatgagct cgtctcgcaa cacccggacc    5820
agaacgcggc cgacaagcta acattttaca ccggatccca tctcgcagaa gtgctgaaag    5880
gagaaacaga cggcatcaaa ctgatattcg gaacgcagga cggacgagag ctagtctcga    5940
aactatacag ggactggccc ctcaaccgcc tcttctaccg gcagatggag gacttcttag    6000
agcgacttac gtccaagtta gacataagcc agggcgtgat caagatcctc gaaatgggtg    6060
cagggaccgg aggaacgact aaatggcttg ttccttTgct ggcgaagctc aacataccgg    6120
ttgagtacac cttcaccgat attgccccgt ctttcgttgc tgcggcgcgc aagaaattct    6180
ccaagcaata cccgttcatg aagttcagaa ctcacgatat cgaaaaggcc cctgcagatg    6240
atcttatcgg cagccagcac gttattatcg ccagcaacgc agttcatgct acgcatagtc    6300
tcagtgaatc cggaaagaac attcgcaagg cactgcggcc tgacggcgtt ctgctgatgc    6360
ttgagatgac agggacactc cactgggtcg acattatttt cggcctcttt gaagggtggt    6420
ggtactttga tgatggccgc acccacgccg tcactcacga gtcccggtgg gcgaaggact    6480
tgcaggctgt tggatacggc cacgtcgact ggacggatgg cgtacgtccg gaaaacaagc    6540
tcgagaagct catcatcgcg ttcgcatcag gcgggaggta tgaaagactt cacattcccc    6600
gacctctaga aagtgcctcc gctgactgtg cagcgcgaca agcagtcgtc gataggtacg    6660
tgcaggagat gaccgctggc tttggagctg caacagggt gtctccttct gctcctctgg    6720
cacatcaaga acccaaggc tgctgcgtcc tggtgactgg tgccacgggt agcctggat    6780
gtcaccttct tgcggcactc acctcccttc ccaccatcgc cagcgtggta tgtctcaatc    6840
gccgcagtcg acaagatccc ctcgagcgtc aacaccgttc gcttcttgag aaaaaaatct    6900
ttctttccga ggagactgct gccagggtca gagtgattga gacagacatg tcaaagcccc    6960
aactcggcct tttggaagag gaatataact atctcctcaa tagcgtgact catattgttc    7020
acaacgcctg gctcatgaat gccaaattgc cccttaggag gttcgaacct cagctccaga    7080
tcatgcggaa tctgctggat ctcgcttacg ggatctccct tcaacgacct atggagaagg    7140
tctccttcca attcatctca tccatcgcga cagtgggcca ctggccaatt tggactggta    7200
agtccagcgt ccccgaggag cgcatggcga tcgagtcggt ccttcccacc gggtatgggg    7260
acgcaaaata catctgcgaa cgcatgatcg acgagaccct ccataaatat ccagacagat    7320
tccgggccat ggtagtgcgc cctggacaag tcgccggctc aagcaccagt ggatattgga    7380
ataccatgga gcattttTct tttctagtga atcgtctcca gactctaaat gccctacctg    7440
actttgatgg tgtgctgtca tggaccccgg tggatgtcgt ggccagcacg ctcgtggatc    7500
tcctcctgct tccggaagat aaaacccgt attccatcta tcacattgat aacccagtcc    7560
gccagccctg gaaggagatg aacgtggtac ttgcagatgc gctgcatata ccccggtcga    7620
acatcattcc attcgagaaa tggattcagc gggtcaagga ctatccccgc caagttgagg    7680
```

```
gtgcagaggg agacaatcct gcgattctgc tggtcgattt ccttgataac aatttcatcc    7740
gcatgtcttg tggggccttt ttgctggaaa cgaagaaatc gcgcgagcat tcgaaaactc    7800
tcgcaaatct aggaccggtc agtgcagaga cagcgaggct gttcattaaa agttggatag    7860
atatgggatt tttaagtcca tga                                           7883

<210> SEQ ID NO 17
<211> LENGTH: 6414
<212> TYPE: DNA
<213> ORGANISM: Chatomium globosum

<400> SEQUENCE: 17
atggcgaacc tcatggaaat tgccattatc ggcatgtctt gccgtttgcc agatgacata     60
aagactcctg gtgactttta ccgcatgcta tgccgcaaaa gagcaggatg gtcacaagtg    120
cccgccgacc gcttcaacgc gaaggcatat cataactcgg acccgaataa gaagggttgc    180
tttaactctg aaggtggcta cttcatccaa gacgacatct acatgtttga cgccggattc    240
ttcgatatca ccaagaagga agctgagtca atggaccctg cacagcggtt gttgctagaa    300
tgcgcatatg aagccttgga gaatgccgga gcaccgaaag agtcggtagc aggtaagaag    360
gttggtgtgt tcatcggcgg taactacggg gaacaccggg ttgccaacct ccgcgacttg    420
gacaacaccc caagcttcga tgccaccggc aaccaaggag ccttcctcgc cggtaggctg    480
gcttactact ttgacttacg aggcccaaca attaccgtcg acactgcgtg ctcgtccagc    540
atgcatgctt tgcacctcgc tgtgcagagt atccggtcag gggagtcgga gcaagccatc    600
gtgggcgcgt cccacctcat aaccgacccg gacatctggg catccatggg aaacctccgc    660
ctgttctcgg ctgacggcag gacccacgct ttcgaccacc gcgccaagtc ggggtatgcg    720
cggggcgaag gcgccgggtg cttaatcctg aagccgctgc accaggcccg ggctgataat    780
gaccatatct tttccgtcat cacgcacacg ggtattagcc acaacggacg taccgtcggc    840
atcgtggctc cctgccccga cgcccaggag aagctggtta cccgagtgct cagggaggcg    900
ggcatccacc cctgggaagt gggcttttt gaggctcacg gaacaggtac aaagaaaggg    960
gacccgatcg aagccagggg tatttacaac gctgtcggtc gttatttttc gcccgagaac   1020
ccgctccaca ttgggtccgt gaagcccaat gttggccatc tggaatgtgc cagcggcatc   1080
atttcgatca tcaagggagc tctcatgctg tactacggtt tcatcctgcc caatgccgac   1140
ttcgagcggg taaatgaagc catcccattg gcggcgtgga acatgcgtgt ggcaacacga   1200
cagaagccgt ggccgaggaa caccaaccgt ctctgtatca acaacttcgg ctttagcgga   1260
tccaactcga cttgcgtcct gagcactacc ccgagatgca gaagcattga aatcgccgat   1320 aacgcgcct acagccctct caggctcttc gtactctcgg ccaacgatga acgcacttt   1380 cgcaagtccg tgagcaaact ggggatttgg atcgaacagc acgccgagct ttaccaaacc   1440
accatgccgc ggaacctggc ctacacactt tgccaacgcc ggtcacactt gcaatgcgg   1500 atggccgttg ttgcgggcat gtgtagcgac gtcaccaagg ccatcaacag ccacgaggcc   1560
gtcccgacac gggcacccag cgtgcctcct aaagtggcat tcgtgtacac tgggcagggc   1620
gcccagtggt tgccatggg ccgggagctc atgaaaacgc atcccgtgtt cctagactct   1680
atcaaacgcg ctgacaatgt actaggcgtc ttacgtgccg atttcaccgc ctctgaggaa   1740
ctcaacagag atgaggattc gaccagggtc ggcctggccc agatcagcca gcccatctgc   1800
accgcagtgc agctagccct aacgaccctt tttgcctcct tcggtgtgac gcccggcgcc   1860
```

```
gtcacgggcc actcgagcgg agagattgga gcggcttatg ccgcaggcgc cttgaccttt    1920
gtggacgcca tgaccatcgc ttactggagg ggtcaggtag tcatcgagct gcgaaacagc    1980
catccgcagc tgagaggcgc tatgatggcg gtgtctcata acgcggacga cattcaggag    2040
ttggtggagg cgatgaaccg tattcatcaa cctcaggtga cgatcgcttg cgtgaattcg    2100
cccatgtcgg tcactctgtc cggtgacgag gcgggcatcg acctgatagc cgaacacttg    2160
cagagcgcca atatctttca tcggaagctt ttcgttgatg tggcatacca ctcccggcat    2220
atgggcataa ttgccccgc atataggttc ttgatcggcc tcattgaacc gttggacggg     2280
cgcaaccgcg atgtccaatt cttttcatcg ctccgtggct gcaaggttcg ccctgagagg    2340
ttgggaccac gatactgggt cgacaatctc accgaggccg tccaattttc cacgtccttg    2400
gagcagctct gcaacgaata ctcgcccgac atactcgtag agatcgggcc ccacgccgca    2460
ctcaaggggc ccatcctgca aggatcaag gagttttttgg gtccggcggc catgaagatc     2520
tcgtatctcc ccaccctggt ccgcggccag gatgccacgc ggacatgcct ggaaacggcc    2580
ggccagcttt tccttcacgg ctacccctg aacttcttcg agatcaacca taaccgcgaa     2640
gaggcagaga ggccggagct gcttgcagcc ctgtacacat acccgtggtc gcgccaaaga    2700
tactgctacg agtccagaat tacccaccag caccggttca agccattccc aagatacgac    2760
gcgctgggca cgttggctga ctggtccgat tctctaaacc cgacatggcg aaacattatc    2820
cgcacagaag acttgcccaa ggtcaggag taccaggcgt cagcccagac cgcatatatg      2880
aacgagctat ctactgtggc gtttgaaatc agggaccttg tggtttctga gcatctgtac    2940
ttgatggacg accaagacgt tgaggtactc gtaagcttcc aggcctcgaa ttcaggggac    3000
aagagaagcc acgggttcaa gattttgtcc tacgggccaa cccaggagtg gacggagcac    3060
tgcactggga ctgtgacagc aatgccgac atgccgtgt ctgagcgccc ggagatcgac       3120
tgtggctcaa agctgtatgc atccgagcta aaggaatatc atgaagaaga ggtgtatttc    3180
aggctgatgg gaaaggggtt cacatacca gaggctttca ggaccttgac caatgtcaga     3240
gtgaaggagc accaagtgac gggggtgtca gatcttcgcg agctcttcat catggacgac    3300
ctccactacg gagctcaccc gggtatcgtc gagtccatgc tccaggcaac gttattcacc    3360
cacaagaacg aggatggcag gccgtctgag gtaccatgcc tcctgtcctc gatccgtcac    3420
atagctattg ttgcggattg gcgcccgagt ctgggcaacc agacggctgt gaaagcaact    3480
ctggatgaaa acagggcttc ttccacggtg gaactctttg gcgccattgg taatgtggcc    3540
gtggggtcgg cggccgtttc catgctgggc gtgaggttca aggcgttggt gcccttcccg    3600
ccgaaagccc caccgcgcga gttgtgcttc aagatgcatt gggaccaact ggacgagggc    3660
gcgttggaca tgaactcagc cgtgcccagg gtcggaaagg atacgccaat cttcgtggcc    3720
gttgtcactc gattcaacga gaacgtcttc aacgacccat tcatgtggag cttggtcctg    3780
catctgaata acacggtgcg tgccggcttt cgccgggctt tatggatgtg gccagtcccc    3840
tacgactacc cttgggattg gagtagctgc tttgtcatta ttcccgaact ggacacggct    3900
gcaatctact ctgctgacca ctgtcacatc ccgatcaata tcgtcacgaa gatactcact    3960
gagtcccgtg gcgtcatgtg ggtgacgaaa ggggcttatc gcattccaca gacgccgact    4020
gtgaacttag gtctcggttt ggtccggaca gcccgctcgg aaaggggcgc ggtcgcaagc    4080
acgctcgact tggatcctgg ttacaacacc tccatcgatc tacaagccaa gctggtcgtt    4140
gacgcattcg ccctatcggt gctctcggaa aatccagagg ctgagatgga gtttgccgaa    4200
gtggacggga agcttgtcgt tccccggatt cttcccgacc ctgaactcaa tctggacgtc    4260
```

```
caccgctcct tgggccacgc cgtgccatat ctccaagcat atgagccatc tcgccggctg    4320
caacttcacc gtggcacaga tgcctcttct cccgaggacc tctatttcga ggacagctgc    4380
tttggcgtgt tgggggcgga cgaagttgag attaaggtcc atgcgactgc tctatcagtc    4440
gacgacgtca caacagggac cgtggacgag ccaggcgcga ccattcaccg cagctgcgcc    4500
ggctatgtca cccgtattgg tgcacaggtc gatgacatct ccgtgggaca gaaggtttgc    4560
gccctcacca acagtcccta cgcgacctac gttcgggcaa gctctactag tgtcgcactc    4620
ctcccagacg gcatcgacat ggaggtggct gcgtgcatcc ccgtccactt cctccccgta    4680
cattacgcct tcaaagagat tgcccgagtc aagcgattcg accgtgtgct catccaagtc    4740
tcggggccca tcggatttgc cgcacttagg gtggcgcaca agttcggggc cgactactat    4800
gctctagtca cgaacgatga gcaccagata ctggtagaga caatattgcc gtccaaccgc    4860
gtccttgacg cacgaaacat ccatctggcc gagcagattt gggaggtcac ggagggccgg    4920
gggatggatg tctgttttgg catatcaggg tgcgaaaatg gcagcacgtg ggagtgcctc    4980
cgtgcttttg ggatatttgt tgagatcaag gggccaggta atcacaagag gacgcaagcc    5040
cacctgcgcg caaacacggt cttcgcgtcc gtcgacatgc tcagtattgc tgtcgagtat    5100
ccggaagata tgaaggaagc cttgacggag gttgtctcca actttgacgc gggcgaactt    5160
tcgccgggca tctgcatcac aacgtttatg atctcgagcc tgcccgaggg gatagcactg    5220
atacgggacg gttatatggc ccacgtggtg attgcgacac aggaggggga tgaatcggtg    5280 atgacccctga aggaaaagtc gggcgacttg ttccaaagcc cagggaccca tatcattgtc    5340
ggtggaacgg gcggcttggg tcgatccgtg gctaaataca tgatccggaa cggcgcacgc    5400
actattgcgc tgcttttcgag aagtggtggc gaagacgtga ttgaccatct gcgagacgag    5460
atgacacaat acggagccga tgtgtttgtg ttgaggtgcg atgttagcaa acttcaccat    5520
gtccggcgag acatttacta ttgtgcgaag catctgcccc cgattcgcgg cgtggtccac    5580
gctgcaatgg tgcttcggga cggtctactc gaaaacatga ccggtcaaga ttactacgac    5640
gtcatcgcgc caaaggcaca cggcgcatgc aaccttgata ttgcccttgc atggatgggc    5700
atcaaagtgg attattttgt cgccttctcc tcagcggcgg gcatcatcgg cagccgcgga    5760
caggccgctt acgctgctgc aaacaccttc ctcgactcgc taatggaatc gcggagacac    5820
cggggtttgc ccggcaactc gctggatctg accgcggtca caggggtcgg gtaccttgct    5880
gaaaacgcca acagggagag ggaaatcctg cgcaactttg gggacgagac gcttgacgaa    5940
gcggaggtct tggcgcttct ctcagccgcc gtccgtggtg ttgctccctg tcaaaccctg    6000
acagggctga agttgcatct tggcagcgat ggccaatggc cctacttcgc caacgacgcc    6060
cgctttgcgt atttgaaggc cgaaggcttg gcagccgccg aggaggaagg actcgtggtg    6120
aaggaagatg tgtctccggg ggaggcgttc cggggggcaa ggtcggacga ggaggcagca    6180
tatgttgcgg cccggggtct tgcagagaag ctttcggagg tcttgagcgt tgcggtggag    6240
gatgtggatg tcgacagaaa catcacgtcg tacgggttag actcgctcac ggctattgag    6300
cttcggaatt ggatcgctaa ggagcttcgt gtcaatctcc agattttgga gctgttgtcg    6360
agcgggaccc tcagcgatct ggcagcgttg attgtgcaga aggcaaagtc gtga          6414
```

<210> SEQ ID NO 18
<211> LENGTH: 6784
<212> TYPE: DNA
<213> ORGANISM: Chatomium globosum

<400> SEQUENCE: 18

```
atggaggagg ccatgctcga cgaaagctgg gctgagcggc cggcattcct cctctttggg      60
gaccagtctc tcgacagtca tggcttttc gctcaattct accgccaatc caaacacggc     120
gagctagcaa gggtcttctt gcagcaggcg aaccacgccc tgctgggtgt ggtcgagaag     180
ctccctgctt tggagcgagc aacactcccc aatttccgaa cattgcggca gctcaacgaa     240
caatatcata gcacggaaca gaagcactcc ggaattgacg cggcgctgtt gacaatatcg     300
caaattgcgc actacctcga gtgagtctac cctatctagc tgagcacacc gctttttttac    360 gtctgttgtt ttggctcgcc ccctctgacc acggcacttt tagtcacgct gaaaagaact     420
gtggcgatat cacacggcct cataagactt ttctcgtcgg gctttgctct gggctctggg     480
ccgcagccgc tatctcggtg gcgccctcgc tcccagacct ggttcatatc ggcgtccaag     540
ccgttctctt ggctttcaag acgggttcct acgttcacgc cattgggaa cggttgagcc      600 cggcgtttga gcgttctgaa agctggagct acatcttctc ggtgtcgagc gttgaggatg     660
tcacccaaac gttggacgct tttcacgata cctcggtgag tagcccgcca accccggcc      720 gccgtgccca gttgggccgc ataactaaca cgctgtttaa tagaaccttc ctcctgctag     780
ccgcgcgtat attagcgcgg tatccgataa tggtattgta gtatctggtc caccgagcac     840
gctagatgcg atagtcaaca acaagatctt tccgcctaac ccgatcgcca ttccggttca     900
tggcccctac cacgcgccac atttgcattc caccgcagac atcgaaagaa tttagagct      960 tgacaaccca gaaacgaagg acgccttcta caagacgtca ccgcgatcgc ccatcatgga    1020
ctgctcaacc gggacatggt tctcccccat ggacacgaaa tcgctcctga tatcggtcgc    1080
ctctaccatc ttgaacaaag gattgatgtt caaaaaggtt ctcaacggtt gcgtcgaggc    1140
tgctcgccta tttcaagacg acaagtgcct cgtaatcccc cttggtccaa cccaaaatcc    1200
gtctacgctt aagaggcgcc tccagcagga gactggattg gaagtcactc ttcgcatgcc    1260 gcctccatt tcatcggagg caacggcatc aagatagggg aaccacggat caagcgggaa    1320
gcccaagctt gccattgtcg gcatggcagg gcgattccct gacgctgcca gccacgaagc    1380
cctgtggaaa ctgctggaaa gtggcctcgc tgtccatcgt gaggcgccac cggatcgctt    1440
caatgtcaag acgcacgttg atccctccgg caaaggaaag aacatgagcc acactccata    1500
cggctgctgg atcaaagacc cgggtctgtt tgaccaccgc gtcttcaaca tgtcgccgcg    1560
cgaggcgcgc aacacagacc ctatgcagag gatggctttg accacggcgt acgaggctct    1620
agagatgtcg ggatacgtcc ccaacaggac gccgtccaca aggcttgatc ggatcggtac    1680
cttctatggc cagacctcgg acgattggcg cgaaataaat gctgcccagg acgtggacac    1740
gtacttcatc acgggaggtg tccgcgcctt tggacctggc cgcatcaact atcactttgg    1800
cttcagcggg ccgagcctca acattgatac cgcttgctcc tccagcgcgg ctgccatgca    1860
ggtggcatgc tcgcgctct gggcccgaga ttgcgacacg ccatcgtcg gcggcctgtc     1920 gtgcatgacc aacccggaca tcttcgccgg actcagtaaa ggccagttcc tgtcaaagaa    1980
agggccatgc gctaccttg acaatgatgc cgatgggtac tgccgcggtg acggctgtgc     2040
atccgtcgtc gtcaagcgtc tggatgacgc cctggccgac caagacaggg ttctcgccgt    2100
catcctcggc accgcaacca accactcagc ggatgctatc tccatcacgc atccccacgg    2160
gccgacgcag tcgatcctgt ccacagccat tctcgacgag gccggagttg atccccatga    2220
tgttgactac gtggagatgc acggcaccgg cacccaggct ggagacggca ccgagatgaa    2280
gtcggtcacc gacatctttg cgcccgcaaa ccggccgagg cccgaagaca gaccactctt    2340
```

```
tctcggagca gtcaaagcaa acgtcgggca cggcgaagcc gcttccgcag ttaccgccct    2400
catcaaggta ctcctgatgc ttgagaagaa cactatccca ccccatgtcg ggatccagaa    2460
cggcggggag atcaacaaga cgttccctaa ggactttgtc gcccggaacg tcaacattgc    2520
attccgtcca gttcccttca gaagaaggga tggcaagccc aggcgcgtct tcgtgaacaa    2580
cttcagcgcc gcgggtggta acactggtct cctagtcgag gaccccccga caattccgcg    2640
cgcgaaaccg gatcctcgca cccaccacgt tatcactttg tcggggcggg tctgggagtc    2700
cgtgaaggga aatgctgaac gtctcctcga gtggacggag cggaaccgcg acacaccgct    2760
ctcgcacatt tcttacagca caacagcaag aaagctgcac cacgtctgcc gtatgagcgt    2820
gacgggcagg gatattggag atttacaggc ggccctcaga gaacgcatca gggacctgga    2880
cctgaatcaa gctgtaccgg tcccgcatca gccgagagtg gtcatgatgt tcacggggca    2940
agggtcgcaa tacgccgcaa tggggaagga gttttacgac cactactcgg tgttccgcga    3000
gagcatcgac ggcttcattg acctggcccg cctgcagggc ttcccctctt ttctccctct    3060
cattgatggc accgaccaga acttgtccga gatgtcaccc atcgtgttgc aacttggctt    3120
ggcatgcttc gagatggccg ccgcccgcct ctgggcttcg tggggaatca agcccgccgc    3180
cgtcgtgggc cacagcctgg gagagtatgc cgctctcgaa gtagctggcg tgctctcggc    3240
tagcgatgtc atttatctag tcggttctcg tgccaagctg ctcgtcgaaa agtgccaatc    3300
tggcagccac ggcatggtcg ccgtccaagc cccggtcgag acggtcttgg aactgatggg    3360
caccgaagct gatggcttaa acatcgcctg catcaacagc ctccgcgaga ccgtcattag    3420
cggcgagact gaaaagtcaa aggatatggc cacctatatg agcgaccagg gttacaagtc    3480 caacccctg cgtgtgccct tcgctttcca ctctccccag gtggaagtta ttttggatga    3540
ttttgagaag ctcgcacagg gcgttaccta caaaaccccc aagatcccca tcatctccac    3600
agtccatgga aaggtcatcc agggcaagtc gatcgatgct gggtacctgc gcaaacacgc    3660
gcgagacaca gtctacttcc tcgacgggct tatcgaggct cagaagtcga gcaccatcga    3720
tgacaagacc gtttggctcg agatgggccc tcacccggtt ctttcggcca tggtcaaggc    3780
tacatttggc gctagtacgg tagcggttcc cacactacgc cgtactgagc cctgttacaa    3840
gacgttgacg agcacgctcg ccaccttgca caacgcgcac ctcaagataa acttcaacga    3900
atatcaccgc gatttcgccg actcagtgcg tctgttgaat tgcccacgt attccttcaa     3960 cgataacaac tactggatcc agtacgcggg cgattggtgt ctcgcgaagc acaacctctc    4020
ggtcgctgca gcggaacaaa agcctgtaac gccctgggtc gccacgacga cagtccacaa    4080
gctcaacaga gaaattgtcg aaggtggcgt ggcgatcgtc gagaccgagt ccgagctcta    4140
ccaagagcaa cttcgaaatg tggtctgtgg ccaccaggtc aacggcgccc cctgtgccc    4200 atcatcgctg tacggcgaca tggccatgac cgtgtgcgac tatgcctaca gcttctgcg    4260 gcctcagtca acgggcatcg gctgtaacgt cgcggatatg caggtcttta gccgctcat    4320 ctttgacgac aaagccaaaa gtcacatcct tcggttgaca gtgactgcta atgccgaggc    4380
tggcgaagcc gacctggtct tccacacggc tcaagatggc aagaaagtcg agcatgctca    4440
ctgcaaagtc tactacggca atcatgacga gtggcaggac gagttcgacc gggccgccta    4500
ccttatcaag tcccgtgtcg acttccttat ggaggcagaa aaacgtggtg ccgcctccaa    4560
gattggccgc ggcttggcgt acaagctctt ctccgccttg gtcgactacg cacacgcta    4620 ccgcggcatg gaggaggtta tcttgatag cactacttgt gaagcgacgg cgaagatccg    4680
```

```
cttccagacg acagcccagg atggaacctt tacttcagc ccctaccata tcgacagcgc    4740
ttgccacatc tctggcttta tcatcaacgg caccgacgct gtggattcgc gtgaacgggt    4800
cttcatctcc cacggctggg gctccatgag atttaccgag atcccggatg caaacaagga    4860
gtaccgcagt tacatccgga tgcagccggt gaagggcacc gagatgatgg ctggcgatgc    4920
gtacgtcttc gatggcgaca agatcattgg catgacgggc cgcatcaagt tccaagccat    4980
caagcgccac actctcaaca tgatgcttcc tccgcgaggg gcccaggcaa tctcgggccc    5040
agctccctcg gcgatcaaag cggccccctc taagaagaag aagaacgaga ctgtaaacgc    5100
ttccaacata gacagggtga accagaggct caagaccgtg acatcctcag tcatggatat    5160
ccttgtcaga gaaataggct gtagccacgg ggagctcgtt gacgacgcct cgtttgacaa    5220
tctcggcgct gattccctaa tggctctaca agtctcttcc aagatacgcg aagagctaga    5280
actcgacatt gaagcgcaag cctggctcga ttaccctacc gtcggcgctt tcaaaaccta    5340
cctggccaac tttgagaagc aggtcgcaa agaaagggca ccatccacag ggtctgcaag    5400
aacgacagac gacgagtcac gcgaagttga atatgactcg gacgtcacga caccgaccga    5460
agccagtgtt accgattctg tcaagggaga tgcgcaggac gacgtcgagc caggcgactc    5520
tgcccagaac caggaacttc gaaccatcat ccgcgaatcc attgccacgg aagcgggcgt    5580
ggacgtgcag gaagtcatta gcgcgtccga ctggacgagt ctcggggtgg actctctctt    5640
gggtttagga atcagtagcc gaattcgtga gctagctggc atagaggtcc ccaacgatct    5700
cttccttgag cacccaacgc tcaaagatgt ggagcgcgtt ttgggcgtca ccgacgtccc    5760
caaaaagccc gccacccgcc aacggaaaag caccaaggaa aagctcaaag caccccccgc    5820
tgcagcctcc gctaaggagc atcctcggat ttctttggag gaacccgccc ctccaaaacc    5880
gccgagacct agccacattg tcgacaagta ccccaccgc acatcgagtt cagtcctcct    5940
gtctggggct tcccgcgacc aaaccaaaca actctttatg atcccggatg gcagcggatc    6000
tgccacgtcg tataccgaaa tcgccaaagt cggtggcggg tggtgtgtct ggggtctttt    6060
ctcgcccttc atgaggacgc ccgaggagta tcagtgtggt gtctatggca tggccgccaa    6120
gtttatcgac cagatgaagt accgccagcc ccatggcccg tactcacttg cgggttggag    6180
tgccggcggc gtcattgcat tcgaaatagt ctaccaattg gtccaggccg gggaagaggt    6240
cgcgaacctg atcatcatcg atgccccttg cccctcaca attgaaccgc ttccgcaggg    6300
gcttcacgcg tggttcgcgt caattggcct gctcggcgaa ggcaacgaca agaagattcc    6360
agagtggttg cttccccact ttgccgcctc catcacagcc ctcagcgagt acgatgccag    6420
accgattccc aaagacaaat gccccaatgt catggcaatc tggtgtgagg atggtgtatg    6480
ccatctaccc accgatccca ggccagagcc gtatccaaag gccacgccc tcttcctgct    6540
ggaaaaccgc accgactttg gccaaacag atgggaggag tgtttggacg tcgaccgcat    6600
gcagttcagg cacatgcctg caaccactt ctccatgatc catggcgatc aggtatgttg    6660
tgtcttttta ctcgggctcc atctattcat agcaccccac ttcaagaggc caagaaacat    6720
gctaactcgg gcgacacagg ccaaaattct tgaaggtttt ttgcgggagg ctcttctgga    6780
ttga                                                                 6784
```

<210> SEQ ID NO 19
<211> LENGTH: 7728
<212> TYPE: DNA
<213> ORGANISM: Chatomium globosum

<400> SEQUENCE: 19

```
atggcccgtc agcccgagat tttcgcaagc gagcccattg ccattgtggg cagcagctgc    60
cgtctcccgg gcggcgcaac ctccccgtcc cggctgtggg atctcctgga gacgcctcgc   120
gacgtggtgc agaaaatccc ggcgagccgc ttcaacactg agcaattcta ccatgcagac   180
agccagcacc atggaagtac caacgtcaag catgcctacc tccttgagga agatccgcgt   240
ggcttcgacc gtgacttctt ctctatcaac cccaaggaag ccgaggctat ggatcctcag   300
caacggatgc tcctcgagac ggtatatgag ggaatagaat ctgccgggta ctcaatgcag   360
cagctgcgtg atcgtccac ggctgtgttt gtcggctgca tgttctacga ttaccagtac    420
acagcaatcc ggggcgtcga tagcctgcct cagtaccacg cgacgggaac tgggtcatcc   480
atcttgtcca atcgggtatc gtacttttac gactggcacg gtccgtcggt cactatcgac   540
acagcctgtt cgtcgagtct ggttgccatg catcaggcag tcagtgccct ccggaacggc   600
gaggctcgca tggctgttgc ggccggctcg aatcttatcc tgggtcctga gcccttcatt   660
agcgagtcca agctcaacat gctgtcgcca aacgggcgat cgtttatgtg ggattcgcag   720
gcagatggat acacgcgcgg cgaaggcttc ggtgttgtct tcctcaagac gctgagccaa   780
gccctggccg acggggatca cattgagtgc attatccgtg agacgggcgt caactcggac   840
ggaaagacgc cgggcatcac catgccgagc cacgagtccc aggcgcggct catccgggac   900
acgtacgcca gatgcggtct cgatctttcg cgagaatccg atcgtccgca atactttgag   960
gctcacggca ctggcacgcc ggcgggcgac ccaatcgaag cccgcgcgat ccagagcgtt  1020
ttcttcccca atgacacaga cgccgacaaa tatgagcagc gcgagcttat ggtgggtagc  1080
atcaagacaa tagtcggcca caccgagggc acagccggtg ttgcgggaat tcttaaggcg  1140
tcgttggccc tgcagcacgg ccgcatcccg gcgaacctgc acttccagaa cctgaacccc  1200
aagatccagc cgtactacaa caacctccgc atcccgaccg agacagttcc ctggcccacc  1260
atccccagg gcggcgtgcg gcgagtcagc gtcaacagct tcggctttgg cggcacgaac  1320
gcccacgcca tcctcgagag ctacgaggga ggcggtgccg gacctgccga cgagggttcc  1380
gactcgggct ttgacacggc ctcgacctcc tcccaggcag aatccggtgt cggtgacggt  1440
gaccacgggc tcaagctcaa agaagcccag gaggctgcgg tcgggccgtt cgtcctgtcg  1500
gcccactcga gcgccgctct ggccgccaac gccagcgcgc tcgccagcca tctccgcgcc  1560
cacccggaca aggtcgacct cacagccctg gcatacacgc tgttccggcg cacccgttc   1620
gccttccgcg ccgccttctc cgcctgctcc acagccgagc agctcgcttc caagctcgaa  1680
gaatccgtca agactctcga gcgcaaaccg ggcgtccctt cgaccttccc cgacgccctc  1740
ccgccccgca tcctcggcat cttcacgggc cagggcgcgc agtgggcgac catggggcgg  1800
gaactctacc acgcgcctc cgccgcaggg cccttccgcg tcgccatcga cgccatgcag  1860
cacagcctgg acacgctgcc cgctgccgag gaccgcccga cctggcggct ggccgaccaa  1920
ctcctcgccg acagggagac ctcgcgcgtc gccgaggccg ccatctccca gccgctgtgc  1980
acggcgctgc aggtcgcgct ggtggacacg ctgcgggcgg cggggatcga gttcgcgggc  2040
gcggtggggc actcgtcggg cgagatcgcg gccgcgtaca cggcgggcta tctcagcggc  2100
gcggacgcca tccgcgtggc ctactaccgc ggcctgcacg cgcacctggc caggggccc   2160
ggcgagggtg ccggggcgcg cggcaagatg atggcggtgg ggatgggctg ggagcaggtg  2220
acggtgttct gcgccgagtt tgacggcgcg ctggtcacgg ccgcgagtaa ccggccacg   2280
agctgcacgc tggcgggcga tgcggacgcg gtggataggg cctttgtgcg cttgcagcat  2340
```

```
gagggtacct tcgcgcgggt tctgcaggtc gacacggcgt accactcgca tcatatgaag   2400
ccgtgcgcgg acccgtatat caagtcgttg aaggagtgtg gtgtgaaggt gcagacgccg   2460
cagaagcgcg gcggccagca gcagtgtcgg tggtactcga gtgtgtggga caacgatgac   2520
cacaaggcgg atggtaaggt tttcgagggc cagtactggg ttgacaacct gacgcggccg   2580
gtgaagttta gccaggcgtt ggcgcgggcg ctggaccaag accacgtctt tgatctggcg   2640
cttgaggttg ggccccaccc cgcactcaag ggaccggctt cggaaacgat taagacgttg   2700
tccggtggtg ttgtctcgct gccctacacc agcgccctga gcgagggca gaatgcggtg   2760 gagtccttca cggatgccct gggtacccTt tggtgtctgt tcccgtcgcc gcccactgga   2820
cgccctatga tcacctttga cggcgtgcgt cgggccttgc aacacgatac cgcagacaac   2880
atggagatgg aagatctcaa agtcctgaaa ggtctgccgc cttactcgtg gaatcatgcc   2940
actcccatct ggaaggagtc gcgggcctct cgtctcttcc gcgtcggcaa ccgcctcggc   3000
cacggccgac acgagctctt gggccaccct gtcgtgtatg gcggtggcgc gcgcgacagc   3060
aagcgcgagg tgcactggaa gcaggtgctc agacttcagg agcttccttg gctggctggg   3120
catgtcattc agggagaagt cttgttcccg gcgtcgggct acctgtccat ggcgtacgag   3180
gccgcgcttc aacttgctct cgacgatgac gagaagaaac agagacgggt ccagctcgtc   3240
gagctccatg atgtcgacat tgtgcgcgcg atgcgcctcg aacaagattc cggtctggaa   3300
ctggtactta ctgttcgcgt gacgagccag tcggacgact gcatcactgc ccaggtggca   3360
tgctacagcg gacccgtcga cgcgccgcaa ccgctagacg cgccgcagac gtcactttca   3420
gcccacttca ccgaggggt gcggctatgg ctcggcgggt tcgagtccga taaagaggag   3480
gaaggtaatg tcctgcctca acgggccggg gagagtgcca ggcccctgcc gatggacgca   3540
ctggacatgg acaagctcta ctccagcctg gctgaagttg gtctgcagta cgccagcccc   3600
tttaaagcca aagccatcct acgccgcctt caccgcacca cggtgacctt ggccacgccg   3660
cccgaatcct cggcgctcca cacctgcatg catcctgccc ctatcgacac ggctgcccag   3720
ggtctgctcg ctgccttctc cttcccgggc gatgatcgct tgtcaaccat ctacttgcca   3780
acaagggttg actgtgtccg gatcgtcccc ccaagcagcc gactctctgc ggcccacaac   3840
gggaatgacg accccagcca gcagcaactc actgccgacg cgacggtgac ctcgacagcc   3900
ggctccacta tcgtgggtga cattgacgtc tttaatacgg ccgacgaagt caaggtccag   3960
atccgtggca tttgcctgac agcggtaggc cagcagcgcg atgcttggct atacgccgga   4020
acgaagtgga tccgggatgc agactcaggc atcgaaccgg agcgtacgtc gacgatgacc   4080
ggggaatggg acgctcagta cgaggcgctg tctcgcgcgg cctacttcta tctccggcag   4140
ttccgcaaga tcctaccgca ggagatgatc atcatgagca agtcgtacaa acgcaacgtg   4200
aagtggacgc tggagtatct gctgccgcag attgagagcg gcgcacaccc gagcttgctc   4260
gggttcaagg ccgagtggaa agacgacacg cgcgagatca tccaggctct gagagaggag   4320
agcatcagca gccagaagaa tgacgtggaa agacaccact cgaaatgca ctggacttc    4380 ctgcgttccg tgggcgacaa gctcatctcg gtcgtccgca gcatgacgcc gtgggtgcgc   4440
atctggactc cccagcaact cgagtgggtg tatgccgacg ggatcggcta ccgctccgcc   4500
aaccacaacg cggccgctta catcgcccag ctcgcgcacc ggtacccgcg catgaacatc   4560
gtcgacgtgg gcgccggcaa cggcggcacc tcgggggccg tgctcagggc gctgcaggag   4620
cagcagttgc agtacgcgtc gtacaactac accgaccgat cgcccgagat tctcgaccga   4680
gcccgcgtcc tgcacggcca ccacaagaac ttgaccttca agaagctcga catcgacaaa   4740
```

-continued

```
gacccggccg agcagggctt cccggacgcg accttcgatg tggtcatcgc gtccaacatc      4800
ctccacaagc tcacgagcct ggcggactcg ctacgccgct gccggcagat gctgcgtccc      4860
ggcggccagc tgatcctgct cgagctgacc gacgacttcc tcatgtccca gatcgtcaag      4920
ctggcgctgc ccgactttt cgtcggcgcc gaggacggcc gcgtcaacgg ccccaacgtc       4980
ggcgtcgaac gatgggacga gctcctccgg gccacgggct tgcgggcgt ggacaggacg       5040
agcaccaaga ccgtctcata ctgctccgtc atcgtggcac acgccgtcga cgacaaggtc      5100
cagctcctgc gggagccgct tgcagccgcg cccgaggcgt tggcaccgtc gctaggcgac      5160
gtcttcatcg tggctggtgg cggtgcgacc actcccgacc tggcatccca gtgccagacc      5220
ctcctgcaaa ccgccacacc atccaccacc gtcaccatca tccccagcct cgatgccgta      5280
agcgcagccg acaacatttc cccggctcg accgttctct gcctggccga gctagaccag       5340
cccgtcttcc agagcagcga cgaaaacgat gcagtggcgc agcgtttccg cggactgcag      5400
gagctgatgt ccacggccgg gtctgtcctg tgggtgacgg cgggcgcgcg gtccgggcgc      5460
gatccggtcg ccaacatggt cgtcggcatg ggcagcacgc tgcgggccga gcgcggctcg      5520
tcgctccggc tgcagttcct cgacgtcgac acgccctcgg cgctgctgga ggtgccgagt      5580
gcgggccccg ccttgctagc taagctgctc ctccgcctcg ctatcttcaa cccggcgagc      5640
ggcgatgact tgttttggac gcaagagccc gagctggcac tgggtgacga cggcgcgctc      5700
tacatccccc gcgtgttggc gcttgatgcg ccgaatcgga ggaacgcagc ccggcgacgt      5760
gcagtcacgc agcaggttgc cctgccctcg aggtcggcag gggaggctgt cgtcctggag      5820
cgtggccagg aggcggcatg ggagctgaag atagccgcgc gcttggaac cacgccgagt       5880
ggggagggta agggagggt gcgcgtgcag gttactgcgt cttccttgca gcaattcacc       5940
tgcagcaacg gcggctcgtc ttcggaattg tatgtctgca tcggccgaga cgtggcatct      6000
ggcgataagg ttgtcgccct ttccgcagtg aatggctctc ttgtctccat tgctaaagac      6060
cacgtcttgc gacgctggtc gcaatccgac gaaggagacg acttggcatg gctgcaagca      6120
ttcctggcgc aggcatctgc cagtcgcctg ctcctcgatg tccagggccc cgcgtggatc      6180
cacggtgctc cggtgcagct cggcgaagct ctcgaggcgg tggcccgcaa gaagggcatc      6240
gccgtcttcc aaaccacgtc gacagcaggc gcaactggcg tggcgacctt tgtgcaccct      6300
tacgcgcggg aggatgattt gttggctctc ccgcttcctg agggcctgcg gacctttgtc      6360
gatctctcac caagccaaag tggcgctgcc attaaggcta tctgctctgc ccggtcgatc      6420
gaggtcaagc aagctgagcg ggctggtctg acggccggtt ttgaggcctg cgaactggag      6480
catctggcca agaaccatga cgtcgtctcg gacagcggta gcgtcggcga gagcgctgtg      6540
acgcttgagc aggcttcggc gggacagctg tccgtggagc agcagcgctc ccccacagcc      6600
gtggtggact ggcgcgcggc cgagacagtc accgctgacg tctccccgtt gaagcacagc      6660
ggcctgtttg cgcccgacaa aacctatctc ctctgcggta tgacgggcga catgggcatc      6720
tcggtgtgcc tctggatggc tgaacacggc gcccgccacg tggtgctgat gagtcggaac      6780
ccgaagattt cgcctcgtat cctggaccac ctagccggga aattcggcgc catcgtgcgc      6840
cccatggccg tcgacatcac caacctctcc agcctgcgcg ccgccgtcac cgccctcaag      6900
accgacatgc ctcccatcgg cggcgtgatg aacggtgcca tgatcctacg cgaccgtctc      6960
ttccagaaca tgccatggga cgacttctcg accgtgctgg gccccaaggt cgccggttct      7020
cgcaacctgg acgccaggca gtcagcctac gcggccgcca accaatacat gaccggcctg      7080
```

| | |
|---|---|
| gtgcgacaac gccgccggcg tgggctggcg gcgtcggtgc tgcacatcgc catcctcacg | 7140 |
| ggcttcggct acatccaccg cagtgacgcc gcgcacgccg agaccatgaa caaggcgctc | 7200 |
| cgcacgcgct acaacaacca agcagagccg gacctgcacg cgatgctggc cgaggccgtt | 7260 |
| gtcggcggcc gtgtccgcga cagtgacggg gacggcacga ccggtgcgga gctcatcacg | 7320 |
| ggtctgcgca ccgtgtttga gggcgagacc tcgaaagacg cgcgtcttgc gcgctatctg | 7380 |
| cgggatgacg aggggatga tttgggcgcc ggtgcggagg gtgggggtgc ggcgatgagt | 7440 |
| gtgcaggcac agctgcgcga ggtgggggcc gatgatgacg ccggccagca gagagtggtg | 7500 |
| ttggaaaagg ccttcgccat tgcgttgggc aagctgctcg agatggaccc cgagacgatc | 7560 |
| gacccggcgc ggccggtggc tagcctgggt gtcgactcgc tggtggcgat cgcatccgc | 7620 |
| gagtggatgc tgcgtgagat gggcgtcgat gtctcagtca tcaaggtcat gtccgacaca | 7680 |
| tatcctatgt cgcgcatgtg cgacgacgtc ttgagaaatt gcaattga | 7728 |

<210> SEQ ID NO 20
<211> LENGTH: 11094
<212> TYPE: DNA
<213> ORGANISM: Chatomium globosum

<400> SEQUENCE: 20

| | |
|---|---|
| atgtcactca atgatatgga ttctcgggat ggaccactcg agcctatcgc catcgtcggc | 60 |
| agtgcttgca ggttccccgg cggagtttcc tcctcatcgg agctatggga tctgctgcgc | 120 |
| cagcctcgag atgttctgag cgagatctcg cagagccgct tcaatgccaa caagttttac | 180 |
| catcctgata tgaaccatag cgggacgata aacgtccgcc attcttattt tctcacacag | 240 |
| gatccccaca gctttgatgc accattcttt ggcatcaaac ccctggaggc cgatgccgtc | 300 |
| gacccacaac agcgtctctt gctcgaaaca acctacaacg ccctcgaaga cgccggcatc | 360 |
| ccgctgccca agataaaagg ctcacggacc ggtgtgttta ttgggctcat gaccgaggat | 420 |
| tattccaata tcattgggag ggaccttcaa aacgtcccgc aatactttgc ctcgggcacg | 480 |
| gcgagaagca tcatctcgaa ccgggtttcc tacgtcttcg acctgcgcgg gccttccatg | 540 |
| accatcgata ccgcttgttc atcaagtctc gtggccttgc atttagcagt ccaaagcttg | 600 |
| agaagcggcg agtcggactg tgcccttgtt ggcgggtcca acttgttgtt gagccccgag | 660 |
| caatacatcg cggggacaaa actcaagctc ttcagcccaa gtggccgaag ccgcatgtgg | 720 |
| gataaagatg cggatggcta cggacgtgga gaggggggttg ctgttctagt cctaaaaagg | 780 |
| gtatctcagg ccttaagtga ttgtgattcc atcgaatgcc tggtcaggga gactggcgtc | 840 |
| aaccaggatg ggaaaacaaa aggcataacc atgccaagcg cggaggctca gatcgacctt | 900 |
| atcaagacaa cgtatctaag atccggtctc gatctgtcac gaccctccga acggccgcag | 960 |
| tattttgaag ctcatgggac tgggacacct gctgggggacc caatcgaagc ggaggccatc | 1020 |
| aacaaagcca ttttcggtca agccaatcac cagcacagcg gatcacaacc gctatacgtg | 1080 |
| ggctccatca aaacggtact cggccacgca gaaagtgctg ctggtgttgc tggggttatg | 1140 |
| aaggcgtctc ttgcattaca acatggagtt ctgcctccca acatgctgct aaacgaactc | 1200 |
| agtcaaacag tcaagccttt ctacagcaac ctgcagatcc ttcaggaggc ccaaagctgg | 1260 |
| ccgccggtat caagcggacc acggaggtct gagatcactc tggtgtcacc attcaacttt | 1320 |
| tctgccgcgt ccgacaagtc tcttcgggcc aacctcattg cctatgccga ttttgtcagg | 1380 |
| gacacctctt caataagtct acgagactta tcgtggactt tgaatgttcg aaggtcaaca | 1440 |
| ctgttagcga ggacctccat cgcagcattg acaaccgacg aactcgaaaa gaagctgaga | 1500 |

```
aaggcggcag ctctggagac accgttcaac tcccacaccc acccaggagt ttccggttcc   1560
attcttgcca tttttaccgg acagggagca caatgggcaa cgatgggttt gcaaatttac   1620
aaaagttcag tactcgttca aaactgcttc caaaagcttc aagcatccct ggactcgcta   1680
cctccccacc acgcccccgg ctggaagtta tgcgaggagt tgttcaagga tcgcgaaagt   1740
tctcgtttgg gggatgctgc catctcacaa ccactctgca ctgctgtgca agtggcactc   1800
gtcgacttgt tcatggctgc caaggtcaaa tttacagcag tcgttgggca ttcgtcgggg   1860
gagattgccg cagcttatgc ggctgggtat cttacggccg agtctgcgat ccgaatcgct   1920
tattacagag ctttttttct tgacatgaat agcgtttcag gtcaaatgtt ggcggttggc   1980
acttctcacc aggacgcccg agagctttgc gagttgcctt cgttgcacgg caagatcact   2040
atagcagctt acaactccgc ctcgagtgtt actctttctg gggattcgga tgccattcgg   2100
gatgcaaagg aaattcttga agacgaagaa aagtttgctc ggattcttca agtcaaccaa   2160
gcctatcact cgccccgcat aaaacaatat gccgatccat acgaaaaggc gctggaagcg   2220
gcccagatat ccgtccaaca gcccccaaga aatcgtccgg tttggatttc gaccgtgata   2280
acagaaccag ctgacaggat cggtttggat tctctggctc acagctactg ggccgataac   2340
atggtcaaac cggtgcgctt cctgcaggct actgagtatg cgacgggtgt ctatggtccc   2400
tttgatgctg tggtcgaggt tgggccacat ccagttctgc agcgtccgac aaccgacatc   2460
ctgcaagaaa ttacggggca agacgtcccc tacatctcga ccctggttcg taatcagcac   2520
gacaccttgt tctcttgcgga atgcctgggc tcactctggg aaattatcgg tgattccgcc   2580
gtcgattttg ccgcgttcga atcatctgtg cacggcacat tcgccgcaca gccgaaggtc   2640
ctcaagaacc ttccaccata cacatgggac catgatcgcc aatattggca tgagacgcgg   2700
tacacgaaag ctttcctaac gagcggggat gtgccgcatc ccttgctcgg aaccatatgc   2760
cctgatggga ctatgcagga gatcaagttc aggaactact cgagccctca acaacaaccg   2820
tggctctcac accataaaat ccaaggccag gttgttttcc cggccgccgc ttacatttcc   2880
tctgcgctgg aggccattgc ccaactttac cccgaggaaa aggaactggt tgagcttgcc   2940
gatattcaca tcggcaaagc catcatgttc ccagacaatg gacgtcaat cgagacggca   3000 ttgtctctca aaatacttga ggataatcct gaacggctgg atgcagagtt tatcttccat   3060
tccgaggctg ttgaaaaacg gtcgaaccag atggtgaaaa acgcgagagg caggattcgg   3120
gtgatccgaa atgggccagt gaagtctctt ccggtcccca atccggatca agacataggc   3180
gggtttgtgg atgtcgaccc ggagagattc tacgactggg caagcgagaa aggttacggt   3240
tacgaaggag cctttcgaag cctgaagcat acccgcagaa agttgaacca ggcggttggt   3300
tccatcgcat ttccgccaga cgccagaaag gatggatttg caatagctca tcctggtgtt   3360
ttagactgtg ctttgcaggc tgttctactt gcgtacagct acccaggtga tgggagactt   3420
cgctcggtct atctacctac caaaatcgac ttgataaggg taacgatggc cggctggctg   3480
gcagaatctc atcaacccga ctcttccttc gcctttgctg catctgctga ctcttaccac   3540
ggcggggagt ttgttggaga cgtcgatatt caggcatcct atgacaatgg tatcatttc   3600 cagcttcagg tcttcacgg tgtagcattg gatcccccat cgccagaaaa cgatgtgaat   3660
ctctttatcg aaacgtcctg gggcccagaa acacttcaaa gttcaccgac tcattggagc   3720
ggtcctgtct gctcaagcta ccgagatttg gcgctgttgt tggaaagagt tgcctacttc   3780
tatcttcgaa agctagcagc acttttttcca cccaaaagca gaaacgggtt gccgtggaat   3840
```

```
tacctccgtc ttctggacta cgcggactcc tgcttggaaa gcgttgatgg tggcgaacac      3900
cggcatacaa ccaacacgga cttggagata cttcgggctg tcggtgaagg tttacccaag      3960
gcccttcgtg gagaattgaa tcttctcgag acgatcacca acaacggtct cttacgaaag      4020
tactaccaag atgccttggg tatgaggagt atctcgggg agatatgtcg tgtgatgcac       4080
catgtgtctc acagatttgc taacctcaac attttggaaa ttggtgctgg tactggagct      4140
gccacaacct cggtcctcgc ggcggttgga cacgctattg ggtcgtatac atttaccgac      4200
atttccagcg gctttttttcc tgaagcccgg gcacaatttg cgtcccatca gccgaaaatg     4260
atgttcaaga ccctggacat cgagaagccg gttgcggatc aaggattcac cgaaatggcc      4320
tatgacgtgg tggtagcatc cctagtgctg catgccacac gtaacctttt ggccaccatg      4380
tccaatgcca aaggctcct ccgacctggc ggctacctca tcatactaga ggtgacagac       4440
aatactccat tgagattggg gctcatattt ggaggcatgc ccggttggtg gcttggagac      4500
gcggatgatc ggaaactctc cccatgcgtc tccatcccgg cttgggggga tcttatgcgc      4560
aagtcaggct tttctagcat ccacaccatc gcttcccaca gcaaagacct tcctgttcct      4620
ctttcggtaa tggtcacaca agctgtggac gaccgagtaa agcttctcat cgaacccctg      4680
aatccgacga ttaaatcata tgggtttggt tgcgtcgtca ttgttggaga gcatacagca      4740
tctaggacac tggccgagac cgccgtcaag cattacaaca ccatcgatct cataccatca      4800
ctccatggaa taggaaccgc caacgttccc ctgtcatcga ccgtagtctg tatggtcgat      4860
ctaggagcag tgtcgatatt ccaggacttg aaaggtcgtg atttatcggc cctgcaaacc      4920
atcttcaacc gcagcaaaat agtcatctgg gtgacagccg cgcccaaga gaccaacccc      4980 aacaaggcga tgttcatcgg cctccaaaga acactcgcgc ttgaactacc ccatgtccgg      5040
atgcagatca ttaacttcga acgagaagcg gatatcgaca cccaggtaat cgcaaccaag      5100
cttttacaac ttgaagcata cggtctttgg gaaagcatga atctcccgac tgattttctc      5160
tggcatattg aaccggagtt gacagtgcga gatagtcaag ttatggtgcc gcggatgcgg      5220
cttgcaaagg ctcggaatgc aaggtacaac gctgcgcgac ggcaactgac caaagcggcg      5280
gcggccaaaa gcacgctcgg tatctccatc atcgacaggg cagttaacgg caagggaatc      5340
ctcatcgtta gcccacctcg gtacctcggg gatgtcttag caacgatcgc tgctgcgcga      5400
ggcatcgact gggtctcgt caccactgac cgggcgattg ggaatatcgg gagtccctgg       5460
gtgtttattc atccattgga cacaaaaagg tcgattaaac gtgtacttcc accggcaatc      5520
ggaatattct tggacatggg caaaaacacg gagattggtg ctacaatccg ggcatgtttg      5580
cccacggatt gccaacaaat ataccttccc gggttgagtg aagccttcac ccggtggatg      5640
gcggaacacg cgccaggca tattgctatc tccagccgga accccgtcat tgaacgagt        5700 tgggtaaagt ccatggccac tttgggatgc aatgtgagat tgtttgatgg tcggtccgtc      5760
caaaacgtgt accacagaat caccggatcg atgccgccta tagccggcgt cgtccaaggg      5820
gccatggtgt tgcgagatgc tgttttttcca gagctcacga tcaaccactg gaagaagtc      5880 acgaaaccaa aaattgaggg aagtattcat cttgatcaga tcttcgacga cccttccttg      5940
gacttctttg tattcatctc ctctgtcgct tacttggccg gaaatgccgg gcaaggcgtc      6000
tactccgcgg ccaacgcttt catgacgagc ctagccgcgc agagacggag ccggggcctt      6060
gctgcttcag tgatccacct gggcgccgtg gtcggcgttg ggtacataac ccgtgagctg      6120
acccccgaaa agcaacgggc attacatcag gcccgggtact cctttctatc agagcaggat      6180
ttccacgaga tcttttgccga agggggtcttt gcaagtctgc cagattccgg cgatgtattc      6240
```

```
gaaatctcaa ccgggctgag gctcgagaac actgttaaag actccccagc aaagtgggca    6300
agaaatccaa tgtttcacca tcttgtaaca aggtcggata acatactgg gcttgacggt     6360 atcatcaaca agctgcaagc tgtcctaggt tttgatgaag aaaagttgat tctagaatta    6420
agtcctgacg aacttgccat cgattcactc gtcgccctcg acatccagtc ctggttccgc    6480
gcagaactcg acgtggatat ccccatattg ggactgctga atgccccgtc cattcgggaa    6540
ataattttgg ctgcccaaaa cctatcattg gaaaccacag cgagccttat cgcagaacct    6600
tcaggcatgg accaagaact aggcgacctg tcagctccca gcggcccacc cacctccgtt    6660
tcaagcagca acaccgcaac aactcccccct tcccctacga tgacgcccaa gacggataat   6720
caaagccagc atctccaaga cacccccagag gtatttgata caagcttaga aggcaaaagc   6780
tctcaactta agaatggggg gatcatgttc gaacgaacgg ttccgctctc ctttgcgcag    6840
tcgagatttt ggtttcttca atcgttcgct gaagatccca gcgcattcaa catcacatcg    6900
gtgcttcgac tccagggccg catcgatatc gaaaggttga aaatgctgt tcaggttgtc     6960 ggacaacgac acgaagctct ccgcaccgcg ttctacaccg acaaggtcac taaggatcat    7020
atgcagggga ttcttccaat catggttccc catctggaga ctgcgacagt tcagaccgag    7080
cgtcagctcg aggaaatagt gcaggaattt gagagacatg tgtacgatgt gtcaaaggga    7140
gaaacgctcc gcataacact gctttccttg tcggaagcag ttcaccgact catcttcggc    7200
taccatcaca tcatactaga tggcatcggg ttccaaatct tcttttttgga gctagaaaaa   7260 gcattcagcg gtaccctgaa cacagcttca tccgatgttc tgcaatacc ggactattca     7320 ctcaggcaga tacaacagta ccgtaacgga tcatggtctc aggaaatcga ctattggaag    7380
cagcagtttg cgaccattcc agaacctcta cccctactgt ttatctccca caggcacact    7440
cgtcttgtca cgccctcctt tcggacgcac tcgatcacaa ctcggctgga cgaagttttg    7500
cagtcgcagg tcatccaaac ctgccggcat tttaaggtca aacagttcca cttcttcacc    7560
gccgtctttg ctgtggtgct cgcccgttat gcaaacacct tcccagagga cctttgcatc    7620
ggcgtggcgg atggtaatcg gaaggatctc gataccacgc gcagcctcgg cctcttttctc   7680 aacctcctcc ccttgcggtt ccggcaaaca ccagatgtca ccttcgcaaa ggcgttgctg    7740
aatgcccaaa agatcattga aaacgcctac acaaattctc gtgttccttt tgatgtgctc    7800
cttggtgagt tggacatccg gcggtcagtt acccacacgc cattgttcca gacgtttttg    7860
aattaccgcc agaacatccg agagacgacc acgttctgcg gctgtgaagt caagggtgaa    7920
ttggtatcgg gcgccgaaa tgcctatgat gttagcttgg acatcgtgga cagtaatgat    7980
cgggggagcc tcatcactct taccgtcaac gcggatttat acgacaaaca tggtgccgca    8040
gcggtgcaga acagttacct caaccttctt caagccttcg cccataaccc tgcagctagg    8100
gtttgctggc cgcctcttca taccgaggag gacgtcaagt taggaatttc acaaggacat    8160
ggtgctgagg ttgattctcg atggccaccc acagtcgtgg accgcattga cgagatgata    8220
aaagcgcacg ccaacaaagt ggcgttgact gatggcgcag gagagagcct cacatatgca    8280
gacatggctc gcaaagtcca cagtattgcc actgagttgg cagcccgagg agtgcaaaag    8340
gggtctcgtg tgggcatttt ccagataccc ggcacggcat gggtgtgctc cttgcttgcc    8400
gttctccgca cgggagcggt tggcgtgccc ttggacctca atgttggcat tggccggcta    8460
tccttattac ttcaagactg catccctcag gttatcctcg tcgatggatc gaccttcgga    8520
cagagcggat ttgtgtccaa ttcgaaggca ctgatcttgg aagtgtcaac ccttcccaac    8580
```

```
ctacaacatc ctagggccac cattgtgcca aaccaggcca aggcgcatga cgacgccatc   8640
atcacatata ccagcggttc cacaggtgtt cccaagggtg tggttatacg gcaccattcg   8700
taccaaaatt tcctcgagtt tacgcttccc agatggggaa tcacggaagg caagctaacc   8760
gttctccaac aatcgccta cgcgttcgac atttccattc ttcaaatctt cgccagtctt   8820
tgctacggcg ggaccctggt catcccagat cttgccaaac ggcgggaccc aagagcgctg   8880
tgcgaccttg tggcctcgca aggtattacc atgacattcg caacaccgac cgagtacctc   8940
tcttgggcca aacacggcac ccagcaatta cgtgactcac aatggcggtg cgccatgact   9000
gggggcgaac ccctgaccaa ttcgcttctc ggagtattca agtctctaac caaggcggac   9060
ctccagctga taaactgtta tgggccgaca gaggcttcca tcggatgcgc agataaagtg   9120
gtagacttcc acaaaagcct cgattctaac ctcgagatgt cggtcctgcc caattatagg   9180
ttggttgtcg ttgacgatga ttttcaacca gttcctgctg gcattcccgg gcaaattctc   9240
atcggcggcg ctggagtagc agcgggttac ctgaatccgc cagacgaggg tgccaaggca   9300
tttattgttg accaacgggc cacgagttc cagaagtctc gacgctgggt tacacttcac   9360
tcctccgggg atcgtgggcg attgaacccc aacggcgggt tagttctaca tggcagaatc   9420
ggcggcagca cccaaaccaa actccgaggc attaggattg atctggccga tattgaaaac   9480
accataatag aggccatgtc acctgatgtg gttcaggcgg tggtatcccg gagagaggat   9540
tcagaaacag ggggagagtt tctcgtggcc ttcctgttgc tgtctgggga taacgctggt   9600
cccgccccgg acgattacgt ggtcaatctc ccagacgagc tatctcttcc actttatatg   9660
cgcccctcca tggcccctcat cgtcgaccaa ctcccaacca tggtctcagg caagattgac   9720
cgagcagcgg tggacttgat ccccatcaag gcatcgtcgg cttataccccc gacaatcgag   9780 gctaccaccc tcaacacaac cgaacagatt ctgttgagtt tgtggagaga ggttatacca   9840
aacgagatta catggcaccg aagaattcgc agcgactccg actttttttcg ggcaggggggc   9900 aactccctcg cggtggtgga cttacaaggc ttgatcaagg agcgcctcca tatcacggtg   9960
cccatttatc gtttgtttga atcggctaca cttggtcaga tggctatgct tctcgaccgt  10020
ggaacagcag cctcccgcga atcgcaaaac aaaccagtcg actggggcca tgagaccag  10080 ctctcagcgg acatcgcgga actggcagca gggaggccaa ttgatcatgc tgacgggagc  10140
ttggcgtttc ccagcacagt tgttctcaca ggatcaactg gcttttttagg ccaagaactt  10200 ctccgtcagc tcattgcgga cacgcgagtt acacgaatac attgcatcgc tgtgagacaa  10260
accaaggaac ggctaccaag ccttttcaca aacaccaaag tctcgttgca ttttggagat  10320
ctcggagacc gtcaactagg acttcgcgaa ggttcgaccc gggagatctt ctctaccgcg  10380
gacgttgttc tgcatgttgg agcagacgtg tcattcctca agtcatacccc gagccttcga  10440 ctagtcaacg tggcctcaac aaaggaactc gtccgttttt gtgcccctcg aatatttca   10500 ctccacttcg tttcatcagc cacagttggg cggctggtcg acagagcat ctttaggccg   10560 ggttcggtga ggcaatatcc tccgtcacag gaagcagacg gctacacagc ctccaaatgg   10620
gtatccgaag tctatctcga gaatgccagc aatgactttg gcctccccgt ctggatacat   10680
cgcccaagta gtatcacggg atcaggcgct tccaaaaccg atctcatgag caacctcctc   10740
caatacgccc aacagatcaa cgcaatgccc tatttgggtg cgaaagggggg ttactttgac   10800 ttcgtttcgg tcgagactac ggctcggatg atcattgagg aaatgtccag aagcattcga   10860
aagcaggaat ccaagttca gtatcttcac gaatcgggcg agattgaaat tgcaacgaac   10920
gacgctgaat cgattttggg acgccaaaac ggagaaccat ttagggttgt ctcaatttct  10980
```

```
gaatggatac aactcgcaac agccgcgggc atggatccct tactggctct gtatctcgaa    11040
cgctccgcaa cgggaggggg ggtcctgttt ccgcgattgc tggggacagt ttag          11094

<210> SEQ ID NO 21
<211> LENGTH: 7578
<212> TYPE: DNA
<213> ORGANISM: Chatomium globosum

<400> SEQUENCE: 21
atggcttctg ccagtacatt gattctgttt gggcctggtg ttatgacctt ggacgaaccc      60
tacttcaacc gcatcttcac atgtatcaag gacgacgccc atcacagcca atgggctctg     120
catgctgcgg aggaccttga gagttgttgg gactccttgt gcaaatcgat tccgaagctg     180
caacgcgttg atggccggaa gcatgctcgg acattagctg actggcttcg agctggaacc     240 ataccaccccg ggtcgactgt tgcgaatttg ccaaatgcga tcctcggtcc gctggtcctt     300
ctggcacagc ttatcgagta cattcagcat ctgaaatccg tcaacggaac cgagcgaggg     360
ttcctcaagt ggatgcctcc cggcccgcag acagaagcag tcggttgctg tctgggatgt     420
ttcagtgcca ttgtggtatc cggcagttcg tcctgggccc agttctgcca caatgccgct     480
gctgcactcc gggtgatgtt tgtaatctgc gctctatctg atgcgcaaga tagccctgac     540
gagactggac cgtctacatg cctgaacgcc ttttggagag gcacacaatc agcgtccact     600
ctgacgacgg ctttggaagc ctatcccaac gcttacgtcg ctgtcctata cgacgagaat     660
cgggcaacta taacaacctc cgcgggcact gctcctgctc tggcgacata tcttgaaacc     720
gtcgggatca aagccagcct gtctgaattc cacggccgtt ccacaccccc ggaagtctat     780
gaacgtgaca tccaagccct attcagcttc tgtcaaactt gccccacgtt tcaagttcca     840
gatgctgccc atttcaccat gcctacgcgg atcaacgcgg agactccgat cagtggtcaa     900
gaaaatcccc ttgaagcggc tacacgcgca ttccttgcgc aacagttcaa ctggatcgga     960
acctttcgtg cagctgctgc cggctgcttg aaagacaaaa atgcccttgt cctggagttt    1020
gggccggaac gttgtatccc cccgacgctc ctccgcagat tgagcagaca ggtaactcac    1080
ttcgacctcg aggagagcct ccgcagatct ctcggtggtg attcaaaccc ggatgcgcgg    1140
ccagttgtat ccgagaccga tattgctgtt atcggcatgg cttgtaacgt ggctggggct    1200
caggatctag gacagtactg gcagataatg ctggatggca cgtcgcagca ccgcgaactc    1260
atacccaacg accggtttgt catggagacc acacatcggc ctggcgagga gggcagcgag    1320
aagaagaaat ggtacggcaa cttcttgac gacacggccg tctttgacca caaattcttc    1380
aagaagtctc ctcgtgaggc cctccatatg gacccgcagc agagactcat tctgcagacg    1440
gcctatcagg ctgtcgcgca ggcgggctat tactttcagc ccaaaggcaa caagtcgtcc    1500
gaccgccgga ttggttgcta cattggcgca gttaccaacg actatgagta caacatctcg    1560
catgctatcc cgaacgcatt ttcagctaca ggcgccttgc gaagctatat cgctggaaag    1620
gtcagccatt tctttggctg gacaggaccg gcaatgaccc ttgatactgc gtgttcggca    1680
tccacggtgg ccattgattt ggccatccag gctattctca gtggcgaatg ctctgcggcc    1740
ctcattcgac agatctttgg gggttctgcc cgcgcgggca tgaagccgtt gcagattggc    1800
tccgcaaagg gcttggttgg ccatacagaa ggcgcctcgg ggattgtagc attgatcaag    1860
gttttgctga tgattctgga aagccgcatc ccgttgcaag ccagtttcaa tacgctcaac    1920
cccgccattc aatactcacc ctcggacaac atggagattg ccaaagcttc ccttccttgg    1980
```

| | |
|---|---|
| acggacgacc gcaaggtagc catgatcaac aactacggag cagcaggttc caatgcctcc | 2040 |
| atactcattc agcaggcgcc aaaaatgacc caaggcgaga atgccatgtc aacaggctct | 2100 |
| gcttcctcct gtcggtggcc tttctacatt tccgggctcg acgacaaggc catccaagca | 2160 |
| tacgcagcca aactccacct atttttgcga gagaggccgg tctctggaca tcaccttgac | 2220 |
| atcgagaatg tgtcattcaa cgtaaatcga caatcgatga acgggtccct tggccgagct | 2280 |
| gccatgtttg ctgccgggtc catcgacgaa ctggaacaac agctgggttc tttggagact | 2340 |
| gccgctactc ctgtctctac acgacccgtc atcctggcgt ttggcgggca ggtcggcaag | 2400 |
| gttgttggac ttgaccgcga ggtgtttgac aaatccacta tcctgcgaca tcatctcgac | 2460 |
| gattgtgata gggcttgcaa gtcaattcag gcgggcagta tttaccctac aatcttttcaa | 2520 |
| cgcgagccca taaacgaccc ctcggtcctg cagccggtgc tcttctcttt gcagtatgca | 2580 |
| tgtgccaaaa gctggatcga ctgtggcgtc gagccagccg ctcttgtcgg gcattcgttt | 2640 |
| ggagagctca ccgcgctctg catttcgggc gtcttgagtc tggaggatac cttacgaatg | 2700 |
| gtccacggca ggtctaaggt tattcgagac agctggggcg cagagcctgg gtccatggtg | 2760 |
| gcagtggagg gtgatccggc agatgtcgaa aacgtcatcg ccgctgtcaa tgcacagcta | 2820 |
| gacaacaaag gtgacggccg acatggcatg gcgtgtattg cgtgcgtcaa cggtccacga | 2880 |
| agcttcacgc ttgctgggtc tgtcgctgcg tgcgacgcgg tgcaacagca catcgaggcc | 2940 |
| cgggatgcag actcgatccg tccaaccatc aagcacaaga gaatccatgt aacaaacgcc | 3000 |
| ttccattctg ggctcgtcga gcccttgaag ccagagctgc tggctgtcgg cagccagctc | 3060 |
| acgttccgcc agcctaggat cccgctcgag cgggaaactg aaggataccg caaatgccct | 3120 |
| tccgacgcct cctacgttgc cgaacatatg agagaccctg tgtactggct tcaagccgtc | 3180 |
| gaaaggctgg ccagcaagta tcccgacgcc atctggctgg aggctggctc caactccacc | 3240 |
| atcaccaaca tggcaagcaa ggcgcttggg atgccaagga gtgcaacctt cctaccagtc | 3300 |
| aacataacag gcgacgatag gtgtttacaa catttggtcg acatcaccat gggactttgg | 3360 |
| agggctggcg tacatgttgc cttctggccg cactcgcgcg cacaaacaca tcaatatgcg | 3420 |
| cccatcatgc ttcctcccta ccagtttgag agaaatcgcc actggcttga ctttaagccg | 3480 |
| cccttgaaac aagttgggca ggagacgcag ccatccgaac aggccaaaag cggtgcggag | 3540 |
| ggaggattcc tcccaccttc gggccctac acgtttgttg ctacaaaga caacaagacc | 3600 |
| aagaaggaat cccggtttct catcaacaat tcaataaagt catacgtcgg catcgtatct | 3660 |
| gggcatgtaa ttgcgaaaca ggcgcccgtg ctcccggtac cattcgcaat cgacttggcg | 3720 |
| attcaggcca tcacgagcat ctgtccagag ctgaccaaca tcaacaacaa gttgcagccc | 3780 |
| agaatctacg agattgtgaa ccacagtccc ttgattcaca ctgacccacc tagaactgta | 3840 |
| ttcatcgatt ttgaacgcca cgatgataat ggaggcgcag agagaagctg gatcttcaag | 3900 |
| tttgtgagca aactcagaga gaccggtgag gagaccttgc atatgcacgg gaaactgtcc | 3960 |
| ttccagtctc gcgacgacgg tcgcctccat gctgaactcg gcaagcttga acgctttgta | 4020 |
| acccacgagc gctgtctgcg agccttggaa agcaacgacg ggtccgaaga ggtcatccag | 4080 |
| gggcggagta tctacaaagt cggcgacaat cttttccact acggcgacag gttcagggc | 4140 |
| cttcaaaaac tggttgggcg atccagcgag tcggccggcc ggctcgctcg ggaaggtct | 4200 |
| gcggaggcat tcgtcttcga tcctacccta gcagatgcct tcgaacaagt tggcagcatc | 4260 |
| tgggccaact gtatgcccg ggatcggcct acttctatct atcttgtcag cgagatggag | 4320 |
| caatggatca ggtcaccaga tcttgagagc ccgcgggacg ttgacagcca agggagtgg | 4380 |

```
gatatcttgg cacagcataa gcgacttcca tctggcgact tcttgacgga tatctttgtc   4440
ttcggctcgg caagccaatc tcttgaggag gtcatgctcg ggattcgata caaatcagtt   4500
ccagttggcc agctgctcac gggtgttcct atccccccta gaagcgcata ccctcttgcg   4560
gaaccatcaa taaagcccct aacgacggga gctccaccgt tgaaccctgt gctcgtcggt   4620
gaaagcattg atcggcaatc ggattctcag ccggccatcg cgccaccaca tgtgaggaat   4680
gtcagcaatg tcaagaaggc aaaggatgct ctgtggccca ggctccaacg ggtcttagca   4740
gagatatctg gcctcgagct tgatgagatt acgcgagctg attcactcgc tgatgttggg   4800
atcgactctt tgatggggct agagctggca cgggatattg agacagaatt tgactgtacc   4860
ctggagcaat cccagctcat cagcatcgtc gacataacag gcattctgga tcttctccag   4920
tctgtgcttg acctcgagga aatcgctgct tcctccgatt cttccgacac agcgtcttcg   4980
gaaccaaaca gtgctgtatc agcagccagc cgtggaacct cgctttccga cacgccgtcg   5040
acggccgaga gagttctgac acggctctt agcctaccgg catctataac cattgaagcc   5100
ttccgcgaat ccaaagacca caccgactcc ttcctgaaga gccagggatg cgcaggttat   5160
cttgacggcg tgtatcaaaa gcaagttagg ctgtgcctgg tacttactac ccaggcgttc   5220
aaggaactgg gctgtgatct tgaggcagcc cagcccggcg atgtgttaca gcctgttcca   5280
tttgtcgcgc accaccggcg cttccacgag tacctgtaca agatgctgga agagacgcga   5340
atcattgata tcgaggaggg gggcgtggtc cgacggaccg gccttccgct tccttctcag   5400
tctgccgacg caatcattga gggtctcatg aaaaacccca aaggctactc gtcgtcccac   5460
cagctgctat ataaagttgg ctcgaggatg gcggacgtct tggctggcaa ggtcgatggt   5520
ccagccctga tctttggaga tgccaaaaat cgtgaatcgg cagcccattt ctacggcgag   5580
tttccgttta caaggccta cattgagcaa atgggcgatt tcctgacccg gctggctcgc   5640
aagggggct tgttgtccca gagcggtctc agtaccccct tgaagatcat ggagatgggt   5700
gctgggacgg gcggcactac aagggtgctt gcgcccatac tggcagaatt cgggatcccc   5760
gtcgagtaca ccttcaccga tctctcgcca tccctcgtat cccaagccaa gaagaagttt   5820
aagcagtacc ctttatgaa attcgccgtc cacgacatcg aacagccccc ggacccagaa   5880
ctgatgggat cgcagcatat tgtcgtggct accaatgccg tacatgccac gcactccatt   5940
gacgcttcga cgcgcaacat ccgcaagttc ctgcgctcag atggcgttct gatgctgctc   6000
gagatgatgg gcacattgca ctgggttgat gtcgtctggg ggactctaga gggctggtgg   6060
cttttttgacg acggccggac gcatgccatt gtgaaggaaa agaggtggga gcagagcctc   6120
ctcaacgcag gcttcaagca cgtcgagtgg acagacggca atctgcctga agttggcgtt   6180
caacggtttg tcatcgctat ggcagctgat ctcgagccgg gcctggccaa gcaaccaagc   6240
attcctccct cacccgagca cgacgagcat gatagcgagg agtatctcaa gggtcgaaag   6300
ctagctgcgc acaaatacat agcgagcgca actcgaggct tcgcgatacc cgaggtctcg   6360
ccagtcgtcc agggacctac aactgacgac ccctccgact cctctatcca ctctgttctc   6420
gtgactggtg caacaggcag tctgggcagc cacatcgtgt cgcacctcgc cagcctaccc   6480
tcgattggca ccgtgttctg cctcaaccgc acgcggccca ccaggaagga tgaacagcct   6540
atcagcccac agcaacgcca gcgggaagca ttcgagtcca ggggcatcga gctgaacgaa   6600
acgatgcgtg ccaaactaga ggtcatagag acggacactt cgcagccaca actaggtctc   6660
gacgtggccc agtacggccg actcgtgggg cgtgtgacgc acatcattca caacgccttc   6720
```

-continued

| | |
|---|---|
| cccgtcaacg gactgcgcgc cctcgaacag aacgagccac aattcatcgt catgcgcaac | 6780 |
| ctcgttgacc tcgcagcagg catctcggca caccgaaagg cccgggacga aaatttcaag | 6840 |
| tgtacctttc aacagatctc ctccctctca gccgtgggca agtatcccctt tagacaggga | 6900 |
| aatggccgcc aagtgcccga ggcccccatg gatatcgaat gttccctccc caatggatac | 6960 |
| ggaggcgcca agattatatg cgaacgaatc ctaaatgaca cgctgggccg ccatccagac | 7020 |
| cgcttccgcg caatgacagt gcggctgggt caggtgtcgg gctcgaagcg gacgggtac | 7080 |
| tggaaccacg tggaggtgct ggccttcctg ttcaagtcgg cacagacact acgggcgttc | 7140 |
| cccgccgtcg aaggcgtctt gaactggctc cctctcgaag aagcctccac ggcgctggcg | 7200 |
| gagcttctcc tccggcccag tgatgatgaa tggtatcccg tctatcacgt ggacaaccca | 7260 |
| gtcccccggg catgggcgga tgtggtgccc gtgtttgccg aggcgctagg cgtgcctcaa | 7320 |
| gacaagggca tagtgtccct gcaggaatgg cgcaggcggg tggccgagtt tccgggagag | 7380 |
| aatccctggg acaacccggc ggcaaaggcc caagactttt tcgaacacaa gttcgagctc | 7440 |
| atgtcttgtg gaggggtgac tatggccact accagagcgt gtaggcactc accaaccttg | 7500 |
| agagctgcgc aaccggtgag tgatgagctg atcagaaagt atgttgaggt ctggaagact | 7560 |
| acaggattcc tgcgttga | 7578 |

<210> SEQ ID NO 22
<211> LENGTH: 16281
<212> TYPE: DNA
<213> ORGANISM: Artificial Sequence
<220> FEATURE:
<223> OTHER INFORMATION: vector

<400> SEQUENCE: 22

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| ttgagtgttt tttatttgtt gtatttttt tttttagag aaaatcctcc aatatcaaat | 360 |
| taggaatcgt agtttcatga ttttctgtta caccaacttt tttgtgtggt gccctcctcc | 420 |
| ttgtcaatat taatgttaaa gtgcaattct ttttccttat cacgttgagc cattagtatc | 480 |
| aattttgctta cctgtattcc tttactatcc tccttttttct ccttcttgat aaatgtatgt | 540 |
| agattgcgta tatagtttcg tctaccctat gaacatattc catttttgtaa tttcgtgtcg | 600 |
| tttctattat gaatttcatt tataaagttt atgtacaaat atcataaaaa aagagaatct | 660 |
| ttttaagcaa ggattttctt aacttcttcg gcgacagcat caccgacttc ggtggtactg | 720 |
| ttggaaccac ctaaatcacc agttctgata cctgcatcca aacctttttt aactgcatct | 780 |
| tcaatggcct taccttcttc aggcaagttc aatgacaatt tcaacatcat tgcagcagac | 840 |
| aagatagtgg cgatagggtc aaccttattc tttggcaaat ctggagcaga accgtggcat | 900 |
| ggttcgtaca aaccaaatgc ggtgttcttg tctggcaaag aggccaagga cgcagatggc | 960 |
| aacaaaccca aggaacctgg gataacggag gcttcatcgg agatgatatc accaaacatg | 1020 |
| ttgctggtga ttataatacc atttaggtgg gttgggttct taactaggat catggcggca | 1080 |
| gaatcaatca attgatgttg aaccttcaat gtagggaatt cgttcttgat ggtttcctcc | 1140 |
| acagttttc tccataatct tgaagaggcc aaaagattag ctttatccaa ggaccaaata | 1200 |

```
ggcaatggtg gctcatgttg tagggccatg aaagcggcca ttcttgtgat tctttgcact      1260
tctggaacgg tgtattgttc actatcccaa gcgacaccat caccatcgtc ttcctttctc      1320
ttaccaaagt aaatacctcc cactaattct ctgacaacaa cgaagtcagt acctttagca      1380
aattgtggct tgattggaga taagtctaaa agagagtcgg atgcaaagtt acatggtctt      1440
aagttggcgt acaattgaag ttcttttacgg attttttagta aaccttgttc aggtctaaca    1500
ctaccggtac cccatttagg accagccaca gcacctaaca aaacggcatc aaccttcttg      1560
gaggcttcca gcgcctcatc tggaagtggg acacctgtag catcgatagc agcaccacca      1620
attaaatgat tttcgaaatc gaacttgaca ttggaacgaa catcagaaat agctttaaga      1680
accttaatgg cttcggctgt gatttcttga ccaacgtggt cacctggcaa acgacgatc       1740 ttcttagggg cagacatagg ggcagacatt agaatggtat atccttgaaa tatatatata      1800
tattgctgaa atgtaaaagg taagaaaagt tagaaagtaa gacgattgct aaccaccatat    1860 tggaaaaaac aataggtcct taaataatat tgtcaacttc aagtattgtg atgcaagcat      1920
ttagtcatga acgcttctct attctatatg aaagccggt tccggcctct caccttttcct    1980 ttttctccca attttttcagt tgaaaaaggt atatgcgtca ggcgacctct gaaattaaca    2040
aaaaatttcc agtcatcgaa tttgattctg tgcgatagcg ccctgtgtg ttctcgttat      2100 gttgaggaaa aaaataatgg ttgctaagag attcgaactc ttgcatctta cgatacctga     2160
gtattcccac agttaactgc ggtcaagata tttcttgaat caggcgcctt agaccgctcg     2220
gccaaacaac caattacttg ttgagaaata gagtataatt atcctataaa tataacgttt     2280
ttgaacacac atgaacaagg aagtacagga caattgattt tgaagagaat gtggattttg     2340
atgtaattgt tgggattcca tttttaataa ggcaataata ttaggtatgt ggatatacta     2400
gaagttctcc tcgaccgtcg atatgcggtg tgaaataccg cacagatgcg taaggagaaa     2460
ataccgcatc aggaaattgt aaacgttaat attttgttaa aattcgcgtt aaattttttgt    2520 taaatcagct cattttttaa ccaataggcc gaaatcggca aaatccctta taaatcaaaa     2580
gaatagaccg agatagggtt gagtgttgtt ccagtttgga acaagagtcc actattaaag     2640
aacgtggact ccaacgtcaa agggcgaaaa accgtctatc agggcgatgg cccactacgt    2700
gaaccatcac cctaatcaag ttttttgggg tcgaggtgcc gtaaagcact aaatcggaac     2760
cctaaaggga gcccccgatt tagagcttga cggggaaagc cggcgaacgt ggcgagaaag     2820
gaagggaaga aagcgaaagg agcgggcgct agggcgctgg caagtgtagc ggtcacgctg     2880
cgcgtaacca ccacacccgc cgcgcttaat gcgccgctac agggcgcgtc gcgccattcg     2940
ccattcaggc tgcgcaactg ttgggaaggg cgatcggtgc gggcctcttc gctattacgc     3000
cagctggcga aagggggatg tgctgcaagg cgattaagtt gggtaacgcc agggttttcc     3060
cagtcacgac gttgtaaaac gacggccagt gagcgcgcgt aatacgactc actatagtat    3120
attaccctgt tatccctagc ggatctgccg gtagaggtgg ggtcaataag agcgacctca    3180
tactatacct gagaaagcaa cctgacctac aggaaagagt tactcaagaa taagaatttt    3240
cgttttaaaa cctaagagtc actttaaaat ttgtatacac ttattttttt tataacttat    3300
ttaataataa aaatcataaa tcataagaaa ttcgcttatt tagaagtggc gcgccgaatt    3360
cactagtgat tgattaattt ttgttcaccg ttcaagtctt cctcggagat tagcttttgt    3420
tcaccgttca aatcttcttc agaaatcaac ttttgttcac cgtcgagtcc gttcaagtct    3480
tcttctgaga ttaattttttg ttcaccgttc aagtcttcct cggagattag cttttgttca   3540
```

```
ccgttcaaat cttcttcaga aatcaacttt tgttcaccgt cgagtccgtt caagtcttct   3600
tctgagatta attttttgttc accgttcaag tcttcctcgg agattagctt ttgttcaccg   3660
```



```
ccgttcaaat cttcttcaga aatcaacttt tgttcaccgt cgagtccgtt caagtcttct   3600
tctgagatta attttttgttc accgttcaag tcttcctcgg agattagctt ttgttcaccg   3660
ttcaaatctt cttcagaaat caacttttgt tcaccgtcga gtccgttcaa gtcttcttct   3720
gagattaatt tttgttcacc gttcaagtct tcctcggaga ttagcttttg ttcaccgttc   3780
aaatcttctt cagaaatcaa cttttgttca ccgtcgagtc cgttcaagtc ttcttctgag   3840
attaattttt gttcaccgtt caagtcttcc tcggagatta gcttttgttc accgttaatt   3900
aacccggggg cgaattgggt accgggcccc cctcgaggt cgacggtatc gataagttat   3960
attgaatttt caaaaattct tactttttt ttggatggac gcaaagaagt taataatca   4020
tattacatgg cattaccacc atatacatat ccatatctaa tcttacttat atgttgtgga   4080
aatgtaaaga gccccattat cttagcctaa aaaaccttc tctttggaac tttcagtaat   4140
acgcttaact gctcattgct atattgaagt acggattaga agccgccgag cgggcgacag   4200
ccctccgacg gaagactctc ctccgtgcgt cctcgtcttc accggtcgcg ttcctgaaac   4260
gcagatgtgc ctcgcgccgc actgctccga acaataaaga ttctacaata ctagcttta   4320
tggttatgaa gaggaaaaat tggcagtaac ctggccccac aaaccttcaa attaacgaat   4380
caaattaaca accataggat gataatgcga ttagtttttt agccttattt ctggggtaat   4440
taatcagcga agcgatgatt tttgatctat taacagatat ataaatggaa aagctgcata   4500
accacttta ctaatactt caacatttc agtttgtatt acttcttatt caaatgtcat   4560
aaaagtatca acaaaaatt gttaatatac ctctatactt taacgtcaag gagaaaaaac   4620
tataatgcac catcaccatc accatcatca tcatcattct tctggtctgg tgccacgcgg   4680
ttctggtatg gttacgccgg cagccagcca agaccctcct gccattccag ccaggcagaa   4740
tgccagtgcg actgctgcca tggcagtgaa tgccaaagac actgtggagc aagagcgtaa   4800
cgttgtcctt ctatttggct gccaatggct cacgttcact gcatccgact tccgccagct   4860
ccgaaaagct gtcctcgata atcctgagct tcactggatg ctcgatgttc taagcgaatt   4920
gccaggctat taccgcgctg ctgccggaac tagttgtgtc ccatccttgc gggcgatcag   4980
gggagaagag gaccttcggg agttggaaag atggttccga tgcgatgatc tatccacagc   5040
caaatttcca ctgtgctata cacagctcgc accgttgctc atgatgaccc attttgtgca   5100
gtattcacag tggctgaaga tgcagccaaa tggaaggaac cccgtggttg aaattgtcgg   5160
attttgtatt ggactcctga gcagtattgc agtctctgcg acgaggatgg gcagcctgaa   5220
gatgtacggc tctgttgcaa tgcgtttagc tatgttatta ggggcaatgg gagatttaca   5280
gcaagctggg gaagagtata cgtctctagc aattgggtgg aagcgtcctg aattagagga   5340
cgaggtggaa ggcttgctcg aaaaatatcc ggggtcatat attaccgttc aatatgacga   5400
gaacagagca acaatcatgg ctcctcggcg aagtgttgct gccctgcaac aaactctcca   5460
gtctgctgga ttttcagcca acgcggttga atacaatggc cgatatcact ggccaggcca   5520
cgaaaagagc ctgaccccat tgattcatct ctgcaatact cattccggtc ttcaactacc   5580
tgacgcatca gagctgctcc accctccgcg tgcaaacagc actgcagaac cggttcgttc   5640
gggctgcctc cacgagctgg tcctccgcgc tgtccttgct caacagtgtc tgtggcacaa   5700
gactttctct gccgtatacc gagaacatct caccacaccc agctctatag tcgtcgagtt   5760
cgggccggaa cgatgcgtgc cccgacact gtttcgccgt cttccacaac gcatcgtcca   5820
cttcgctgat gtagagcttc cggccaccat aagccgcgac catgagctag ccacgaggcc   5880
cccggcagaa accgacatag ccatagtcgg tatggcctgc cgtgttgcgg gcgctgatga   5940
```

```
ccttgacgaa ttctgggatc ttttgtgttc tggccagtca cagcaccgcg agatgccacg    6000
agaaagatac gcaaactacg agactccttg gcgccctgag gcgagtcatc gctcatggct    6060
cggtaatttt gtccgcgata ttgatgcctt tgaccacaag ttcttcagga aatcaccgcg    6120
ggaagcgatg tcacaggatc cccagcaacg gctcatgctt caagtcgcct atcaagcgct    6180
ggagtcagca ggctactttt cccaaccatc cccaggaaaa gatataggat gctttattgc    6240
aacctgtaca gtggactacg aacacaacgt gaattgccat ccagcttccg cctatgcagc    6300
gacagggctg ttgagaagct tcctagccgg aaaactctca catcactttg ggtggcgggg    6360
cccctcacta tgtgtggata cagcgtgttc tggctctgct gtagcattgc atcatgcatg    6420
tcgggcaata ctgagcggcg attgcacggc cgccctggtg ggcggcgcca atgccatcac    6480
cagtcctctc gcatatgata atctcgcagg ggcatcattt ctttcgccta caggtccgtg    6540
taagccattt gacgcgaagg ctgacggtta ttgtcgcggt gaaggcttcg cagcgatcta    6600
tatcaaaaag ttatcacacg caattgcaga tggagatcag gtcctggcaa ctattgcaag    6660
tacagctgtg gaacagaatg acaactgtac acctattgtt gtgccggaca ctgcttcgtt    6720
ggctggtctg tttaagaagg taacgcagcg tgcgcatctt cactcaaggg acatcagtat    6780
cgtcgaagct catggaacag gcactcaagc tggggatcca gccgagtatg agagcgtgcg    6840
ggacgtgcta ggtggtccaa ggagggtagg gaatttagct ttaggctctg taaaaggcct    6900
ggtcgggcac actgagggtg tatccggaat tattgccctg tgcaaggtcg tcctgatgat    6960
cctgaacgga cagatccctc ctcaacccgg gttccattct ctgaatccac atatcagggc    7020
catgccagac gaccatatcg agataggaac aagagtcaaa ccttgggaag ttggatttcg    7080
cgcagcgctg ataaacaatt atggagcttg tgggtctaat gcatcaatgg tcatcacaca    7140
gggaccgcaa aaggatgaag ttcaagaacg gggtattcac gcagaaaatg ttgcgctgcc    7200
gtttcgcgtg tgcggtttag acaaggcccg tctgcaggca tatgcggcac gtttgcggag    7260
gttcctctct cgctcagagc gaggcatatc ttttgctaat atcgcgttca atctcacgcg    7320
aaaatcgaac ccggccctgg agtgccagtg cgtcttccaa acccgatcag agtcggagct    7380
taaagacatc ctgactggtc tggaggaagg ggacaataaa tatataattc aagtgaagaa    7440
acccaaacgc ccactggtgt gtgttttgg aggacaggta gggagaagta ttggactcga    7500
ccgcacgttc tataacgcat ttcctttgtt caaacatcat ctcgactcct gtgatgatat    7560
tcttaaagcg aatggggatt caagcatcta ccctggtata tttgcaacgg ccccgtact    7620 ggatattgtg cagctccata cgcagctttt tgcattgcag tatgcttgcg ctcgcagctg    7680
gatggattgt ggagtggagg tcacagcggt tataggccac agcttcggcg agctaacagc    7740
attgtgtata tctggcgcgc tgtctctacc agacgccttg actcttatcg tgcgccgtgc    7800
tgttctgatc cgtgacaaat ggggtgctga cccgggtgct atgctcgccg tagaaggaga    7860
caggtctacc ttggagaaac accttgaatc gtcctccgca aacatagcat gctttaatgg    7920
ccctcgaagt tttaccgtcg cagggcctac cgcagttatt gacttccttc aggaagaact    7980
gggggctgat tccgcatttc gactgaagcg ccttgaggtc acaaatgctt tccattccac    8040
cctggtggac ccgttgcttc ctgcactcgc aagtgccata gatggtttag ctcttaacac    8100
cgcaactatt ccgatcgagc gtgctactga acaccaagca gcagatacaa taccgttgag    8160
catcgtggca gaccatctcc gtcagcctgt ttatttcaat aatgctgtac agcgcctcgc    8220
tgcacgtcat ggccctgcta tctggcttga ggcaggctcc aactccacga ttacctcgct    8280
```

```
agcacggaga gcgcttggtt tgggcgtctc tggcaacact ttccattcgg tgaatgtaac    8340
atccacgtcg gcattgatga acctcactga tgtcacggtc gggctctgga gcgataatgt    8400
gccttgcaca ttctggggtt atcacgctcg ccaaaccaga gaatatgctc ccctttttgct   8460 accaccttac cagtttgaaa gaacgcgaca ctggatggaa aataagcccc ttcccttgaa    8520
atataaccag gcgcaagcgg ttatggaagg taagatggaa gagcctcttt tttcatttat    8580
cggttacgaa gaccatgccc gtctgttgag taaatacctc atccatacgg accatccaaa    8640
ctatattgca gcagtctccg ggcatacagc cgcgaagacc gccccaatcg cacccgcaac    8700
tctgctgctt gattatgcaa tcgagctgct cagatctctt cccaacaacc aaaggaaaat    8760
acccagagtg tttgatgtcg ggagtgatgc gccactactg ctagattcaa accgcgaggt    8820
gtggatcgag gtttccgctg aagatgataa aaggacttgg gccttaaggt ttcagagtca    8880
gacgaaaggg ggtcaatctg actcccggct tctacattgc acagcacata tatcgatgca   8940
tgacgtccga tgctctaggt tacaaaccga gttcacacag tacgcaaggc tagtcagcca    9000
cgccaggtgt gccgacctcc taacagaccc agaagttgat gatatcctgc agggccgaaa    9060
tgtgtatcgg tcattcgcag aaatagtgga gtattctgag cagtatcagg gtgtgaaaag    9120
gctagttggg aaaggtagag aaagcgccgg tcgagttgtc aaatcatatt ctgggaaaac    9180
atgggcagat cccttttgt gtgactcctt cagccagtgt gctgggtttt gggtgaattg     9240
catgaccgac agagctgaag acgaagttta tgtcgcgagt ggaattgagc agtggatgcg    9300
cacgccatta tacgcggata tggcgactgc taggccggat acctggcatg tatgggctcg    9360
tcaccagcaa tctgagggat tatatacaag cgacgtcttt tgttcacac ctgatggaga    9420 gctggtggag atgtttctcg gcttgcggta ttcgcgcgta gcaaaaagcc tgtttacccg     9480
cctacttcgt ggctccacgc tgaaagttga ctgcaggaca aaagatactg ctaaccagga    9540
aaataactca ataaaggatc tggtcagtcg tgttaaggct gttgtggccg agatctgcgc    9600
ggtgaagccc agcgagatac aggatgatag tcatctagcc gatgcgggcg ttgattcgct    9660
gatggcaatg gagcttgccc gcgaattaga ggttgccttc aaatgcacga tagctttgga    9720
ggcgctcgtt gaggcagaga catttcatga tcttgtgcaa gcggttcaaa gtgcactggg    9780
agagacgtat gaagactcca cgtttgcag tggcaaccag tgcagcacaa ctgacgaggc    9840
caccgaattc cctagcacta gctggtcaat tacaagtgta tccgatacgg cagacttggt    9900
actaccgctt gatggcgtac tggatgctct ggatgaaacc aaaggactga ccgatcagtt    9960
cctagcggac aataaatgca gtggtcgtct tctcaacttc actcctttga tggttgaaat   10020
gtgcattgta ttgacactgg aagcattgga ggaattgggg agcaacatcc gatctgctcg   10080
tgcaaacgac cgcctcccgc gcattgaatt tgatacgcag cacggcccac tagttgagta   10140
cctatacggg cggctattgg aggcgggatt gataaaacta gacggatcga cagtcattcg   10200
cacggagatc tgcgctccaa cagaatcgag cagtacactt ctccacaaga tcgaacgcga   10260
gtacccagaa tatggcggtg caagtaaact caccttctac actggcagta gacttgcctc   10320
ggttctgcgc ggggagcagg acgggctgca gctcatcttc ggcacagcgg agggccagcg   10380
gcttgtatcg tggatgtatg gcgatgagcc gcataatgtg gcgggttaca agctaatggg   10440
agagtttatc cggcgacttg tcgacaagct acctccagcc gcagccagag aagggatgac   10500
cttgagaatt ctcgaaatgg gtgcaggcac aggtggtggc acgaagtgga tgcttcctct   10560
gctggcagcg cttccagttc cggtagaata tacctttagc gacatatccc ccgcattttct 10620 agctcaggcg cgacgcaaat ttcgcgacta tcaatttgtc cggtattgcg tgcatgatat   10680
```

```
cgaaaaaccg ccatcagagg acctaggaaa ataccatatc atcatggcga gcaatgcggt   10740
ccatgcgacc tcaaatctgc aggtgtccac gggtaatatg cgacaggccc tgcgaccgga   10800
tggcgtgttg atgttgctag agatgactag gccggttttt gcgatagacc tggtattcgg   10860
gttatttcgt ggctggtggg ttttcaacga tggacgacg catgcaatta ccaacgagca    10920
acggtggaaa gacgacctgc aagcagtagg atacggtcac gtcgattgga cggacggcga   10980
atccaacgag gtcggcgtcc agcgtgtaat ttttgctact gccggaggag agcaatatca   11040
cccggtctcg ccccaagagg atgccgcaag actgcggaca gtggtggagt atgtttacca   11100
acacaccgca ggctttacaa tgccagcatt gccgccacgg atcagagctc cagctaacca   11160
tgcatgcatt ttagtcactg gggccacagg tagccttggt agccatttgg ttgcgcgcct   11220
cgtacagctt tcgaatgttc aagctgttat ctgcctgaac cgggtaagcc gaatgggccc   11280
gcgggttcga caaaggaag cagtggcggc gcggggccta tctcttgagt caaaagaaga    11340
gaccaaacta atggttattg agactgacac tgcaaacgac cgtatgggac tatccgttga   11400
gcagtgcagg taccttcaag aaaacgtaac tcacataatt cacaatgctt ggcccatgaa   11460
cggtgccgca ccgctgtcga agttcgaggg acagttccgt gcgctgcgaa atttgatcga   11520
tctggctaga tgcattgcca ctgctcaacg acacccagtc cgattccagt tcatatcttc   11580
gattggtacg gtcaatggag gtggagcgct ggaagaacgt acgcggattg aacaggtgat   11640
gagcaacggg tataacgagg cgaagttcgt ctgcgagcga atgattcacg agacgctgca   11700
gcggtatccg gcagtattcc aggcaacaat tgtacggcca ggacagattt ctggatccga   11760
ggaaacaggg tactggaaca cggccgagca ttttccggcc atggtgaaat cgtcccagag   11820
ccttggtgct ttcccttcac tggcggggcg gttgggatgg acgccagtag atgtagcagc   11880
tcgtattatc gccgaactgc tactggacga gggaatcccc gaggaaatct atcacgtcga   11940
ccatcctaca ggtcagaact ggaccactgt cgtagacgtg ctcgccgagg agctggaagc   12000
caccgaggtg ccgttcaagg attggattca gcgagttaga aaccgtggtg gcagcaggga   12060
gaatccagca gggtttatgg cagactggct ggagacgaat ttcgaaagga tgtcgtgtca   12120
gggaccgcta gacacaaggg tggcaagaag acattccaaa acgttgagag agatgggggg   12180 aggggagg gatgaacacg tgaggcgggt tgtccgcagt tggaaggagt gcggtttctt    12240
aacacaagca cagaccagac agggcattcc aggagccgtt gctttaatcg tcgcacacca   12300
ccaccaccac caccccgggt taattaacat cttttaccca tacgatgttc ctgactatgc   12360
gggctatccg tatgacgtcc cggactatgc aggatcctat ccatatgacg ttccagatta   12420
cgctgctcag tgctgaggcg cgccacttct aaataagcga atttcttatg atttatgatt   12480
tttattatta aataagttat aaaaaaaata agtgtataca aattttaaag tgactcttag   12540
gttttaaaac gaaaattctt attcttgagt aactctttcc tgtaggtcag gttgctttct   12600
caggtatagt atgaggtcgc tcttattgac cacacctcta ccggcagatc cgctagggat   12660
aacagggtaa tatagttccc tttagtgagg gttaattgcg cgcttggcgt aatcatggtc   12720
atagctgttt cctgtgtgaa attgttatcc gctcacaatt ccacacaaca taggagccgg   12780
aagcataaag tgtaaagcct ggggtgccta atgagtgagg taactcacat taattgcgtt   12840
gcgctcactg cccgctttcc agtcgggaaa cctgtcgtgc cagctgcatt aatgaatcgg   12900
ccaacgcgcg gggagaggcg gtttgcgtat tgggcgctct tccgcttcct cgctcactga   12960
ctcgctgcgc tcggtcgttc ggctgcggcg agcggtatca gctcactcaa aggcggtaat   13020
```

```
acggttatcc acagaatcag gggataacgc aggaaagaac atgtgagcaa aaggccagca   13080
aaaggccagg aaccgtaaaa aggccgcgtt gctggcgttt ttccataggc tccgcccccc   13140
tgacgagcat cacaaaaatc gacgctcaag tcagaggtgg cgaaacccga caggactata   13200
aagataccag gcgtttcccc ctggaagctc cctcgtgcgc tctcctgttc cgaccctgcc   13260
gcttaccgga tacctgtccg cctttctccc ttcgggaagc gtggcgcttt ctcatagctc   13320
acgctgtagg tatctcagtt cggtgtaggt cgttcgctcc aagctgggct gtgtgcacga   13380
accccccgtt cagcccgacc gctgcgcctt atccggtaac tatcgtcttg agtccaaccc   13440
ggtaagacac gacttatcgc cactggcagc agccactggt aacaggatta gcagagcgag   13500
gtatgtaggc ggtgctacag agttcttgaa gtggtggcct aactacggct acactagaag   13560
gacagtattt ggtatctgcg ctctgctgaa gccagttacc ttcggaaaaa gagttggtag   13620
ctcttgatcc ggcaaacaaa ccaccgctgg tagcggtggt ttttttgttt gcaagcagca   13680
gattacgcgc agaaaaaaag gatctcaaga agatcctttg atcttttcta cggggtctga   13740
cgctcagtgg aacgaaaact cacgttaagg gattttggtc atgagattat caaaaaggat   13800
cttcacctag atccttttaa attaaaaatg aagttttaaa tcaatctaaa gtatatatga   13860
gtaaacttgg tctgacagtt accaatgctt aatcagtgag gcacctatct cagcgatctg   13920
tctatttcgt tcatccatag ttgcctgact ccccgtcgtg tagataacta cgatacggga   13980
gggcttacca tctggcccca gtgctgcaat gataccgcga gacccacgct caccggctcc   14040
agatttatca gcaataaacc agccagccgg aagggccgag cgcagaagtg gtcctgcaac   14100
tttatccgcc tccatccagt ctattaattg ttgccgggaa gctagagtaa gtagttcgcc   14160
agttaatagt ttgcgcaacg ttgttgccat tgctacaggc atcgtggtgt cacgctcgtc   14220
gtttggtatg gcttcattca gctccggttc ccaacgatca aggcgagtta catgatcccc   14280
catgttgtgc aaaaaagcgg ttagctcctt cggtcctccg atcgttgtca gaagtaagtt   14340
ggccgcagtg ttatcactca tggttatggc agcactgcat aattctctta ctgtcatgcc   14400
atccgtaaga tgcttttctg tgactggtga gtactcaacc aagtcattct gagaatagtg   14460
tatgcggcga ccgagttgct cttgcccggc gtcaatacgg gataataccg cgccacatag   14520
cagaacttta aaagtgctca tcattggaaa acgttcttcg gggcgaaaac tctcaaggat   14580
cttaccgctg ttgagatcca gttcgatgta acccactcgt gcacccaact gatcttcagc   14640
atcttttact ttcaccagcg tttctgggtg agcaaaaaca ggaaggcaaa atgccgcaaa   14700
aaagggaata agggcgacac ggaaatgttg aatactcata ctcttccttt ttcaatatta   14760
ttgaagcatt tatcagggtt attgtctcat gagcggatac atatttgaat gtatttagaa   14820
aaataaacaa ataggggttc cgcgcacatt tccccgaaaa gtgccacctg aacgaagcat   14880
ctgtgcttca ttttgtagaa caaaaatgca acgcgagagc gctaatttt caaacaaaga   14940 atctgagctg catttttaca gaacagaaat gcaacgcgaa agcgctattt taccaacgaa   15000
gaatctgtgc ttcatttttg taaaacaaaa atgcaacgcg agagcgctaa ttttcaaac   15060 aaagaatctg agctgcattt ttacagaaca gaaatgcaac gcgagagcgc tattttacca   15120
acaaagaatc tatacttctt ttttgttcta caaaaatgca tcccgagagc gctattttc   15180 taacaaagca tcttagatta cttttttttct cctttgtgcg ctctataatg cagtctcttg   15240
ataacttttt gcactgtagg tccgttaagg ttagaagaag gctactttgg tgtctatttt   15300
ctcttccata aaaaaagcct gactccactt cccgcgttta ctgattacta gcgaagctgc   15360
gggtgcattt tttcaagata aaggcatccc cgattatatt ctataccgat gtggattgcg   15420
```

| | | | | |
|---|---|---|---|---|
| catactttgt | gaacagaaag | tgatagcgtt | gatgattctt | cattggtcag | aaaattatga | 15480 |
| acggtttctt | ctattttgtc | tctatatact | acgtatagga | aatgtttaca | ttttcgtatt | 15540 |
| gttttcgatt | cactctatga | atagttctta | ctacaatttt | tttgtctaaa | gagtaatact | 15600 |
| agagataaac | ataaaaaatg | tagaggtcga | gtttagatgc | aagttcaagg | agcgaaaggt | 15660 |
| ggatgggtag | gttatatagg | gatatagcac | agagatatat | agcaaagaga | tacttttgag | 15720 |
| caatgtttgt | ggaagcggta | ttcgcaatat | tttagtagct | cgttacagtc | cggtgcgttt | 15780 |
| ttggtttttt | gaaagtgcgt | cttcagagcg | cttttggttt | tcaaaagcgc | tctgaagttc | 15840 |
| ctatactttc | tagagaatag | gaacttcgga | ataggaactt | caaagcgttt | ccgaaaacga | 15900 |
| gcgcttccga | aaatgcaacg | cgagctgcgc | acatacagct | cactgttcac | gtcgcaccta | 15960 |
| tatctgcgtg | ttgcctgtat | atatatatac | atgagaagaa | cggcatagtg | cgtgtttatg | 16020 |
| cttaaatgcg | tacttatatg | cgtctattta | tgtaggatga | aaggtagtct | agtacctcct | 16080 |
| gtgatattat | cccattccat | gcggggtatc | gtatgcttcc | ttcagcacta | cccttttagct | 16140 |
| gttctatatg | ctgccactcc | tcaattggat | tagtctcatc | cttcaatgct | atcatttcct | 16200 |
| ttgatattgg | atcatactaa | gaaaccatta | ttatcatgac | attaacctat | aaaaataggc | 16260 |
| gtatcacgag | gccctttcgt | c | | | | 16281 |

```
<210> SEQ ID NO 23
<211> LENGTH: 16512
<212> TYPE: DNA
<213> ORGANISM: Artificial Sequence
<220> FEATURE:
<223> OTHER INFORMATION: vector

<400> SEQUENCE: 23
```

| | | | | | | |
|---|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcgggctgg | cttaactatg | cggcatcaga | gcagattgta | ctgagagtgc | 180 |
| accatatcga | ctacgtcgta | aggccgtttc | tgacagagta | aaattcttga | gggaactttc | 240 |
| accattatgg | gaaatgcttc | aagaaggtat | tgacttaaac | tccatcaaat | ggtcaggtca | 300 |
| ttgagtgttt | tttatttgtt | gtatttttt | tttttagag | aaaatcctcc | aatatcaaat | 360 |
| taggaatcgt | agtttcatga | ttttctgtta | cacctaactt | tttgtgtggt | gccctcctcc | 420 |
| ttgtcaatat | taatgttaaa | gtgcaattct | ttttccttat | cacgttgagc | cattagtatc | 480 |
| aatttgctta | cctgtattcc | tttactatcc | tcctttttct | ccttcttgat | aaatgtatgt | 540 |
| agattgcgta | tatagtttcg | tctacccctat | gaacatattc | cattttgtaa | tttcgtgtcg | 600 |
| tttctattat | gaatttcatt | tataaagttt | atgtacaaat | atcataaaaa | aagagaatct | 660 |
| ttttaagcaa | ggatttttctt | aacttcttcg | gcgacagcat | caccgacttc | ggtggtactg | 720 |
| ttggaaccac | ctaaatcacc | agttctgata | cctgcatcca | aaccttttt | aactgcatct | 780 |
| tcaatggcct | taccttcttc | aggcaagttc | aatgacaatt | tcaacatcat | tgcagcagac | 840 |
| aagatagtgg | cgatagggtc | aaccttattc | tttggcaaat | ctggagcaga | accgtggcat | 900 |
| ggttcgtaca | aaccaaatgc | ggtgttcttg | tctggcaaag | aggccaagga | cgcagatggc | 960 |
| aacaaaccca | aggaacctgg | gataacggag | gcttcatcgg | agatgatatc | accaaacatg | 1020 |
| ttgctggtga | ttaataccc | atttaggtgg | gttgggttct | taactaggat | catgcggca | 1080 |
| gaatcaatca | attgatgttg | aaccttcaat | gtagggaatt | cgttcttgat | ggtttcctcc | 1140 |

```
acagtttttc tccataatct tgaagaggcc aaaagattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttctttacgg attttagta aaccttgttc aggtctaaca     1500
ctaccggtac cccatttagg accagccaca gcacctaaca aaacggcatc aaccttcttg    1560
gaggcttcca cgcgcctcatc tggaagtggg acacctgtag catcgatagc agcaccacca   1620
attaaatgat tttcgaaatc gaacttgaca ttggaacgaa catcagaaat agctttaaga    1680
accttaatgg cttcggctgt gatttcttga ccaacgtggt cacctggcaa acgacgatc     1740
ttcttagggg cagacatagg ggcagacatt agaatggtat atccttgaaa tatatatata    1800
tattgctgaa atgtaaaagg taagaaaagt tagaaagtaa gacgattgct aaccacctat    1860
tggaaaaaac aataggtcct taaataatat tgtcaacttc aagtattgtg atgcaagcat    1920
ttagtcatga acgcttctct attctatatg aaaagccggt tccggcctct cacctttcct    1980
ttttctccca atttttcagt tgaaaaggt atatgcgtca ggcgacctct gaaattaaca     2040
aaaaatttcc agtcatcgaa tttgattctg tgcgatagcg ccctgtgtg ttctcgttat     2100
gttgaggaaa aaataatgg ttgctaagag attcgaactc ttgcatctta cgatacctga    2160
gtattcccac agttaactgc ggtcaagata ttcttgaat caggcgcctt agaccgctcg     2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca ttttaataa ggcaataata ttaggtatgt ggatatacta     2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttgt     2520
taaatcagct cattttttaa ccaataggcc gaaatcggca aaatcccttta taaatcaaaa    2580
gaatagaccg ataagggtt gagtgttgtt ccagtttgga acaagagtcc actattaaag     2640
aacgtggact ccaacgtcaa agggcgaaaa accgtctatc agggcgatgg cccactacgt    2700
gaaccatcac cctaatcaag tttttggg tcgaggtgcc gtaaagcact aaatcggaac      2760
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg tgctgcaagg cgattaagtt gggtaacgcc agggttttcc     3060
cagtcacgac gttgtaaaac gacggccagt gagcgcgcgt aatacgactc actatagtat    3120
attccctgt tatccctagc ggatctgccg gtagaggtgt ggtcaataag agcgacctca     3180
tactatacct gagaaagcaa cctgacctac aggaaagagt tactcaagaa taagaatttt    3240
cgttttaaaa cctaagagtc actttaaaat ttgtatacac ttattttttt tataacttat    3300
ttaataataa aaatcataaa tcataagaaa ttcgcttatt tagaagtggc gcgccgaatt    3360
cactagtgat tgattaattt ttgttcaccg ttcaagtctt cctcggagat tagcttttgt    3420
tcaccgttca aatcttcttc agaaatcaac ttttgttcac cgtcgagtcc gttcaagtct    3480
tcttctgaga ttaattttg ttcaccgttc aagtcttcct cggagattag cttttgttca    3540
```

```
ccgttcaaat cttcttcaga aatcaacttt tgttcaccgt cgagtccgtt caagtcttct   3600
tctgagatta attttttgttc accgttcaag tcttcctcgg agattagctt ttgttcaccg   3660
ttcaaatctt cttcagaaat caacttttgt tcaccgtcga gtccgttcaa gtcttcttct   3720
gagattaatt tttgttcacc gttcaagtct tcctcggaga ttagcttttg ttcaccgttc   3780
aaatcttctt cagaaatcaa cttttgttca ccgtcgagtc cgttcaagtc ttcttctgag   3840
attaattttt gttcaccgtt caagtcttcc tcggagatta gcttttgttc accgttaatt   3900
aacccggggg cgaattgggt accgggcccc cctcgaggt cgacggtatc gataagttat   3960
attgaatttt caaaaattct tactttttt ttggatggac gcaaagaagt ttaataatca   4020
tattacatgg cattaccacc atatacatat ccatatctaa tcttacttat atgttgtgga   4080
aatgtaaaga gccccattat cttagcctaa aaaaccttc tctttggaac tttcagtaat   4140
acgcttaact gctcattgct atattgaagt acggattaga agccgccgag cgggcgacag   4200
ccctccgacg gaagactctc ctccgtgcgt cctcgtcttc accggtcgcg ttcctgaaac   4260
gcagatgtgc ctcgcgccgc actgctccga acaataaaga ttctacaata ctagctttta   4320
tggttatgaa gaggaaaaat tggcagtaac ctggccccac aaaccttcaa attaacgaat   4380
caaattaaca accataggat gataatgcga ttagtttttt agccttattt ctggggtaat   4440
taatcagcga agcgatgatt tttgatctat taacagatat ataaatggaa agctgcata   4500 accactttaa ctaatacttt caacattttc agtttgtatt acttcttatt caaatgtcat   4560
aaaagtatca acaaaaaatt gttaatatac ctctatactt taacgtcaag gagaaaaaac   4620
tataatgcac catcaccatc accatcatca tcatcattct tctggtctgg tgccacgcgg   4680
ttctggtatg cttggtcatc gggacttcac tacattgcct ctttcacggc gtgagtttct   4740 cctcttttggc cctctggccc tgtcgtttga ccaggctgcc tttgagcatc ttcgcaaaac   4800
gattgtcaac agcgaagagc accgttgggc tctagaggta ctcggcagcc ttccccaata   4860
ctatgcgacc attgtcaacg ctttttcctgg aatcaatggt aggaatgagg ttcaactcga   4920
agatctcaaa ggtgcccttc acagtggaaa gcctctcgcg accagcttcc cactgcccaa   4980
cacccttctt attcctctgg taatggtcct ccacttgacc gaatactcca gattccttca   5040
ggagatcagt gaggaacttg aatctggtat tgatctcttc gatgcgtccc gtcacaataa   5100
ggagactgtt ggtttctgca ctggtctcct cagtgccatg gcagtttcca cgcgcggcag   5160
ccgggaagat tttcgcaaat atgcggctgt tgccgtgcga cttggcctgc tcgttggtgt   5220
ggtggtggat tctcatgata tatcatccgc gcaagggccc agcaagtcta tcagtgcgtc   5280
ttggaattct gcgcaaaagc gtgaagacgc acggcgtatc atggatgaat tccccaggc   5340 gtacatctct gtctattatg acgaagaccg tgctactatc acagcccag catccgagat   5400 ttctgatctg catcggcgtt tgcgagcttc tggcattgta acagccgaga tcggcctgaa   5460
tggatgtttc catgctgatt gttatcttga tcaactggat ccaattatcc agttttgcga   5520
ctctcagccc gacttccagc ttccggatgc atccaaggtt gttattccta cccgatccaa   5580
tgctactgga gagttaatcc gcgacggtgc tttgcaccag cacgccctgc ggtctatcct   5640
ggtcgaaccc cctcagtggt tcgagagctt cactgcagtg cgtgacgctt gcgcagagga   5700
tgaaggggcc attatattct ccttcggtcc cgagcggtgc gttcctccgt ctctcctccg   5760
ggtgttgagc cagaaagtgg tgaccgtgga agatctcgac gttttaaaga gataccagta   5820
ctcctactcc gagaacgata ttgctgttgt cgggatgtcc tgcaaggtgg ctggtgccaa   5880
```

```
caatcttgaa gaattctggg accttctttg taccggaaag tcccaacata gggaagttcc    5940
gaaggaacga ttcagctttg agacagtctt ccgagatgtc gattctaaga ggaagtggtt    6000
tggcaatttt attgacggcc atgatcagtt cgatcacaaa ttcttcaaaa agagcccccg    6060
cgagagcgct acaatggatc ctcagcagcg tcatttgctc cagattgcct accaggctgt    6120
tgagcaatct ggatactttc attcggccaa tccagacaga cagattggtt gctacatggg    6180
tgtgtgtgcc tgcgactatg agaataatat tgcctgccat gctcccaatg cgttctcagc    6240
tacgggaaac ctgcaaggtt tcatcgccgg caaagtcagt catttctttg gatggactgg    6300
acctggactc acaattgaca ctgcctgctc atcctccgcc gttgcagtac accaagcatg    6360
caaggccatc attaccggag agtgcactgc tgccctggcc ggcggcacac atgttatgac    6420
gaacccgcta tggttccaga accttgctgg agcgtcattt ctcagcacca ctgggcagtg    6480
caagcccttt gacgccaaag cagatggcta ctgtagaggt gagggtattg caactgtttt    6540
tctgaagaaa ctctctgctg ccgttgccga cggggatcag attcttgggg ttatcacggc    6600
cactgctgtg cagcagaacc agaattgcac ccctatcttc gtcccaacg tgccatcact    6660 ttccgacctg tttcgtgtcg tggtgaagca atctcgacta caaccatcgg acgtgactgt    6720
ggttgaggcg cacggcaccg gaactgctgt tggagacccg gctgagtacg acagcattcg    6780
atcagtgcta ggtggctcga gccgggagaa aacgcttgct ctcagctccg tcaagggcct    6840
agttggtcac attgagtgca cctccggcat tgtctcgctc atcaaagtac tcttaatgct    6900
gcagaagcgg atgatcccac cccaggcaag cttcactacc attaacccgg ccattaaggc    6960
tactcctgca gacaaaatca acataccgac cactgtcaag acttgggacg ccgaattctg    7020
cgcagctttg attaataact acggtgcctc gggctccaac gcatccattg tcgtcactca    7080 accgccgtt ggtacagtta agccaagtgc agaaacctca ggtcttaaat accccttccg    7140
attctgcggc atggatgaac aaagtctgcg ccggtactcc aaaatctttc ggcagtttct    7200
caaccgaaaa agctactctg cgcaggatct ctcgttgcgg aatatctcct tcaatgtaaa    7260
tcgacaaagc aaccgtcagc tagatcgaac tctactcttc agcgtcaaga cactagagga    7320
actcgaacag aagctcgtca cttttcgagaa tgataatgac agtattacat ctctcgcact    7380
gcccaagtcc aagccagtcg tcctctgctt tggaggtcaa gtctcaacat tgtcgggct    7440 ggatcgcact gtatacgagc gcgtggctat tttacggaag catctccata ctgtcgatgc    7500
agtagctcgc tcgatcggac tgaagagcat cttccccagg atctttgaga ctacacccgt    7560
tagtgacact gtccatttgc agatcatgct atttgcatct cagtacgcct gcgcacgcag    7620
ctggatcgac tctggcatcc agcctgttgc tgtagttggt catagcttcg gtgaactcac    7680
tagcctttgc gtctcgcagt cattgtcttt agaagacgcc gtcaagatga tcgcagctcg    7740
tgcgacccta atcagggacg cttgggggccc agagaaaggc gccatgcttg cagtggaagc    7800
ggatctggaa gacgtccaga aattactcgc tgagtcgagt gctggatgtc aagatgtaca    7860
accagccacg attgcctgct ataacggacc caggagcttt acacttgctg gtgcggttgc    7920
agcgattgac gccgttgctg aggccctcgc cacacctgcg ttctcctcca tgaagaacaa    7980
gcgccttaac gtgacgaatg cattccattg tgctctagta gatcccctcc ttgatcgact    8040
cgaggagagt gcccgggaac tgactttccg tgcgcctgtg attcccgtcc agagagcaac    8100
cgagtatcag acagaggagc ttcctacctc cagatttgtc gctgatcata ttcgttctcc    8160
ggtctttttc aaccacgcaa ttcacagact ggcggataag tatccttctt gtgtcttctt    8220
agaagcaggc tccaactcga ccgtcaccaa catggccagt cgtgcacttg gcaatcccag    8280
```

```
cagctcccac ttccaggcaa tcaacatcac gagccataac ggatggaata accttgtaga   8340
tgcaactatg aatatgtgga aatcggggct aggtgtccat ttctgggctc atcagcccag   8400
ccagaccaag gaatacgctc ttctcctgct accaccgtat cagttcgagc cttctcgcca   8460
ctggatagaa ttgaagaatc cgccaaagct gacagccgca ccagcaattg aggaagttaa   8520
aaaagaagag gctaaggtac cgaatacttt attgacattt gtggggtacc aagacagtga   8580
gaggcagcag gcaagattcc gagtcaatac tatgatcccc aaatacgaca agctcatccg   8640
aggccatatc attgcacaaa ccgctcccat ctgcccagca accgtacagc ttgacctggt   8700
catcgagtct atccggagta tccgtccgga gcttgcaagc actgaacacg agcctcagat   8760
ccatgccgta gagaatctgg cgccaatatg cgtgaatcca ctgagagctg tgtgggtgga   8820
ggtcacagcc gacgacgtcg ctcaaggaac ctcctggaat ttccaggtat acagcgacga   8880
tctacagaac ggtttctcca aaaccatcca tacaaccggt cgagttatct tccggtccat   8940
tagtgatgtg tccctaaagt atgagtttgc ccggtttgag cggcacttca ggcaccaaac   9000
gtgtgtcgaa ctaatgcgcg gcggtgaagt cgatgaagta ttacagaaca gaaatatcta   9060
caagatgttc gccgagattg tcgattatgg cgaggactac cgtgggctcc agaagcttgt   9120
gagcaagggc aatcagtccg ctggatatgt ggtgaagaaa tacaaccctg agtcctggct   9180
tgatgggcat ctagccgaca gtttctgtca agtgggaggc atttacgtca actgtatgac   9240
ggatcgtgtt ccaaatgata tgttcatcgc caacggcatc gagcagtgga tgcgttcacc   9300
caaaatgcgt caacaggacc ctcgacccga gtcgtaccat gtgctggcaa cgcaccatcg   9360
gccctctgat aaggcatttc tgactgatgt gttcgctttc gactcgacta ctggtgtctt   9420
aatcgaagtt attctgggta tcagctacgt caagattccc aaagcctcga tgagcaagtt   9480
actctctcgc cttacagtga atgatagtgc tagttgtcct accaacatgc ctctgctttc   9540
aaaatcagcc agtgtgaacc tgtttgatgc tccagagaac ctcagcactc catcactgtc   9600
tgttgctcct acccagcagt ctgctcccgc cctcagcctc tccaaagtaa aaaaggtcaa   9660
gaacgatggg ccagacaagg ggcagctcac gcaacgaatc aagtccatcc tggcggaact   9720
ttccggtctc gaaattgcag agataaagga cgatagcgag cttgccgacc tcggaatcga   9780
ttctctcatg ggtatggaaa tggcacatga gatagagaag gctttcacaa tttcgctgcc   9840
tgagagtgac ctcatggagg tcgtagacgt gccgagccta attaaatgcg tacggaaagc   9900
tatgagcggc gatgctgatt ccgctgaata caccaccgag cagagtacat ccgaagcggc   9960
ggacagcgac gataaatcca cgaattatac cactcctagc actccaggcg aggaagctct  10020
cgacatggac aagtctatgc gcgagtttct agggaaagag ggcacggagt taaatctccc  10080
ctttgagacg gtcatgaagg cattcaatga gaccaagaac atgacggacg acaggattgc  10140
agagtaccag caaactcggt acgtcgaaag cgttcttcca atgcagagcc agatgtgtgt  10200
gtctctcgtg ttggaggcat ttgatcaact caacatgagg attcgcaccg ctcctgcagg  10260
ggagaaattc acgcgtatct ctcatccgaa ggaacatact cggctagtcg actacctata  10320
caagatgcta gaggacgcaa gccttatcaa cattgacgga gaggtcatca cccgaacggc  10380
catccaggtt ccacggccta gcaaagagat tttcgatgag ctcgtctcgc aacacccgga  10440
ccagaacgcg gccgacaagc taacatttta caccggatcc catctcgcag aagtgctgaa  10500
aggagaaaca gacggcatca aactgatatt cggaacgcag gacggacgag agctagtctc  10560
gaaactatac agggactggc ccctcaaccg cctcttctac cggcagatgg aggacttctt  10620
```

```
agagcgactt acgtccaagt tagacataag ccagggcgtg atcaagatcc tcgaaatggg   10680
tgcagggacc ggaggaacga ctaaatggct tgttcctttg ctggcgaagc tcaacatacc   10740
ggttgagtac accttcaccg atattgcccc gtctttcgtt gctgcggcgc gcaagaaatt   10800
ctccaagcaa tacccgttca tgaagttcag aactcacgat atcgaaaagg ccccctgcaga  10860
tgatcttatc ggcagccagc acgttattat cgccagcaac gcagttcatg ctacgcatag   10920
tctcagtgaa tccggaaaga acattcgcaa ggcactgcgg cctgacgcg ttctgctgat    10980
gcttgagatg acagggacac tccactgggt cgacattatt ttcggcctct ttgaagggtg   11040
gtggtacttt gatgatggcc gcacccacgc cgtcactcac gagtcccggt gggcgaagga   11100
cttgcaggct gttggatacg gccacgtcga ctggacggat ggcgtacgtc cggaaaacaa   11160
gctcgagaag ctcatcatcg cgttcgcatc aggcgggagg tatgaaagac ttcacattcc   11220
ccgacctcta gaaagtgcct ccgctgactg tgcagcgcga caagcagtcg tcgataggta   11280
cgtgcaggag atgaccgctg gctttggagc tgcaacaggg gtgtctcctt ctgctcctct   11340
ggcacatcaa gaacccaagg gctgctgcgt cctggtgact ggtgccacgg gtagcctggg   11400
atgtcacctt cttgcggcac tcacctccct tcccaccatc gccagcgtgg tatgtctcaa   11460
tcgccgcagt cgacaagatc ccctcgagcg tcaacaccgt tcgcttcttg agaaaaaaat   11520
ctttctttcc gaggagactg ctgccagggt cagagtgatt gagacagaca tgtcaaagcc   11580
ccaactcggc cttttggaag aggaatataa ctatctcctc aatagcgtga ctcatattgt   11640
tcacaacgcc tggctcatga atgccaaatt gccccttagg aggttcgaac ctcagctcca   11700
gatcatgcg aatctgctgg atctcgctta cgggatctcc cttcaacgac ctatggagaa    11760
ggtctccttc caattcatct catccatcgc gacagtgggc cactggccaa tttggactgg   11820
taagtccagc gtccccgagg agcgcatggc gatcgagtcg gtccttccca ccgggtatgg   11880
ggacgcaaaa tacatctgcg aacgcatgat cgacgagacc ctccataaat atccagacag   11940
attccgggcc atggtagtgc gccctggaca agtcgccggc tcaagcacca gtggatattg   12000
gaataccatg gagcattttt cttttctagt gaaatcgtct cagactctaa atgccctacc   12060
tgactttgat ggtgtgctgt catggacccc ggtggatgtc gtggccagca cgctcgtgga   12120
tctcctcctg cttccggaag ataaaacccc gtattccatc tatcacattg ataacccagt   12180
ccgccagccc tggaaggaga tgaacgtggt acttgcagat gcgctgcata taccccggtc   12240
gaacatcatt ccattcgaga atggattca gcgggtcaag gactatcccc gccaagttga    12300
gggtgcagag ggagacaatc ctgcgattct gctggtcgat ttccttgata caatttcat    12360
ccgcatgtct tgtgggggcc ttttgctgga aacgaagaaa tcgcgcgagc attcgaaaac   12420
tctcgcaaat ctaggaccgg tcagtgcaga gacagcgagg ctgttcatta aaagttggat   12480
agatatggga ttttttaagtc caggagccgt tgctttaatc gtcgcacacc accaccacca   12540
ccaccccggg ttaattaaca tcttttaccc atacgatgtt cctgactatg cgggctatcc   12600
gtatgacgtc ccggactatg caggatccta tccatatgac gttccagatt acgctgctca   12660
gtgctgaggc gcgccacttc taaataagcg aatttcttat gatttatgat tttattatt    12720
aaataagtta taaaaaaaat aagtgtatac aaattttaaa gtgactctta ggttttaaaa   12780
cgaaaattct tattcttgag taactctttc ctgtaggtca ggttgctttc tcaggtatag   12840
tatgaggtcg ctcttattga ccacacctct accggcagat ccgctaggga taacagggta   12900
atatagttcc ctttagtgag ggttaattgc gcgcttggcg taatcatggt catagctgtt   12960
tcctgtgtga aattgttatc cgctcacaat tccacacaac ataggagccg gaagcataaa   13020
```

```
gtgtaaagcc tggggtgcct aatgagtgag gtaactcaca ttaattgcgt tgcgctcact   13080
gcccgctttc cagtcgggaa acctgtcgtg ccagctgcat taatgaatcg ccaacgcgc   13140 ggggagaggc ggtttgcgta ttgggcgctc ttccgcttcc tcgctcactg actcgctgcg   13200
ctcggtcgtt cggctgcggc gagcggtatc agctcactca aaggcggtaa tacggttatc   13260
cacagaatca ggggataacg caggaaagaa catgtgagca aaaggccagc aaaaggccag   13320
gaaccgtaaa aaggccgcgt tgctggcgtt tttccatagg ctccgccccc ctgacgagca   13380
tcacaaaaat cgacgctcaa gtcagaggtg gcgaaacccg acaggactat aaagatacca   13440
ggcgtttccc cctggaagct ccctcgtgcg ctctcctgtt ccgaccctgc cgcttaccgg   13500
atacctgtcc gcctttctcc cttcgggaag cgtggcgctt tctcatagct cacgctgtag   13560
gtatctcagt tcggtgtagg tcgttcgctc caagctgggc tgtgtgcacg aaccccccgt   13620
tcagcccgac cgctgcgcct tatccggtaa ctatcgtctt gagtccaacc cggtaagaca   13680
cgacttatcg ccactggcag cagccactgg taacaggatt agcagagcga ggtatgtagg   13740
cggtgctaca gagttcttga agtggtggcc taactacggc tacactagaa ggacagtatt   13800
tggtatctgc gctctgctga agccagttac cttcggaaaa agagttggta gctcttgatc   13860
cggcaaacaa accaccgctg gtagcggtgg tttttttgtt tgcaagcagc agattacgcg   13920
cagaaaaaaa ggatctcaag aagatccttt gatcttttct acggggtctg acgctcagtg   13980
gaacgaaaac tcacgttaag ggattttggt catgagatta tcaaaaagga tcttcaccta   14040
gatcctttta aattaaaaat gaagttttaa atcaatctaa agtatatatg agtaaacttg   14100
gtctgacagt taccaatgct taatcagtga ggcacctatc tcagcgatct gtctatttcg   14160
ttcatccata gttgcctgac tccccgtcgt gtagataact acgatacggg agggcttacc   14220
atctggcccc agtgctgcaa tgataccgcg agacccacgc tcaccggctc cagatttatc   14280
agcaataaac cagccagccg gaagggccga gcgcagaagt ggtcctgcaa ctttatccgc   14340
ctccatccag tctattaatt gttgccggga agctagagta agtagttcgc cagttaatag   14400
tttgcgcaac gttgttgcca ttgctacagg catcgtggtg tcacgctcgt cgtttggtat   14460
ggcttcattc agctccggtt cccaacgatc aaggcgagtt acatgatccc ccatgttgtg   14520
caaaaaagcg gttagctcct tcggtcctcc gatcgttgtc agaagtaagt tggccgcagt   14580
gttatcactc atggttatgg cagcactgca taattctctt actgtcatgc catccgtaag   14640
atgcttttct gtgactggtg agtactcaac caagtcattc tgagaatagt gtatgcggcg   14700
accgagttgc tcttgcccgg cgtcaatacg ggataatacc gcgccacata gcagaacttt   14760
aaaagtgctc atcattggaa aacgttcttc ggggcgaaaa ctctcaagga tcttaccgct   14820
gttgagatcc agttcgatgt aacccactcg tgcacccaac tgatcttcag catcttttac   14880
tttcaccagc gtttctgggt gagcaaaaac aggaaggcaa aatgccgcaa aaaagggaat   14940
aagggcgaca cggaaatgtt gaatactcat actcttcctt tttcaatatt attgaagcat   15000
ttatcagggt tattgtctca tgagcggata catatttgaa tgtatttaga aaataaaca   15060 aataggggtt ccgcgcacat ttccccgaaa agtgccacct gaacgaagca tctgtgcttc   15120
attttgtaga acaaaaatgc aacgcgagag cgctaatttt tcaaacaaag aatctgagct   15180
gcatttttac agaacagaaa tgcaacgcga aagcgctatt ttaccaacga agaatctgtg   15240
cttcattttt gtaaacaaa aatgcaacgc gagagcgcta ttttcaaa caaagaatct   15300 gagctgcatt tttacagaac agaaatgcaa cgcgagagcg ctatttacc aacaaagaat   15360
```

| | |
|---|---|
| ctatacttct tttttgttct acaaaaatgc atcccgagag cgctattttt ctaacaaagc | 15420 |
| atcttagatt acttttttc tcctttgtgc gctctataat gcagtctctt gataactttt | 15480 |
| tgcactgtag gtccgttaag gttagaagaa ggctactttg gtgtctattt tctcttccat | 15540 |
| aaaaaaagcc tgactccact tcccgcgttt actgattact agcgaagctg cgggtgcatt | 15600 |
| ttttcaagat aaaggcatcc ccgattatat tctataccga tgtggattgc gcatactttg | 15660 |
| tgaacagaaa gtgatagcgt tgatgattct tcattggtca gaaaattatg aacggtttct | 15720 |
| tctattttgt ctctatatac tacgtatagg aaatgtttac attttcgtat tgttttcgat | 15780 |
| tcactctatg aatagttctt actacaattt ttttgtctaa agagtaatac tagagataaa | 15840 |
| cataaaaat gtagaggtcg agtttagatg caagttcaag gagcgaaagg tggatgggta | 15900 |
| ggttatatag ggatatagca cagagatata tagcaaagag atacttttga gcaatgtttg | 15960 |
| tggaagcggt attcgcaata ttttagtagc tcgttacagt ccggtgcgtt tttggttttt | 16020 |
| tgaaagtgcg tcttcagagc gcttttggtt ttcaaaagcg ctctgaagtt cctatacttt | 16080 |
| ctagagaata ggaacttcgg aataggaact tcaaagcgtt tccgaaaacg agcgcttccg | 16140 |
| aaaatgcaac gcgagctgcg cacatacagc tcactgttca cgtcgcacct atatctgcgt | 16200 |
| gttgcctgta tatatatata catgagaaga acggcatagt gcgtgtttat gcttaaatgc | 16260 |
| gtacttatat gcgtctattt atgtaggatg aaaggtagtc tagtacctcc tgtgatatta | 16320 |
| tcccattcca tgcggggtat cgtatgcttc cttcagcact acccttagc tgttctatat | 16380 |
| gctgccactc ctcaattgga ttagtctcat ccttcaatgc tatcatttcc tttgatattg | 16440 |
| gatcatacta agaaaccatt attatcatga cattaaccta taaaaatagg cgtatcacga | 16500 |
| ggccctttcg tc | 16512 |

<210> SEQ ID NO 24
<211> LENGTH: 15108
<212> TYPE: DNA
<213> ORGANISM: Artificial Sequence
<220> FEATURE:
<223> OTHER INFORMATION: vector

<400> SEQUENCE: 24

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| ttgagtgttt tttatttgtt gtattttttt tttttagag aaaatcctcc aatatcaaat | 360 |
| taggaatcgt agtttcatga ttttctgtta cacctaactt tttgtgtggt gccctcctcc | 420 |
| ttgtcaatat taatgttaaa gtgcaattct ttttccttat cacgttgagc cattagtatc | 480 |
| aatttgctta cctgtattcc tttactatcc tcctttttct ccttcttgat aaatgtatgt | 540 |
| agattgcgta tatagtttcg tctaccctat gaacatattc cattttgtaa tttcgtgtcg | 600 |
| tttctattat gaatttcatt tataaagttt atgtacaaat atcataaaaa aagagaatct | 660 |
| ttttaagcaa ggattttctt aacttcttcg gcgacagcat caccgacttc ggtggtactg | 720 |
| ttggaaccac ctaaatcacc agttctgata cctgcatcca aaccttttt aactgcatct | 780 |
| tcaatggcct taccttcttc aggcaagttc aatgacaatt tcaacatcat tgcagcagac | 840 |
| aagatagtgg cgatagggtc aaccttattc tttggcaaat ctggagcaga accgtggcat | 900 |

```
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140
acagttttc  tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattgggaga taagtctaaa agagagtcgg atgcaaagtt acatggtctt   1440
aagttggcgt acaattgaag ttctttacgg attttagta  aaccttgttc aggtctaaca   1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat gctttaaga   1680
accttaatgg cttcggctgt gatttcttga ccaacgtggt cacctggcaa aacgacgatc   1740
ttcttagggg cagacatagg ggcagacatt agaatggtat atccttgaaa tatatatata   1800
tattgctgaa atgtaaaagg taagaaaagt tagaaagtaa gacgattgct aaccaccctat  1860
tggaaaaaac aataggtcct taaataatat tgtcaacttc aagtattgtg atgcaagcat   1920
ttagtcatga acgcttctct attctatatg aaaagccggt tccggcctct caccctttcct  1980
ttttctccca attttttcagt tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaataatgg  ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca ttttttaataa ggcaataata ttaggtatgt ggatatacta   2400
gaagttctcc tcgaccgtcg atatgcggtg tgaaataccg cacagatgcg taaggagaaa   2460
ataccgcatc aggaaattgt aaacgttaat attttgttaa aattcgcgtt aaattttttgt  2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gcccccgatt tagagcttga cggggaaagc cggcgaacgt ggcgagaaag   2820
gaagggaaga aagcgaaagg agcgggcgct agggcgctgg caagtgtagc ggtcacgctg   2880
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aaggggatg  tgctgcaagg cgattaagtt gggtaacgcc agggttttcc   3060
cagtcacgac gttgtaaaac gacggccagt gagcgcgcgt aatacgactc actatagtat   3120
attaccctgt tatccctagc ggatctgccg gtagaggtgg ggtcaataag agcgacctca   3180
tactatacct gagaaagcaa cctgacctac aggaaagagt tactcaagaa taagaatttt   3240
```

```
cgttttaaaa cctaagagtc actttaaaat ttgtatacac ttattttttt tataacttat    3300
ttaataataa aaatcataaa tcataagaaa ttcgcttatt tagaagtggc gcgccgaatt    3360
cactagtgat tgattaattt ttgttcaccg ttcaagtctt cctcggagat tagcttttgt    3420
tcaccgttca atcttcttc agaaatcaac ttttgttcac cgtcgagtcc gttcaagtct    3480
tcttctgaga ttaattttg ttcaccgttc aagtcttcct cggagattag cttttgttca    3540
ccgttcaaat cttcttcaga aatcaacttt tgttcaccgt cgagtccgtt caagtcttct    3600
tctgagatta atttttgttc accgttcaag tcttcctcgg agattagctt tgttcaccg    3660 ttcaaatctt cttcagaaat caacttttgt tcaccgtcga gtccgttcaa gtcttcttct    3720
gagattaatt tttgttcacc gttcaagtct tcctcggaga ttagcttttg ttcaccgttc    3780
aaatcttctt cagaaatcaa cttttgttca ccgtcgagtc cgttcaagtc ttcttctgag    3840
attaattttt gttcaccgtt caagtcttcc tcggagatta gcttttgttc accgttaatt    3900
aacccggggg cgaattgggt accgggcccc cctcgaggt cgacggtatc gataagttat    3960
attgaatttt caaaaattct tactttttt ttggatggac gcaaagaagt ttaataatca    4020
tattacatgg cattaccacc atatacatat ccatatctaa tcttacttat atgttgtgga    4080
aatgtaaaga gccccattat cttagcctaa aaaaaccttc tctttggaac tttcagtaat    4140
acgcttaact gctcattgct atattgaagt acggattaga agccgccgag cgggcgacag    4200
ccctccgacg gaagactctc ctccgtgcgt cctcgtcttc accggtcgcg ttcctgaaac    4260
gcagatgtgc ctcgcgccgc actgctccga acaataaaga ttctacaata ctagcttta    4320 tggttatgaa gaggaaaaat tggcagtaac ctggccccac aaaccttcaa attaacgaat    4380
caaattaaca accataggat gataatgcga ttagttttt agccttattt ctggggtaat    4440
taatcagcga agcgatgatt tttgatctat taacagatat ataaatggaa aagctgcata    4500
accactttaa ctaatacttt caacattttc agtttgtatt acttcttatt caaatgtcat    4560
aaaagtatca acaaaaaatt gttaatatac ctctatactt taacgtcaag gagaaaaaac    4620
tataatgcac catcaccatc accatcatca tcatcattct tctggtctgg tgccacgcgg    4680
ttctggtatg gcgaacctca tggaaattgc cattatcggc atgtcttgcc gtttgccaga    4740
tgacataaag actcctggtg acttttaccg catgctatgc cgcaaaagag caggatggtc    4800
acaagtgccc gccgaccgct tcaacgcgaa ggcatatcat aactcggacc cgaataagaa    4860
gggttgcttt aactctgaag gtggctactt catccaagac gacatctaca tgtttgacgc    4920
cggattcttc gatatcacca agaaggaagc tgagtcaatg gaccctgcac agcggttgtt    4980
gctagaatgc gcatatgaag ccttggagaa tgccggagca ccgaaagagt cggtagcagg    5040
taagaaggtt ggtgtgttca tcggcggtaa ctacggggaa caccgggttg ccaacctccg    5100
cgacttggac aacaccccaa gcttcgatgc caccggcaac caaggagcct tcctcgccgg    5160
taggctggct tactactttg acttacgagg cccaacaatt accgtcgaca ctgcgtgctc    5220
gtccagcatg catgctttgc acctcgctgt gcagagtatc cggtcagggg agtcggagca    5280
agccatcgtg ggcgcgtccc acctcataac cgacccggac atctgggcat ccatgggaaa    5340
cctccgcctg ttctcggctg acggcaggac ccacgctttc gaccaccgcg ccaagtcggg    5400
gtatgcgcgg ggcgaaggcg ccgggtgctt aatcctgaag ccgctgcacc aggcccgggc    5460
tgataatgac catatctttt ccgtcatcac gcacacgggt attagccaca acggacgtac    5520
cgtcggcatc gtggctccct gccccgacgc ccaggagaag ctggttaccc gagtgctcag    5580
ggaggcgggc atccacccct gggaagtggg ctttttttgag gctcacggaa caggtacaaa    5640
```

```
gaaaggggac cgatcgaag ccaggggtat ttacaacgct gtcggtcgtt attttcgcc      5700
cgagaacccg ctccacattg ggtccgtgaa gcccaatgtt ggccatctgg aatgtgccag    5760
cggcatcatt tcgatcatca agggagctct catgctgtac tacggtttca tcctgcccaa    5820
tgccgacttc gagcgggtaa atgaagccat cccattggcg gcgtggaaca tgcgtgtggc    5880
aacacgacag aagccgtggc cgaggaacac caaccgtctc tgtatcaaca acttcggctt    5940
tagcggatcc aactcgactt gcgtcctgag cactaccccg agatgcagaa gcattgaaat    6000
cgccgataac ggcgcctaca gccctctcag gctcttcgta ctctcggcca acgatgaaac    6060
ggcacttcgc aagtccgtga gcaaactggg gatttggatc gaacagcacg ccgagcttta    6120
ccaaaccacc atgccgcgga acctggccta cactttgc caacgccggt cacacttgca      6180
atggcggatg gccgttgttg cgggcatgtg tagcgacgtc accaaggcca tcaacagcca    6240
cgaggccgtc ccgacacggg cacccagcgt gcctcctaaa gtggcattcg tgtacactgg    6300
gcagggcgcc cagtggtttg ccatgggccg ggagctcatg aaaacgcatc ccgtgttcct    6360
agactctatc aaacgcgctg acaatgtact aggcgtctta cgtgccgatt tcaccgcctc    6420
tgaggaactc aacagagatg aggattcgac cagggtcggc ctggcccaga tcagccagcc    6480
catctgcacc gcagtgcagc tagccctaac cgacctttt gcctccttcg gtgtgacgcc      6540
cggcgccgtc acgggccact cgagcggaga gattggagcg gcttatgccg caggcgcctt    6600
gacctttgtg gacgccatga ccatcgctta ctggaggggt caggtagtca tcgagctgcg    6660
aaacagccat ccgcagctga gaggcgctat gatggcggtg tctcataacg cggacgacat    6720
tcaggagttg gtggaggcga tgaaccgtat tcatcaacct caggtgacga tcgcttgcgt    6780
gaattcgccc atgtcggtca ctctgtccgg tgacgaggcg ggcatcgacc tgatagccga    6840
acacttgcag agcgccaata tctttcatcg gaagcttttc gttgatgtgg cataccactc    6900
ccggcatatg ggcataattg ccccgcata taggttcttg atcggcctca ttgaaccgtt      6960
ggacgggcgc aaccgcgatg tccaattctt ttcatcgctc cgtggctgca aggttcgccc    7020
tgagaggttg ggaccacgat actgggtcga caatctcacc gaggccgtcc aattttccac    7080
gtccttggag cagctctgca acgaatactc gcccgacata ctcgtagaga tcgggcccca    7140
cgccgcactc aaggggccca tcctgcaagg gatcaaggag ttttgggtc ggcggccat      7200
gaagatctcg tatctcccca ccctggtccg cggccaggat gccacgcgga catgcctgga    7260
aacggccggc cagcttttcc ttcacggcta ccccctgaac ttcttcgaga tcaaccataa    7320
ccgcgaagag gcagagaggc cggagctgct tgcagccctg tacacatacc cgtggtcgcg    7380
ccaaagatac tgctacgagt ccagaattac ccaccagcac cggttcaagc cattcccaag    7440
atacgacgcg ctgggcacgt tggctgactg gtccgattct ctaaacccga catggcgaaa    7500
cattatccgc acagaagact tgcccaaggt cagggagtac caggcgtcag cccagaccgc    7560
atatatgaac gagctatcta ctgtggcgtt tgaaatcagg gaccttgtgg tttctgagca    7620
tctgtacttg atggacgacc aagacgttga ggtactcgta agcttccagg cctcgaattc    7680
aggggacaag agaagccacg ggttcaagat tttgtcctac gggccaaccc aggagtggac    7740
ggagcactgc actgggactg tgacagcaat gccagacatg ccggtgtctg agcgcccgga    7800
gatcgactgt ggctcaaagc tgtatgcatc cgagctaaag gaatatcatg aagaagaggt    7860
gtatttcagg ctgatgggaa agggggttcac atacccagag gctttcagga ccttgaccaa    7920
tgtcagagtg aaggagcacc aagtgacggg ggtgtcagat cttcgcgagc tcttcatcat    7980
```

```
ggacgacctc cactacggag ctcacccggg tatcgtcgag tccatgctcc aggcaacgtt    8040
attcacccac aagaacgagg atggcaggcc gtctgaggta ccatgcctcc tgtcctcgat    8100
ccgtcacata gctattgttg cggattggcg cccgagtctg ggcaaccaga cggctgtgaa    8160
agcaactctg gatgaaaaca gggcttcttc cacggtggaa ctctttggcg ccattggtaa    8220
tgtggccgtg gggtcggcgg ccgtttccat gctgggcgtg aggttcaagg cgttggtgcc    8280
cttcccgccg aaagccccac cgcgcgagtt gtgcttcaag atgcattggg accaactgga    8340
cgagggcgcg ttggacatga actcagccgt gcccagggtc ggaaaggata cgccaatctt    8400
cgtggccgtt gtcactcgat tcaacgagaa cgtcttcaac gacccattca tgtggagctt    8460
ggtcctgcat ctgaataaca cggtgcgtgc cggcttgcgc cgggctttat ggatgtggcc    8520
agtcccctac gactacccett gggattggag tagctgcttt gtcattattc ccgaactgga    8580
cacggctgca atctactctg ctgaccactg tcacatcccg atcaatatcg tcacgaagat    8640
actcactgag tcccgtggcg tcatgtgggt gacgaaaggg gcttatcgca ttccacagac    8700
gccgactgtg aacttaggtc tcggtttggt ccggacagcc cgctcggaaa ggggcgcggt    8760
cgcaagcacg ctcgacttgg atcctggtta caacacctcc atcgatctac aagccaagct    8820
ggtcgttgac gcattcgccc tatcggtgct ctcggaaaat ccagaggctg agatggagtt    8880
tgccgaagtg gacgggaagc ttgtcgttcc ccggattctt cccgaccctg aactcaatct    8940
ggacgtccac cgctccttgg gccacgccgt gccatatctc caagcatatg agccatctcg    9000
ccggctgcaa cttcaccgtg gcacagatgc ctcttctccc gaggacctct atttcgagga    9060
cagctgcttt ggcgtgttgg gggcggacga agttgagatt aaggtccatg cgactgctct    9120
atcagtcgac gacgtcacaa cagggaccgt ggacgagcca ggcgcgacca ttcaccgcag    9180
ctgcgccggc tatgtcaccc gtattggtgc acaggtcgat gacatctccg tgggacagaa    9240
ggtttgcgcc ctcaccaaca gtccctacgc gacctacgtt cgggcaagct ctactagtgt    9300
cgcactcctc ccagacggca tcgacatgga ggtggctgcg tgcatccccg tccacttcct    9360
ccccgtacat tacgccttca aagagattgc ccgagtcaag cgattcgacc gtgtgctcat    9420
ccaagtctcg gggcccatcg gatttgccgc acttagggtg gcgcacaagt tcggggccga    9480
ctactatgct ctagtcacga acgatgagca ccagatactg gtagagacaa tattgccgtc    9540
caaccgcgtc cttgacgcac gaaacatcca tctggccgag cagatttggg aggtcacgga    9600
gggccggggg atggatgtct gtttggccat atcagggtgc gaaaatggca gcacgtggga    9660
gtgcctccgt gcttttggga tatttgttga gatcaagggg ccaggtaatc acaagaggac    9720
gcaagcccac ctgcgcgcaa acacggtctt cgcgtccgtc gacatgctca gtattgctgt    9780
cgagtatccg gaagatatga aggaagcctt gacggaggtt gtctccaact ttgacgcggg    9840
cgaactttcg ccgggcatct gcatcacaac gtttatgatc tcgagcctgc ccgaggggat    9900
agcactgata cgggacggtt atatggccca cgtggtgatt gcgacacagg aggggggatga   9960 atcggtgatg accctgaagg aaaagtcggg cgacttgttc caaagcccag ggacccatat   10020
cattgtcggt ggaacgggcg gcttgggtcg atccgtggct aaatacatga tccggaacgg   10080
cgcacgcact attgcgctgc tttcgagaag tggtggcgaa gacgtgattg accatctgcg   10140
agacgagatg acacaatacg gagccgatgt gtttgtgttg aggtgcgatg ttagcaaact   10200
tcaccatgtc cggcgagaca tttactattg tgcgaagcat ctgccccga ttcgcggcgt    10260 ggtccacgct gcaatggtgc ttcgggacgg tctactcgaa aacatgaccg gtcaagatta   10320
ctacgacgtc atcgcgccaa aggcacacgg cgcatgcaac cttgatattg cccttgcatg   10380
```

```
gatgggcatc aaagtggatt attttgtcgc cttctcctca gcggcgggca tcatcggcag   10440
ccgcggacag gccgcttacg ctgctgcaaa caccttcctc gactcgctaa tggaatcgcg   10500
gagacaccgg ggtttgcccg gcaactcgct ggatctgacc gcggtcacag gggtcgggta   10560
ccttgctgaa aacgccaaca gggagaggga atcctgcgc aactttgggg acgagacgct    10620
tgacgaagcg gaggtcttgg cgcttctctc agccgccgtc cgtggtgttg ctccctgtca   10680
aaccctgaca gggctgaagt tgcatcttgg cagcgatggc caatggccct acttcgccaa   10740
cgacgcccgc tttgcgtatt tgaaggccga aggcttggca gccgccgagg aggaaggact   10800
cgtggtgaag gaagatgtgt ctccggggga ggcgttccgg ggggcaaggt cggacgagga   10860
ggcagcatat gttgcggccc ggggtcttgc agagaagctt tcggaggtct tgagcgttgc   10920
ggtggaggat gtggatgtcg acagaaacat cacgtcgtac gggttagact cgctcacggc   10980
tattgagctt cggaattgga tcgctaagga gcttcgtgtc aatctccaga ttttggagct   11040
gttgtcgagc gggaccctca gcgatctggc agcgttgatt gtgcagaagg caaagtcggg   11100
agccgttgct ttaatcgtcg cacaccacca ccaccaccac cccgggttaa ttaacatctt   11160
ttacccatac gatgttcctg actatgcggg ctatccgtat gacgtcccgg actatgcagg   11220
atcctatcca tatgacgttc cagattacgc tgctcagtgc tgaggcgcgc cacttctaaa   11280
taagcgaatt tcttatgatt tatgattttt attattaaat aagttataaa aaaataagt    11340 gtatacaaat tttaaagtga ctcttaggtt ttaaaacgaa aattcttatt cttgagtaac   11400
tctttcctgt aggtcaggtt gctttctcag gtatagtatg aggtcgctct tattgaccac   11460
acctctaccg gcagatccgc tagggataac agggtaatat agttcccttt agtgagggtt   11520
aattgcgcgc ttggcgtaat catggtcata gctgtttcct gtgtgaaatt gttatccgct   11580
cacaattcca cacaacatag gagccggaag cataaagtgt aaagcctggg gtgcctaatg   11640
agtgaggtaa ctcacattaa ttgcgttgcg ctcactgccc gctttccagt cgggaaacct   11700
gtcgtgccag ctgcattaat gaatcggcca acgcgcgggg agaggcggtt tgcgtattgg   11760
gcgctcttcc gcttcctcgc tcactgactc gctgcgctcg gtcgttcggc tgcggcgagc   11820
ggtatcagct cactcaaagg cggtaatacg gttatccaca gaatcagggg ataacgcagg   11880
aaagaacatg tgagcaaaag gccagcaaaa ggccaggaac cgtaaaaagg ccgcgttgct   11940
ggcgtttttc cataggctcc gcccccctga cgagcatcac aaaaatcgac gctcaagtca   12000
gaggtggcga aacccgacag gactataaag ataccaggcg tttccccctg gaagctccct   12060
cgtgcgctct cctgttccga ccctgccgct taccggatac ctgtccgcct ttctcccttc   12120
gggaagcgtg gcgctttctc atagctcacg ctgtaggtat ctcagttcgg tgtaggtcgt   12180
tcgctccaag ctgggctgtg tgcacgaacc ccccgttcag cccgaccgct gcgccttatc   12240
cggtaactat cgtcttgagt ccaacccggt aagacacgac ttatcgccac tggcagcagc   12300
cactggtaac aggattagca gagcgaggta tgtaggcggt gctacagagt tcttgaagtg   12360
gtggcctaac tacggctaca ctagaaggac agtatttggt atctgcgctc tgctgaagcc   12420
agttaccttc ggaaaaagag ttggtagctc ttgatccggc aaacaaacca ccgctggtag   12480
cggtggtttt tttgtttgca agcagcagat tacgcgcaga aaaaaggat ctcaagaaga    12540 tcctttgatc ttttctacgg ggtctgacgc tcagtggaac gaaaactcac gttaagggat   12600
tttggtcatg agattatcaa aaaggatctt cacctagatc cttttaaatt aaaaatgaag   12660
ttttaaatca atctaaagta tatatgagta aacttggtct gacagttacc aatgcttaat   12720
```

```
cagtgaggca cctatctcag cgatctgtct atttcgttca tccatagttg cctgactccc   12780
cgtcgtgtag ataactacga tacgggaggg cttaccatct ggccccagtg ctgcaatgat   12840
accgcgagac ccacgctcac cggctccaga tttatcagca ataaaccagc cagccggaag   12900
ggccgagcgc agaagtggtc ctgcaacttt atccgcctcc atccagtcta ttaattgttg   12960
ccgggaagct agagtaagta gttcgccagt taatagtttg cgcaacgttg ttgccattgc   13020
tacaggcatc gtggtgtcac gctcgtcgtt tggtatggct tcattcagct ccggttccca   13080
acgatcaagg cgagttacat gatcccccat gttgtgcaaa aaagcggtta gctccttcgg   13140
tcctccgatc gttgtcagaa gtaagttggc cgcagtgtta tcactcatgg ttatggcagc   13200
actgcataat tctcttactg tcatgccatc cgtaagatgc ttttctgtga ctggtgagta   13260
ctcaaccaag tcattctgag aatagtgtat gcggcgaccg agttgctctt gcccggcgtc   13320
aatacgggat aataccgcgc cacatagcag aactttaaaa gtgctcatca ttggaaaacg   13380
ttcttcgggg cgaaaactct caaggatctt accgctgttg agatccagtt cgatgtaacc   13440
cactcgtgca cccaactgat cttcagcatc ttttactttc accagcgttt ctgggtgagc   13500
aaaaacagga aggcaaaatg ccgcaaaaaa gggaataagg gcgacacgga aatgttgaat   13560
actcatactc ttcctttttc aatattattg aagcatttat cagggttatt gtctcatgag   13620
cggatacata tttgaatgta tttagaaaaa taaacaaata ggggttccgc gcacatttcc   13680
ccgaaaagtg ccacctgaac gaagcatctg tgcttcattt tgtagaacaa aaatgcaacg   13740
cgagagcgct aattttttcaa acaaagaatc tgagctgcat ttttacagaa cagaaatgca   13800
acgcgaaagc gctattttac caacgaagaa tctgtgcttc attttttgtaa aacaaaaatg   13860 caacgcgaga gcgctaattt ttcaaacaaa gaatctgagc tgcatttttta cagaacagaa   13920 atgcaacgcg agagcgctat tttaccaaca aagaatctat acttcttttt tgttctacaa   13980
aaatgcatcc cgagagcgct attttttctaa caaagcatct tagattactt tttttctcct   14040
ttgtgcgctc tataatgcag tctcttgata acttttttgca ctgtaggtcc gttaaggtta   14100
gaagaaggct actttggtgt ctattttctc ttccataaaa aaagcctgac tccacttccc   14160
gcgtttactg attactagcg aagctgcggg tgcattttttt caagataaag gcatccccga   14220
ttatattcta taccgatgtg gattgcgcat actttgtgaa cagaaagtga tagcgttgat   14280
gattcttcat tggtcagaaa attatgaacg gtttcttcta ttttgtctct atatactacg   14340
tataggaaat gtttacattt tcgtattgtt ttcgattcac tctatgaata gttcttacta   14400 caatttttt gtctaaagag taatactaga gataaacata aaaaatgtag aggtcgagtt   14460
tagatgcaag ttcaaggagc gaaaggtgga tgggtaggtt atatagggat atagcacaga   14520
gatatatagc aaagagatac ttttgagcaa tgtttgtgga agcggtattc gcaatatttt   14580
agtagctcgt tacagtccgg tgcgtttttg gttttttgaa agtgcgtctt cagagcgctt   14640
ttggttttca aaagcgctct gaagttccta tactttctag agaataggaa cttcggaata   14700
ggaacttcaa agcgtttccg aaaacgagcg cttccgaaaa tgcaacgcga gctgcgcaca   14760
tacagctcac tgttcacgtc gcacctatat ctgcgtgttg cctgtatata tatatacatg   14820
agaagaacgg catagtgcgt gtttatgctt aaatgcgtac ttatatgcgt ctatttatgt   14880
aggatgaaag gtagtctagt acctcctgtg atattatccc attccatgcg gggtatcgta   14940
tgcttccttc agcactaccc tttagctgtt ctatatgctg ccactcctca attggattag   15000
tctcatcctt caatgctatc atttcctttg atattggatc atactaagaa accattatta   15060
tcatgacatt aacctataaa aataggcgta tcacgaggcc ctttcgtc                 15108
```

<210> SEQ ID NO 25
<211> LENGTH: 15246
<212> TYPE: DNA
<213> ORGANISM: Artificial Sequence
<220> FEATURE:
<223> OTHER INFORMATION: vector

<400> SEQUENCE: 25

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatcga ctacgtcgta aggccgtttc tgacagagta aaattcttga gggaactttc     240
accattatgg gaaatgcttc aagaaggtat tgacttaaac tccatcaaat ggtcaggtca     300
ttgagtgttt tttatttgtt gtatttttt tttttagag aaaatcctcc aatatcaaat     360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttcct ccttcttgat aaatgtatgt     540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaaccttttt aactgcatct     780
tcaatggcct taccttcttc aggcaagttc aatgacaatt tcaacatcat tgcagcagac     840
aagatagtgg cgatagggtc aaccttattc tttggcaaat ctggagcaga accgtggcat     900
ggttcgtaca aaccaaatgc ggtgttcttg tctggcaaag aggccaagga cgcagatggc     960
aacaaaccca aggaacctgg ataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140 acagttttc tccataatct tgaagaggcc aaaagattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttctttacgg atttttagta aaccttgttc aggtctaaca    1500
ctaccggtac cccatttagg accagccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa aacgacgatc    1740
ttcttagggg cagacatagg ggcagacatt agaatggtat atccttgaaa tatatatata    1800
tattgctgaa atgtaaaagg taagaaaagt tagaaagtaa gacgattgct aaccaccttt    1860
tggaaaaaac aataggtcct taaataatat tgtcaacttc aagtattgtg atgcaagcat    1920
ttagtcatga acgcttctct attctatatg aaaagccggt tccggcctct caccttttcct   1980 ttttctccca atttttcagt tgaaaaaggt atatgcgtca ggcgacctct gaaattaaca    2040
```

-continued

```
aaaaatttcc agtcatcgaa tttgattctg tgcgatagcg ccccctgtgtg ttctcgttat    2100 gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca ttttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aattttttgt    2520
taaatcagct cattttttaa ccataggcc gaaatcggca aaatcccctta taaatcaaaa    2580 gaatagaccg atagggtt gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag tttttgggg tcgaggtgcc gtaaagcact aaatcggaac    2760
cctaagggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg tgctgcaagg cgattaagtt gggtaacgcc agggttttcc    3060
cagtcacgac gttgtaaaac gacggccagt gagcgcgcgt aatacgactc actatagtat    3120
attaccctgt tatccctagc ggatctgccg gtagaggtg ggtcaataag agcgacctca    3180
tactatacct gagaaagcaa cctgacctac aggaaagagt tactcaagaa taagaattttt    3240 cgttttaaaa cctaagagtc actttaaaat ttgtatacac ttatttttttt tataacttat    3300 ttaataataa aaatcataaa tcataagaaa ttcgcttatt tagaagtggc gcgccgaatt    3360
cactagtgat tgattaattt ttgttcaccg ttcaagtctt cctcggagat tagcttttgt    3420
tcaccgttca aatcttcttc agaaatcaac ttttgttcac cgtcgagtcc gttcaagtct    3480
tcttctgaga ttaattttg ttcaccgttc aagtcttcct cggagattag cttttgttca    3540
ccgttcaaat cttcttcaga aatcaacttt tgttcaccgt cgagtccgtt caagtcttct    3600
tctgagatta atttttgttc accgttcaag tcttcctcgg agattagctt tgttcaccg    3660 ttcaaatctt cttcagaaat caacttttgt tcaccgtcga gtccgttcaa gtcttcttct    3720
gagattaatt tttgttcacc gttcaagtct tcctcggaga ttagcttttg ttcaccgttc    3780
aaatcttctt cagaaatcaa cttttgttca ccgtcgagtc cgttcaagtc ttcttctgag    3840
attaattttt gttcaccgtt caagtcttcc tcggagatta gcttttgttc accgttaatt    3900
aacccggggg cgaattgggt accgggcccc cctcgaggt cgacggtatc gataagttat    3960
attgaatttt caaaaattct tacttttttt ttggatggac gcaaagaagt ttaataatca    4020
tattacatgg cattaccacc atatacatat ccatatctaa tcttacttat atgttgtgga    4080
aatgtaaaga gccccattat cttagcctaa aaaaaccttc tctttggaac tttcagtaat    4140
acgcttaact gctcattgct atattgaagt acggattaga agccgccgag cgggcgacag    4200
ccctccgacg gaagactctc ctccgtgcgt cctcgtcttc accggtcgcg ttcctgaaac    4260
gcagatgtgc ctcgcgccgc actgctccga acaataaaga ttctacaata ctagctttta    4320
tggttatgaa gaggaaaaat tggcagtaac ctggccccac aaaccttcaa attaacgaat    4380
caaattaaca accataggat gataatgcga ttagtttttt agccttattt ctggggtaat    4440
```

```
taatcagcga agcgatgatt tttgatctat taacagatat ataaatggaa aagctgcata   4500
accactttaa ctaatacttt caacattttc agtttgtatt acttcttatt caaatgtcat   4560
aaaagtatca acaaaaaatt gttaatatac ctctatactt taacgtcaag gagaaaaaac   4620
tataatgcac catcaccatc accatcatca tcatcattct tctggtctgg tgccacgcgg   4680
ttctggtatg gaggaggcca tgctcgacga aagctgggct gagcggccgg cattcctcct   4740
ctttggggac cagtctctcg acagtcatgg cttttttcgct caattctacc gccaatccaa   4800
acacggcgag ctagcaaggg tcttcttgca gcaggcgaac cacgccctgc tgggtgtggt   4860
cgagaagctc cctgctttgg agcgagcaac actccccaat ttccgaacat gcggcagct   4920
caacgaacaa tatcatagca cggaacagaa gcactccgga attgacgcgg cgctgttgac   4980
aatatcgcaa attgcgcact acctcgatca cgctgaaaag aactgtggcg atatcacacg   5040
gcctcataag acttttctcg tcgggctttg ctctgggctc tgggccgcag ccgctatctc   5100
ggtggcgccc tcgctcccag acctggttca tatcggcgtc caagccgttc tcttggcttt   5160
caagacgggt tcctacgttc acgccattgg ggaacggttg agcccggcgt ttgagcgttc   5220
tgaaagctgg agctacatct tctcggtgtc gagcgttgag gatgtcaccc aaacgttgga   5280
cgctttcac gatacctcga accttcctcc tgctagccgc gcgtatatta gcgcggtatc   5340
cgataatggg attgtagtat ctggtccacc gagcacgcta gatgcgatag tcaacaacaa   5400
gatctttccg cctaacccga tcgccattcc ggttcatggc ccctaccacg cgccacattt   5460
gcattccacc gcagacatcg aaagaatttt agagcttgac aacccagaaa cgaaggacgc   5520
cttctacaag acgtcaccgc gatcgcccat catggactgc tcaaccggga catggttctc   5580
ccccatggac acgaaatcgc tcctgatatc ggtcgcctct accatcttga acaaaggatt   5640
gatgttcaaa aaggttctca acggttgcgt cgaggctgct cgcctatttc aagacgacaa   5700
gtgcctcgta atcccccttg gtccaaccca aaatccgtct acgcttaaga ggcgcctcca   5760
gcaggagact ggattggaag tcactcttcg catgccgcct cctatttcat cggaggcaac   5820
ggcatccaag atagggaacc acggatcaag cgggaagccc aagcttgcca ttgtcggcat   5880
ggcagggcga ttccctgacg ctgccagcca cgaagccctg tggaaactgc tggaaagtgg   5940
cctcgctgtc catcgtgagg cgccaccgga tcgcttcaat gtcaagacgc acgttgatcc   6000
ctccggcaaa ggaaagaaca tgagccacac tccatacggc tgctggatca agacccggg   6060
tctgtttgac caccgcgtct tcaacatgtc gccgcgcgag gcgcgcaaca cagaccctat   6120
gcagaggatg gctttgacca cggcgtacga ggctctagat atgtcgggat acgtccccaa   6180
caggacgccg tccacaaggc ttgatcggat cggtaccttc tatgccagaa cctcggacga   6240
ttggcgcgaa ataaatgctg cccaggacgt ggacacgtac ttcatcacgg gaggtgtccg   6300
cgcctttgga cctggccgca tcaactatca ctttggcttc agcgggccga gcctcaacat   6360
tgataccgct tgctcctcca gcgcggctgc catgcaggtg gcatgctcgg cgctctgggc   6420
ccgagattgc gacacggcca tcgtcggcgg cctgtcgtgc atgaccaacc cggacatctt   6480
cgccggactc agtaaaggcc agttcctgtc aaagaaaggg ccatgcgcta cctttgacaa   6540
tgatgccgat gggtactgcc gcggtgacgg ctgtgcatcc gtcgtcgtca agcgtctgga   6600
tgacgccctg gccgaccaag acagggttct cgccgtcatc ctcggcaccg caaccaacca   6660
ctcagcggat gctatctcca tcacgcatcc ccacgggccg acgcagtcga tcctgtccac   6720
agccattctc gacgaggccg gagttgatcc ccatgatgtt gactacgtgg agatgcacgg   6780
```

```
caccggcacc caggctggag acggcaccga gatgaagtcg gtcaccgaca tctttgcgcc    6840
cgcaaaccgg ccgaggcccg aagacagacc actctttctc ggagcagtca aagcaaacgt    6900
cgggcacggc gaagccgctt ccggagttac cgccctcatc aaggtactcc tgatgcttga    6960
gaagaacact atcccacccc atgtcgggat ccagaacggc ggggagatca acaagacgtt    7020
ccctaaggac tttgtcgccc ggaacgtcaa cattgcattc cgtccagttc ccttcagaag    7080
aagggatggc aagcccaggc gcgtcttcgt gaacaacttc agcgccgcgg gtggtaacac    7140
tggtctccta gtcgaggacc ccccgacaat tccgcgcgcg aaaccggatc ctcgcaccca    7200
ccacgttatc actttgtcgg ggcgggtctg ggagtccgtg aagggaaatg ctgaacgtct    7260
cctcgagtgg acggagcgga accgcgacac accgctctcg cacatttctt acagcacaac    7320
agcaagaaag ctgcaccacg tctgccgtat gagcgtgacg ggcagggata ttggagattt    7380
acaggcggcc ctcagagaac gcatcaggga cctggacctg aatcaagctg taccggtccc    7440
gcatcagccg agagtggtca tgatgttcac ggggcaaggg tcgcaatacg ccgcaatggg    7500
gaaggagttt tacgaccact actcggtgtt ccgcgagagc atcgacggct tcattgacct    7560
ggcccgcctg cagggcttcc cctcttttct ccctctcatt gatggcaccg accagaactt    7620
gtccgagatg tcacccatcg tgttgcaact tggcttggca tgcttcgaga tggccgccgc    7680
ccgcctctgg gcttcgtggg gaatcaagcc cgccgccgtc gtgggccaca gcctgggaga    7740
gtatgccgct ctcgaagtag ctggcgtgct ctcggctagc gatgtcattt atctagtcgg    7800
ttctcgtgcc aagctgctcg tcgaaaagtg ccaatctggc agccacggca tggtcgccgt    7860
ccaagccccg gtcgagacgg tcttggaact gatgggcacc gaagctgatg gcttaaacat    7920
cgcctgcatc aacagcctcc gcgagaccgt cattagcggc gagactgaaa agtcaaagga    7980
tatggccacc tatatgagcg accagggtta caagtccaac cacctgcgtg tgcccttcgc    8040
tttccactct ccccaggtgg aagttatttt ggatgatttt gagaagctcg cacagggcgt    8100
tacctacaaa accccccaaga tccccatcat ctccacagtc catggaaagg tcatccaggg    8160
caagtcgatc gatgctgggt acctgcgcaa acacgcgcga gacacagtct acttcctcga    8220
cgggcttatc gaggctcaga agtcgagcac catcgatgac aagaccgttt ggctcgagat    8280
gggccctcac ccggttcttt cggccatggt caaggctaca tttggcgcta gtacggtagc    8340
ggttccacac ctacgccgta ctgagccctg ttacaagacg ttgacgagca cgctcgccac    8400
cttgcacaac gcgcacctca agataaactt caacgaatat caccgcgatt cgccgactc    8460
agtgcgtctg ttgaatttgc ccacgtattc cttcaacgat aacaactact ggatccagta    8520
cgcgggcgat tggtgtctcg cgaagcacaa cctctcggtc gctgcagcgg aacaaaagcc    8580
tgtaacgccc tgggtcgcca cgacgacagt ccacaagctc aacagagaaa ttgtcgaagg    8640
tggcgtggcg atcgtcgaga ccgagtccga gctctaccaa gagcaacttc gaaatgtggt    8700
ctgtggccac caggtcaacg gcgcccccct gtgcccatca tcgctgtacg gcgacatggc    8760
catgaccgtg tgcgactatg cctacaagct tctgcggcct cagtcaacgg gcatcggctg    8820
taacgtcgcg gatatgcagg tcttaaagcc gctcatcttt gacgacaaag ccaaaagtca    8880
catccttcgg ttgacagtga ctgctaatgc cgaggctggc gaagccgacc tggtcttcca    8940
cacggctcaa gatggcaaga agtcgagca tgctcactgc aaagtctact acggcaatca    9000
tgacgagtgg caggacagt tcgaccgggc cgcctacctt atcaagtccc gtgtcgactt    9060
ccttatggag gcagaaaaac gtggtgccgc ctccaagatt ggccgcgct tggcgtacaa    9120
gctcttctcc gccttggtcg actacggcac acgctaccgc ggcatggagg aggttattct    9180
```

```
tgatagcact acttgtgaag cgacggcgaa gatccgcttc cagacgacag cccaggatgg    9240
aaccttttac ttcagcccct accatatcga cagcgcttgc cacatctctg gctttatcat    9300
caacggcacc gacgctgtgg attcgcgtga acgggtcttc atctcccacg gctggggctc    9360
catgagattt accgagatcc cggatgcaaa caaggagtac cgcagttaca tccggatgca    9420
gccggtgaag ggcaccgaga tgatggctgg cgatgcgtac gtcttcgatg gcgacaagat    9480
cattggcatg acgggccgca tcaagttcca agccatcaag cgccacactc tcaacatgat    9540
gcttcctccg cgaggggccc aggcaatctc gggcccagct ccctcggcga tcaaagcggc    9600
cccctctaag aagaagaaga acgagactgt aaacgcttcc aacatagaca gggtgaacca    9660
gaggctcaag accgtgacat cctcagtcat ggatatcctt gtcagagaaa taggctgtag    9720
ccacggggag ctcgttgacg acgcctcgtt tgacaatctc ggcgctgatt ccctaatggc    9780
tctacaagtc tcttccaaga tacgcgaaga gctagaactc gacattgaag cgcaagcctg    9840
gctcgattac cctaccgtcg gcgctttcaa aacctacctg gccaactttg agaagccagg    9900
tcgcaaagaa agggcaccat ccacagggtc tgcaagaacg acagacgacg agtcacgcga    9960
agttgaatat gactcggacg tcacgacacc gaccgaagcc agtgttaccg attctgtcaa   10020
gggagatgcg caggacgacg tcgagccagg cgactctgcc cagaaccagg aacttcgaac   10080
catcatccgc gaatccattg ccacggaagc gggcgtggac gtgcaggaag tcattagcgc   10140
gtccgactgg acgagtctcg gggtggactc tctcttgggt ttaggaatca gtagccgaat   10200
tcgtgagcta gctggcatag aggtccccaa cgatctcttc cttgagcacc caacgctcaa   10260
agatgtggag cgcgttttgg gcgtcaccga cgtccccaaa aagcccgcca cccgccaacg   10320
gaaaagcacc aaggaaaagc tcaaagcacc ccccgctgca gcctccgcta aggagcatcc   10380
tcggatttct ttggaggaac ccgcccctcc aaaaccgccg agacctagcc acattgtcga   10440 caagtaccccc caccgcacat cgagttcagt cctcctgtct ggggcttccc gcgaccaaac   10500
caaacaactc tttatgatcc cggatggcag cggatctgcc acgtcgtata ccgaaatcgc   10560
caaagtcggt ggcgggtggt gtgtctgggg tcttttctcg cccttcatga ggacgcccga   10620
ggagtatcag tgtggtgtct atggcatggc cgccaagttt atcgaccaga tgaagtaccg   10680
ccagccccat ggcccgtact cacttgcggg ttggagtgcc ggcggcgtca ttgcattcga   10740
aatagtctac caattggtcc aggccgggga agaggtcgcg aacctgatca tcatcgatgc   10800
cccttgcccc ctcacaattg aaccgcttcc gcaggggctt cacgcgtggt tcgcgtcaat   10860
tggcctgctc ggcgaaggca acgacaagaa gattccagag tggttgcttc cccactttgc   10920
cgcctccatc acagccctca gcgagtacga tgccagaccg attcccaaag acaaatgccc   10980
caatgtcatg gcaatctggt gtgaggatgg tgtatgccat ctacccaccg atcccaggcc   11040
agagccgtat ccaaagggcc acgccctctt cctgctggaa aaccgcaccg actttgggcc   11100
aaacagatgg gaggagtgtt tggacgtcga ccgcatgcag ttcaggcaca tgcctggcaa   11160
ccacttctcc atgatccatg gcgatcaggc caaaattctt gaaggttttt tgcgggaggc   11220
tcttctggat ctcgagggag ccgttgcttt aatcgtcgca caccaccacc accaccaccc   11280
cgggttaatt aacatctttt acccatacga tgttcctgac tatgcgggct atccgtatga   11340
cgtcccggac tatgcaggat cctatccata tgacgttcca gattacgctg ctcagtgctg   11400
aggcgcgcca cttctaaata agcgaatttc ttatgattta tgattttat tattaaataa   11460 gttataaaaa aaataagtgt atacaaattt taaagtgact cttaggtttt aaaacgaaaa   11520
```

-continued

```
ttcttattct tgagtaactc tttcctgtag gtcaggttgc tttctcaggt atagtatgag    11580
gtcgctctta ttgaccacac ctctaccggc agatccgcta gggataacag ggtaatatag    11640 ttcccttag tgagggttaa ttgcgcgctt ggcgtaatca tggtcatagc tgtttcctgt     11700
gtgaaattgt tatccgctca caattccaca acatagga gccggaagca taaagtgtaa      11760 agcctgggt gcctaatgag tgaggtaact cacattaatt gcgttgcgct cactgcccgc     11820
tttccagtcg ggaaacctgt cgtgccagct gcattaatga atcggccaac gcgcggggag    11880
aggcggtttg cgtattgggc gctcttccgc ttcctcgctc actgactcgc tgcgctcggt    11940
cgttcggctg cggcgagcgg tatcagctca ctcaaaggcg gtaatacggt tatccacaga    12000
atcaggggat aacgcaggaa agaacatgtg agcaaaaggc cagcaaaagg ccaggaaccg    12060
taaaaaggcc gcgttgctgg cgttttttcca taggctccgc ccccctgacg agcatcacaa    12120
aaatcgacgc tcaagtcaga ggtggcgaaa cccgacagga ctataaagat accaggcgtt    12180
tccccctgga agctccctcg tgcgctctcc tgttccgacc ctgccgctta ccggatacct    12240
gtccgccttt ctcccttcgg gaagcgtggc gctttctcat agctcacgct gtaggtatct    12300
cagttcggtg taggtcgttc gctccaagct gggctgtgtg cacgaacccc ccgttcagcc    12360
cgaccgctgc gccttatccg gtaactatcg tcttgagtcc aacccggtaa gacacgactt    12420
atcgccactg gcagcagcca ctggtaacag gattagcaga gcgaggtatg taggcggtgc    12480
tacagagttc ttgaagtggt ggcctaacta cggctacact agaaggacag tatttggtat    12540
ctgcgctctg ctgaagccag ttaccttcgg aaaaagagtt ggtagctctt gatccggcaa    12600
acaaaccacc gctggtagcg gtggtttttt tgtttgcaag cagcagatta cgcgcagaaa    12660
aaaaggatct caagaagatc ctttgatctt ttctacgggg tctgacgctc agtggaacga    12720
aaactcacgt taagggattt tggtcatgag attatcaaaa aggatcttca cctagatcct    12780
tttaaattaa aaatgaagtt ttaaatcaat ctaaagtata tatgagtaaa cttggtctga    12840
cagttaccaa tgcttaatca gtgaggcacc tatctcagcg atctgtctat ttcgttcatc    12900
catagttgcc tgactccccg tcgtgtagat aactacgata cgggagggct taccatctgg    12960
ccccagtgct gcaatgatac cgcgagaccc acgctcaccg gctccagatt tatcagcaat    13020
aaaccagcca gccggaaggg ccgagcgcag aagtggtcct gcaactttat ccgcctccat    13080
ccagtctatt aattgttgcc gggaagctag agtaagtagt tcgccagtta atagtttgcg    13140
caacgttgtt gccattgcta caggcatcgt ggtgtcacgc tcgtcgtttg gtatggcttc    13200
attcagctcc ggttcccaac gatcaaggcg agttacatga tcccccatgt tgtgcaaaaa    13260
agcggttagc tccttcggtc ctccgatcgt tgtcagaagt aagttggccg cagtgttatc    13320
actcatggtt atggcagcac tgcataattc tcttactgtc atgccatccg taagatgctt    13380
ttctgtgact ggtgagtact caaccaagtc attctgagaa tagtgtatgc ggcgaccgag    13440
ttgctcttgc ccggcgtcaa tacgggataa taccgcgcca catagcagaa ctttaaaagt    13500
gctcatcatt ggaaaacgtt cttcggggcg aaaactctca aggatcttac cgctgttgag    13560
atccagttcg atgtaaccca ctcgtgcacc caactgatct tcagcatctt ttactttcac    13620
cagcgtttct gggtgagcaa aaacaggaag gcaaaatgcc gcaaaaaagg gaataagggc    13680
gacacggaaa tgttgaatac tcatactctt cctttttcaa tattattgaa gcatttatca    13740
gggttattgt ctcatgagcg gatacatatt tgaatgtatt tagaaaaata aacaaatagg    13800
ggttccgcgc acatttcccc gaaaagtgcc acctgaacga agcatctgtg cttcattttg    13860
tagaacaaaa atgcaacgcg agagcgctaa ttttttcaaac aaagaatctg agctgcattt    13920
```

-continued

| | |
|---|---|
| ttacagaaca gaaatgcaac gcgaaagcgc tattttacca acgaagaatc tgtgcttcat | 13980 |
| ttttgtaaaa caaaaatgca acgcgagagc gctaattttt caaacaaaga atctgagctg | 14040 |
| catttttaca gaacagaaat gcaacgcgag agcgctattt taccaacaaa gaatctatac | 14100 |
| ttcttttttg ttctacaaaa atgcatcccg agagcgctat ttttctaaca aagcatctta | 14160 |
| gattactttt tttctccttt gtgcgctcta taatgcagtc tcttgataac tttttgcact | 14220 |
| gtaggtccgt taaggttaga agaaggctac tttggtgtct attttctctt ccataaaaaa | 14280 |
| agcctgactc cacttcccgc gtttactgat tactagcgaa gctgcgggtg cattttttca | 14340 |
| agataaaggc atccccgatt atattctata ccgatgtgga ttgcgcatac tttgtgaaca | 14400 |
| gaaagtgata gcgttgatga ttcttcattg gtcagaaaat tatgaacggt ttcttctatt | 14460 |
| ttgtctctat atactacgta taggaaatgt ttacattttc gtattgtttt cgattcactc | 14520 |
| tatgaatagt tcttactaca attttttgt ctaaagagta atactagaga taaacataaa | 14580 |
| aaatgtagag gtcgagttta gatgcaagtt caaggagcga aggtggatg ggtaggttat | 14640 |
| atagggatat agcacagaga tatatagcaa agagatactt ttgagcaatg tttgtggaag | 14700 |
| cggtattcgc aatattttag tagctcgtta cagtccggtg cgttttggt ttttgaaag | 14760 |
| tgcgtcttca gagcgctttt ggttttcaaa agcgctctga agttcctata ctttctagag | 14820 |
| aataggaact tcggaatagg aacttcaaag cgtttccgaa aacgagcgct tccgaaaatg | 14880 |
| caacgcgagc tgcgcacata cagctcactg ttcacgtcgc acctatatct gcgtgttgcc | 14940 |
| tgtatatata tatacatgag aagaacggca tagtgcgtgt ttatgcttaa atgcgtactt | 15000 |
| atatgcgtct atttatgtag gatgaaaggt agtctagtac ctcctgtgat attatcccat | 15060 |
| tccatgcggg gtatcgtatg cttccttcag cactacccett tagctgttct atatgctgcc | 15120 |
| actcctcaat tggattagtc tcatccttca atgctatcat ttcctttgat attggatcat | 15180 |
| actaagaaac cattattatc atgacattaa cctataaaaa taggcgtatc acgaggccct | 15240 |
| ttcgtc | 15246 |

<210> SEQ ID NO 26
<211> LENGTH: 16422
<212> TYPE: DNA
<213> ORGANISM: Artificial Sequence
<220> FEATURE:
<223> OTHER INFORMATION: vector

<400> SEQUENCE: 26

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| tgagtgtttt tttatttgtt gtattttttt tttttagag aaaatcctcc aatatcaaat | 360 |
| taggaatcgt agtttcatga ttttctgtta cacctaactt tttgtgtggt gccctcctcc | 420 |
| ttgtcaatat taatgttaaa gtgcaattct ttttccttat cacgttgagc cattagtatc | 480 |
| aatttgctta cctgtattcc tttactatcc tcctttttct ccttcttgat aaatgtatgt | 540 |
| agattgcgta tatagtttcg tctacccctat gaacatattc cattttgtaa tttcgtgtcg | 600 |
| tttctattat gaatttcatt tataaagttt atgtacaaat atcataaaaa aagagaatct | 660 |

```
tttttaagcaa ggatttttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140
acagtttttc tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg attttttagta aaccttgttc aggtctaaca   1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa acgacgatc    1740
ttcttagggg cagacatagg ggcagacatt agaatgtat atccttgaaa tatatatata   1800
tattgctgaa atgtaaaagg taagaaaagt tagaaagtaa gacgattgct aaccacctat   1860
tggaaaaaac aataggtcct taaataatat tgtcaacttc aagtattgtg atgcaagcat   1920
ttagtcatga acgcttctct attctatatg aaaagccggt tccggcctct caccttttcct   1980
ttttctccca attttttcagt tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca ttttttaataa ggcaataata ttaggtatgt ggatatacta   2400
gaagttctcc tcgaccgtcg atatgcggtg tgaaataccg cacagatgcg taaggagaaa   2460
ataccgcatc aggaaattgt aaacgttaat attttgttaa aattcgcgtt aaattttttgt   2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag tttttttgggg tcgaggtgcc gtaaagcact aaatcggaac   2760
cctaaaggga gccccgatt tagagcttga cggggaaagc cggcgaacgt ggcgagaaag   2820
gaagggaaga aagcgaaagg agcgggcgct agggcgctgg caagtgtagc ggtcacgctg   2880
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aaggggggatg tgctgcaagg cgattaagtt gggtaacgcc agggttttcc   3060
```

```
cagtcacgac gttgtaaaac gacggccagt gagcgcgcgt aatacgactc actatagtat    3120
attaccctgt tatccctagc ggatctgccg gtagaggtgt ggtcaataag agcgacctca    3180
tactatacct gagaaagcaa cctgacctac aggaaagagt tactcaagaa taagaattt     3240 cgttttaaaa cctaagagtc actttaaaat ttgtatacac ttatttttt tataacttat    3300 ttaataataa aaatcataaa tcataagaaa ttcgcttatt tagaagtggc gcgccgaatt    3360
cactagtgat tgattaattt ttgttcaccg ttcaagtctt cctcggagat tagcttttgt    3420
tcaccgttca aatcttcttc agaaatcaac ttttgttcac cgtcgagtcc gttcaagtct    3480
tcttctgaga ttaattttg ttcaccgttc aagtcttcct cggagattag cttttgttca    3540
ccgttcaaat cttcttcaga atcaacttt tgttcaccgt cgagtccgtt caagtcttct    3600
tctgagatta ttttgttc accgttcaag tcttcctcgg agattagctt tgttcaccg     3660 ttcaaatctt cttcagaaat caactttgt tcaccgtcga gtccgttcaa gtcttcttct    3720
gagattaatt tttgttcacc gttcaagtct tcctcggaga ttagcttttg ttcaccgttc    3780
aaatcttctt cagaaatcaa cttttgttca ccgtcgagtc cgttcaagtc ttcttctgag    3840
attaattttt gttcaccgtt caagtcttcc tcggagatta gcttttgttc accgttaatt    3900
aacccggggg cgaattgggt accgggcccc cctcgaggt cgacggtatc gataagttat    3960
attgaatttt caaaaattct tactttttt ttggatggac gcaaagaagt ttaataatca    4020
tattacatgg cattaccacc atatacatat ccatatctaa tcttacttat atgttgtgga    4080
aatgtaaaga gccccattat cttagcctaa aaaaccttc tctttggaac tttcagtaat    4140
acgcttaact gctcattgct atattgaagt acggattaga agccgccgag cgggcgacag    4200
ccctccgacg gaagactctc ctccgtgcgt cctcgtcttc accggtcgcg ttcctgaaac    4260
gcagatgtgc ctcgcgccgc actgctccga acaataaaga ttctacaata ctagctttta    4320
tggttatgaa gaggaaaaat tggcagtaac ctggccccac aaaccttcaa attaacgaat    4380
caaattaaca accataggat gataatgcga ttagtttttt agccttattt ctggggtaat    4440
taatcagcga agcgatgatt tttgatctat taacagatat ataaatggaa aagctgcata    4500
accactttaa ctaatacttt caacattttc agtttgtatt acttcttatt caaatgtcat    4560
aaaagtatca acaaaaaatt gttaatatac ctctatactt taacgtcaag gagaaaaaac    4620
tataatgcac catcaccatc accatcatca tcatcattct tctggtctgg tgccacgcgg    4680
ttctggtatg gcccgtcagc ccgagatttt cgcaagcgag cccattgcca ttgtgggcag    4740
cagctgccgt ctcccgggcg gcgcaacctc cccgtcccgg ctgtgggatc tcctggagac    4800
gcctcgcgac gtggtgcaga aaatcccggc gagccgcttc aacactgagc aattctacca    4860
tgcagacagc cagcaccatg gaagtaccaa cgtcaagcat gcctacctcc ttgaggaaga    4920
tccgcgtggc ttcgaccgtg acttcttctc tatcaacccc aaggaagccg aggctatgga    4980
tcctcagcaa cggatgctcc tcgagacggt atatgaggga atagaatctg ccgggtactc    5040
aatgcagcag ctgcgtggat cgtccacggc tgtgtttgtc ggctgcatgt tctacgatta    5100
ccagtacaca gcaatccggg gcgtcgatag cctgcctcag taccacgcga cgggaactgg    5160
gtcatccatc ttgtccaatc gggtatcgta cttttacgac tggcacggtc cgtcggtcac    5220
tatcgacaca gcctgttcgt cgagtctggt tgccatgcat caggcagtca gtgccctccg    5280
gaacggcgag gctcgcatgg ctgttgcggc cggctcgaat cttatcctgg gtcctgagcc    5340
cttcattagc gagtccaagc tcaacatgct gtcgccaaac gggcgatcgt ttatgtggga    5400
```

```
ttcgcaggca gatggataca cgcgcggcga aggcttcggt gttgtcttcc tcaagacgct   5460
gagccaagcc ctggccgacg gggatcacat tgagtgcatt atccgtgaga cgggcgtcaa   5520
ctcggacgga aagacgccgg gcatcaccat gccgagccac gagtcccagg cgcggctcat   5580
ccgggacacg tacgccagat gcggtctcga tctttcgcga gaatccgatc gtccgcaata   5640
ctttgaggct cacggcactg gcacgccggc gggcgaccca atcgaagccc gcgcgatcca   5700
gagcgttttc ttccccaatg acacagacgc cgacaaatat gagcagcgcg agcttatggt   5760
gggtagcatc aagacaatag tcggccacac cgagggcaca gccggtgttg cgggaattct   5820
taaggcgtcg ttggccctgc agcacggccg catcccggcg aacctgcact tccagaacct   5880
gaaccccaag atccagccgt actacaacaa cctccgcatc ccgaccgaga cagttccctg   5940
gcccaccatc ccccagggcg gcgtgcggcg agtcagcgtc aacagcttcg gctttggcgg   6000
cacgaacgcc cacgccatcc tcgagagcta cgagggaggc ggtgccggac ctgccgacga   6060
gggttccgac tcgggctttg acacggcctc gacctcctcc caggcagaat ccggtgtcgg   6120
tgacggtgac cacgggctca agctcaaaga agccaggag gctgcggtcg gccgttcgt    6180 cctgtcggcc cactcgagcg ccgctctggc cgccaacgcc agcgcgctcg ccagccatct   6240
ccgcgcccac ccggacaagg tcgacctcac agccctggca tacacgctgt tccggcgcac   6300
cccgttcgcc ttccgcgccg ccttctccgc ctgctccaca gccgagcagc tcgcttccaa   6360
gctcgaagaa tccgtcaaga ctctcgagcg caaaccgggc gtcccttcga ccttccccga   6420
cgccctcccg ccccgcatcc tcggcatctt cacgggccag ggcgcgcagt gggcgaccat   6480
ggggcgggaa ctctaccacg gcgcctccgc cgcagggccc ttccgcgtcg ccatcgacgc   6540
catgcagcac agcctggaca cgctgccgc tgccgaggac cgcccgacct ggcggctggc   6600
cgaccaactc ctcgccgaca gggagacctc gcgcgtcgcc gaggccgcca tctcccagcc   6660
gctgtgcacg gcgctgcagg tcgcgctggt ggacacgctg cgggcggcgg ggatcgagtt   6720
cgcgggcgcg gtggggcact cgtcgggcga gatcgcggcc gcgtacacgg cgggctatct   6780
cagcggcgcg gacgccatcc gcgtggccta ctaccgcggc ctgcacgcgc acctggccag   6840
ggggcccggc gagggtgccg gggcgcgcgg caagatgatg gcggtgggga tgggctggga   6900
gcaggtgacg gtgttctgcg ccgagtttga cggcgcgctg gtcacggccg cgagtaactc   6960
ggccacgagc tgcacgctgg cgggcgatgc ggacgcggtg gatagggcct ttgtgcgctt   7020
gcagcatgag ggtaccttcg cgcgggttct gcaggtcgac acggcgtacc actcgcatca   7080
tatgaagccg tgcgcggacc cgtatatcaa gtcgttgaag gagtgtggtg tgaaggtgca   7140
gacgccgcag aagcgcggcg gccagcagca gtgtcggtgg tactcgagtg tgtgggacaa   7200
cgatgaccac aaggcggatg gtaaggtttt cgagggccag tactgggttg acaacctgac   7260
gcggccggtg aagtttagcc aggcgttggc gcgggcgctg gaccaagacc acgtctttga   7320
tctggcgctt gaggttgggc cccacccgc actcaaggga ccggcttcgg aaacgattaa   7380
gacgttgtcc ggtggtgttg tctcgctgcc ctacaccagc gccctgaagc gagggcagaa   7440
tgcggtggag tccttcacgg atgccctggg tacccttggg tgtctgttcc cgtcgccgcc   7500
cactggacgc cctatgatca cctttgacgg cgtgcgtcgg gccttgcaac acgataccgc   7560
agacaacatg gagatggaag atctcaaagt cctgaaaggt ctgccgcctt actcgtggaa   7620
tcatgccact cccatctgga aggagtcgcg ggcctctcgt ctcttccgcg tcggcaaccg   7680
cctcggccac ggccgacacg agctcttggg ccacccctgtc gtgtatgcg gtggcgcgcg   7740 cgacagcaag cgcgaggtgc actggaagca ggtgctcaga cttcaggagc ttccttggct   7800
```

```
ggctgggcat gtcattcagg gagaagtctt gttcccggcg tcgggctacc tgtccatggc   7860
gtacgaggcc gcgcttcaac ttgctctcga cgatgacgag aagaaacaga gacgggtcca   7920
gctcgtcgag ctccatgatg tcgacattgt gcgcgcgatg cgcctcgaac aagattccgg   7980
tctggaactg gtacttactg ttcgcgtgac gagccagtcg gacgactgca tcactgccca   8040
ggtggcatgc tacagcggac ccgtcgacgc gccgcaaccg ctagacgcgc cgcagacgtc   8100
actttcagcc cacttcaccg gaggggtgcg gctatggctc ggcgggttcg agtccgataa   8160
agaggaggaa ggtaatgtcc tgcctcaacg ggccggggag agtgccaggc ccctgccgat   8220
ggacgcactg gacatggaca agctctactc cagcctggct gaagttggtc tgcagtacgc   8280
cagccccttt aaagccaaag ccatcctacg ccgccttcac cgcaccacgg tgaccttggc   8340
cacgccgccc gaatcctcgg cgctccacac ctgcatgcat cctgcccta tcgacacggc   8400
tgcccagggt ctgctcgctg ccttctcctt cccgggcgat gatcgcttgt caaccatcta   8460
cttgccaaca agggttgact gtgtccggat cgtcccccca agcagccgac tctctgcggc   8520
ccacaacggg aatgacgacc ccagccagca gcaactcact gccgacgcga cggtgacctc   8580
gacagccggc tccactatcg tgggtgacat tgacgtcttt aatacggccg acgaagtcaa   8640
ggtccagatc cgtggcattt gcctgacagc ggtaggccag cagcgcgatg cttggctata   8700
cgccggaacg aagtggatcc gggatgcaga ctcaggcatc gaaccggagc gtacgtcgac   8760
gatgaccggg gaatgggacg ctcagtacga ggcgctgtct cgcgcggcct acttctatct   8820
ccggcagttc cgcaagatcc taccgcagga gatgatcatc atgagcaagt cgtacaaacg   8880
caacgtgaag tggacgctgg agtatctgct gccgcagatt gagagcggcg cacacccgag   8940
cttgctcggg ttcaaggccg agtggaaaga cgacacgcgc gagatcatcc aggctctgag   9000
agaggagagc atcagcagcc agaagaatga cgtggaaaga caccactgcg aaatgcactg   9060
ggacttcctg cgttccgtgg gcgacaagct catctcggtc gtccgcagca tgacgccgtg   9120
ggtgcgcatc tggactcccc agcaactcga gtgggtgtat gccgacggga tcggctaccg   9180
ctccgccaac cacaacgcgg ccgcttacat cgcccagctc gcgcaccggt acccgcgcat   9240
gaacatcgtc gacgtgggcg ccggcaacgg cggcacctcg ggggccgtgc tcagggcgct   9300
gcaggagcag cagttgcagt acgcgtcgta caactacacc gaccgatcgc ccgagattct   9360
cgaccgagcc cgcgtcctgc acggccacca caagaacttg accttcaaga agctcgacat   9420
cgacaaagac ccggccgagc agggcttccc ggacgcgacc ttcgatgtgg tcatcgcgtc   9480
caacatcctc cacaagctca cgagcctggc ggactcgcta cgccgctgcc ggcagatgct   9540
gcgtcccggc ggccagctga tcctgctcga gctgaccgac gacttcctca tgtcccagat   9600
cgtcaagctg gcgctgcccg actttttcgt cggcgccgag gacggccgcg tcaacggccc   9660
caacgtcggc gtcgaacgat gggacgagct cctccgggcc acgggctttg cgggcgtgga   9720
caggacgagc accaagaccg tctcatactg ctccgtcatc gtggcacacg ccgtcgacga   9780
caaggtccag ctcctgcggg agccgcttgc agccgcgccc gaggcgttgg caccgtcgct   9840
aggcgacgtc ttcatcgtgg ctggtggcgg tgcgaccact cccgacctgg catcccagtg   9900
ccagaccctc ctgcaaaccg ccacaccatc caccaccgtc accatcatcc ccagcctcga   9960
tgccgtaagc gcagccgaca acatttcccc cggctcgacc gttctctgcc tggccgagct  10020
agaccagccc gtcttccaga gcagcgacga aaacgatgca gtggcgcagc gtttccgcgg  10080
actgcaggag ctgatgtcca cggccgggtc tgtcctgtgg gtgacggcgg gcgcgcggtc  10140
```

| | |
|---|---|
| cgggcgcgat ccggtcgcca acatggtcgt cggcatgggc agcacgctgc gggccgagcg | 10200 |
| cggctcgtcg ctccggctgc agttcctcga cgtcgacacg ccctcggcgc tgctggaggt | 10260 |
| gccgagtgcg ggccccgcct tgctagctaa gctgctcctc cgcctcgcta tcttcaaccc | 10320 |
| ggcgagcggc gatgacttgt tttggacgca agagcccgag ctggcactgg gtgacgacgg | 10380 |
| cgcgctctac atccccgcg tgttggcgct tgatgcgccg aatcggagga acgcagcccg | 10440 |
| gcgacgtgca gtcacgcagc aggttgccct gccctcgagg tcggcagggg aggctgtcgt | 10500 |
| cctggagcgt ggccaggagg cggcatggga gctgaagata gccgcgccgc ttggaaccac | 10560 |
| gccgagtggg gagggtaagg gaggggtgcg cgtgcaggtt actgcgtctt ccttgcagca | 10620 |
| attcacctgc agcaacggcg gctcgtcttc ggaattgtat gtctgcatcg gccgagacgt | 10680 |
| ggcatctggc gataaggttg tcgcccttc cgcagtgaat ggctctcttg tctccattgc | 10740 |
| taaagaccac gtcttgcgac gctggtcgca atccgacgaa ggagacgact tggcatggct | 10800 |
| gcaagcattc ctggcgcagg catctgccag tcgcctgctc ctcgatgtcc agggccccgc | 10860 |
| gtggatccac ggtgctccgg tgcagctcgg cgaagctctc gaggcggtgg cccgcaagaa | 10920 |
| gggcatcgcc gtcttccaaa ccacgtcgac agcaggcgca actggcgtgg cgacctttgt | 10980 |
| gcacccttac gcgcgggagg atgatttgtt ggctctcccg cttcctgagg gcctgcggac | 11040 |
| ctttgtcgat ctctcaccaa gccaaagtgg cgctgccatt aaggctatct gctctgcccg | 11100 |
| gtcgatcgag gtcaagcaag ctgagcgggc tggtctgacg gccggttttg aggcctgcga | 11160 |
| actggagcat ctggccaaga accatgacgt cgtctcggac agcggtagcg tcggcgagag | 11220 |
| cgctgtgacg cttgagcagg cttcggcggg acagctgtcc gtggagcagc agcgctcccc | 11280 |
| cacagccgtg gtggactggc gcgcggccga gacagtcacc gctgacgtct ccccgttgaa | 11340 |
| gcacagcggc ctgtttgcgc ccgacaaaac ctatctcctc tgcggtatga cgggcgacat | 11400 |
| gggcatctcg gtgtgcctct ggatggctga acacggcgcc cgccacgtgg tgctgatgag | 11460 |
| tcggaacccg aagatttcgc ctcgtatcct ggaccaccta gccgggaaat tcggcgccat | 11520 |
| cgtgcgcccc atggccgtcg acatcaccaa cctctccagc ctgcgcgccg ccgtcaccgc | 11580 |
| cctcaagacc gacatgcctc ccatcggcgg cgtgatgaac ggtgccatga tcctacgcga | 11640 |
| ccgtctcttc cagaacatgc catgggacga cttctcgacc gtgctgggcc ccaaggtcgc | 11700 |
| cggttctcgc aacctggacg ccaggcagtc agcctacgcg gccgccaacc aatacatgac | 11760 |
| cggcctggtg cgacaacgcc gccggcgtgg gctggcggcg tcggtgctgc acatcgccat | 11820 |
| cctcacgggc ttcggctaca tccaccgcag tgacgccgcg cacgccgaga ccatgaacaa | 11880 |
| ggcgctccgc acgcgctaca acaaccaagc agagccggac ctgcacgcga tgctggccga | 11940 |
| ggccgttgtc ggcggccgtg tccgcgacag tgacggggac ggcacgaccg gtgcggagct | 12000 |
| catcacgggt ctgcgcaccg tgtttgaggg cgagacctcg aaagacgcgc gtcttgcgcg | 12060 |
| ctatctgcgg gatgacgagg gggatgattt gggcgccggt gcggagggtg ggggtgcggc | 12120 |
| gatgagtgtg caggcacagc tgcgcgaggt ggggccgat gatgacgccg gccagcagag | 12180 |
| agtggtgttg gaaaaggcct tcgccattgc gttgggcaag ctgctcgaga tggaccccga | 12240 |
| gacgatcgac ccggcgcggc cggtggctag cctgggtgtc gactcgctgg tggcgattcg | 12300 |
| catccgcgag tggatgctgc gtgagatggg cgtcgatgtc tcagtcatca aggtcatgtc | 12360 |
| cgacacatat cctatgtcgc gcatgtgcga cgacgtcttg agaaattgca atggagccgt | 12420 |
| tgctttaatc gtcgcacacc accaccacca ccacccgggg ttaattaaca tcttttaccc | 12480 |
| atacgatgtt cctgactatg cgggctatcc gtatgacgtc ccggactatg caggatccta | 12540 |

-continued

```
tccatatgac gttccagatt acgctgctca gtgctgaggc gcgccacttc taaataagcg   12600
aatttcttat gatttatgat ttttattatt aaataagtta taaaaaaaat aagtgtatac   12660
aaattttaaa gtgactctta ggttttaaaa cgaaaattct tattcttgag taactctttc   12720
ctgtaggtca ggttgctttc tcaggtatag tatgaggtcg ctcttattga ccacacctct   12780
accggcagat ccgctaggga taacagggta atatagttcc ctttagtgag ggttaattgc   12840
gcgcttggcg taatcatggt catagctgtt tcctgtgtga aattgttatc cgctcacaat   12900
tccacacaac ataggagccg gaagcataaa gtgtaaagcc tggggtgcct aatgagtgag   12960
gtaactcaca ttaattgcgt tgcgctcact gcccgctttc cagtcgggaa acctgtcgtg   13020
ccagctgcat taatgaatcg gccaacgcgc ggggagaggc ggtttgcgta ttgggcgctc   13080
ttccgcttcc tcgctcactg actcgctgcg ctcggtcgtt cggctgcggc gagcggtatc   13140
agctcactca aaggcggtaa tacggttatc cacagaatca ggggataacg caggaaagaa   13200
catgtgagca aaaggccagc aaaaggccag gaaccgtaaa aaggccgcgt tgctggcgtt   13260
tttccatagg ctccgccccc ctgacgagca tcacaaaaat cgacgctcaa gtcagaggtg   13320
gcgaaacccg acaggactat aaagatacca ggcgtttccc cctggaagct ccctcgtgcg   13380
ctctcctgtt ccgaccctgc cgcttaccgg atacctgtcc gcctttctcc cttcgggaag   13440
cgtggcgctt tctcatagct cacgctgtag gtatctcagt tcggtgtagg tcgttcgctc   13500
caagctgggc tgtgtgcacg aaccccccgt tcagcccgac cgctgcgcct tatccggtaa   13560
ctatcgtctt gagtccaacc cggtaagaca cgacttatcg ccactggcag cagccactgg   13620
taacaggatt agcagagcga ggtatgtagg cggtgctaca gagttcttga agtggtggcc   13680
taactacggc tacactagaa ggacagtatt tggtatctgc gctctgctga gccagttac   13740 cttcggaaaa agagttggta gctcttgatc cggcaaacaa accaccgctg gtagcggtgg   13800
tttttttgtt tgcaagcagc agattacgcg cagaaaaaaa ggatctcaag aagatccttt   13860
gatcttttct acggggtctg acgctcagtg gaacgaaaac tcacgttaag ggattttggt   13920
catgagatta tcaaaaagga tcttcaccta gatccttta aattaaaaat gaagttttaa   13980
atcaatctaa agtatatatg agtaaacttg gtctgacagt taccaatgct taatcagtga   14040
ggcacctatc tcagcgatct gtctatttcg ttcatccata gttgcctgac tccccgtcgt   14100
gtagataact acgatacggg agggcttacc atctggcccc agtgctgcaa tgataccgcg   14160
agacccacgc tcaccggctc cagatttatc agcaataaac cagccagccg aagggccga   14220 gcgcagaagt ggtcctgcaa ctttatccgc ctccatccag tctattaatt gttgccggga   14280
agctagagta agtagttcgc cagttaatag tttgcgcaac gttgttgcca ttgctacagg   14340
catcgtggtg tcacgctcgt cgtttggtat ggcttcattc agctccggtt cccaacgatc   14400
aaggcgagtt acatgatccc ccatgttgtg caaaaaagcg gttagctcct tcggtcctcc   14460
gatcgttgtc agaagtaagt tggccgcagt gttatcactc atggttatgg cagcactgca   14520
taattctctt actgtcatgc catccgtaag atgcttttct gtgactggtg agtactcaac   14580
caagtcattc tgagaatagt gtatgcggcg accgagttgc tcttgcccgg cgtcaatacg   14640
ggataatacc gcgccacata gcagaacttt aaaagtgctc atcattggaa aacgttcttc   14700
ggggcgaaaa ctctcaagga tcttaccgct gttgagatcc agttcgatgt aacccactcg   14760
tgcacccaac tgatcttcag catcttttac tttcaccagc gtttctgggt gagcaaaaac   14820
aggaaggcaa aatgccgcaa aaaagggaat aagggcgaca cggaaatgtt gaatactcat   14880
```

```
actcttcctt tttcaatatt attgaagcat ttatcagggt tattgtctca tgagcggata    14940
catatttgaa tgtatttaga aaaataaaca aataggggtt ccgcgcacat ttccccgaaa    15000
agtgccacct gaacgaagca tctgtgcttc attttgtaga acaaaaatgc aacgcgagag    15060
cgctaatttt tcaaacaaag aatctgagct gcattttac agaacagaaa tgcaacgcga     15120
aagcgctatt ttaccaacga agaatctgtg cttcatttt gtaaaacaaa aatgcaacgc     15180
gagagcgcta attttcaaa caaagaatct gagctgcatt tttacagaac agaaatgcaa    15240
cgcgagagcg ctattttacc aacaaagaat ctatacttct tttttgttct acaaaaatgc    15300
atcccgagag cgctattttt ctaacaaagc atcttagatt actttttttc tcctttgtgc    15360
gctctataat gcagtctctt gataactttt tgcactgtag gtccgttaag gttagaagaa    15420
ggctactttg gtgtctattt tctcttccat aaaaaaagcc tgactccact tcccgcgttt    15480
actgattact agcgaagctg cgggtgcatt ttttcaagat aaaggcatcc ccgattatat    15540
tctataccga tgtggattgc gcatactttg tgaacagaaa gtgatagcgt tgatgattct    15600
tcattggtca gaaaattatg aacggtttct tctattttgt ctctatatac tacgtatagg    15660
aaatgtttac atttttcgtat tgttttcgat tcactctatg aatagttctt actacaattt    15720
ttttgtctaa agagtaatac tagagataaa cataaaaaat gtagaggtcg agtttagatg    15780
caagttcaag gagcgaaagg tggatgggta ggttatatag ggatatagca cagagatata    15840
tagcaaagag atacttttga gcaatgtttg tggaagcggt attcgcaata ttttagtagc    15900
tcgttacagt ccggtgcgtt tttggttttt tgaaagtgcg tcttcagagc gcttttggtt    15960
ttcaaaagcg ctctgaagtt cctatacttt ctagagaata ggaacttcgg aataggaact    16020
tcaaagcgtt tccgaaaacg agcgcttccg aaaatgcaac gcgagctgcg cacatacagc    16080
tcactgttca cgtcgcacct atatctgcgt gttgcctgta tatatatata catgagaaga    16140
acggcatagt gcgtgtttat gcttaaatgc gtacttatat gcgtctattt atgtaggatg    16200
aaaggtagtc tagtacctcc tgtgatatta tcccattcca tgcggggtat cgtatgcttc    16260
cttcagcact acctttagc tgttctatat gctgccactc ctcaattgga ttagtctcat    16320
ccttcaatgc tatcatttcc tttgatattg gatcatacta agaaaccatt attatcatga    16380
cattaaccta taaaaatagg cgtatcacga ggcccttttcg tc                      16422
```

<210> SEQ ID NO 27
<211> LENGTH: 19788
<212> TYPE: DNA
<213> ORGANISM: Artificial Sequence
<220> FEATURE:
<223> OTHER INFORMATION: vector

<400> SEQUENCE: 27

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatcga ctacgtcgta aggccgtttc tgacagagta aaattcttga gggaactttc     240
accattatgg gaaatgcttc aagaaggtat tgacttaaac tccatcaaat ggtcaggtca     300
ttgagtgttt tttatttgtt gtattttttt tttttagag aaaatcctcc aatatcaaat      360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttct ccttcttgat aaatgtatgt      540
```

```
agattgcgta tatagtttcg tctaccctat gaacatattc catttttgtaa tttcgtgtcg    600 tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140 acagttttc tccataatct tgaagaggcc aaaagattag ctttatccaa ggaccaaata    1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg attttttagta aaccttgttc aggtctaaca   1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacatagg ggcagacatt agaatggtat atccttgaaa tatatatata   1800
tattgctgaa atgtaaaagg taagaaaagt tagaaagtaa gacgattgct aaccacctat   1860
tggaaaaaac aataggtcct taaataatat tgtcaacttc aagtattgtg atgcaagcat   1920
ttagtcatga acgcttctct attctatatg aaaagccggt tccggcctct cacctttcct   1980
ttttctccca attttttcagt tgaaaaaggt atatgcgtca ggcgacctct gaattaaca    2040 aaaaattttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca tttttaataa ggcaataata ttaggtatgt ggatatacta   2400
gaagttctcc tcgaccgtcg atatgcggtg tgaaataccg cacagatgcg taaggagaaa   2460
ataccgcatc aggaaattgt aaacgttaat attttgttaa aattcgcgtt aaattttttgt   2520 taaatcagct cattttttaa ccaataggcc gaaatcggca aaatcccttta taaatcaaaa   2580 gaatagaccg agataggggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gccccccgatt tagagcttga cggggaaagc cggcgaacgt ggcgagaaag   2820
gaagggaaga aagcgaaagg agcgggcgct agggcgctgg caagtgtagc ggtcacgctg   2880
```

```
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg tgctgcaagg cgattaagtt gggtaacgcc agggttttcc     3060
cagtcacgac gttgtaaaac gacggccagt gagcgcgcgt aatacgactc actatagtat    3120
attaccctgt tatccctagc ggatctgccg gtagaggtgt ggtcaataag agcgacctca    3180
tactatacct gagaaagcaa cctgacctac aggaaagagt tactcaagaa taagaatttt    3240
cgttttaaaa cctaagagtc actttaaaat ttgtatacac ttattttttt tataacttat    3300
ttaataataa aaatcataaa tcataagaaa ttcgcttatt tagaagtggc gcgccgaatt    3360
cactagtgat tgattaattt tgttcaccg ttcaagtctt cctcggagat tagcttttgt    3420
tcaccgttca atcttcttc agaaatcaac ttttgttcac cgtcgagtcc gttcaagtct    3480
tcttctgaga ttaattttg ttcaccgttc aagtcttcct cggagattag cttttgttca    3540
ccgttcaaat cttcttcaga atcaacttt tgttcaccgt cgagtccgtt caagtcttct    3600
tctgagatta attttgttc accgttcaag tcttcctcgg agattagctt tgttcaccg     3660 ttcaaatctt cttcagaaat caacttttgt tcaccgtcga gtccgttcaa gtcttcttct    3720
gagattaatt tttgttcacc gttcaagtct tcctcggaga ttagcttttg ttcaccgttc    3780
aaatcttctt cagaaatcaa cttttgttca ccgtcgagtc cgttcaagtc ttcttctgag    3840
attaattttt gttcaccgtt caagtcttcc tcggagatta gcttttgttc accgttaatt    3900
aacccggggg cgaattgggt accgggcccc cctcgaggt cgacggtatc gataagttat     3960
attgaatttt caaaaattct tacttttttt tggatggac gcaaagaagt ttaataatca     4020
tattacatgg cattaccacc atatacatat ccatatctaa tcttacttat atgttgtgga    4080
aatgtaaaga gccccattat cttagcctaa aaaaccttc tctttggaac tttcagtaat    4140
acgcttaact gctcattgct atattgaagt acggattaga agccgccgag cgggcgacag    4200
ccctccgacg gaagactctc ctccgtgcgt cctcgtcttc accggtcgcg ttcctgaaac    4260
gcagatgtgc ctcgcgccgc actgctccga acaataaaga ttctacaata ctagctttta    4320
tggttatgaa gaggaaaaat tggcagtaac ctggccccac aaaccttcaa attaacgaat    4380
caaattaaca accataggat gataatgcga ttagtttttt agccttattt ctggggtaat    4440
taatcagcga agcgatgatt tttgatctat taacagatat ataaatgaa aagctgcata     4500 accactttaa ctaatacttt caacattttc agtttgtatt acttcttatt caaatgtcat    4560
aaaagtatca acaaaaaatt gttaatatac ctctatactt taacgtcaag gagaaaaaac    4620
tataatgcac catcaccatc accatcatca tcatcattct tctggtctgg tgccacgcgg    4680
ttctggtatg tcactcaatg atatggattc tcgggatgga ccactcgagc ctatcgccat    4740
cgtcggcagt gcttgcaggt tccccggcgg agtttcctcc tcatcggagc tatgggatct    4800
gctgcgccag cctcgagatg ttctgagcga gatctcgcag agccgcttca atgccaacaa    4860
gttttaccat cctgatatga accatagcgg gacgataaac gtccgccatt cttattttct    4920
cacacaggat ccccacagct ttgatgcacc attctttggc atcaaacccc tggaggccga    4980
tgccgtcgac ccacaacagc gtctcttgct cgaaacaacc tacaacgccc tcgaagacgc    5040
cggcatcccg ctgcccaaga taaaaggctc acggaccggt gtgtttattg ggctcatgac    5100
cgaggattat tccaatatca ttgggaggga ccttcaaaac gtcccgcaat actttgcctc    5160
gggcacggcg agaagcatca tctcgaaccg ggtttcctac gtcttcgacc tgcgcgggcc    5220
ttccatgacc atcgataccg cttgttcatc aagtctcgtg gccttgcatt tagcagtcca    5280
```

```
aagcttgaga agcggcgagt cggactgtgc ccttgttggc gggtccaact tgttgttgag   5340
ccccgagcaa tacatcgcgg ggacaaaact caagctcttc agcccaagtg gccgaagccg   5400
catgtgggat aaagatgcgg atggctacgg acgtggagag ggggttgctg ttctagtcct   5460
aaaaagggta tctcaggcct taagtgattg tgattccatc gaatgcctgg tcagggagac   5520
tggcgtcaac caggatggga aaacaaaagg cataaccatg ccaagcgcgg aggctcagat   5580
cgaccttatc aagacaacgt atctaagatc cggtctcgat ctgtcacgac cctccgaacg   5640
gccgcagtat tttgaagctc atgggactgg gacacctgct ggggacccaa tcgaagcgga   5700
ggccatcaac aaagccattt tcggtcaagc caatcaccag cacagcggat cacaaccgct   5760
atacgtgggc tccatcaaaa cggtactcgg ccacgcagaa agtgctgctg gtgttgctgg   5820
ggttatgaag gcgtctcttg cattacaaca tggagttctg cctcccaaca tgctgctaaa   5880
cgaactcagt caaacagtca agcctttcta cagcaacctg cagatccttc aggaggccca   5940
aagctggccg ccggtatcaa gcggaccacg gaggtctgag atcactctgg tgtcaccatt   6000
caacttttct gccgcgtccg acaagtctct tcgggccaac ctcattgcct atgccgattt   6060
tgtcagggac acctcttcaa taagtctacg agactttatcg tggactttga atgttcgaag   6120
gtcaacactg ttagcgagga cctccatcgc agcattgaca accgacgaac tcgaaaagaa   6180
gctgagaaag gcggcagctc tggagacacc gttcaactcc cacacccacc caggagtttc   6240
cggttccatt cttgccattt ttaccggaca gggagcacaa tgggcaacga tgggtttgca   6300
aatttacaaa agttcagtac tcgttcaaaa ctgcttccaa aagcttcaag catccctgga   6360
ctcgctacct ccccaccacg cccccggctg gaagttatgc gaggagttgt tcaaggatcg   6420
cgaaagttct cgtttggggg atgctgccat ctcacaacca ctctgcactg ctgtgcaagt   6480
ggcactcgtc gacttgttca tggctgccaa ggtcaaattt acagcagtcg ttgggcattc   6540
gtcgggggag attgccgcag cttatgcggc tgggtatctt acggccgagt ctgcgatccg   6600
aatcgcttat tacagaggct ttttttcttga catgaatagc gtttcaggtc aaatgttggc   6660
ggttggcact tctcaccagg acgcccgaga gctttgcgag ttgccttcgt tgcacggcaa   6720
gatcactata gcagcttaca actccgcctc gagtgttact ctttctgggg attcggatgc   6780
cattcgggat gcaaaggaaa ttcttgaaga cgaagaaaag tttgctcgga ttcttcaagt   6840
caaccaagcc tatcactcgc cccgcataaa acaatatgcc gatccatacg aaaaggcgct   6900
ggaagcggcc cagatatccg tccaacagcc cccaagaaat cgtccggttt ggatttcgac   6960
cgtgataaca gaaccagctg acaggatcgg tttggattct ctggctcaca gctactgggc   7020
cgataacatg gtcaaaccgg tgcgcttcct gcaggctact gagtatgcga cgggtgtcta   7080
tggtcccttt gatgctgtgg tcgaggttgg gccacatcca gttctgcagc gtccgacaac   7140
cgacatcctg caagaaatta cggggcaaga cgtcccctac atctcgaccc tggttcgtaa   7200
tcagcacgac accttgtctc ttgcggaatg cctgggctca ctctgggaaa ttatcggtga   7260
ttccgccgtc gattttgccg cgttcgaatc atctgtgcac ggcacattcg ccgcacagcc   7320
gaaggtcctc aagaaccttc caccatacac atgggaccat gatcgccaat attggcatga   7380
gacgcggtac acgaaagctt tcctaacgag cggggatgtg ccgcatccct tgctcggaac   7440
catatgccct gatgggacta tgcaggagat caagttcagg aactactcga gccctcaaca   7500
acaaccgtgg ctctcacacc ataaaatcca aggccaggtt gttttcccgg ccgccgctta   7560
catttcctct gcgctggagg ccattgccca actttacccc gaggaaaagg aactggttga   7620
```

```
gcttgccgat attcacatcg gcaaagccat catgttccca gacaatggga cgtcaatcga    7680
gacggcattg tctctcaaaa tacttgagga taatcctgaa cggctggatg cagagtttat    7740
cttccattcc gaggctgttg aaaaacggtc gaaccagatg gtggaaaacg cgagaggcag    7800
gattcgggtg atccgaaatg ggccagtgaa gtctcttccg gtccccaatc cggatcaaga    7860
cataggcggg tttgtggatg tcgacccgga gagattctac gactgggcaa gcgagaaagg    7920
ttacggttac gaaggagcct ttcgaagcct gaagcatacc cgcagaaagt tgaaccaggc    7980
ggttggttcc atcgcatttc cgccagacgc cagaaaggat ggatttgcaa tagctcatcc    8040
tggtgtttta gactgtgctt tgcaggctgt tctacttgcg tacagctacc caggtgatgg    8100
gagacttcgc tcggtctatc tacctaccaa aatcgacttg ataagggtaa cgatggccgg    8160
ctggctggca gaatctcatc aacccgactc ttccttcgcc tttgctgcat ctgctgactc    8220
ttaccacggc ggggagtttg ttggagacgt cgatattcag gcatcctatg acaatggtat    8280
cattttccag cttcagggtc ttcacggtgt agcattggat ccccatcgc cagaaaacga    8340 tgtgaatctc tttatcgaaa cgtcctgggg cccagaaaca cttcaaagtt caccgactca    8400
ttggagcggt cctgtctgct caagctaccg agatttggcg ctgttgttgg aaagagttgc    8460
ctacttctat cttcgaaagc tagcagcact ttttccaccc aaaagcagaa acgggttgcc    8520
gtggaattac ctccgtcttc tggactacgc ggactcctgc ttggaaagcg ttgatggtgg    8580
cgaacaccgg catacaacca acacggactt ggagatactt cgggctgtcg gtgaaggttt    8640
acccaaggcc cttcgtggag aattgaatct tctcgagacg atcaccaaca acggtctctt    8700
acgaaagtac taccaagatg ccttgggtat gagggagtat ctcggggaga tatgtcgtgt    8760
gatgcaccat gtgtctcaca gatttgctaa cctcaacatt ttggaaattg gtgctggtac    8820
tggagctgcc acaacctcgg tcctcgcggc ggttggacac gctattgggt cgtatacatt    8880
taccgacatt tccagcggct ttttcctga gcccgggca caatttgcgt cccatcagcc    8940
gaaaatgatg ttcaagaccc tggacatcga gaagccggtt gcggatcaag gattcaccga    9000
aatggcctat gacgtggtgg tagcatccct agtgctgcat gccacacgta acctttggc    9060 caccatgtcc aatgccagaa ggctcctccg acctggcggc tacctcatca tactagaggt    9120
gacagacaat actccattga gattggggct catatttgga ggcatgcccg gttggtggct    9180
tggagacgcg gatgatcgga aactctcccc atgcgtctcc atcccggctt gggggatct     9240 tatgcgcaag tcaggctttt ctagcatcca caccatcgct tcccacagca aagaccttcc    9300
tgttcctctt tcggtaatgg tcacacaagc tgtggacgac cgagtaaagc ttctcatcga    9360 accccctgaat ccgacgatta aatcatatgg gtttggttgc gtcgtcattg ttggagagca    9420
tacagcatct aggacactgg ccgagaccgc cgtcaagcat acaacacca tcgatctcat    9480 accatcactc catggaatag gaaccgccaa cgttcccctg tcatcgaccg tagtctgtat    9540
ggtcgatcta ggagcagtgt cgatattcca ggacttgaaa ggtcgtgatt tatcggccct    9600
gcaaaccatc ttcaaccgca gcaaaatagt catctgggtg acagccggcg cccaagagac    9660
caaccccaac aaggcgatgt tcatcggcct ccaaagaaca ctcgcgcttg aactacccca    9720
tgtccggatg cagatcatta acttcgaacg agaagcggat atcgacaccc aggtaatcgc    9780
aaccaagctt ttacaacttg aagcatacgg tctttgggaa agcatgaatc tcccgactga    9840 tttttctctgg catattgaac cggagttgac agtgcgagat agtcaagtta tggtgccgcg    9900
gatgcggctt gcaaaggctc ggaatgcaag gtacaacgct gcgcgacggc aactgaccaa    9960
agcggcggcg gccaaaagca cgctcggtat ctccatcatc gacagggcag ttaacggcaa    10020
```

```
gggaatcctc atcgttagcc cacctcggta cctcggggat gtcttagcaa cgatcgctgc   10080
tgcgcgaggc atcgacttgg gtctcgtcac cactgaccgg gcgattggga atatcgggag   10140
tccctgggtg tttattcatc cattggacac aaaaaggtcg attaaacgtg tacttccacc   10200
ggcaatcgga atattcttgg acatgggcaa aaacacggag attggtgcta caatccgggc   10260
atgtttgccc acggattgcc aacaaatata ccttcccggg ttgagtgaag ccttcacccg   10320
gtggatggcg gaacacggcg ccaggcatat tgctatctcc agccggaacc ccgtcattga   10380
acggagttgg gtaaagtcca tggccacttt gggatgcaat gtgagattgt ttgatggtcg   10440
gtccgtccaa aacgtgtacc acagaatcac cggatcgatg ccgcctatag ccggcgtcgt   10500
ccaaggggcc atggtgttgc gagatgctgt ttttccagag ctcacgatca accactggca   10560
agaagtcacg aaaccaaaaa ttgagggaag tattcatctt gatcagatct tcgacgaccc   10620
ttccttggac ttctttgtat tcatctcctc tgtcgcttac ttggccggaa atgccgggca   10680
aggcgtctac tccgcggcca acgctttcat gacgagccta gccgcgcaga gacggagccg   10740
gggccttgct gcttcagtga tccacctggg cgccgtggtc ggcgttgggt acataacccg   10800
tgagctgacc cccgaaaagc aacgggcatt acatcaggcc gggtactcct ttctatcaga   10860
gcaggatttc cacgagatct tgccgaagg ggttcttgca agtctgccag attccggcga   10920
tgtattcgaa atctcaaccg ggctgaggct cgagaacact gttaaagact ccccagcaaa   10980
gtgggcaaga aatccaatgt tcaccatct tgtaacaagg tcggataaac atactgggct   11040
tgacggtatc atcaacaagc tgcaagctgt cctaggtttt gatgaagaaa agttgattct   11100
agaattaagt cctgacgaac ttgccatcga ttcactcgtc gccctcgaca tccagtcctg   11160
gttccgcgca gaactcgacg tggatatccc catattggga ctgctgaatg ccccgtccat   11220
tcgggaaata attttggctg cccaaaacct atcattggaa accacagcga gccttatcgc   11280
agaaccttca ggcatggacc aagaactagg cgacctgtca gctcccagcg gcccacccac   11340
ctccgtttca agcagcaaca ccgcaacaac tccccttcc cctacgatga cgcccaagac   11400
ggataatcaa agccagcatc tccaagacac cccagaggta tttgatacaa gcttagaagg   11460
caaaagctct caacttaaga atggggggat catgttcgaa cgaacggttc cgctctcctt   11520
tgcgcagtcg agattttggt ttcttcaatc gttcgctgaa gatcccagcg cattcaacat   11580
cacatcggtg cttcgactcc agggccgcat cgatatcgaa aggttgagaa atgctgttca   11640
ggttgtcgga caacgacacg aagctctccg caccgcgttc tacaccgaca aggtcactaa   11700
ggatcatatg caggggattc ttccaatcat ggttccccat ctggagactg cgacagttca   11760
gaccgagcgt cagctcgagg aaatagtgca ggaatttgag agacatgtgt acgatgtgtc   11820
aaagggagaa acgctccgca taacactgct ttccttgtcg gaagcagttc accgactcat   11880
cttcggctac catcacatca tactagatgg catcgggttc caaatcttct ttttggagct   11940
agaaaaagca ttcagcggta ccctgaacac agcttcatcc gatgttctgc aatacccgga   12000
ctattcactc aggcagatac aacagtaccg taacggatca tggtctcagg aaatcgacta   12060
ttggaagcag cagtttgcga ccattccaga acctctaccc ctactgttta tctcccacag   12120
gcacactcgt cttgtcacgc cctccttcg gacgcactcg atcacaactc ggctggacga   12180
agttttgcag tcgcaggtca tccaaacctg ccggcatttt aaggtcaaac agttccactt   12240
cttcaccgcc gtctttgctg tggtgctcgc ccgttatgca aacaccttcc cagaggacct   12300
ttgcatcggc gtggcggatg gtaatcggaa ggatctcgat accacgcgca gcctcggcct   12360
```

```
ctttctcaac ctcctcccct tgcggttccg gcaaacacca gatgtcacct tcgcaaaggc    12420
gttgctgaat gcccaaaaga tcattgaaaa cgcctacaca aattctcgtg ttccttttga    12480
tgtgctcctt ggtgagttgg acatccggcg gtcagttacc cacacgccat tgttccagac    12540 gttttgaat taccgccaga acatccgaga gacgaccacg ttctgcggct gtgaagtcaa     12600
gggtgaattg gtatcgggcg gccgaaatgc ctatgatgtt agcttggaca tcgtggacag    12660
taatgatcgg gggagcctca tcactcttac cgtcaacgcg gatttatacg acaaacatgg    12720
tgccgcagcg gtgcagaaca gttacctcaa ccttcttcaa gccttcgccc ataaccctgc    12780
agctagggtt tgctggccgc ctcttcatac cgaggaggac gtcaagttag gaatttcaca    12840
aggacatggt gctgaggttg attctcgatg gccacccaca gtcgtggacc gcattgacga    12900
gatgataaaa gcgcacgcca acaaagtggc gttgactgat ggcgcaggag agagcctcac    12960
atatgcagac atggctcgca agtccacag tattgccact gagttggcag cccgaggagt     13020
gcaaaagggg tctcgtgtgg gcattttcca gatacccggc acggcatggg tgtgctcctt    13080 gcttccgtt ctccgcacgg gagcggttgg cgtgcccttg acctcaatg ttggcattgg      13140 ccggctatcc ttattacttc aagactgcat ccctcaggtt atcctcgtcg atggatcgac    13200
cttcggacag agcggatttg tgtccaattc gaaggcactg atcttggaag tgtcaaccct    13260
tcccaaccta caacatccta gggccaccat tgtgccaaac caggccaagg cgcatgacga    13320
cgccatcatc acatatacca gcggttccac aggtgttccc aagggtgtgg ttatacggca    13380
ccattcgtac caaaatttcc tcgagtttac gcttcccaga tggggaatca cggaaggcaa    13440
gctaaccgtt ctccaacaat cggcctacgc gttcgacatt tccattcttc aaatcttcgc    13500
cagtctttgc tacggcggga ccctggtcat cccagatctt gccaaacggc gggacccaag    13560
agcgctgtgc gaccttgtgg cctcgcaagg tattaccatg acattcgcaa caccgaccga    13620
gtacctctct tgggccaaac acggcaccca gcaattacgt gactcacaat ggcggtgcgc    13680
catgactggg ggcgaacccc tgaccaattc gcttctcgga gtattcaagt ctctaaccaa    13740
ggcggacctc cagctgataa actgttatgg gccgacagag gcttccatcg gatgcgcaga    13800
taaagtggta gacttccaca aaagcctcga ttctaacctc gagatgtcgg tcctgcccaa    13860
ttataggttg gttgtcgttg acgatgattt tcaaccagtt cctgctggca ttcccgggca    13920
aattctcatc ggcggcgctg gagtagcagc gggttacctg aatccgccag acgagggtgc    13980
caaggcattt attgttgacc aacgggccac ggagttccag aagtctcgac gctgggttac    14040
acttcactcc tccgggggatc gtgggcgatt gaacccaac ggcgggttag ttctacatgg     14100
cagaatcggc ggcagcaccc aaaccaaact ccgaggcatt aggattgatc tggccgatat    14160
tgaaaacacc ataatagagg ccatgtcacc tgatgtggtt caggcggtgg tatcccggag    14220
agaggattca gaaacagggg gagagtttct cgtggccttc ctgttgctgt ctggggataa    14280
cgctggtccc gccccggacg attacgtggt caatctccca gacgagctat ctcttccact    14340
ttatatgcgc ccctccatgg ccctcatcgt cgaccaactc ccaaccatgg tctcaggcaa    14400
gattgaccga gcagcggtgg acttgatccc catcaaggca tcgtcggctt ataccccgac    14460
aatcgaggct accaccctca acacaaccga acagattctg ttgagtttgt ggagagaggt    14520
tataccaaac gagattacat ggcaccgaag aattcgcagc gactccgact tttttcgggc    14580 aggggggcaac tccctcgcgg tggtggactt acaaggcttg atcaaggagc gcctccatat    14640
cacggtgccc atttatcgtt tgtttgaatc ggctacactt ggtcagatgg ctatgcttct    14700
cgaccgtgga acagcagcct cccgcgaatc gcaaaacaaa ccagtcgact ggggccatga    14760
```

| | |
|---|---|
| gacccagctc tcagcggaca tcgcggaact ggcagcaggg aggccaattg atcatgctga | 14820 |
| cgggagcttg gcgtttccca gcacagttgt tctcacagga tcaactggct ttttaggcca | 14880 |
| agaacttctc cgtcagctca ttgcggacac gcgagttaca cgaatacatt gcatcgctgt | 14940 |
| gagacaaacc aaggaacggc taccaagcct tttcacaaac accaaagtct cgttgcattt | 15000 |
| tggagatctc ggagaccgtc aactaggact tcgcgaaggt tcgacccggg agatcttctc | 15060 |
| taccgcggac gttgttctgc atgttggagc agacgtgtca ttcctcaagt catacccgag | 15120 |
| ccttcgacta gtcaacgtgg cctcaacaaa ggaactcgtc cgttttgtg ccctcggaa | 15180 |
| tatttcactc cacttcgttt catcagccac agttgggcgg ctggtcggac agagcatctt | 15240 |
| taggccgggt tcggtgaggc aatatcctcc gtcacaggaa gcagacggct acacagcctc | 15300 |
| caaatgggta tccgaagtct atctcgagaa tgccagcaat gactttggcc tccccgtctg | 15360 |
| gatacatcgc ccaagtagta tcacgggatc aggcgcttcc aaaaccgatc tcatgagcaa | 15420 |
| cctcctccaa tacgcccaac agatcaacgc aatgccctat ttgggtgcga aggggggtta | 15480 |
| ctttgacttc gtttcggtcg agactacggc tcggatgatc attgaggaaa tgtccagaag | 15540 |
| cattcgaaag caggaatcca aagttcagta tcttcacgaa tcgggcgaga ttgaaattgc | 15600 |
| aacgaacgac gctgaatcga ttttgggacg ccaaaacgga gaaccattta gggttgtctc | 15660 |
| aatttctgaa tggatacaac tcgcaacagc cgcgggcatg gatcccttac tggctctgta | 15720 |
| tctcgaacgc tccgcaacgg gagggggggt cctgtttccg cgattgctgg ggacagttgg | 15780 |
| agccgttgct ttaatcgtcg cacaccacca ccaccaccac cccgggttaa ttaacatctt | 15840 |
| ttacccatac gatgttcctg actatgcggg ctatccgtat gacgtcccgg actatgcagg | 15900 |
| atcctatcca tatgacgttc cagattacgc tgctcagtgc tgaggcgcgc cacttctaaa | 15960 |
| taagcgaatt tcttatgatt tatgattttt attattaaat aagttataaa aaaataagt | 16020 |
| gtatacaaat tttaaagtga ctcttaggtt ttaaaacgaa aattcttatt cttgagtaac | 16080 |
| tctttcctgt aggtcaggtt gctttctcag gtatagtatg aggtcgctct tattgaccac | 16140 |
| acctctaccg gcagatccgc tagggataac agggtaatat agttcccttt agtgagggtt | 16200 |
| aattgcgcgc ttggcgtaat catggtcata gctgtttcct gtgtgaaatt gttatccgct | 16260 |
| cacaattcca cacaacatag gagccggaag cataaagtgt aaagcctggg gtgcctaatg | 16320 |
| agtgaggtaa ctcacattaa ttgcgttgcg ctcactgccc gctttccagt cgggaaacct | 16380 |
| gtcgtgccag ctgcattaat gaatcggcca acgcgcgggg agaggcggtt tgcgtattgg | 16440 |
| gcgctcttcc gcttcctcgc tcactgactc gctgcgctcg tcgttcggc tgcggcgagc | 16500 |
| ggtatcagct cactcaaagg cggtaatacg gttatccaca gaatcagggg ataacgcagg | 16560 |
| aaagaacatg tgagcaaaag gccagcaaaa ggccaggaac cgtaaaaagg ccgcgttgct | 16620 |
| ggcgtttttc cataggctcc gcccccctga cgagcatcac aaaaatcgac gctcaagtca | 16680 |
| gaggtggcga aacccgacag gactataaag ataccaggcg tttccccctg gaagctccct | 16740 |
| cgtgcgctct cctgttccga ccctgccgct taccggatac ctgtccgcct ttctcccttc | 16800 |
| gggaagcgtg gcgctttctc atagctcacg ctgtaggtat ctcagttcgg tgtaggtcgt | 16860 |
| tcgctccaag ctgggctgtg tgcacgaacc ccccgttcag cccgaccgct gcgccttatc | 16920 |
| cggtaactat cgtcttgagt ccaacccggt aagacacgac ttatcgccac tggcagcagc | 16980 |
| cactggtaac aggattagca gagcgaggta tgtaggcggt gctacagagt tcttgaagtg | 17040 |
| gtggcctaac tacggctaca ctagaaggac agtatttggt atctgcgctc tgctgaagcc | 17100 |

| | |
|---|---|
| agttaccttc ggaaaaagag ttggtagctc ttgatccggc aaacaaacca ccgctggtag | 17160 |
| cggtggtttt tttgtttgca agcagcagat tacgcgcaga aaaaaaggat ctcaagaaga | 17220 |
| tcctttgatc ttttctacgg ggtctgacgc tcagtggaac gaaaactcac gttaagggat | 17280 |
| tttggtcatg agattatcaa aaaggatctt cacctagatc cttttaaatt aaaaatgaag | 17340 |
| ttttaaatca atctaaagta tatatgagta aacttggtct gacagttacc aatgcttaat | 17400 |
| cagtgaggca cctatctcag cgatctgtct atttcgttca tccatagttg cctgactccc | 17460 |
| cgtcgtgtag ataactacga tacgggaggg cttaccatct ggccccagtg ctgcaatgat | 17520 |
| accgcgagac ccacgctcac cggctccaga tttatcagca ataaaccagc cagccggaag | 17580 |
| ggccgagcgc agaagtggtc ctgcaacttt atccgcctcc atccagtcta ttaattgttg | 17640 |
| ccgggaagct agagtaagta gttcgccagt taatagtttg cgcaacgttg ttgccattgc | 17700 |
| tacaggcatc gtggtgtcac gctcgtcgtt tggtatggct tcattcagct ccggttccca | 17760 |
| acgatcaagg cgagttacat gatcccccat gttgtgcaaa aaagcggtta gctccttcgg | 17820 |
| tcctccgatc gttgtcagaa gtaagttggc cgcagtgtta tcactcatgg ttatggcagc | 17880 |
| actgcataat tctcttactg tcatgccatc cgtaagatgc ttttctgtga ctggtgagta | 17940 |
| ctcaaccaag tcattctgag aatagtgtat gcggcgaccg agttgctctt gcccggcgtc | 18000 |
| aatacgggat aataccgcgc cacatagcag aactttaaaa gtgctcatca ttggaaaacg | 18060 |
| ttcttcgggg cgaaaactct caaggatctt accgctgttg agatccagtt cgatgtaacc | 18120 |
| cactcgtgca cccaactgat cttcagcatc ttttactttc accagcgttt ctgggtgagc | 18180 |
| aaaaacagga aggcaaaatg ccgcaaaaaa gggaataagg gcgacacgga aatgttgaat | 18240 |
| actcatactc ttcctttttc aatattattg aagcatttat cagggttatt gtctcatgag | 18300 |
| cggatacata tttgaatgta tttagaaaaa taaacaaata ggggttccgc gcacatttcc | 18360 |
| ccgaaaagtg ccacctgaac gaagcatctg tgcttcattt tgtagaacaa aaatgcaacg | 18420 |
| cgagagcgct aatttttcaa acaaagaatc tgagctgcat ttttacagaa cagaaatgca | 18480 |
| acgcgaaagc gctattttac caacgaagaa tctgtgcttc attttttgtaa aacaaaaatg | 18540 |
| caacgcgaga gcgctaattt ttcaaacaaa gaatctgagc tgcattttta cagaacagaa | 18600 |
| atgcaacgcg agagcgctat tttaccaaca aagaatctat acttcttttt tgttctacaa | 18660 |
| aaatgcatcc cgagagcgct attttttctaa caaagcatct tagattactt ttttttctcct | 18720 |
| ttgtgcgctc tataatgcag tctcttgata acttttttgca ctgtaggtcc gttaaggtta | 18780 |
| gaagaaggct actttggtgt ctatttttctc ttccataaaa aaagcctgac tccacttccc | 18840 |
| gcgtttactg attactagcg aagctgcggg tgcatttttt caagataaag gcatcccga | 18900 |
| ttatattcta taccgatgtg gattgcgcat actttgtgaa cagaaagtga tagcgttgat | 18960 |
| gattcttcat tggtcagaaa attatgaacg gtttcttcta ttttgtctct atatactacg | 19020 |
| tataggaaat gtttacattt tcgtattgtt ttcgattcac tctatgaata gttcttacta | 19080 |
| caattttttt gtctaaagag taatactaga gataaacata aaaaatgtag aggtcgagtt | 19140 |
| tagatgcaag ttcaaggagc gaaaggtgga tgggtaggtt atataggat atagcacaga | 19200 |
| gatatatagc aaagagatac ttttgagcaa tgtttgtgga agcggtattc gcaatatttt | 19260 |
| agtagctcgt tacagtccgg tgcgtttttg gttttttgaa agtgcgtctt cagagcgctt | 19320 |
| ttggttttca aaagcgctct gaagttccta tactttctag agaataggaa cttcggaata | 19380 |
| ggaacttcaa agcgtttccg aaaacgagcg cttccgaaaa tgcaacgcga gctgcgcaca | 19440 |
| tacagctcac tgttcacgtc gcacctatat ctgcgtgttg cctgtatata tatatacatg | 19500 |

-continued

```
agaagaacgg catagtgcgt gtttatgctt aaatgcgtac ttatatgcgt ctatttatgt    19560
aggatgaaag gtagtctagt acctcctgtg atattatccc attccatgcg gggtatcgta    19620
tgcttccttc agcactaccc tttagctgtt ctatatgctg ccactcctca attggattag    19680
tctcatcctt caatgctatc atttcctttg atattggatc atactaagaa accattatta    19740
tcatgacatt aacctataaa aataggcgta tcacgaggcc ctttcgtc                 19788
```

<210> SEQ ID NO 28
<211> LENGTH: 16272
<212> TYPE: DNA
<213> ORGANISM: Artificial Sequence
<220> FEATURE:
<223> OTHER INFORMATION: vector

<400> SEQUENCE: 28

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatcga ctacgtcgta aggccgtttc tgacagagta aaattcttga gggaactttc     240
accattatgg gaaatgcttc aagaaggtat tgacttaaac tccatcaaat ggtcaggtca     300
ttgagtgttt tttatttgtt gtatttttt ttttttagag aaaatcctcc aatatcaaat      360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttct ccttcttgat aaatgtatgt      540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaacctttt aactgcatct      780 tcaatggcct taccttcttc aggcaagttc aatgacaatt tcaacatcat tgcagcagac     840
aagatagtgg cgatagggtc aaccttattc tttggcaaat ctggagcaga accgtggcat     900
ggttcgtaca aaccaaatgc ggtgttcttg tctggcaaag aggccaagga cgcagatggc     960
aacaaaccca aggaacctgg gataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140 acagttttc tccataatct tgaagaggcc aaaagattag ctttatccaa ggaccaaata     1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttcttacgg attttagta aaccttgttc aggtctaaca      1500
ctaccggtac cccatttagg accagccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa aacgacgatc    1740
```

```
ttcttagggg cagacatagg ggcagacatt agaatggtat atccttgaaa tatatatata    1800
tattgctgaa atgtaaaagg taagaaaagt tagaaagtaa gacgattgct aaccacctat    1860
tggaaaaaac aataggtcct taaataatat tgtcaacttc aagtattgtg atgcaagcat    1920
ttagtcatga acgcttctct attctatatg aaaagccggt tccggcctct caccttcct    1980
ttttctccca attttttcagt tgaaaaaggt atatgcgtca ggcgacctct gaaattaaca    2040
aaaaatttcc agtcatcgaa tttgattctg tgcgatagcg ccctgtgtg ttctcgttat    2100
gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca tttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttgt    2520
taaatcagct cattttttaa ccaataggcc gaaatcggca aaatcccta taaatcaaaa    2580
gaatagaccg agatagggtt gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag tttttggg tcgaggtgcc gtaaagcact aaatcggaac    2760
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga agggggatg tgctgcaagg cgattaagtt gggtaacgcc agggttttcc    3060
cagtcacgac gttgtaaaac gacggccagt gagcgcgcgt aatacgactc actatagtat    3120
attaccctgt tatccctagc ggatctgccg gtagaggtgt ggtcaataag agcgacctca    3180
tactatacct gagaaagcaa cctgacctac aggaaagagt tactcaagaa taagaatttt    3240
cgttttaaaa cctaagagtc actttaaaat ttgtatacac ttatttttt tataacttat    3300
ttaataataa aaatcataaa tcataagaaa ttcgcttatt tagaagtggc gcgccgaatt    3360
cactagtgat tgattaattt tgttcaccg ttcaagtctt cctcggagat tagcttttgt    3420
tcaccgttca aatcttcttc agaaatcaac ttttgttcac cgtcgagtcc gttcaagtct    3480
tcttctgaga ttaattttg ttcaccgttc aagtcttcct cggagattag cttttgttca    3540
ccgttcaaat cttcttcaga aatcaactt tgttcaccgt cgagtccgtt caagtcttct    3600
tctgagatta attttgttc accgttcaag tcttcctcgg agattagctt tgttcaccg    3660
ttcaaatctt cttcagaaat caactttgt tcaccgtcga gtccgttcaa gtcttcttct    3720
gagattaatt tttgttcacc gttcaagtct tcctcggaga ttagcttttg ttcaccgttc    3780
aaatcttctt cagaaatcaa cttttgttca ccgtcgagtc cgttcaagtc ttcttctgag    3840
attaattttt gttcaccgtt caagtcttcc tcggagatta gcttttgttc accgttaatt    3900
aacccgggg cgaattgggt accgggcccc cctcgaggt cgacggtatc gataagttat    3960
attgaatttt caaaaattct actttttttt ttggatggac gcaaagaagt ttaataatca    4020
tattacatgg cattaccacc atatacatat ccatatctaa tcttacttat atgttgtgga    4080
aatgtaaaga gccccattat cttagcctaa aaaaaccttc tctttggaac tttcagtaat    4140
```

-continued

```
acgcttaact gctcattgct atattgaagt acggattaga agccgccgag cgggcgacag    4200
ccctccgacg gaagactctc ctccgtgcgt cctcgtcttc accggtcgcg ttcctgaaac    4260
gcagatgtgc ctcgcgccgc actgctccga acaataaaga ttctacaata ctagctttta    4320
tggttatgaa gaggaaaaat tggcagtaac ctggccccac aaaccttcaa attaacgaat    4380
caaattaaca accataggat gataatgcga ttagtttttt agccttattt ctggggtaat    4440
taatcagcga agcgatgatt tttgatctat taacagatat ataaatggaa aagctgcata    4500
accactttaa ctaatacttt caacattttc agtttgtatt acttcttatt caaatgtcat    4560
aaaagtatca acaaaaaatt gttaatatac ctctatactt taacgtcaag gagaaaaaac    4620
tataatgcac catcaccatc accatcatca tcatcattct tctggtctgg tgccacgcgg    4680
ttctggtatg gcttctgcca gtacattgat tctgtttggg cctggtgtta tgaccttgga    4740
cgaaccctac ttcaaccgca tcttcacatg tatcaaggac gacgcccatc acagccaatg    4800
ggctctgcat gctgcggagg accttgagag ttgttgggac tccttgtgca aatcgattcc    4860
gaagctgcaa cgcgttgatg gccggaagca tgctcggaca ttagctgact ggcttcgagc    4920
tggaaccata ccacccgggt cgactgttgc gaatttgcca aatgcgatcc tcggtccgct    4980
ggtccttctg gcacagctta tcgagtacat tcagcatctg aaatccgtca acggaaccga    5040
gcgagggttc ctcaagtgga tgcctcccgg cccgcagaca gaagcagtcg gttgctgtct    5100
gggatgtttc agtgccattg tggtatccgg cagttcgtcc tgggcccagt tctgccacaa    5160
tgccgctgct gcactccggg tgatgtttgt aatctgcgct ctatctgatg cgcaagatag    5220
ccctgacgag actggaccgt ctacatgcct gaacgccttt tggagaggga cacaatcagc    5280
gtccactctg acgacggctt tggaagccta tcccaacgct tacgtcgctg tcctatacga    5340
cgagaatcgg gcaactataa caacctccgc gggcactgct cctgctctgg cgacatatct    5400
tgaaaccgtc gggatcaaag ccagcctgtc tgaattccac ggccgtttcc acaccccgga    5460
agtctatgaa cgtgacatcc aagccctatt cagcttctgt caaacttgcc ccacgtttca    5520
agttccagat gctgcccatt tcaccatgcc tacgcggatc aacgcggaga ctccgatcag    5580
tggtcaagaa aatccccttg aagcggctac acgcgcattc cttgcgcaac agttcaactg    5640
gatcggaacc tttcgtgcag ctgctgccgg ctgcttgaaa gacaaaaatg cccttgtcct    5700
ggagtttggg ccggaacgtt gtatccccccc gacgctcctc cgcagattga gcagacaggt    5760
aactcacttc gacctcgagg agagcctccg cagatctctc ggtggtgatt caaacccgga    5820
tgcgcggcca gttgtatccg agaccgatat tgctgttatc ggcatggctt gtaacgtggc    5880
tggggctcag gatctaggac agtactggca gataatgctg gatggcacgt cgcagcaccg    5940
cgaactcata cccaacgacc ggtttgtcat ggagaccaca catcggcctg gcgaggaggg    6000
cagcgagaag aagaaatggg acggcaactt tcttgacgac acggccgtct ttgaccacaa    6060
attcttcaag aagtctcctc gtgaggccct ccatatggac ccgcagcaga gactcattct    6120
gcagacggcc tatcaggctg tcgcgcaggc gggctattac tttcagccca aggcaacaa    6180 gtcgtccgac cgccggattg gttgctacat tggcgcagtt accaacgact atgagtacaa    6240
catctcgcat gctatcccga acgcattttc agctacaggc ccttgcgaa gctatatcgc    6300 tggaaaggtc agccatttct ttggctggac aggaccggca atgacccttg atactgcgtg    6360
ttcggcatcc acggtggcca ttgatttggc catccaggct attctcagtg gcgaatgctc    6420
tgcggccctc attcgacaga tctttggggg ttctgcccgc gcgggcatga agccgttgca    6480
```

```
gattggctcc gcaaagggct tggttggcca tacagaaggc gcctcgggga ttgtagcatt    6540
gatcaaggtt ttgctgatga ttctggaaag ccgcatcccg ttgcaagcca gtttcaatac    6600
gctcaacccc gccattcaat actcaccctc ggacaacatg gagattgcca aagcttccct    6660
tccttggacg gacgaccgca aggtagccat gatcaacaac tacggagcag caggttccaa    6720
tgcctccata ctcattcagc aggcgccaaa aatgacccaa ggcgagaatg ccatgtcaac    6780
aggctctgct tcctcctgtc ggtggccttt ctacatttcc gggctcgacg acaaggccat    6840
ccaagcatac gcagccaaac tccacctatt tttgcgagag aggccggtct ctggacatca    6900
ccttgacatc gagaatgtgt cattcaacgt aaatcgacaa tcgatgaacg ggtcccttgg    6960
ccgagctgcc atgtttgctg ccgggtccat cgacgaactg gaacaacagc tgggttcttt    7020
ggagactgcc gctactcctg tctctacacg acccgtcatc ctggcgtttg gcggcaggt     7080
cggcaaggtt gttggacttg accgcgaggt gtttgacaaa tccactatcc tgcgacatca    7140
tctcgacgat tgtgataggg cttgcaagtc aattcaggcg ggcagtattt accctacaat    7200
cttccaacgc gagcccataa acgacccctc ggtcctgcag ccggtgctct tctctttgca    7260
gtatgcatgt gccaaaagct ggatcgactg tggcgtcgag ccagccgctc ttgtcgggca    7320
ttcgttgga gagctcaccg cgctctgcat ttcgggcgtc ttgagtctgg aggatacctt     7380
acgaatggtc cacggcaggt ctaaggttat tcgagacagc tggggcgcag agcctgggtc    7440
catggtggca gtggagggtg atccggcaga tgtcgaaaac gtcatcgccg ctgtcaatgc    7500
acagctagac aacaaaggtg acggccgaca tggcatggcg tgtattgcgt gcgtcaacgg    7560
tccacgaagc ttcacgcttg ctgggtctgt cgctgcgtgc gacgcggtgc aacagcacat    7620
cgaggcccgg gatgcagact cgatccgtcc aaccatcaag cacaagagaa tccatgtaac    7680
aaacgccttc cattctgggc tcgtcgagcc cttgaagcca gagctgctgg ctgtcggcag    7740
ccagctcacg ttccgccagc ctaggatccc gctcgagcgg gaaactgaag gataccgcaa    7800
atgcccttcc gacgcctcct acgttgccga acatatgaga gaccctgtgt actggcttca    7860
agccgtcgaa aggctggcca gcaagtatcc cgacgccatc tggctggagg ctggctccaa    7920
ctccaccatc accaacatgg caagcaaggc gcttgggatg ccaaggagtg caaccttcct    7980
accagtcaac ataacaggcg acgataggtg tttacaacat ttggtcgaca tcaccatggg    8040
actttggagg gctggcgtac atgttgcctt ctggccgcac tcgcgcgcac aaacacatca    8100
atatgcgccc atcatgcttc ctccctacca gtttgagaga aatcgccact ggcttgactt    8160
taagccgccc ttgaaacaag ttgggcagga gacgcagcca tccgaacagg ccaaaagcgg    8220
tgcggaggga ggattcctcc caccttcggg ccctacacg tttgttggct acaaagacaa     8280
caagaccaag aaggaatccc ggtttctcat caacaattca ataaagtcat acgtcggcat    8340
cgtatctggg catgtaattg cgaaacaggc gcccgtgctc ccggtaccat cgcaatcga    8400
cttggcgatt caggccatca cgagcatctg tccagagctg accaacatca caacaagtt     8460
gcagcccaga atctacgaga ttgtgaacca cagtcccttg attcacactg acccacctag    8520
aactgtattc atcgattttg aacgccacga tgataatgga ggcgcagaga gaagctggat    8580
cttcaagttt gtgagcaaac tcagagagac cggtgaggag accttgcata tgcacgggaa    8640
actgtccttc cagtctcgcg acgacggtcg cctccatgct gaactcggca gcttgaacg     8700
cttttgtaacc cacagagcgct gtctgcgagc cttggaaagc aacgacgggt ccgaagaggt    8760
catccagggg cggagtatct acaaagtcgg cgacaatctt ttccactacg gcgacaggtt    8820
caggggcctt caaaaactgg ttgggcgatc cagcgagtcg gccggccggc tcgctcgggg    8880
```

```
aaggtctgcg gaggcattcg tcttcgatcc tacoctagca gatgccttcg aacaagttgg   8940
cagcatctgg gccaactgta tggcccggga tcggcctact tctatctatc ttgtcagcga   9000
gatggagcaa tggatcaggt caccagatct tgagagcccg cgggacgttg acagccaagg   9060
ggagtgggat atcttggcac agcataagcg acttccatct ggcgacttct tgacggatat   9120
ctttgtcttc ggctcggcaa gccaatctct tgaggaggtc atgctcggga ttcgatacaa   9180
atcagttcca gttggccagc tgctcacggg tgttcctatc cccctagaa gcgcataccc    9240
tcttgcggaa ccatcaataa agcccctaac gacgggagct ccaccgttga accctgtgct   9300
cgtcggtgaa agcattgatc ggcaatcgga ttctcagccg gccatcgcgc caccacatgt   9360
gaggaatgtc agcaatgtca agaaggcaaa ggatgctctg tggcccaggc tccaacgggt   9420
cttagcagag atatctggcc tcgagcttga tgagattacg cgagctgatt cactcgctga   9480
tgttgggatc gactctttga tggggctaga gctggcacgg gatattgaga cagaatttga   9540
ctgtaccctg gagcaatccc agctcatcag catcgtcgac ataacaggca ttctggatct   9600
tctccagtct gtgcttgacc tcgaggaaat cgctgcttcc tccgattctt ccgacacagc   9660
gtcttcggaa ccaaacagtg ctgtatcagc agccagccgt ggaacctcgc tttccgacac   9720
gccgtcgacg gccgagaaga gttctgacac ggctcttagc ctaccggcat ctataaccat   9780
tgaagccttc cgcgaatcca aagaccacac cgactccttc ctgaagagcc agggatgcgc   9840
aggttatctt gacggcgtgt atcaaaagca agttaggctg tgcctggtac ttactaccca   9900
ggcgttcaag gaactgggct gtgatcttga ggcagcccag cccggcgatg tgttacagcc   9960
tgttccattt gtcgcgcacc accggcgctt ccacgagtac ctgtacaaga tgctggaaga  10020
gacgcgaatc attgatatcg aggaggggggg cgtggtccga cggaccggcc ttccgcttcc  10080
ttctcagtct gccgacgcaa tcattgaggg tctcatgaaa aaccccaaag gctactcgtc  10140
gtcccaccag ctgctatata agttggctc gaggatggcg gacgtcttgg ctggcaaggt   10200
cgatggtcca gccctgatct ttggagatgc caaaaatcgt gaatcggcag cccatttcta  10260
cggcgagttt ccgtttaaca aggcctacat tgagcaaatg ggcgatttcc tgacccggct  10320
ggctcgcaag gggggcttgt tgtcccagag cggtctcagt accccttga agatcatgga   10380
gatgggtgct gggacgggcg gcactacaag ggtgcttgcg cccatactgg cagaattcgg  10440
gatccccgtc gagtacacct tcaccgatct ctcgccatcc ctcgtatccc aagccaagaa  10500
gaagtttaag cagtacccctt ttatgaaatt cgccgtccac gacatcgaac agccccgga   10560
cccagaactg atgggatcgc agcatattgt cgtggctacc aatgccgtac atgccacgca  10620
ctccattgac gcttcgacgc gcaacatccg caagttcctg cgctcagatg gcgttctgat  10680
gctgctcgag atgatgggca cattgcactg ggttgatgtc gtctggggga ctctagaggg  10740
ctggtggctt tttgacgacg gccggacgca tgccattgtg aaggaaaaga ggtgggagca  10800
gagcctcctc aacgcaggct tcaagcacgt cgagtggaca gacggcaatc tgcctgaagt  10860
tggcgttcaa cggtttgtca tcgctatggc agctgatctc gagccgggcc tggccaagca  10920
accaagcatt cctccctcac ccgagcacga cgagcatgat agcgaggagt atctcaaggg  10980
tcgaaagcta gctgcggaca aatacatagc gagcgcaact cgaggcttcg cgatacccga  11040
ggtctcgcca gtcgtccagg gacctacaac tgacgacccc tccgactcct ctatccactc  11100
tgttctcgtg actggtgcaa caggcagtct gggcagccac atcgtgtcgc acctcgccag  11160
cctacccctcg attggcaccg tgttctgcct caaccgcacg cggcccacca ggaaggatga  11220
```

```
acagcctatc agcccacagc aacgccagcg ggaagcattc gagtccaggg gcatcgagct   11280
gaacgaaacg atgcgtgcca aactagaggt catagagacg gacacttcgc agccacaact   11340
aggtctcgac gtggcccagt acggccgact cgtgggggcgt gtgacgcaca tcattcacaa   11400
cgccttcccc gtcaacggac tgcgcgccct cgaacagaac gagccacaat tcatcgtcat   11460
gcgcaacctc gttgacctcg cagcaggcat ctcggcacac cgaaaggccc gggacgaaaa   11520
tttcaagtgt accttcaac agatctcctc cctctcagcc gtgggcaagt atcccttag   11580 acagggaaat ggccgccaag tgcccgaggc ccccatggat atcgaatgtt ccctcccaa   11640 tggatacgga ggcgccaaga ttatatgcga acgaatccta aatgacacgc tgggccgcca   11700
tccagaccgc ttccgcgcaa tgacagtgcg gctgggtcag gtgtcgggct cgaagcggac   11760
ggggtactgg aaccacgtgg aggtgctggc cttcctgttc aagtcggcac agacactacg   11820
ggcgttcccc gccgtcgaag gcgtcttgaa ctggctccct ctcgaagaag cctccacggc   11880
gctggcggag cttctcctcc ggcccagtga tgatgaatgg tatcccgtct atcacgtgga   11940
caacccagtc ccccgggcat gggcggatgt ggtgcccgtg tttgccgagg cgctaggcgt   12000
gcctcaagac aagggcatag tgtccctgca ggaatggcgc aggcgggtgg ccgagtttcc   12060
gggagagaat ccctgggaca acccggcggc aaaggcccaa gacttttttcg aacacaagtt   12120 cgagctcatg tcttgtggag gggtgactat ggccactacc agagcgtgta ggcactcacc   12180
aaccttgaga gctgcgcaac cggtgagtga tgagctgatc agaaagtatg ttgaggtctg   12240
gaagactaca ggattcctgc gtggagccgt tgctttaatc gtcgcacacc accaccacca   12300
ccaccccggg ttaattaaca tcttttaccc atacgatgtt cctgactatg cgggctatcc   12360
gtatgacgtc ccggactatg caggatccta tccatatgac gttccagatt acgctgctca   12420
gtgctgaggc gcgccacttc taaataagcg aatttcttat gatttatgat ttttattatt   12480
aaataagtta taaaaaaat aagtgtatac aaattttaaa gtgactctta ggttttaaaa   12540
cgaaaattct tattcttgag taactctttc ctgtaggtca ggttgctttc tcaggtatag   12600
tatgaggtcg ctcttattga ccacacctct accggcagat ccgctaggga taacagggta   12660
atatagttcc ctttagtgag ggttaattgc gcgcttggcg taatcatggt catagctgtt   12720
tcctgtgtga aattgttatc cgctcacaat tccacacaac ataggagccg gaagcataaa   12780
gtgtaaagcc tggggtgcct aatgagtgag gtaactcaca ttaattgcgt tgcgctcact   12840
gcccgctttc cagtcgggaa acctgtcgtg ccagctgcat taatgaatcg gccaacgcgc   12900
ggggagaggc ggtttgcgta ttgggcgctc ttccgcttcc tcgctcactg actcgctgcg   12960
ctcggtcgtt cggctgcggc gagcggtatc agctcactca aaggcggtaa tacggttatc   13020
cacagaatca ggggataacg caggaaagaa catgtgagca aaaggccagc aaaaggccag   13080
gaaccgtaaa aaggccgcgt tgctggcgtt tttccatagg ctccgccccc ctgacgagca   13140
tcacaaaaat cgacgctcaa gtcagaggtg gcgaaacccg acaggactat aaagatacca   13200
ggcgtttccc cctggaagct ccctcgtgcg ctctcctgtt ccgaccctgc cgcttaccgg   13260
atacctgtcc gcctttctcc cttcgggaag cgtggcgctt tctcatagct cacgctgtag   13320
gtatctcagt tcggtgtagg tcgttcgctc caagctgggc tgtgtgcacg aaccccccgt   13380
tcagcccgac cgctgcgcct tatccggtaa ctatcgtctt gagtccaacc cggtaagaca   13440
cgacttatcg ccactggcag cagccactgg taacaggatt agcagagcga ggtatgtagg   13500
cggtgctaca gagttcttga agtggtggcc taactacggc tacactagaa ggacagtatt   13560
tggtatctgc gctctgctga agccagttac cttcggaaaa agagttggta gctcttgatc   13620
```

```
cggcaaacaa accaccgctg gtagcggtgg ttttttttgtt tgcaagcagc agattacgcg    13680
cagaaaaaaa ggatctcaag aagatccttt gatcttttct acggggtctg acgctcagtg    13740
gaacgaaaac tcacgttaag ggattttggt catgagatta tcaaaaagga tcttcaccta    13800
gatcctttta aattaaaaat gaagttttaa atcaatctaa agtatatatg agtaaacttg    13860
gtctgacagt taccaatgct taatcagtga ggcacctatc tcagcgatct gtctatttcg    13920
ttcatccata gttgcctgac tccccgtcgt gtagataact acgatacggg agggcttacc    13980
atctggcccc agtgctgcaa tgataccgcg agacccacgc tcaccggctc cagatttatc    14040
agcaataaac cagccagccg gaagggccga gcgcagaagt ggtcctgcaa ctttatccgc    14100
ctccatccag tctattaatt gttgccggga agctagagta agtagttcgc cagttaatag    14160
tttgcgcaac gttgttgcca ttgctacagg catcgtggtg tcacgctcgt cgtttggtat    14220
ggcttcattc agctccggtt cccaacgatc aaggcgagtt acatgatccc ccatgttgtg    14280
caaaaaagcg gttagctcct tcggtcctcc gatcgttgtc agaagtaagt tggccgcagt    14340
gttatcactc atggttatgg cagcactgca taattctctt actgtcatgc catccgtaag    14400
atgcttttct gtgactggtg agtactcaac caagtcattc tgagaatagt gtatgcggcg    14460
accgagttgc tcttgcccgg cgtcaatacg ggataatacc gcgccacata gcagaacttt    14520
aaaagtgctc atcattggaa aacgttcttc ggggcgaaaa ctctcaagga tcttaccgct    14580
gttgagatcc agttcgatgt aacccactcg tgcacccaac tgatcttcag catcttttac    14640
tttcaccagc gtttctgggt gagcaaaaac aggaaggcaa aatgccgcaa aaaagggaat    14700
aagggcgaca cggaaatgtt gaatactcat actcttcctt tttcaatatt attgaagcat    14760
ttatcagggt tattgtctca tgagcggata catatttgaa tgtatttaga aaaataaaca    14820
aataggggtt ccgcgcacat ttccccgaaa agtgccacct gaacgaagca tctgtgcttc    14880
attttgtaga acaaaaatgc aacgcgagag cgctaatttt tcaaacaaag aatctgagct    14940
gcatttttac agaacagaaa tgcaacgcga aagcgctatt ttaccaacga agaatctgtg    15000
cttcattttt gtaaaacaaa aatgcaacgc gagagcgcta attttttcaaa caaagaatct    15060 gagctgcatt tttacagaac agaaatgcaa cgcgagagcg ctattttacc aacaaagaat    15120
ctatacttct tttttgttct acaaaaatgc atcccgagag cgctattttt ctaacaaagc    15180
atcttagatt acttttttc tcctttgtgc gctctataat gcagtctctt gataactttt    15240
tgcactgtag gtccgttaag gttagaagaa ggctactttg gtgtctattt tctcttccat    15300
aaaaaaagcc tgactccact tcccgcgttt actgattact agcgaagctg cgggtgcatt    15360
ttttcaagat aaaggcatcc ccgattatat tctataccga tgtggattgc gcatactttg    15420
tgaacagaaa gtgatagcgt tgatgattct tcattggtca gaaaattatg aacggtttct    15480
tctattttgt ctctatatac tacgtatagg aaatgtttac attttcgtat tgttttcgat    15540
tcactctatg aatagttctt actacaattt ttttgtctaa agagtaatac tagagataaa    15600
cataaaaaat gtagaggtcg agtttagatg caagttcaag gagcgaaagg tggatgggta    15660
ggttatatag ggatatagca cagagatata tagcaaagag atactttga gcaatgtttg    15720 tggaagcggt attcgcaata ttttagtagc tcgttacagt ccggtgcgtt tttggttttt    15780
tgaaagtgcg tcttcagagc gcttttggtt ttcaaaagcg ctctgaagtt cctatacttt    15840
ctagagaata ggaacttcgg aataggaact tcaaagcgtt tccgaaaacg agcgcttccg    15900
aaaatgcaac gcgagctgcg cacatacagc tcactgttca cgtcgcacct atatctgcgt    15960
```

| | |
|---|---|
| gttgcctgta tatatatata catgagaaga acggcatagt gcgtgtttat gcttaaatgc | 16020 |
| gtacttatat gcgtctattt atgtaggatg aaaggtagtc tagtacctcc tgtgatatta | 16080 |
| tcccattcca tgcggggtat cgtatgcttc cttcagcact accctttagc tgttctatat | 16140 |
| gctgccactc ctcaattgga ttagtctcat ccttcaatgc tatcatttcc tttgatattg | 16200 |
| gatcatacta agaaaccatt attatcatga cattaaccta taaaaatagg cgtatcacga | 16260 |
| ggcccttcg tc | 16272 |

```
<210> SEQ ID NO 29
<211> LENGTH: 7707
<212> TYPE: DNA
<213> ORGANISM: Chaetomium globosum

<400> SEQUENCE: 29
```

| | |
|---|---|
| atggcatcac cttcactttt agtctttggg ccgcagtcga gcctgctgtc ggaagactgg | 60 |
| ctcgtgcaac tgcggtcgac tttgctggga aaccgtaaac ttgagggcct agttaccgca | 120 |
| ataactcagc ttgaatccat ctggaacgat cttgctctcg ccgacccatc tttcaaaggc | 180 |
| atccctggcc aggaacattt ccgggcccct tccaactgga tcagcagccc tggcaactcg | 240 |
| gacccgccag cggagctttc ccgactcaac ctgctcctca cccccttac cgtcatcgct | 300 |
| cacctagtcg aatacttcaa ctacttggag gtgtccggcc tttcccatga caactcctc | 360 |
| aatagcactt ccatcaatgg cggcggattc caaggcttct gtaccggatt gctggccgca | 420 |
| gtgacgttgt cattggccaa ggatgaagga gaggcggtaa aactctcaac atcggtattg | 480 |
| gggcttgccg tggctctcgg cgcatatgtc gacttggatg gatgttttgc gaatccaccg | 540 |
| agggaatttt cctgtctctc ggttcgctgg aagagcagtg aagagagcct atcggttttc | 600 |
| aaagcgatag aggaacatgc tgaggcatac gtttctgtca actccgatgt attgagtgcc | 660 |
| accgtcaccc ttcccaagca aacgcaagac gagctcgttg caaaactcac tgatctcggg | 720 |
| gtcaccgctc gtccgtaccc actctcgggc cgctttcact cctccatcca cgaggaacat | 780 |
| gtggagaaga tcgtctctct cgggaactcc aacaccaagt tccgattccc ggtggcttgt | 840 |
| gggttgccta atctcgtcag ggacggcacg gggtccccca ttggcaacag cactcccctt | 900 |
| catgaggtga ttgcgaggtc tatgttggtt cagcggtcag aatggagcag cacaattcgg | 960 |
| tctgccctgc cggaacctgc ttctactggc acggaggctg tcgtgtttgg acttgtggac | 1020 |
| tgcataccctc gatccctggt cactgaaggt ggccttaccg tcactcgacc tggcttccag | 1080 |
| aagacggggg catacgtcta ccctgaagac gcggtagccg tcgtcggact ggcctgccga | 1140 |
| tttcccggcg cggattcgct cgaagagtat tggcagctac ttctgtctaa gcttccatg | 1200 |
| ctcggcaagc tcccaaccga acggttccca acaaaagggt tgcgccggac accaaaggac | 1260 |
| gacattccct tcatcggaaa cttcctccgt gatggctacg cctttgacaa caagttttc | 1320 |
| aaccgatctc cgcgcgaggc ctcggccatg gatccgcagc acaaattaat tctgcaggtc | 1380 |
| gcgtacgaag ctctcgagac ggcgggatat ttcagccatg gctcgtcacc tagcgacgtc | 1440 |
| ggctgttacg tcggtgtagc ggcgtctgac tacgaggaca atgtcgcgtc ccatctcccg | 1500 |
| acagccttct ccgtcctcgg catggtccgc gcgtttgtga gcggcaagat cagccatttc | 1560 |
| tttaacttga gtggcccgtc tatggtattc gacacggctt gttcttcctc tgctgtggcc | 1620 |
| atccacactc gcatgccagg ctctcaggaa tggggagtgc tctcatggcc ctcggctggc | 1680 |
| ggagtcaacg ttattacaag cccagtcctg catcagaacc tcgcggcagc aaattttcta | 1740 |
| agccctacag gcgaatccaa ggccttcgat gcgcgtgctg acgggtactg ccgcggggag | 1800 |

```
ggcgcgggaa tggtcgtcct gaagaagtac tctacagcgc ttgccgacgg cgatcacatt    1860
tacggaatca tcgcagggtc tgcggtcaac cagaatgaca actgtgcggc cattaccgtc    1920
cctgtatcaa agtcgcagac cgcgctgtac aagcgagtgc tcaagatggg acggatggac    1980
cctgagaagg tttcgtatgt cgaggcacac ggaaccggca ccccgaaagg agacccaatc    2040
gaatgtgcaa gcatccgaga ggtattcgga aaccagccct cgcgcaagct gcactttggc    2100
tccgtcaaag caagcatcgg ccatacgaaa gccgcgtctg gcgtggcagg cctcatcaag    2160
gtcttgctca tgatgcacca tcggacgatc ccgccgcagg ccagcttcca gacactcaac    2220
cctaatatcc caccccctggg tccgtccaat atggaaattg ctctgacacc cagggactgg    2280
aatggcgaat tcctcgccgc atgcgtcaat aactacggcg cggccggcag caatgccgcc    2340
atgcttattt gccagcctcc acgtctcacc acgacgccga aggcccgccg tggaagggac    2400
agccttccca tgaaatacccc cgtcatgcta agagccaagt ccgcagccag ccttcaagcc    2460
tactgcaatg cgttgacgca attcttggac aaggcgtctg ctcataccag cgatgaccaa    2520
ctcctggctg acgttgccta tgggctcgcc acccaccaga acatcagctt gccctactct    2580
ctcggcacca ccgtcgattc tcttgctcgc ctgcgccagg aactgagcgc ctgcgcttcc    2640
gccacactgc ccgaagagca aacggcaaaa gccaaatccc ggcctgtcat catggtcttc    2700
tccgggcaaa cgggcaacac cgtcaaccta tccgaagaag catccggtc ctccctgctt     2760 ctccagagcc acctgaaccg ctgcgaccgc attctccgat cgctgggcca cccgagcatc    2820
ttccccgcca tcttctccaa gcagcccatc tccgacaccc tggtgctcca ctgcgccgtg    2880
tttgcgctgc agtactcctg cgcttgggcc tggatcgacg cggggtcca gatcgatgcc     2940 atgatcggcc atagctttgg ccagctgacc gcgctctgcg tggccggtgc catgtccctc    3000
gaggatgggc tgaagctgat tgctggccga gctatccttg ttcgggacca gtggggtccg    3060
gaaagggggg ctatgatctc tgtcggcgcg ggcgagcaac agacgcagga gctggtggcg    3120
agcgctcatc aagctggcat cgaggttgag attgcttgct tcaacgccaa ggataaccat    3180
gtcgtggttg ttctgcgtc ttccattgcc gcctttgagg acctggttgc aggccagggc     3240
agtgaggtcc gtttgaagcg gctggaggtc actcacgggt tcattccgt gtttgtcgat     3300 gggattatgc cggagtacaa ggcgctgctg gatagcattt cctttttccca gcccaagatc    3360 catgttgaga cttgctcgcc gggctcagct tggaacacgg tcaactcgga gcttgttgcc    3420
caacagtctc gcgatgccgt ccactttagt gctgccattt cccgcatcca gaagaagttc    3480
agtgattgcg tgtggctgga agccggttcg ggcacggcgg ccatcccct tgctcgccga     3540 gccctgcagg cggaacaggt cgacatcgcg aagcatgctt ccacgcagt caaactcgga     3600 gcgccggacg ccatggagtt gctggcgcag acgacgcttg atttgtggaa cagcgggacc    3660
aaggccatgt tctggcccctt ccatcgctcc caaaagcacc agtacaatgt cctgcagctt    3720
cctccgtacc agttcgagaa gcggcaccac tggctggagt atgtggatcg ccacggcagt    3780
gatgcccctg tccccgtggc ggcgatcgag gcaaagccgg ccgacatggt atccttctcc    3840
cagtatgccg acgacacggg gaacctcgcg atcttcaaca tcaaccagga gaccagcgag    3900
ttccaagcag ccattgaagg ccaccgcgtc ctcggccatc cgctctgtcc cgtctccttg    3960
tacatcgaag ttgcgacacg ggcggcggct ctgctccacc ccaacttctc gactgagacg    4020
catgcatcgg gcgttgatgc gctggaaatc ttcacgcctc ttggtcttga cacggcacgg    4080
caagcccagg ttacgcttct cagcattggc gaggacgagt gggagttcac cgtccatagc    4140
```

```
tttccgcttg gcgacacggc gtcgagaaag accaggcacg ccacggccag aattcgcatc    4200
acgtccctgc ttgacaagag caccgcggcc atgtttgcgc gcttccagcg tctggccaag    4260
tacgaggaat gcgaagctct cttTgccgac ggagccgccg caggcatcca ggggccgttg    4320
gtgtacaaga tgttcgacaa ggtcgtcaat tactcgggga tctaccgtgg cgtgctgaag    4380
attgcgtcca agaaccagaa agtgagcggt ctcgttcagc taccagacgc tacggcgaag    4440
ggagcagaca tggagaagtc ggcctgcaat ccactggcca ttgacaactt cacccaagtt    4500
gccggcctcc acgtcaacgg gcttgatgag tgcggaaacg acgaagtgta catctgctcg    4560
caggtcgatg agattcgcgc ccttcagagc ctcaagagac ctgatggtgg cagtgctggc    4620
ccgtggctgg tgcatgccaa ctttagcagg caaggggaca gagagctcct gaacgatatc    4680
ttcgtcttcg atacgtcagc taagactcta gtcatgacca tcctgggggt ccgatttacc    4740
aagaccaacg tgaatatgct gcagaaggta ctggctcgtg caaacacagc gcactctcat    4800
caagcccagg caaaggttga acctccccgt accgctgcgg cgcagatcaa gtccgccatc    4860
agcacccagc tcatccgcac tgccaatgct ccggagcgta gccggaaccg caagagggct    4920
ctcgaagaca aggtcaacag caacattaga attggcctca agcaactact gcaagaggta    4980
gcggacgtgt ctcccgagca gatccatgac agcactctcc tcgtcgatgt cggcatcgac    5040
tccctgatgg ccaccgaggt gcagacggcc atcggcgaca ggtttggcgt cctcctcaca    5100
actgctgagt tccaatccat tgaggacttt ggatccttgt gcgcagcagt gcagccggcc    5160
cagagcagtg ctcggagctc ctccgaggac gacctgtctg acgataacga gctcctagcc    5220
tcctctcact cggccacgcc tgcatccagt gtcgagtacg agtttcaaaa cgacgagctc    5280
gtggccaaac tgcagaagtt ggtggcaggc catcttgatg tctcagaggc tattgcgcca    5340
gaccttttgc tagcagacgc cggcgtggac tccttgttgg gaatcgagct gggggcagat    5400
attgaaaagg agtttggacg gaccatcgac atgatgcagc tcagtccgac ctgcactttt    5460
gctgacctgg cccctgcagc ggaaaaggac ctcctcgcac acgcggccga ggacttccgc    5520
gcgatccgtt cggattacct tcgcttcgca aaggaaaccg gctgggcagg attccgacag    5580
aatgcgtacc ccaagcagag gcaactggtg ctgagctacg tcctcgaggc tttcgcccag    5640
ttgggctgtg acattgcccg tgttgagggg ggcgatgtcc tccccaatgt cccgcatatg    5700
ccgaagcatg ccaaagtcgt aggccagttc tacaaggttc tccaagaggc tagccttgtc    5760
cgcaaacagg gggacaagct ggtcaggtcc caaacccgt gccccaagac cgatgcggaa    5820
gaactagtcc agcagatgat cgtcgcctat ccccagcacg cctccgagct caagctgcta    5880
cgatccacgg gctccaagct ggcagacgtc ctgtcgggca aggtcgatcc cctccagatc    5940
atcttccgca caaggccga cagagatctg ctcgaggatg tctataccaa ctcgccaatg    6000
ttctcgaccg gaaccaaggt gctagccaac ttcttcacca aagcactcga aatccaccgc    6060
ggcggcgagc aagtacgcat cctcgagctt ggtgccggca cggcggtac gaccaagacg    6120 atcctcgaga cgctctcgtc gatgggagtc aacttttcgt acaccttcac cgacctgtcg    6180
tcgtcgctcg tggcggcggc caagaggaag tttgccaagt acggggacgc cgtcaacttc    6240
tccgtcctcg acgtcgaaaa gccaccgccg cagcacctcg ttgggaacta ccacatcgcc    6300
ctcgcgtcca actgcgtcca tgccaccaag agcctgctgg tttcgtcgac caatacctgc    6360
aagatgcttc gtcaagacgg tatgctctgc ctgctggagc tgacgagaaa cctgtactgg    6420
ctggactgtg tctttggtct gctcgagggc tggtggctct ttgaggatgg ccgggaacat    6480
gtccttgcgg atgagttcct ctggaaggat accctgctga gagccgggtt caagcacgtt    6540
```

```
gactggagcg atgacgacag cgaggagtcg gatcagttcc gtctggtggt gggattcaag      6600
tctgcgccgg accacctaat ctccgcggtt gagaagctac agctcgcggc agcggcggcc      6660
aaaaaggcgg ccgccaagct ggtgaccaaa gaaaccgtcg agtaccaccg cgtcggagat      6720
gtctccctcc aagccgacat ctactacccc gaccagcccg acgacggcac cgccaagcgc      6780
cccatcgctc tcatgatcca cggcggcgga cacatcatgc tctcgcgcaa agacatccgc      6840
ccgcggcaaa cccgcctcct cctctcacgg ggtctcctcc ccatcagcat cgactaccgg      6900
ctctgccccg aagtgaccct ccccgccggc ccatgaccg acgtcggcac agctctacac      6960
tgggcgcgca ccacgctccc ctctctccta cctaacgcca cccggccgga catccgcgcg      7020
gacggcagcc gggtcgtggt cattggctgg tcgacgggcg gcaccctctc catgacgctg      7080
ccgttcacgg cgccggcgcg gggcattgcg ccgcccgagg cggtgctggc gttttattgc      7140
ccgacggatt atcaggatgg gttttggagg gagccgaatt ttcccgagga gacgacggag      7200
agagaggccg gggtggagta tgatttgcta gaggggggtaa gggacggcgc gattaccgcg      7260
tataatgtgc cggcggcgca gcgggcgacg ggagggtgga tgtcgttgga ggatccgcgg      7320
tcgaggatcg cgctgcatat gaattggaag gggcaggcgt tgccggtttt gttgggggggg     7380 ttgccgagta agggcaaggc gggtgagggg gtggattgga agaatcggcc gcagccgagt      7440
gatgaggagg tggcggcggt gagtccgtat gcgcaggtgg tggcggggag ttataggacg      7500
ccaacgttct tgattcatgg cacgagggat gatttgatcc cgtggcagca tacgagagg      7560 attaaggatg cgttggtgga gagggcgtg ccggcgggg cggcgattgt gcaggatgcg      7620
gttcatttgt ttgatttgta tgggagtgag ggctgggagg cggtcttgga ggggtatgag      7680
ttcttgttca agcagattgg cgtctag                                         7707

<210> SEQ ID NO 30
<211> LENGTH: 5412
<212> TYPE: DNA
<213> ORGANISM: Aspergillus terreus

<400> SEQUENCE: 30
atggaggtac atgagatga agtgttgtca gtcgactctg gcgtctcaac tcccccgtcg        60
acaggaagtg gatttcggag gccactagag accccgggaa cagaaatcgg gaatctcaat      120
cttaaccctc agaatgaggt tgccgttgtt ggaatggcct gccggcttgc cggggggcaat     180 aattctccgg aagaactgtg gcagtccatt ctaaacagga aggatgcctc tggcgagatc      240
ccaagcatgc gctgggagcc gtattaccgt cgggatattc gcaaccccaa gatcctagat      300
caaacgacaa agcgcggcta cttcttggac cacgtcgaga attttgatgc cgcgttcttt      360
ggcgtttccc ccaaagaggc cgagcagatg gaccccccagc agcggttgtc acttgaggtg      420
acttgggagg ccctggaaga cgcaggaatc ccaccgcaga gtttgtccgg ctcagaaaca      480
gccgtgttta tgggagtcaa ttcggatgat tattccaagc tcttactgga agatattccg      540
aacgtggagg cctggatggg catcggcact gcgtactgcg gagtcccgaa ccgcatctcc      600
taccacctga acctcatggg acccagcact gccgttgatg ccgcctgtgc ctcctctctc      660
gttgccatcc atcacggacg acaagccatc ctgcaaggga gagcgaagt cgctattgtc      720 ggaggagtca cgcccctctg cgggccagga ctgactcgcg tactcgacaa ggcaggagcg      780
acctccacgg aaggtcgctg tctctctttc gacgaagatg cgaagggcta cggccgtggt      840
gaaggagctg cggtggtgat cttgaaacgg ctgtccaccg ccatccggga cggagaccac      900
```

```
attcgcgcca tcatcaaggg cagtgccgta gcacaggatg gcaaaaccaa cggcatcatg    960
gctcccaacg ccaaggcaca agagcttgtg gcgtggaatg cgcttcggac agccggagtc   1020
gaccctctga cggttgggta tgtggaagct cacgcaacgt caaccccctct tggcgatcct  1080
accgaggtca gcgccgtctc agcagtctac ggcaaaggca gaccggaagg gaatccttgc   1140
ttcattggct ctgtcaaacc caacgtgggc catttggaag cgggcgctgg cgccgtcggt   1200
ttcatcaaag cagtcatggc agttgaaaag gccatttttcc ccccacaaac caacctgaag  1260
agactcaatt ctcgcattga ctggggccaa gccggagtga aggtcgtcca ggagacactg   1320
gaatggcctg gcaatgagga tgacgtccgc cgagccggtg tttgctctta cggatatggt   1380
ggtacggtct cccatgcaat catcgaggag tttgcgcaac agctccagcg gccgactacc   1440
aacacaaccg atgaagaccc tctgcctcgg attcttctcc tgtcggcacc tcaagagaga   1500
cgccttgctt tgcaggcacg gacacaggcc tcctggattg ccgcggaggg cagaaataga   1560
accctggagt cgattgcaac caccttgagc actcgtcgtg ggcaccatga ctaccgggct   1620
gccatcatcg cagagaacca tgatgacgct gttcagaaac tgtctgacat tgtcaatggt   1680
aaagcagccg aatggacgac gtcgagtcgt gttctcgatg ccagttgctc caaggacgtg   1740
gtgtgggttt tctccggtca tggcgcacaa tggactgcaa tggctacgga tctcctcaaa   1800
gacattgtgt tctatcaaac aatcagccgt ctggacccga ttgtggagcg cgaaatgggc   1860
ttctcggcat tgcattccct tgcaagtggc gatttcgaat cgtccatcaa ggtgcaagtg   1920
ctcacctatc tcgtacaggt gggactggct gccatcttgc gctcgaaggg attggagccc   1980
caggctgtca tcggtcattc agttggcgaa attgccgcct cagtcgcggc tggctgtctg   2040
actgcagaag aaggcgccct gattgtcacc cgcagagcaa acctctatcg gcgtgtgatg   2100
ggcgcgggcg caatggttct cgtcaacatt ccatttgtcg acatggagaa agagcttcaa   2160
ggccggacgg acctcgtggc cgccattgac tcctcgccat cttcatgtgt tgtttccggt   2220
gccactgagg ctgtcctggc actcgtggaa gacctcaagt ctcgtggtgt caacgctttc   2280
cgggtcaaga cggatattcc cttccaccac ccgatgctgg atcaactgtc cgagcccttg   2340
cgagaggcca tggcagggtc cctgtcgcca cgcaagccca gagtccgtct ttactcgacg   2400
tcggcagaag acccacgcag tatggttgct cgggatatat attactggac cagcaacatg   2460
gtcaacccgg tccggttgac ggccgcagtg caggcagcag tggacgatgg cctgcgattg   2520
ttccttgaag tctcttctca tcccattgtg tcccactctg tccgagagac catgttggac   2580
ctgggtgtgg aggacttcac cgtgaccaac accatggctc gcaataagcc tgccgacaag   2640
accattctgt ccagcattgc gcagcttcac tgtcggggcg ccgtcgtcaa ttggaagaag   2700
cagctgccgg gccctgggc gctggatgtg cccttgacga cctgggacca caagccctac   2760
tggcggcata ttcacactgg ccctatcagt gcctcgactt tgcacgatgt ggacaaacac   2820
acgctgttgg gtcagcgcgt tcccgttgcg ggagaaacaa ctatggtgtt caccacccag   2880
atggatgacc agaccaagcc tttcccagga agccatccac tgcacggctc tgagattgtt   2940
ccggctgctg cccttgtcaa cactttcctg catgccaccg ggctaccac cctttccaac    3000
attacccttc gcgtgccagt ggccatcagc cagccgcgcg acatccaggt ggtggtgtca   3060
cagaatcaaa tcaagatctg ctcccgtctc actcagaagg cgggttctgg ggcagacgaa   3120
ggttcctggc tgacacacac tacgggtcag tgggaggctg gtggaagcaa gaacgccccg   3180
gcgcaactcg atattgctgc tatcaaggct cgtctcgcta taacaaatt ggcggacaac    3240
ttctccatcg actatttgga caaggttggc gtttcagcaa tgggctttcc ttgggcagtt   3300
```

-continued

```
acagagcact acggcaccct gcaggagatg atcgctcgcg ttgatgtcgc gccagacgtc    3360
cccgcgacca gtccactccc ctgggatgct gcctcttggg ccccgatcct cgatgcggcc    3420
acctcagtgg gatccactct cttttcgat cagcctcgcc tgcgcatgcc ggctcacatt     3480 cacgggttc aagtctacac cacgcagccg cctctcaagg tgggttacct gtacgtggaa     3540
aaggctggcg atcgggatct ggcggtgcat gtcagtgtct gcgacgagct cggaaccgtc    3600
ttagctcgat tcgaatccat gcgcttttcc gagatcgaag gcacgccggg cagtaacggc    3660
agcgaggaga gtcttgtcca tcagctcgca tggcctcccg cgatctacag cgagaagccg    3720
ctgacaatca acaatgtcgt cctcgtttcc cgggataaga acgtcgcaga tctctactgt    3780
gggtccttga aagatcgtgt gtcatctatc acggtgctgg atgctgctgc cgacctgctt    3840
tccctttcgc aggattccag cagtgtcttg caagcaaaag atacagcggt ggtgtacgtg    3900
cccggtcccc tccacagcgc ggattctatc ccgactgcgg cccattcttt cctcatggaa    3960
ttgctcctcc tggtcaaaat cattgtcaat ggctctttgc ccaccaaggt ctttgtcctt    4020
acggaccgcg tctgcgagag tgagtctgct acggctctcg ctcagtctcc gatccacggt    4080
gtctcccgta tcattgctgc ggagcaccca gatcaatggg gcggactgat tgacgtcgaa    4140
acgccgggcc agttcccact cgagacgatg aagtatgtgc aggaggcgga caacatccgc    4200
atctcggatg gcatacccag aattgctcgt ctgcgcccgc ttcctcgcga caagctccta    4260
ccgcctagca agcagacttc cctgctcccc cgacccgaaa gtacctactt gattacgggt    4320
ggactgggcg ctctggggtt ggaggtcgca cagttcctgg tggaaaaggg tgctcgtcga    4380
ttgatcctcg tttctcggcg tgccttgcct ccgcgccggg agtgggcaga catccttgct    4440
gatgcatcat cctcgctggc gccggcgctg gagacaatcc aggcccttga agcacaggga    4500
gccactgtcc acactcttgc agtggacatt tcctctcctg acgcagcgcc tcaactggct    4560
gtcgccattg attctctgtc gctaccccca gtccgcggcg tggtccacgc agcaggcgtt    4620
ctggacagcc agctggtcct ctccgccacg tcagactctg tcgagcgcgt gctggcgccc    4680
aagatcaccg gagcgctggt ccttggcacc gtcttcccc caaggccct cgatttcttc      4740 atgctattct cctcgtgcgg acagctacta ggcttcccgg gtcaagcatc ctacgcgtcc    4800
ggaaacgcgt tccttgatgc attcgcaacc tcgcgccgac accaaggaga caacgctgtc    4860
gccgtgcagt ggaccagctg gcgctccctc ggcatggcag ccagtaccga cttcatcaac    4920
gctgagctgg ccagcaaggg catcactgac atcacgcgcg acgagggatt ccgcgcatgg    4980
atgcatattt ccaaatatga tatcgaccag gccgcggtct tgcgcagtct ggccttcgag    5040
gccgatgaac ccctccccac ccctatcctt acggatattg ccgtccgcaa ggctggctcc    5100
gcctcctccg cggatgctcc ctctgctgca ccgaaagaga cgaacgaaat gccggaatcg    5160
atcccggagc gtcgtacctg gttggatgag cgaatccgtg attgtgtggc ccgcgtgctt    5220
cagctgggga gcagcgacga ggttgattcc aaggccgctc tgagtgacct gggagtcgac    5280
agtgtcatga ccgttagctt gagaggtcag ctgcagaaga cgttgggggt caaggtgcca    5340
cccacactga cctggagttg cccgacggtg tcacatctgg tgggatggtt tttggaaaag    5400
atgggaaatt ga                                                        5412
```

<210> SEQ ID NO 31
<211> LENGTH: 49
<212> TYPE: DNA
<213> ORGANISM: Artificial Sequence
<220> FEATURE:

<223> OTHER INFORMATION: primer

<400> SEQUENCE: 31
tggtctggtg ccacgcggtt ctggtatgga ggtacatgga gatgaagtg                49

<210> SEQ ID NO 32
<211> LENGTH: 48
<212> TYPE: DNA
<213> ORGANISM: Artificial Sequence
<220> FEATURE:
<223> OTHER INFORMATION: primer

<400> SEQUENCE: 32
caacggcaac ctcattctga gggttaagat tgagattccc gatttctg                 48

<210> SEQ ID NO 33
<211> LENGTH: 48
<212> TYPE: DNA
<213> ORGANISM: Artificial Sequence
<220> FEATURE:
<223> OTHER INFORMATION: primer

<400> SEQUENCE: 33
cagaaatcgg gaatctcaat cttaaccctc agaatgaggt tgccgttg                 48

<210> SEQ ID NO 34
<211> LENGTH: 47
<212> TYPE: DNA
<213> ORGANISM: Artificial Sequence
<220> FEATURE:
<223> OTHER INFORMATION: primer

<400> SEQUENCE: 34
tgcgacgatt aaagcaacgg ctccatttcc catcttttcc aaaaacc                  47

<210> SEQ ID NO 35
<211> LENGTH: 14706
<212> TYPE: DNA
<213> ORGANISM: Artificial Sequence
<220> FEATURE:
<223> OTHER INFORMATION: vector

<400> SEQUENCE: 35
gacgtcaggt ggcactttc ggggaaatgt gcgcggaacc cctatttgtt tatttttcta     60
aatacattca aatatgtatc cgctcatgag acaataaccc tgataaatgc ttcaataata    120
ttgaaaaagg aagagtatga gtattcaaca tttccgtgtc gcccttattc ccttttttgc    180
ggcattttgc cttcctgttt ttgctcaccc agaaacgctg gtgaaagtaa aagatgctga    240
agatcagttg ggtgcacgag tgggttacat cgaactggat ctcaacagcg gtaagatcct    300
tgagagtttt cgccccgaag aacgttttcc aatgatgagc acttttaaag ttctgctatg    360
tggcgcggta ttatcccgta ttgacgccgg gcaagagcaa ctcggtcgcc gcatacacta    420
ttctcagaat gacttggttg agtactcacc agtcacagaa aagcatctta cggatggcat    480
gacagtaaga gaattatgca gtgctgccat aaccatgagt gataacactg cggccaactt    540
acttctgaca acgatcggag gaccgaagga gctaaccgct tttttgcaca acatggggga    600
tcatgtaact cgccttgatc gttgggaacc ggagctgaat gaagccatac caaacgacga    660
gcgtgacacc acgatgcctg tagcaatggc aacaacgttg cgcaaactat taactggcga    720
actacttact ctagcttccc ggcaacaatt aatagactgg atggaggcgg ataaagttgc    780
aggaccactt ctgcgctcgg cccttccggc tggctggttt attgctgata aatctggagc    840

```
cggtgagcgt gggtctcgcg gtatcattgc agcactgggg ccagatggta agccctcccg     900
tatcgtagtt atctacacga cggggagtca ggcaactatg gatgaacgaa atagacagat     960
cgctgagata ggtgcctcac tgattaagca ttggtaactg tcagaccaag tttactcata    1020
tatactttag attgatttaa aacttcattt ttaatttaaa aggatctagg tgaagatcct    1080
ttttgataat ctcatgacca aaatccctta acgtgagttt tcgttccact gagcgtcaga    1140
ccccgtagaa aagatcaaag gatcttcttg agatcctttt tttctgcgcg taatctgctg    1200
cttgcaaaca aaaaaaccac cgctaccagc ggtggtttgt ttgccggatc aagagctacc    1260
aactcttttt ccgaaggtaa ctggcttcag cagagcgcag ataccaaata ctgtccttct    1320
agtgtagccg tagttaggcc accacttcaa gaactctgta gcaccgccta catacctcgc    1380
tctgctaatc ctgttaccag tggctgctgc cagtggcgat aagtcgtgtc ttaccgggtt    1440
ggactcaaga cgatagttac cggataaggc gcagcggtcg ggctgaacgg ggggttcgtg    1500
cacacagccc agcttggagc gaacgaccta caccgaactg agatacctac agcgtgagct    1560
atgagaaagc gccacgcttc ccgaagggag aaaggcggac aggtatccgg taagcggcag    1620
ggtcggaaca ggagagcgca cgagggagct tccaggggga aacgcctggt atctttatag    1680
tcctgtcggg tttcgccacc tctgacttga gcgtcgattt ttgtgatgct cgtcaggggg    1740
gcggagccta tggaaaaacg ccagcaacgc ggccttttta cggttcctgg ccttttgctg    1800
gccttttgct cacatgttct ttcctgcgtt atcccctgat tctgtggata accgtattac    1860
cgcctttgag tgagctgata ccgctcgccg cagccgaacg accgagcgca gcgagtcagt    1920
gagcgaggaa gcggaagagc gcccaatacg caaaccgcct ctccccgcgc gttggccgat    1980
tcattaatgc agctggcacg acaggtttcc cgactggaaa gcgggcagtg agcgcaacgc    2040
aattaatgtg agttagctca ctcattaggc accccaggct ttacacttta tgcttccggc    2100
tcgtatgttg tgtggaattg tgagcggata acaatttcac acaggaaaca gctatgacca    2160
tgattacgcc aagcgcgcaa ttaaccctca ctaaagggaa caaaagctgg agctccaccg    2220
cggtggcggc cgctctagaa ctagtggatc caagtacgga ttagaagccg ccgagcgggc    2280
gacagccctc cgacggaaga ctctcctccg tgcgtcctcg tcttcaccgg tcgcgttcct    2340
gaaacgcaga tgtgcctcgc gccgcactgc tccgaacaat aaagattcta caatactagc    2400
ttttatggtt atgaagagga aaaattggca gtaacctggc cccacaaacc ttcaaattaa    2460
cgaatcaaat taacaaccat aggatgataa tgcgattagt ttttttagcct tatttctggg    2520
gtaattaatc agcgaagcga tgatttttga tctattaaca gatatataaa tggaaaagct    2580
gcataaccac tttaactaat actttcaaca ttttcagttt gtattacttc ttattcaaat    2640
gtcataaaag tatcaacaaa aaattgttaa tatacctcta actttaacg tcaaggagaa    2700
aaaactataa tgcaccatca ccatcaccat catcatcatc attcttctgg tctggtgcca    2760
cgcggttctg gtatggaggt acatggagat gaagtgttgt cagtcgactc tggcgtctca    2820
actcccccgt cgacaggaag tggatttcgg aggccactag agaccccggg aacagaaatc    2880
gggaatctca atcttaaccc tcagaatgag gttgccgttg ttggaatggc ctgccggctt    2940
gccggggggca ataattctcc ggaagaactg tggcagtcca ttctaaacag gaaggatgcc    3000
tctggcgaga tcccaagcat gcgctgggag ccgtattacc gtcgggatat tcgcaacccc    3060
aagatcctag atcaaacgac aaagcgcggc tacttcttgg accacgtcga gaattttgat    3120
gccgcgttct ttggcgtttc ccccaaagag gccgagcaga tggaccccca gcagcggttg    3180
```

```
tcacttgagg tgacttggga ggccctggaa gacgcaggaa tcccaccgca gagtttgtcc    3240
ggctcagaaa cagccgtgtt tatgggagtc aattcggatg attattccaa gctcttactg    3300
gaagatattc cgaacgtgga ggcctggatg ggcatcggca ctgcgtactg cggagtcccg    3360
aaccgcatct cctaccacct gaacctcatg ggacccagca ctgccgttga tgccgcctgt    3420
gcctcctctc tcgttgccat ccatcacgga cgacaagcca tcctgcaagg ggagagcgaa    3480
gtcgctattg tcggaggagt caacgccctc tgcgggccag gactgactcg cgtactcgac    3540
aaggcaggag cgacctccac ggaaggtcgc tgtctctctt tcgacgaaga tgcgaagggc    3600
tacggccgtg gtgaaggagc tgcggtggtg atcttgaaac ggctgtccac cgccatccgg    3660
gacggagacc acattcgcgc catcatcaag ggcagtgccg tagcacagga tggcaaaacc    3720
aacggcatca tggctcccaa cgccaaggca caagagcttg tggcgtggaa tgcgcttcgg    3780
acagccggag tcgaccctct gacggttggg tatgtggaag ctcacgcaac gtcaaccccct   3840 cttggcgatc ctaccgaggt cagcgccgtc tcagcagtct acggcaaagg cagaccggaa    3900
gggaatcctt gcttcattgg ctctgtcaaa cccaacgtgg gccatttgga agcgggcgct    3960
ggcgccgtcg gtttcatcaa agcagtcatg gcagttgaaa aggccatttt ccccccacaa    4020
accaacctga agagactcaa ttctcgcatt gactggggcc aagccggagt gaaggtcgtc    4080
caggagacac tggaatggcc tggcaatgag gatgacgtcc gccgagccgg tgtttgctct    4140
tacggatatg gtggtacggt ctcccatgca atcatcgagg agtttgcgca acagctccag    4200
cggccgacta ccaacacaac cgatgaagac cctctgcctc ggattcttct cctgtcggca    4260
cctcaagaga gacgccttgc tttgcaggca cggacacagg cctcctggat gccgcggag     4320 ggcagaaata gaaccctgga gtcgattgca accaccttga gcactcgtcg tgggcaccat    4380
gactaccggg ctgccatcat cgcagagaac catgatgacg ctgttcagaa actgtctgac    4440
attgtcaatg gtaaagcagc cgaatggacg acgtcgagtc gtgttctcga tgccagttgc    4500
tccaaggacg tggtgtgggt tttctccggt catggcgcac aatggactgc aatggctacg    4560
gatctcctca aagacattgt gttctatcaa acaatcagcc gtctggaccc gattgtggag    4620
cgcgaaatgg gcttctcggc attgcattcc cttgcaagtg gcgatttcga atcgtccatc    4680
aaggtgcaag tgctcaccta tctcgtacag gtgggactgg ctgccatctt gcgctcgaag    4740
ggattggagc cccaggctgt catcggtcat tcagttggcg aaattgccgc tcagtcgcg    4800 gctggctgtc tgactgcaga agaaggcgcc ctgattgtca cccgcagagc aaacctctat    4860
cggcgtgtga tgggcgcggg cgcaatggtt ctcgtcaaca ttccatttgt cgacatggag    4920
aaagagcttc aaggccggac ggacctcgtg gccgccattg actcctcgcc atcttcatgt    4980
gttgtttccg gtgccactga ggctgtcctg gcactcgtgg aagacctcaa gtctcgtggt    5040
gtcaacgctt tccgggtcaa gacggatatt cccttccacc acccgatgct ggatcaactg    5100
tccgagccct gcgagaggc catggcaggg tccctgtcgc cacgcaagcc cagagtccgt    5160
ctttactcga cgtcggcaga agaccacgcg agtatggttg ctcgggatat atattactgg    5220
accagcaaca tggtcaaccc ggtccggttg acggccgcag tgcaggcagc agtggacgat    5280
ggcctgcgat tgttccttga agtctcttct catcccattg tgtcccactc tgtccgagag    5340
accatgttgg acctgggtgt ggaggacttc accgtgacca acaccatggc tcgcaataag    5400
cctgccgaca agaccattct gtccagcatt gcgcagcttc actgtcgggg cgccgtcgtc    5460
aattggaaga agcagctgcc gggccttgg gcgctggatg tgcccttgac gacctgggac    5520
cacaagccct actggcggca tattcacact ggccctatca gtgcctcgac tttgcacgat    5580
```

-continued

```
gtggacaaac acacgctgtt gggtcagcgc gttcccgttg cgggagaaac aactatggtg    5640
ttcaccaccc agatggatga ccagaccaag cctttcccag gaagccatcc actgcacggc    5700
tctgagattg ttccggctgc tgcccttgtc aacactttcc tgcatgccac cggggctacc    5760
acccttccca acattaccct tcgcgtgcca gtggccatca gccagccgcg cgacatccag    5820
gtggtggtgt cacagaatca aatcaagatc tgctcccgtc tcactcagaa ggcgggttct    5880
ggggcagacg aaggttcctg gctgacacac actacgggtc agtgggaggc tggtggaagc    5940
aagaacgccc cggcgcaact cgatattgct gctatcaagg ctcgtctcgc taataacaaa    6000
ttggcggaca acttctccat cgactatttg acaaggttg gcgtttcagc aatgggcttt    6060
ccttgggcag ttacagagca ctacggcacc ctgcaggaga tgatcgctcg cgttgatgtc    6120
gcgccagacg tccccgcgac cagtccactc ccctgggatg ctgcctcttg ggccccgatc    6180
ctcgatgcgg ccacctcagt gggatccact ctcttttcg atcagcctcg cctgcgcatg    6240
ccggctcaca ttcacggggt tcaagtctac accacgcagc cgcctctcaa ggtgggttac    6300
ctgtacgtgg aaaaggctgg cgatcgggat ctggcggtgc atgtcagtgt ctgcgacgag    6360
ctcggaaccg tcttagctcg attcgaatcc atgcgctttt ccgagatcga aggcacgccg    6420
ggcagtaacg gcagcgagga gagtcttgtc catcagctcg catggcctcc cgcgatctac    6480
agcgagaagc cgctgacaat caacaatgtc gtcctcgttt cccgggataa gaacgtcgca    6540
gatctctact gtgggtcctt gaaagatcgt gtgtcatcta tcacggtgct ggatgctgct    6600
gccgacctgc tttcccttc gcaggattcc agcagtgtct tgcaagcaaa agatacagcg    6660
gtggtgtacg tgcccggtcc cctccacagc gcggattcta tcccgactgc ggcccattct    6720
ttcctcatgg aattgctcct cctggtcaaa atcattgtca atggctcttt gcccaccaag    6780
gtctttgtcc ttacggaccg cgtctgcgag agtgagtctg ctacggctct cgctcagtct    6840
ccgatccacg gtgtctcccg tatcattgct gcggagcacc cagatcaatg gggcggactg    6900
attgacgtcg aaacgccggg ccagttccca ctcgagacga tgaagtatgt gcaggaggcg    6960
gacaacatcc gcatctcgga tggcataccc agaattgctc gtctgcgccc gcttcctcgc    7020
gacaagctcc taccgcctag caagcagact tccctgctcc cccgacccga agtacctac    7080 ttgattacgg gtggactggg cgctctgggg ttggaggtcg cacagttcct ggtgaaaaag    7140
ggtgctcgtc gattgatcct cgtttctcgg cgtgccttgc ctccgcgccg ggagtgggca    7200
gacatccttg ctgatgcatc atcctcgctg gcgccggcgc tggagacaat ccaggccctt    7260
gaagcacagg gagccactgt ccacactctt gcagtggaca tttcctctcc tgacgcagcg    7320
cctcaactgg ctgtcgccat tgattctctg tcgctacccc cagtccgcgg cgtggtccac    7380
gcagcaggcg ttctggacag ccagctgtc ctctccgcca cgtcagactc tgtcgagcgc    7440
gtgctggcgc caagatcac cggagcgctg gtccttggca ccgtcttccc ccccaaggcc    7500
ctcgatttct tcatgctatt ctcctcgtgc ggacagctac taggcttccc gggtcaagca    7560
tcctacgcgt ccggaaacgc gttccttgat gcattcgcaa cctcgcgccg acaccaagga    7620
gacaacgctg tcgccgtgca gtggaccagc tggcgctccc tcggcatggc agccagtacc    7680
gacttcatca acgctgagct ggccagcaag ggcatcactg acatcacgcg cgacgaggga    7740
ttccgcgcat ggatgcatat ttccaaatat gatatcgacc aggccgcggt cttgcgcagt    7800
ctggccttcg aggccgatga acccctcccc acccctatcc ttacggatat tgccgtccgc    7860
aaggctggct ccgcctcctc cgcggatgct ccctctgctg caccgaaaga gacgaacgaa    7920
```

```
atgccggaat cgatcccgga gcgtcgtacc tggttggatg agcgaatccg tgattgtgtg    7980
gcccgcgtgc ttcagctggg gagcagcgac gaggttgatt ccaaggccgc tctgagtgac    8040
ctgggagtcg acagtgtcat gaccgttagc ttgagaggtc agctgcagaa gacgttgggg    8100
gtcaaggtgc cacccacact gacctggagt tgcccgacgg tgtcacatct ggtgggatgg    8160
tttttggaaa agatgggaaa tggagccgtt gctttaatcg tcgcacacca ccaccaccac    8220
caccccgggt taattaacat cttttaccca tacgatgttc ctgactatgc gggctatccg    8280
tatgacgtcc cggactatgc aggatcctat ccatatgacg ttccagatta cgctgctcag    8340
tgctgaggcg cgccacttct aaataagcga atttcttatg atttatgatt tttattatta    8400
aataagttat aaaaaaaata agtgtataca aattttaaag tgactcttag gttttaaaac    8460
gaaaattctt attcttgagt aactctttcc tgtaggtcag gttgctttct caggtatagt    8520
atgaggtcgc tcttattgac cacacctcta ccggcagatc cgctagggat aacagggtaa    8580
tatagttccc tttagtgctc gagggggggc ccggtaccca attcgcccta tagtgagtcg    8640
tattacgcgc gctcactggc cgtcgtttta caacgtcgtg actgggaaaa ccctggcgtt    8700
acccaactta atcgccttgc agcacatccc cctttcgcca gctggcgtaa tagcgaagag    8760
gcccgcaccg atcgcccttc ccaacagttg cgcagcctga atggcgaatg gcgcgacgcg    8820
ccctgtagcg gcgcattaag cgcggcgggt gtggtggtta cgcgcagcgt gaccgctaca    8880
cttgccagcg ccctagcgcc cgctcctttc gctttcttcc cttcctttct cgccacgttc    8940
gccggctttc cccgtcaagc tctaaatcgg gggctccctt tagggttccg atttagtgct    9000
ttacggcacc tcgaccccaa aaaacttgat tagggtgatg gttcacgtag tgggccatcg    9060
ccctgataga cggttttttcg ccctttgacg ttggagtcca cgttctttaa tagtggactc    9120
ttgttccaaa ctggaacaac actcaaccct atctcggtct attctttga tttataaggg    9180 attttgccga tttcggccta ttggttaaaa aatgagctga tttaacaaaa atttaacgcg    9240
aattttaaca aaatattaac gtttacaatt tcctgatgcg gtattttctc cttacatctg    9300
tgcggtattt cacaccgcat atgaatggtc aggtcattga gtgtttttta tttgttgtat    9360
tttttttttt ttagagaaaa tcctccaata tcaaattagg aatcgtagtt tcatgatttt    9420
ctgttacacc taacttttg tgtggtgccc tcctccttgt caatattaat gttaaagtgc    9480
aattcttttt ccttatcacg ttgagccatt agtatcaatt tgcttacctg tattccttta    9540
ctatcctcct ttttctcctt cttgataaat gtatgtagat tgcgtatata gtttcgtcta    9600
ccctatgaac atattccatt ttgtaatttc gtgtcgtttc tattatgaat ttcatttata    9660
aagtttatgt acaaatatca taaaaaaaga gaatcttttt aagcaaggat tttcttaact    9720
tcttcggcga cagcatcacc gacttcggtg gtactgttgg aaccacctaa atcaccagtt    9780
ctgatacctg catccaaaac cttttttaact gcatcttcaa tggccttacc ttcttcaggc    9840 aagtcaatg acaatttcaa catcattgca gcagacaaga tagtggcgat agggtcaacc    9900
ttattctttg gcaaatctgg agcagaaccg tggcatggtt cgtacaaacc aaatgcggtg    9960
ttcttgtctg gcaaagaggc caaggacgca gatggcaaca acccaaggaa acctgggata    10020
acggaggctt catcggagat gatatcacca aacatgttgc tggtgattat aataccattt    10080
aggtgggttg ggttcttaac taggatcatg gcggcagaat caatcaattg atgttgaacc    10140
ttcaatgtag ggaattcgtt cttgatggtt tcctccacag tttttctcca taatcttgaa    10200
gaggccaaaa cattagcttt atccaaggac caaataggca atggtggctc atgttgtagg    10260
gccatgaaag cggccattct tgtgattctt tgcacttctg gaacggtgta ttgttcacta    10320
```

```
tcccaagcga caccatcacc atcgtcttcc tttctcttac caaagtaaat acctcccact    10380
aattctctga caacaacgaa gtcagtacct ttagcaaatt gtggcttgat tggagataag    10440
tctaaaagag agtcggatgc aaagttacat ggtcttaagt tggcgtacaa ttgaagttct    10500
ttacggattt ttagtaaacc ttgttcaggt ctaacactac cggtaccccca tttaggacca    10560 cccacagcac ctaacaaaac ggcatcaacc ttcttggagg cttccagcgc ctcatctgga    10620
agtgggacac ctgtagcatc gatagcagca ccaccaatta aatgattttc gaaatcgaac    10680
ttgacattgg aacgaacatc agaaatagct ttaagaacct taatggcttc ggctgtgatt    10740
tcttgaccaa cgtggtcacc tggcaaaacg acgatcttct tagggcaga cattagaatg     10800 gtatatcctt gaaatatata tatatatatt gctgaaatgt aaaaggtaag aaaagttaga    10860
aagtaagacg attgctaacc accatatgga gcttagctac aaatcccact ggctatatgt    10920
atcaatgata ttcgaatacg ctttgaggag atacagccta atatccgaca aactgtttta    10980
cagatttacg atcgtacttg ttacccatca ttgaattttg aacatccgaa cctgggagtt    11040
ttccctgaaa cagatagtat atttgaacct gtataataat atatagtcta gcgctttacg    11100
gaagacaatg tatgtatttc ggttcctgga gaaactattg catctattgc ataggtaatc    11160
ttgcacgtcg catccccggt tcattttctg cgtttccatc ttgcacttca atagcatatc    11220
tttgttaacg aagcatctgt gcttcatttt gtagaacaaa aatgcaacgc gagagcgcta    11280
atttttcaaa caaagaatct gagctgcatt tttacagaac agaaatgcaa cgcgaaagcg    11340
ctattttacc aacgaagaat ctgtgcttca ttttttgtaaa acaaaaatgc aacgcgagag    11400
cgctaatttt tcaaacaaag aatctgagct gcattttac agaacagaaa tgcaacgcga    11460
gagcgctatt ttaccaacaa agaatctata cttctttttt gttctacaaa aatgcatccc    11520
gagagcgcta tttttctaac aaagcatctt agattacttt ttttctcctt tgtgcgctct    11580
ataatgcagt ctcttgataa cttttttgcac tgtaggtccg ttaaggttag aagaaggcta    11640
ctttggtgtc tattttctct tccataaaaa aagcctgact ccacttcccg cgtttactga    11700
ttactagcga agctgcgggt gcatttttc aagataaagg catccccgat tatattctat     11760
accgatgtgg attgcgcata ctttgtgaac agaaagtgat agcgttgatg attcttcatt    11820
ggtcagaaaa ttatgaacgg ttttcttctat tttgtctcta tatactacgt ataggaaatg    11880
tttacatttt cgtattgttt tcgattcact ctatgaatag ttcttactac aattttttg     11940 tctaaagagt aatactagag ataaacataa aaaatgtaga ggtcgagttt agatgcaagt    12000
tcaaggagcg aaaggtggat gggtaggtta tataggata tagcacagag atatatagca     12060
aagagatact tttgagcaat gtttgtggaa gcggtattcg caatatttta gtagctcgtt    12120
acagtccggt gcgttttttgg tttttgaaa gtgcgtcttc agagcgcttt tggttttcaa    12180
aagcgctctg aagttcctat actttctagc tagagaatag gaacttcgga ataggaactt    12240
caaagcgttt ccgaaaacga gcgcttccga aaatgcaacg cgagctgcgc acatacagct    12300
cactgttcac gtcgcaccta tatctgcgtg ttgcctgtat atatatatac atgagaagaa    12360
cggcatagtg cgtgtttatg cttaaatgcg tacttatatg cgtctattta tgtaggatga    12420
aaggtagtct agtacctcct gtgatattat cccattccat gcggggtatc gtatgcttcc    12480
ttcagcacta cccttttagct gttctatatg ctgccactcc tcaattggat tagtctcatc    12540
cttcaatgct atcattttcct ttgatattgg atcgatccga tgataagctg tcaaacatga    12600
gaatttcgag ctcgaattca tcgatttaaa ctggatggcg gcgttagtat cgaatcgaca    12660
```

| | |
|---|---|
| gcagtatagc gaccagcatt cacatacgat tgacgcatga tattactttc tgcgcactta | 12720 |
| acttcgcatc tgggcagatg atgtcgaggc gaaaaaaaat ataaatcacg ctaacatttg | 12780 |
| attaaaatag aacaactaca atataaaaaa actatacaaa tgacaagttc ttgaaaacaa | 12840 |
| gaatcttttt attgtcagta ctctttattt gtacaattca tccataccat gggtaatacc | 12900 |
| agcagcagta acaaattcta acaagaccat gtggtctctc ttttcgtttg gatctttgga | 12960 |
| taaggcagat tgagtggata agtaatggtt gtctggtaac aagactggac catcaccaat | 13020 |
| tggagtattt tgttgataat ggtcagctaa ttgaacagaa ccatcttcaa tgttgtgtct | 13080 |
| aattttgaag ttaactttga taccattctt ttgtttgtca gccatgatgt aaacattgtg | 13140 |
| agagttatag ttgtattcca atttgtgacc taaaatgtta ccatcttctt taaaatcaat | 13200 |
| accttttaat tcgattctat taactaaggt atcaccttca aacttgactt cagctctggt | 13260 |
| cttgtagtta ccgtcatctt tgaaaaaaat agttctttct tgaacataac cttctggcat | 13320 |
| ggcagacttg aaaagtcat gttgtttcat atgatctggg tatctagaaa acattgaac | 13380 |
| accataagtt aaagtagtga ctaaggttgg ccatggaact ggcaatttac cagtagtaca | 13440 |
| aataaatttt aaggtcaatt taccgtaagt agcatcacct tcaccttcac cggagacaga | 13500 |
| aaatttgtga ccattaacat caccatctaa ttcaaccaaa attgggacaa caccagtgaa | 13560 |
| taattcttca cctttagaca tgttaattaa accagcaccg tcaccgtttt gctggccgca | 13620 |
| tcttctcaaa tatgcttccc agcctgcttt tctgtaacgt tcaccctcta ccttagcatc | 13680 |
| ccttcccttt gcaaatagtc ctcttccaac aataataatg tcagatcctg tagagaccac | 13740 |
| atcatccacg ttctatact gttgacccaa tgcgtctccc ttgtcatcta aacccacacc | 13800 |
| gggtgtcata atcaaccaat cgtaaccttc atctcttcca cccatgtctc tttgagcaat | 13860 |
| aaagccgata acaaaatctt tgtcgctctt cgcaatgtca acagtaccct tagtatattc | 13920 |
| tccagtagat agggagccct tgcatgacaa ttctgctaac atcaaaaggc ctctaggttc | 13980 |
| ctttgttact tcttctgccg cctgcttcaa accgctaaca atacctgggc ccaccacacc | 14040 |
| gtgtgcattc gtaatgtctg cccattctgc tattctgtat acacccgcag agtactgcaa | 14100 |
| tttgactgta ttaccaatgt cagcaaattt tctgtcttcg aagagtaaaa aattgtactt | 14160 |
| ggcggataat gccttagcg gcttaactgt gccctccatg gaaaaatcag tcaagatatc | 14220 |
| cacatgtgtt tttagtaaac aaattttggg acctaatgct tcaactaact ccagtaattc | 14280 |
| cttggtggta cgaacatcca atgaagcaca caagtttgtt tgcttttcgt gcatgatatt | 14340 |
| aaatagcttg gcagcaacag gactaggatg agtagcagca cgttcctat atgtagctttt | 14400 |
| cgacatgatt tatcttcgtt tcctgcatgt ttttgttctg tgcagttggg ttaagaatac | 14460 |
| tgggcaattt catgtttctt caacactaca tatgcgtata tataccaatc taagtctgtg | 14520 |
| ctccttcctt cgttcttcct tctgttcgga gattaccgaa tcaaaaaaat ttcaaagaaa | 14580 |
| ccgaaatcaa aaaaagaat aaaaaaaaaa tgatgaattg aattgaaaag ctaattcttg | 14640 |
| aagacgaaag ggcctcgtga tacgcctatt tttataggtt aatgtcatga taataatggt | 14700 |
| ttctta | 14706 |

<210> SEQ ID NO 36
<211> LENGTH: 6784
<212> TYPE: DNA
<213> ORGANISM: Chaetomium globosum

<400> SEQUENCE: 36

| | |
|---|---|
| atggaggagg ccatgctcga cgaaagctgg gctgagcggc cggcattcct cctctttggg | 60 |

-continued

```
gaccagtctc tcgacagtca tggcttttc gctcaattct accgccaatc caaacacggc      120
gagctagcaa gggtcttctt gcagcaggcg aaccacgccc tgctgggtgt ggtcgagaag      180
ctccctgctt tggagcgagc aacactcccc aatttccgaa cattgcggca gctcaacgaa      240
caatatcata gcacggaaca gaagcactcc ggaattgacg cggcgctgtt gacaatatcg      300
caaattgcgc actacctcga gtgagtctac cctatctagc tgagcacacc gcttttttac      360
gtctgttgtt ttggctcgcc ccctctgacc acggcacttt tagtcacgct gaaaagaact      420
gtggcgatat cacacggcct cataagactt ttctcgtcgg gctttgctct gggctctggg      480
ccgcagccgc tgtctcggtg gcgccctcgc tcccagacct ggttcatatc ggcgtccaag      540
ccgttctctt ggctttcaag acgggttcct acgttcacgc cattggggaa cggttgagcc      600
cggcgtttga gcgttctgaa agctggagct acatcttctc ggtgtcgagc gttgaggatg      660
tcacccaaac gttggacgct tttcacgata cctcggtgag tagcccgcca accccggcc       720 gccgtgccca gttgggccgc ataactaaca cgctgtttaa tagaaccttc ctcctgctag      780
ccgcgcgtat attagcgcgg tatccgataa tggtattgta gtatctggtc caccgagcac      840
gctagatgcg atagtcaaca acaagatctt tccgcctaac ccgatcgcca ttccggttca      900
tggcccctac cacgcgccac atttgcattc caccgcagac atcgaaagaa ttttagagct      960
tgacaaccca gaaacgaagg acgccttcta caagacgtca ccgcgatcgc ccatcatgga     1020
ctgctcaacc gggacatggt tctcccccat ggacacgaaa tcgctcctga tatcggtcgc     1080
ctctaccatc ttgaacaaag gattgatgtt caaaaaggtt ctcaacggtt gcgtcgaggc     1140
tgctcgccta tttcaagacg acaagtgcct cgtaatcccc cttggtccaa cccaaaatcc     1200
gtctacgctt aagaggcgcc tccagcagga gactggattg gaagtcactc ttcgcatgcc     1260
gcctcctatt tcatcggagg caacggcatc caagataggg aaccacggat caagcgggaa     1320
gcccaagctt gccattgtcg gcatggcagg gcgattccct gacgctgcca gccacgaagc     1380
cctgtggaaa ctgctggaaa gtggcctcgc tgtccatcgt gaggcgccac cggatcgctt     1440
caatgtcaag acgcacgttg atccctccgg caaaggaaag aacatgagcc acactccata     1500
cggctgctgg atcaaagacc cgggtctgtt tgaccaccgc gtcttcaaca tgtcgccgcg     1560
cgaggcgcgc aacacagacc ctatgcagag gatggctttg accacggcgt acgaggctct     1620
agagatgtcg ggatacgtcc ccaacaggac gccgtccaca aggcttgatc ggatcggtac     1680
cttctatggc cagacctcgg acgattggcg cgaaataaat gctgcccagg acgtggacac     1740
gtacttcatc acgggaggtg tccgcgcctt tggacctggc cgcatcaact atcactttgg     1800
cttcagcggg ccgagcctca acattgatac cgcttgctcc tccagcgcgg ctgccatgca     1860
ggtggcatgc tcgcgctct gggcccgaga ttgcgacacg gccatcgtcg gcggcctgtc      1920
gtgcatgacc aacccggaca tcttcgccgg actcagtaaa ggccagttcc tgtcaaagaa     1980
agggccatgc gctacctttg acaatgatgc cgatgggtac tgccgcggtg acggctgtgc     2040
atccgtcgtc gtcaagcgtc tggatgacgc cctggccgac caagacaggg ttctcgccgt     2100
catcctcggc accgcaacca accactcagc ggatgctatc tccatcacgc atccccacgg     2160
gccgacgcag tcgatcctgt ccacagccat tctcgacgag gccggagttg atccccatga     2220
tgttgactac gtggagatgc acggcaccgg cacccaggct ggagacggca ccgagatgaa     2280
gtcggtcacc gacatctttg cgcccgcaaa ccggccgagg cccgaagaca gaccactctt     2340
tctcggagca gtcaaagcaa acgtcgggca cggcgaagcc gcttccggag ttaccgccct     2400
```

-continued

```
catcaaggta ctcctgatgc ttgagaagaa cactatccca ccccatgtcg ggatccagaa    2460
cggcggggag atcaacaaga cgttccctaa ggactttgtc gcccggaacg tcaacattgc    2520
attccgtcca gttcccttca gaagaaggga tggcaagccc aggcgcgtct tcgtgaacaa    2580
cttcagcgcc gcgggtggta acactggtct cctagtcgag gaccccccga caattccgcg    2640
cgcgaaaccg gatcctcgca cccaccacgt tatcactttg tcgggcggg tctgggagtc     2700
cgtgaaggga aatgctgaac gtctcctcga gtggacggag cggaaccgcg acacaccgct    2760
ctcgcacatt tcttacagca caacagcaag aaagctgcac cacgtctgcc gtatgagcgt    2820
gacgggcagg gatattggag atttacaggc ggccctcaga gaacgcatca gggacctgga    2880
cctgaatcaa gctgtaccgg tcccgcatca gccgagagtg gtcatgatgt tcacggggca    2940
agggtcgcaa tacgccgcaa tggggaagga gttttacgac cactactcgg tgttccgcga    3000
gagcatcgac ggcttcattg acctggcccg cctgcagggc ttccctctct ttctccctct    3060
cattgatggc accgaccaga acttgtccga gatgtcaccc atcgtgttgc aacttggctt    3120
ggcatgcttc gagatggccg ccgcccgcct ctgggcttcg tggggaatca gcccgccgc    3180
cgtcgtgggc cacagcctgg gagagtatgc cgctctcgaa gtagctggcg tgctctcggc    3240
tagcgatgtc atttatctag tcggttctcg tgccaagctg ctcgtcgaaa gtgccaatc    3300
tggcagccac ggcatggtcg ccgtccaagc cccggtcgag acggtcttgg aactgatggg    3360
caccgaagct gatggcttaa acatcgcctg catcaacagc ctccgcgaga ccgtcattag    3420
cggcgagact gaaaagtcaa aggatatggc cacctatatg agcgaccagg gttacaagtc    3480
caaccacctg cgtgtgccct tcgctttcca ctctccccag gtggaagtta ttttggatga    3540
ttttgagaag ctcgcacagg gcgttaccta caaaaccccc aagatcccca tcatctccac    3600
agtccatgga aaggtcatcc agggcaagtc gatcgatgct gggtacctgc gcaaacacgc    3660
gcgagacaca gtctacttcc tcgacgggct tatcgaggct cagaagtcga gcaccatcga    3720
tgacaagacc gtttggctcg agatgggccc tcacccggtt ctttcggcca tggtcaaggc    3780
tacatttggc gctagtacgg tagcggttcc cacactacgc cgtactgagc cctgttacaa    3840
gacgttgacg agcacgctcg ccaccttgca caacgcgcac ctcaagataa acttcaacga    3900
atatcaccgc gatttcgccg actcggtgcg tctgttgaat ttgcccacgt attccttcaa    3960
cgatgacaac tactgatcc agtacgcggg cgattggtgt ctcgcgaagc acaacctctc    4020
ggtcgctgca gcggaacaaa agcctgtaac gccctgggtc gccacgacga cagtccacaa    4080
gctcaacaga gaaattgtcg aaggtggcgt ggcgatcgtc gagaccgagt ccgagctcta    4140
ccaagagcaa cttcgaaatg tggtctgtgg ccaccaggtc aacggcgccc ccctgtgccc    4200
atcatcgctg tacggcgaca tggccatgac cgtgtgcgac tatgcctaca gcttctgcg    4260
gcctcagtca acgggcatcg gctgtaacgt cgcggatatg caggtcttta agccgctcat    4320
ctttgacgac aaagccaaaa gtcacatcct tcggttgaca gtgactgcta atgccgaggc    4380
tggcgaagcc gacctggtct tccacacggc tcaagatggc aagaaagtcg agcatgctca    4440
ctgcaaagtc tactacggca atcatgacga gtggcaggac gagttcgacc gggccgccta    4500
ccttatcaag tcccgtgtcg acttccttgt ggaggcagaa aaacgtggtg ccgcctccaa    4560
gattggccgc ggcttggcgt acaagctctt ctccgccttg gtcgactacg gcacacgcta    4620
ccgcggcatg gaggaggtta ttcttgatag cactacttgt gaagcgacgg cgaagatccg    4680
cttccagacg acagcccagg atggaacctt ttacttcagc ccctaccata tcgacagcgc    4740
ttgccacatc tctggcttta tcatcaacgg caccgacgct gtggattcgc gtgaacgggt    4800
```

| | |
|---|---|
| cttcatctcc cacggctggg gctccatgag atttaccgag atcccggatg caaacaagga | 4860 |
| gtaccgcagt tacatccgga tgcagccggt gaagggcacc gagatgatgg ctggcgatgc | 4920 |
| gtacgtcttc gatggcgaca agatcattgg catgacgggc cgcatcaagt tccaagccat | 4980 |
| caagcgccac actctcaaca tgatgcttcc tccgcgaggg gcccaggcaa tctcgggccc | 5040 |
| agctccctcg gcgatcaaag cggcccctc taagaagaag aagaacgaga ctgtaaacgc | 5100 |
| ttccaacata gacagggtga accagaggct caagaccgtg acatcctcag tcatggatat | 5160 |
| ccttgtcaga gaaataggct gtagccacgg ggagctcgtt gacgacgcct cgtttgacaa | 5220 |
| tctcggcgct gattccctaa tggctctaca agtctcttcc aagatacgcg aagagctaga | 5280 |
| actcgacatt gaagcgcaag cctggctcga ttaccctacc gtcggcgctt tcaaaaccta | 5340 |
| cctggccaac tttgagaagc caggtcgcaa agaaagggca ccatccacag ggtctgcaag | 5400 |
| aacgacagac gacgagtcac gcgaagttga atatgactcg gacgtcacga caccgaccga | 5460 |
| agccagtgtt accgattctg tcaagggaga tgcgcaggac gacgtcgagc caggcgactc | 5520 |
| tgcccagaac caggaacttc gaaccatcat ccgcgaatcc attgccacgg aagcgggcgt | 5580 |
| ggacgtgcag gaagtcatta gcgcgtccga ctggacgagt ctcggggtgg actctctctt | 5640 |
| gggtttagga atcagtagcc gaattcgtga gctagctggc atagaggtcc ccaacgatct | 5700 |
| cttccttgag cacccaacgc tcaaagatgt ggagcgcgtt ttgggcgtca ccgacgtccc | 5760 |
| caaaaagccc gccacccgcc aacggaaaag caccaaggaa aagctcaaag cacccccgc | 5820 |
| tgcagcctcc gctaaggagc atcctcggat ttctttggag gaaccgccc ctccaaaacc | 5880 |
| gccgagacct agccacattg tcgacaagta ccccaccgc atcgagtt cagtcctcct | 5940 |
| gtctggggct tcccgcgacc aaaccaaaca actctttatg atcccggatg gcagcggatc | 6000 |
| tgccacgtcg tataccgaaa tcgccaaagt cggtggcggg tggtgtgtct ggggtctttt | 6060 |
| ctcgcccttc atgagggcgc ccgaggagta tcagtgtggt gtctatggca tggccgccaa | 6120 |
| gtttatcgac cagatgaagt accgccagcc ccatggcccg tactcacttg cgggttggag | 6180 |
| tgccggcggc gtcattgcat tcgaaatagt ctaccaattg gtccaggccg gggaagaggt | 6240 |
| cgcgaacctg atcatcatcg atgccccttg cccctcaca attgaaccgc ttccgcaggg | 6300 |
| gcttcacgcg tggttcgcgt caattggcct gctcggcgaa ggcaacgaca agaagattcc | 6360 |
| agagtggttg cttccccact tgccgcctc catcacagcc ctcagcgagt acgatgccag | 6420 |
| accgattccc aaagacaaat gccccaatgt catggcaatc tggtgtgagg atggtgtatg | 6480 |
| ccatctaccc accgatccca ggccagagcc gtatccaaag ggccacgccc tcttcctgct | 6540 |
| ggaaaaccgc accgactttg ggccaaacag atgggaggag tgtttggacg tcgaccgcat | 6600 |
| gcagttcagg cacatgcctg caaccactt ctccatgatc catggcgatc aggtatgttg | 6660 |
| tgtcttttta ctcgggctcc atctattcat agcaccccac ttcaagaggc caagaaacat | 6720 |
| gctaactcgg gcgacacagg ccaaaattct tgaaggtttt ttgcgggagg ctcttctgga | 6780 |
| ttga | 6784 |

<210> SEQ ID NO 37
<211> LENGTH: 320
<212> TYPE: DNA
<213> ORGANISM: Chaetomium globosum

<400> SEQUENCE: 37

| | |
|---|---|
| atggaggagg ccatgctcga cgaaagctgg gctgagcggc cggcattcct cctctttggg | 60 |

```
gaccagtctc tcgacagtca tggctttttc gctcaattct accgccaatc caaacacggc    120
gagctagcaa gggtcttctt gcagcaggcg aaccacgccc tgctgggtgt ggtcgagaag    180
ctccctgctt tggagcgagc aacactcccc aatttccgaa cattgcggca gctcaacgaa    240
caatatcata gcacggaaca gaagcactcc ggaattgacg cggcgctgtt gacaatatcg    300
caaattgcgc actacctcga                                                320

<210> SEQ ID NO 38
<211> LENGTH: 292
<212> TYPE: DNA
<213> ORGANISM: Chaetomium globosum

<400> SEQUENCE: 38
tcacgctgaa aagaactgtg gcgatatcac acggcctcat aagactttc tcgtcgggct      60 ttgctctggg ctctgggccg cagccgctgt ctcggtggcg ccctcgctcc cagacctggt    120
tcatatcggc gtccaagccg ttctcttggc tttcaagacg ggttcctacg ttcacgccat    180
tggggaacgg ttgagcccgg cgtttgagcg ttctgaaagc tggagctaca tcttctcggt    240
gtcgagcgtt gaggatgtca cccaaacgtt ggacgctttt cacgatacct cg           292

<210> SEQ ID NO 39
<211> LENGTH: 5889
<212> TYPE: DNA
<213> ORGANISM: Chaetomium globosum

<400> SEQUENCE: 39
aaccttcctc ctgctagccg cgcgtatatt agcgcggtat ccgataatgg tattgtagta     60
tctggtccac cgagcacgct agatgcgata gtcaacaaca agatctttcc gcctaacccg    120
atcgccattc cggttcatgg cccctaccac gcgccacatt tgcattccac cgcagacatc    180
gaaagaattt tagagcttga caacccagaa acgaaggacg ccttctacaa gacgtcaccg    240
cgatcgccca tcatggactg ctcaaccggg acatggttct cccccatgga cacgaaatcg    300
ctcctgatat cggtcgcctc taccatcttg aacaaggat tgatgttcaa aaaggttctc    360
aacggttgcg tcgaggctgc tcgcctattt caagacgaca agtgcctcgt aatccccctt    420
ggtccaaccc aaaatccgtc tacgcttaag aggcgcctcc agcaggagac tggattggaa    480
gtcactcttc gcatgccgcc tcctatttca tcggaggcaa cggcatccaa gatagggaac    540
cacggatcaa gcgggaagcc caagcttgcc attgtcggca tggcagggcg attccctgac    600
gctgccagcc acgaagccct gtggaaactg ctggaaagtg gcctcgctgt ccatcgtgag    660
gcgccaccgg atcgcttcaa tgtcaagacg cacgttgatc cctccggcaa aggaaagaac    720
atgagccaca ctccatacgg ctgctggatc aaagacccgg gtctgtttga ccaccgcgtc    780
ttcaacatgt cgccgcgcga ggcgcgcaac acagaccta tgcagaggat ggctttgacc    840
acggcgtacg aggctctaga gatgtcggga tacgtcccca caggacgcc gtccacaagg    900 cttgatcgga tcggtacctt ctatggccag acctcggacg attggcgcga aataaatgct    960
gcccaggacg tggacacgta cttcatcacg ggaggtgtcc gcgcctttgg acctggccgc   1020
atcaactatc actttggctt cagcgggccg agcctcaaca ttgataccgc ttgctcctcc   1080
agcgcggctg ccatgcaggt ggcatgctcg gcgctctggg cccgagattg cgacacggcc   1140
atcgtcggcg gcctgtcgtg catgaccaac ccggacatct tcgccggact cagtaaaggc   1200
cagttcctgt caaagaaagg gccatgcgct acctttgaca atgatgccga tgggtactgc   1260
cgcggtgacg gctgtgcatc cgtcgtcgtc aagcgtctgg atgacgccct ggccgaccaa   1320
```

```
gacagggttc tcgccgtcat cctcggcacc gcaaccaacc actcagcgga tgctatctcc    1380
atcacgcatc cccacgggcc gacgcagtcg atcctgtcca cagccattct cgacgaggcc    1440
ggagttgatc cccatgatgt tgactacgtg gagatgcacg gcaccggcac ccaggctgga    1500
gacggcaccg agatgaagtc ggtcaccgac atctttgcgc ccgcaaaccg gccgaggccc    1560
gaagacagac cactctttct cggagcagtc aaagcaaacg tcgggcacgg cgaagccgct    1620
tccggagtta ccgccctcat caaggtactc ctgatgcttg agaagaacac tatcccaccc    1680
catgtcggga tccagaacgg cggggagatc aacaagacgt ccctaagga ctttgtcgcc    1740
cggaacgtca acattgcatt ccgtccagtt cccttcagaa gaagggatgg caagcccagg    1800
cgcgtcttcg tgaacaactt cagcgccgcg ggtggtaaca ctggtctcct agtcgaggac    1860
cccccgacaa ttccgcgcgc gaaaccggat cctcgcaccc accacgttat cactttgtcg    1920
gggcgggtct gggagtccgt gaagggaaat gctgaacgtc tcctcgagtg gacggagcgg    1980
aaccgcgaca caccgctctc gcacatttct tacagcacaa cagcaagaaa gctgcaccac    2040
gtctgccgta tgagcgtgac gggcagggat attggagatt tacaggcggc cctcagagaa    2100
cgcatcaggg acctggacct gaatcaagct gtaccggtcc cgcatcagcc gagagtggtc    2160
atgatgttca cggggcaagg gtcgcaatac gccgcaatgg ggaaggagtt ttacgaccac    2220
tactcggtgt tccgcgagag catcgacggc ttcattgacc tggcccgcct gcagggcttc    2280
ccctcttttc tccctctcat tgatggcacc gaccagaact tgtccgagat gtcacccatc    2340
gtgttgcaac ttggcttggc atgcttcgag atggccgccg cccgcctctg gcttcgtgg    2400
ggaatcaagc ccgccgccgt cgtgggccac agcctgggag agtatgccgc tctcgaagta    2460
gctggcgtgc tctcggctag cgatgtcatt tatctagtcg gttctcgtgc caagctgctc    2520
gtcgaaaagt gccaatctgg cagccacggc atggtcgccg tccaagcccc ggtcgagacg    2580
gtcttggaac tgatgggcac cgaagctgat ggcttaaaca tcgcctgcat caacagcctc    2640
cgcgagaccg tcattagcgg cgagactgaa aagtcaaagg atatggccac ctatatgagc    2700
gaccagggtt acaagtccaa ccacctgcgt gtgcccttcg ctttccactc tccccaggtg    2760
gaagttattt tggatgattt tgagaagctc gcacagggcg ttacctacaa acccccaag    2820
atccccatca tctccacagt ccatggaaag gtcatccagg gcaagtcgat cgatgctggg    2880
tacctgcgca aacacgcgcg agacacagtc tacttcctcg acgggcttat cgaggctcag    2940
aagtcgagca ccatcgatga caagaccgtt tggctcgaga tgggccctca cccggttctt    3000
tcggccatgg tcaaggctac atttggcgct agtacggtag cggttcccac actacgccgt    3060
actgagccct gttacaagac gttgacgagc acgctcgcca ccttgcacaa cgcgcacctc    3120
aagataaact tcaacgaata tcaccgcgat ttcgccgact cggtgcgtct gttgaatttg    3180
cccacgtatt ccttcaacga tgacaactac tggatccagt acgcgggcga ttggtgtctc    3240
gcgaagcaca acctctcggt cgctgcagcg gaacaaaagc ctgtaacgcc ctgggtcgcc    3300
acgacgacag tccacaagct caacagagaa attgtcgaag gtggcgtggc gatcgtcgag    3360
accgagtccg agctctacca agagcaactt cgaaatgtgg tctgtggcca ccaggtcaac    3420
ggcgccccc tgtgcccatc atcgctgtac ggcgacatgg ccatgaccgt gtgcgactat    3480
gcctacaagc ttctgcggcc tcagtcaacg ggcatcggct gtaacgtcgc ggatatgcag    3540
gtctttaagc cgctcatctt tgacgacaaa gccaaaagtc acatccttcg gttgacagtg    3600
actgctaatg ccgaggctgg cgaagccgac ctggtcttcc acacggctca agatggcaag    3660
```

```
aaagtcgagc atgctcactg caaagtctac tacggcaatc atgacgagtg gcaggacgag    3720
ttcgaccggg ccgcctacct tatcaagtcc cgtgtcgact tccttgtgga ggcagaaaaa    3780
cgtggtgccg cctccaagat tggccgcggc ttggcgtaca agctcttctc cgccttggtc    3840
gactacggca cacgctaccg cggcatggag gaggttattc ttgatagcac tacttgtgaa    3900
gcgacggcga agatccgctt ccagacgaca gcccaggatg gaacctttta cttcagcccc    3960
taccatatcg acagcgcttg ccacatctct ggctttatca tcaacggcac cgacgctgtg    4020
gattcgcgtg aacgggtctt catctcccac ggctggggct ccatgagatt taccgagatc    4080
ccggatgcaa acaaggagta ccgcagttac atccggatgc agccggtgaa gggcaccgag    4140
atgatggctg gcgatgcgta cgtcttcgat ggcgacaaga tcattggcat gacgggccgc    4200
atcaagttcc aagccatcaa gcgccacact ctcaacatga tgcttcctcc gcagggggcc    4260
caggcaatct cgggcccagc tccctcggcg atcaaagcgg ccccctctaa gaagaagaag    4320
aacgagactg taaacgcttc caacatagac agggtgaacc agaggctcaa gaccgtgaca    4380
tcctcagtca tggatatcct tgtcagagaa ataggctgta ccacgggga gctcgttgac    4440 gacgcctcgt ttgacaatct cggcgctgat tccctaatgg ctctacaagt ctcttccaag    4500
atacgcgaag agctagaact cgacattgaa gcgcaagcct ggctcgatta ccctaccgtc    4560
ggcgctttca aaacctacct ggccaacttt gagaagccag gtcgcaaaga aagggcacca    4620
tccacagggt ctgcaagaac gacagacgac gagtcacgcg aagttgaata tgactcggac    4680
gtcacgacac cgaccgaagc cagtgttacc gattctgtca agggagatgc gcaggacgac    4740
gtcgagccag gcgactctgc ccagaaccag gaacttcgaa ccatcatccg cgaatccatt    4800
gccacggaag cgggcgtgga cgtgcaggaa gtcattagcg cgtccgactg gacgagtctc    4860 gggg tggact ctctcttggg tttaggaatc agtagccgaa ttcgtgagct agctggcata    4920
gaggtcccca acgatctctt ccttgagcac ccaacgctca agatgtggga gcgcgttttg    4980
ggcgtcaccg acgtccccaa aaagcccgcc accgccaac ggaaaagcac caaggaaaag    5040
ctcaaagcac ccccgctgc agcctccgct aaggagcatc ctcggatttc tttggaggaa    5100
cccgcccctc caaaaccgcc gagacctagc cacattgtcg acaagtaccc ccaccgcaca    5160
tcgagttcag tcctcctgtc tggggcttcc cgcgaccaaa ccaaacaact ctttatgatc    5220
ccggatggca gcggatctgc cacgtcgtat accgaaatcg ccaaagtcgg tggcgggtgg    5280
tgtgtctggg gtcttttctc gcccttcatg agggcgcccg aggagtatca gtgtggtgtc    5340
tatggcatgg ccgccaagtt tatcgaccag atgaagtacc gccagcccca tggcccgtac    5400
tcacttgcgg gttggagtgc cggcggcgtc attgcattcg aaatagtcta ccaattggtc    5460
caggccgggg aagaggtcgc gaacctgatc atcatcgatg cccccttgccc cctcacaatt    5520 gaaccgcttc cgcaggggct tcacgcgtgg ttcgcgtcaa ttggcctgct cggcgaaggc    5580
aacgacaaga agattccaga gtggttgctt ccccactttg ccgcctccat cacagccctc    5640
agcgagtacg atgccagacc gattcccaaa gacaaatgcc ccaatgtcat ggcaatctgg    5700
tgtgaggatg gtgtatgcca tctacccacc gatcccaggc cagagccgta tccaaagggc    5760
cacgccctct tcctgctgga aaaccgcacc gactttgggc caaacagatg ggaggagtgt    5820
ttggacgtcg accgcatgca gttcaggcac atgcctggca accacttctc catgatccat    5880
ggcgatcag                                                           5889

<210> SEQ ID NO 40
<211> LENGTH: 45
```

```
<212> TYPE: DNA
<213> ORGANISM: Chaetomium globosum

<400> SEQUENCE: 40
gccaaaattc ttgaaggttt tttgcgggag gctcttctgg attga              45

<210> SEQ ID NO 41
<211> LENGTH: 60
<212> TYPE: DNA
<213> ORGANISM: Artificial Sequence
<220> FEATURE:
<223> OTHER INFORMATION: primer

<400> SEQUENCE: 41
tcttctggtc tggtgccacg cggttctggt atggaggagg ccatgctcga cgaaagctgg    60

<210> SEQ ID NO 42
<211> LENGTH: 49
<212> TYPE: DNA
<213> ORGANISM: Artificial Sequence
<220> FEATURE:
<223> OTHER INFORMATION: primer

<400> SEQUENCE: 42
atcgcaaatt gcgcactacc tcgatcacgc tgaaaagaac tgtggcgat              49

<210> SEQ ID NO 43
<211> LENGTH: 49
<212> TYPE: DNA
<213> ORGANISM: Artificial Sequence
<220> FEATURE:
<223> OTHER INFORMATION: primer

<400> SEQUENCE: 43
tatcgcaaat tgcgcactac ctcgatcacg ctgaaaagaa ctgtggcga              49

<210> SEQ ID NO 44
<211> LENGTH: 49
<212> TYPE: DNA
<213> ORGANISM: Artificial Sequence
<220> FEATURE:
<223> OTHER INFORMATION: primer

<400> SEQUENCE: 44
gttggacgct tttcacgata cctcgaacct tcctcctgct agccgcgcg              49

<210> SEQ ID NO 45
<211> LENGTH: 49
<212> TYPE: DNA
<213> ORGANISM: Artificial Sequence
<220> FEATURE:
<223> OTHER INFORMATION: primer

<400> SEQUENCE: 45
gttggacgct tttcacgata cctcgaacct tcctcctgct agccgcgcg              49

<210> SEQ ID NO 46
<211> LENGTH: 98
<212> TYPE: DNA
<213> ORGANISM: Artificial Sequence
<220> FEATURE:
<223> OTHER INFORMATION: primer

<400> SEQUENCE: 46
cttctccatg atccatggcg atcaggccaa aattcttgaa ggttttttgc gggaggctct    60
```
tctggatgga gccgttgctt taatcgtcgc acaccacc    98

<210> SEQ ID NO 47
<211> LENGTH: 6546
<212> TYPE: DNA
<213> ORGANISM: Chaetomium globosum

<400> SEQUENCE: 47

| | |
|---|---|
| atggaggagg ccatgctcga cgaaagctgg gctgagcggc cggcattcct cctctttggg | 60 |
| gaccagtctc tcgacagtca tggctttttc gctcaattct accgccaatc caaacacggc | 120 |
| gagctagcaa gggtcttctt gcagcaggcg aaccacgccc tgctgggtgt ggtcgagaag | 180 |
| ctccctgctt tggagcgagc aacactcccc aatttccgaa cattgcggca gctcaacgaa | 240 |
| caatatcata gcacggaaca gaagcactcc ggaattgacg cggcgctgtt gacaatatcg | 300 |
| caaattgcgc actacctcga tcacgctgaa aagaactgtg gcgatatcac acggcctcat | 360 |
| aagacttttc tcgtcgggct tgctctgggc tctgggccg cagccgctgt ctcggtggcg | 420 |
| ccctcgctcc cagacctggt tcatatcggc gtccaagccg ttctcttggc tttcaagacg | 480 |
| ggttcctacg ttcacgccat tggggaacgg ttgagcccgg cgtttgagcg ttctgaaagc | 540 |
| tggagctaca tcttctcggt gtcgagcgtt gaggatgtca cccaaacgtt ggacgctttt | 600 |
| cacgatacct cgaaccttcc tcctgctagc cgcgcgtata ttagcgcggt atccgataat | 660 |
| ggtattgtag tatctggtcc accgagcacg ctagatgcga tagtcaacaa caagatcttt | 720 |
| ccgcctaacc cgatcgccat tccggttcat ggcccctacc acgcgccaca tttgcattcc | 780 |
| accgcagaca tcgaaagaat tttagagctt gacaacccag aaacgaagga cgccttctac | 840 |
| aagacgtcac cgcgatcgcc catcatggac tgctcaaccg ggacatggtt ctcccccatg | 900 |
| gacacgaaat cgctcctgat atcggtcgcc tctaccatct tgaacaaagg attgatgttc | 960 |
| aaaaaggttc tcaacggttg cgtcgaggct gctcgcctat ttcaagacga caagtgcctc | 1020 |
| gtaatccccc ttggtccaac ccaaaatccg tctacgctta agaggcgcct ccagcaggag | 1080 |
| actggattgg aagtcactct tcgcatgccg cctcctattt catcggaggc aacggcatcc | 1140 |
| aagatagggga accacggatc aagcgggaag cccaagcttg ccattgtcgg catggcaggg | 1200 |
| cgattccctg acgctgccag ccacgaagcc ctgtggaaac tgctggaaag tggcctcgct | 1260 |
| gtccatcgtg aggcgccacc ggatcgcttc aatgtcaaga cgcacgttga tccctccggc | 1320 |
| aaaggaaaga acatgagcca cactccatac ggctgctgga tcaaagaccc gggtctgttt | 1380 |
| gaccaccgcg tcttcaacat gtcgccgcgc gaggcgcgca acacagaccc tatgcagagg | 1440 |
| atggctttga ccacggcgta cgaggctcta gagatgtcgg gatacgtccc caacaggacg | 1500 |
| ccgtccacaa ggcttgatcg gatcggtacc ttctatggcc agacctcgga cgattggcgc | 1560 |
| gaaataaatg ctgcccagga cgtggacacg tacttcatca cgggaggtgt ccgcgccttt | 1620 |
| ggacctggcc gcatcaacta tcactttggc ttcagcgggc cgagcctcaa cattgatacc | 1680 |
| gcttgctcct ccagcgcggc tgccatgcag gtggcatgct cggcgctctg ggcccgagat | 1740 |
| tgcgacacgg ccatcgtcgg cggcctgtcg tgcatgacca acccggacat cttcgccgga | 1800 |
| ctcagtaaag gccagttcct gtcaaagaaa gggccatgcg ctacctttga caatgatgcc | 1860 |
| gatgggtact gccgcggtga cggctgtgca tccgtcgtcg tcaagcgtct ggatgacgcc | 1920 |
| ctggccgacc aagacagggt tctcgccgtc atcctcggca ccgcaaccaa ccactcagcg | 1980 |
| gatgctatct ccatcacgca tcccacgggc ccgacgcagt cgatcctgtc cacagccatt | 2040 |
| ctcgacgagg ccggagttga tccccatgat gttgactacg tggagatgca cggcaccggc | 2100 |

```
acccaggctg gagacggcac cgagatgaag tcggtcaccg acatctttgc gcccgcaaac    2160
cggccgaggc ccgaagacag accactcttt ctcggagcag tcaaagcaaa cgtcgggcac    2220
ggcgaagccg cttccggagt taccgccctc atcaaggtac tcctgatgct tgagaagaac    2280
actatcccac cccatgtcgg gatccagaac ggcggggaga tcaacaagac gttccctaag    2340
gactttgtcg cccggaacgt caacattgca ttccgtccag ttcccttcag aagaagggat    2400
ggcaagccca ggcgcgtctt cgtgaacaac ttcagcgccg cgggtggtaa cactggtctc    2460
ctagtcgagg accccccgac aattccgcgc gcgaaaccgg atcctcgcac ccaccacgtt    2520
atcactttgt cggggcgggt ctgggagtcc gtgaagggaa atgctgaacg tctcctcgag    2580
tggacggagc ggaaccgcga cacaccgctc tcgcacattt cttacagcac aacagcaaga    2640
aagctgcacc acgtctgccg tatgagcgtg acgggcaggg atattggaga tttacaggcg    2700
gccctcagag aacgcatcag ggacctggac ctgaatcaag ctgtaccggt cccgcatcag    2760
ccgagagtgg tcatgatgtt cacggggcaa gggtcgcaat acgccgcaat ggggaaggag    2820
ttttacgacc actactcggt gttccgcgag agcatcgacg gcttcattga cctggcccgc    2880
ctgcagggct tcccctcttt tctccctctc attgatggca ccgaccagaa cttgtccgag    2940
atgtcaccca tcgtgttgca acttggcttg gcatgcttcg agatggccgc cgcccgcctc    3000
tgggcttcgt ggggaatcaa gcccgccgcc gtcgtgggcc acagcctggg agagtatgcc    3060
gctctcgaag tagctggcgt gctctcggct agcgatgtca tttatctagt cggttctcgt    3120
gccaagctgc tcgtcgaaaa gtgccaatct ggcagccacg gcatggtcgc cgtccaagcc    3180
ccggtcgaga cggtcttgga actgatgggc accgaagctg atggcttaaa catcgcctgc    3240
atcaacagcc tccgcgagac cgtcattagc ggcgagactg aaaagtcaaa ggatatggcc    3300
acctatatga gcgaccaggg ttacaagtcc aaccacctgc gtgtgcccct cgctttccac    3360
tctccccagg tggaagttat tttggatgat tttgagaagc tcgcacaggg cgttacctac    3420
aaaaccccca agatccccat catctccaca gtccatggaa aggtcatcca gggcaagtcg    3480
atcgatgctg ggtacctgcg caaacacgcg cgagacacag tctacttcct cgacgggctt    3540
atcgaggctc agaagtcgag caccatcgat gacaagaccg tttggctcga gatgggccct    3600 caccccggttc tttcggccat ggtcaaggct acatttggcg ctagtacggt agcggttccc    3660
acactacgcc gtactgagcc ctgttacaag acgttgacga gcacgctcgc caccttgcac    3720
aacgcgcacc tcaagataaa cttcaacgaa tatcaccgcg atttcgccga ctcggtgcgt    3780
ctgttgaatt tgcccacgta ttccttcaac gatgacaact actggatcca gtacgcgggc    3840
gattggtgtc tcgcgaagca caacctctcg gtcgctgcag cggaacaaaa gcctgtaacg    3900
ccctgggtcg ccacgacgac agtccacaag ctcaacagag aaattgtcga aggtggcgtg    3960
gcgatcgtcg agaccgagtc cgagctctac caagagcaac ttcgaaatgt ggtctgtggc    4020
caccaggtca acggcgcccc cctgtgccca tcatcgctgt acggcgacat ggccatgacc    4080
gtgtgcgact atgcctacaa gcttctgcgg cctcagtcaa cgggcatcgg ctgtaacgtc    4140
gcggatatgc aggtctttaa gccgctcatc tttgacgaca agccaaaaag tcacatcctt    4200
cggttgacag tgactgctaa tgccgaggct ggcgaagccg acctggtctt ccacacggct    4260
caagatggca agaaagtcga gcatgctcac tgcaaagtct actacggcaa tcatgacgag    4320
tggcaggacg agttcgaccg ggccgcctac cttatcaagt cccgtgtcga cttccttgtg    4380
gaggcagaaa acgtggtgc cgcctccaag attggccgcg gcttggcgta caagctcttc    4440
```

```
tccgccttgg tcgactacgg cacacgctac cgcggcatgg aggaggttat tcttgatagc    4500
actacttgtg aagcgacggc gaagatccgc ttccagacga cagcccagga tggaacctttt   4560 tacttcagcc cctaccatat cgacagcgct tgccacatct ctggctttat catcaacggc    4620
accgacgctg tggattcgcg tgaacgggtc ttcatctccc acggctgggg ctccatgaga    4680
tttaccgaga tcccggatgc aaacaaggag taccgcagtt acatccggat gcagccggtg    4740
aagggcaccg agatgatggc tggcgatgcg tacgtcttcg atggcgacaa gatcattggc    4800
atgacgggcc gcatcaagtt ccaagccatc aagcgccaca ctctcaacat gatgcttcct    4860
ccgcgagggg cccaggcaat ctcgggccca gctccctcgg cgatcaaagc ggcccctct    4920 aagaagaaga agaacgagac tgtaaacgct tccaacatag acagggtgaa ccagaggctc    4980
aagaccgtga catcctcagt catggatatc cttgtcagag aaataggctg tagccacggg    5040
gagctcgttg acgacgcctc gtttgacaat ctcggcgctg attccctaat ggctctacaa    5100
gtctcttcca agatacgcga agagctagaa ctcgacattg aagcgcaagc ctggctcgat    5160 tacccctaccg tcggcgcttt caaaacctac ctggccaact ttgagaagcc aggtcgcaaa   5220
gaaagggcac catccacagg gtctgcaaga acgacagacg acgagtcacg cgaagttgaa    5280
tatgactcga acgtcacgac accgaccgaa gccagtgtta ccgattctgt caagggagat    5340
gcgcaggacg acgtcgagcc aggcgactct gcccagaacc aggaacttcg aaccatcatc    5400
cgcgaatcca ttgccacgga agcgggcgtg gacgtgcagg aagtcattag cgcgtccgac    5460
tggacgagtc tcggggtgga ctctctcttg ggtttaggaa tcagtagccg aattcgtgag    5520
ctagctggca tagaggtccc caacgatctc ttccttgagc acccaacgct caaagatgtg    5580
gagcgcgttt tgggcgtcac cgacgtcccc aaaaagcccg ccacccgcca acggaaaagc    5640
accaaggaaa agctcaaagc accccccgct gcagcctccg ctaaggagca tcctcggatt    5700
tctttggagg aacccgcccc tccaaaaccg ccgagaccta gccacattgt cgacaagtac    5760
ccccaccgca catcgagttc agtcctcctg tctggggctt cccgcgacca aaccaaacaa    5820
ctctttatga tcccggatgg cagcggatct gccacgtcgt ataccgaaat cgccaaagtc    5880
ggtggcgggt ggtgtgtctg gggtcttttc tcgcccttca tgagggcgcc cgaggagtat    5940
cagtgtggtg tctatggcat ggccgccaag tttatcgacc agatgaagta ccgccagccc    6000 catgcccgt actcacttgc gggttggagt gccggcggcg tcattgcatt cgaaatagtc     6060
taccaattgg tccaggccgg ggaagaggtc gcgaacctga tcatcatcga tgccccttgc    6120 ccccctcacaa ttgaaccgct tccgcagggg cttcacgcgt ggttcgcgtc aattggcctg   6180
ctcggcgaag gcaacgacaa gaagattcca gagtggttgc ttccccactt tgccgcctcc    6240
atcacagccc tcagcgagta cgatgccaga ccgattccca aagacaaatg ccccaatgtc    6300
atggcaatct ggtgtgagga tggtgtatgc catctaccca ccgatcccag gccagagccg    6360
tatccaaagg gccacgccct cttcctgctg gaaaaccgca ccgactttgg gccaaacaga    6420
tgggaggagt gtttggacgt cgaccgcatg cagttcaggc acatgcctgg caaccacttc    6480
tccatgatcc atggcgatca ggccaaaatt cttgaaggtt ttttgcggga ggctcttctg    6540
gattga                                                               6546
```

HETEROLOGOUS EXPRESSION OF FUNGAL POLYKETIDE SYNTHETIC GENE IN YEAST AND A METHOD OF PREPARING A COMPOUND PRODUCED BY A PROTEAN ENCODED BY THE POLYKETIDE SYNTHETIC GENE BY THE HETEROLOGOUS EXPRESSION

TECHNICAL FIELD

The present invention relates to a method of preparing an expression vector containing linked sequences by removing introns from a eukaryotic gene containing the introns, and linking only the exon sequences. Specifically, it relates to a method of preparing an expression vector containing linked exon sequences comprising amplifying exon sequences as multiple fragments by PCR from a fungal giant gene containing introns, and linking the fragments with a vector that has been treated with a restriction enzyme using a gap repair cloning method; a method of preparing an expression vector containing a full-length cDNA sequence by synthesizing cDNA fragments from a giant gene and linking the fragments; a transformant having introduced therein an expression vector prepared by the method; a protein produced by the transformant; and a method of preparing a compound produced by the protein using the expression vector.

BACKGROUND ART

Analysis of fungal genome sequences has revealed the existence of a number of genes that are predicted to be biosynthetic genes for secondary metabolites, but production of a protein encoded by the gene (biosynthetic enzyme for secondary metabolite) has not been identified.

To obtain a protein encoded by a genome sequence, it is ordinarily necessary to first prepare mRNA, synthesize cDNA with reverse transcriptase, and then introduce the cDNA into an expression vector. In general, synthesis of full-length cDNA is quite difficult if a gene has a giant reading frame, so that there may be some reading frames that cannot be covered by cDNA libraries. Also it is difficult to introduce and express such a gene in a host that is different from the source organism (heterologous expression).

Many secondary metabolites have already been used as lead compounds for drugs, and examples of secondary metabolites that have been used in this way include natural polyketides and peptides. These natural products are known to be biosynthesized by polyketide synthases (PKS) and non-ribosomal peptide synthetases (NRPS), respectively (Non-Patent Documents 1 to 3).

Regarding the genes found in fungal genome sequences that are predicted to be biosynthetic genes for secondary metabolites, it is anticipated that the secondary metabolites synthesized by the proteins encoded by the genes will be useful. However, because fungi are eukaryotes and their genes contain introns, and the genes are very large, it is difficult to synthesize a full-length cDNA by conventional methods as described above. It has not been possible to synthesize the proteins encoded by genes that are predicted to be biosynthetic genes for secondary metabolites.

Accordingly, there is a need for methods for removing the introns from a fungal giant biosynthetic gene, and expressing a protein encoded by the gene.

Non-Patent Document 1: Leadlay, P. et al., Nature, 1990
Non-Patent Document 2: Katz, L. et al., Science, 1991
Non-Patent Document 3: Samson, S. et al., Nature, 1985
Non-Patent Document 4: Hisao Moriya et al., PLos ONE 2010

DISCLOSURE OF THE INVENTION

An object of the present invention is to extract only exon sequences from a fungal giant gene for which full-length cDNA cannot be synthesized with reverse transcriptase, and link these sequences to prepare an expression vector containing the linked sequences, and to synthesis and link cDNA fragments of such a giant gene to prepare an expression vector comprising a full-length cDNA sequence, and to express the protein encoded by the gene using the expression vector.

To achieve the objects, the inventors amplified by PCR the sequences that were predicted to be exon sequences in a hypothetical biosynthesis gene present in the genome of a fungus *Chaetomium globosum*, linked the exon sequences with a vector that had been treated with a restriction enzyme via homologous recombination in a budding yeast to prepare an expression vector, and expressed the expression vector in a yeast host system. That is, the inventors employed for the first time the gap repair cloning method to remove intron sequences from a gene, thereby achieving the present invention.

The present invention provides a method of preparing an expression vector by linking exon sequences of a eukaryotic gene containing an intron or from the genome sequence of a presumed eukaryotic gene containing an intron to form the expression vector containing the linked sequences, said method comprising the steps of:

(a) amplifying exon sequences from a genome extracted from a eukaryote by PCR to prepare multiple fragments, wherein the forward primer used in the PCR has, in order from the 5' end to the 3' end, a sequence complementary to the sequence of the 3' terminal part of the sense strand of a fragment to which the amplified fragment is to be linked, or a sequence complementary to the sequence of the 3' terminal part of the sense strand of a restriction enzyme-treated terminal part of the vector, and a sequence complementary to the sequence of the 5' terminal part of the sense strand of the fragment to be amplified, and wherein the reverse primer has, in order from the 5' end to the 3' end, a sequence complementary to the sequence of the 3' terminal part of the antisense strand of a fragment to which the amplified fragment is to be linked, or a sequence complementary to the sequence of the 3' terminal part of the antisense strand of a restriction enzyme-treated terminal part of the vector, and a sequence complementary to the sequence of the 5' terminal part of the antisense strand of the fragment to be amplified, whereby a sequence homologous to a terminal part of a fragment to be linked to the fragment to be amplified or a sequence homologous to a restriction enzyme-treated terminal part of the vector are added to the end of the fragment to be amplified; and (b) simultaneously transforming a budding yeast or fission yeast with the fragments obtained in the step (a) and a restriction enzyme-treated vector to obtain the expression vector containing fragments linked to the fragments and fragments linked to the vector that are joined via homologous recombination.

The present invention also provides a method of preparing an expression vector comprising a full-length cDNA sequence from a eukaryotic gene containing an intron or of the genome sequence of a presumed eukaryotic gene containing an intron, said method comprising the steps of:

(a) synthesizing cDNA fragments from mRNA extracted from a eukaryote and amplifying the cDNA fragments by PCR, wherein the forward primer used in the PCR has, in order from the 5' end to the 3' end, a sequence complementary to the sequence of the 3' terminal part of the sense strand of a fragment to which the amplified fragment is to be linked, or a sequence complementary to the sequence of the 3' terminal part of the sense strand of a restriction enzyme-treated terminal part of the vector, and a sequence complementary to the sequence of the 5' terminal part of the sense strand of the fragment to be amplified, and wherein the reverse primer has, in order from the 5' end to the 3' end, a sequence complementary to the sequence of the 3' terminal part of the antisense strand of a fragment to which the amplified fragment is to be linked, or a sequence complementary to the sequence of the 3' terminal part of the antisense strand of the restriction enzyme-treated terminal part of the vector, and a sequence complementary to the sequence of the 5' terminal part of the antisense strand of the fragment to be amplified, whereby a sequence homologous to a terminal part of a fragment to be linked to the fragment to be amplified or a sequence homologous to a restriction enzyme-treated terminal part of the vector are added to the end of the fragment to be amplified; and (b) simultaneously transforming a budding yeast or fission yeast with the cDNA fragments obtained in the step (a) and a restriction enzyme-treated vector to obtain the expression vector containing fragments linked to the fragments and fragments linked to the vector that are joined via homologous recombination.

The method can be applied to a gene of a fungus (a eukaryote), and the fungus may be of the genus *Penicilium, Chaetomium* or *Aspergillus*.

In a preferred method a gene or genome sequence of the presumed gene may be of 4 to 20 kb in length.

In a preferred method a gene or genome sequence of the presumed gene may encode a polyketide synthase or nonribosomal peptide synthetase.

In a preferred method, the linked sequence may be a polynucleotide comprising a nucleotide sequence represented by any one of SEQ ID NOs:15 to 21, 29 and 47.

The present invention also provides a transformant having introduced therein an expression vector prepared by the method of the invention.

The present invention also provides a protein produced by the transformant of the invention.

The present invention also provides a method of preparing a compound produced by a protein encoded by a gene or genome sequence of a presumed gene containing an intron by using an expression vector prepared by the method of the invention.

The method may comprises the steps of culturing a transformant having an introduced expression vector, and collecting the compound from the culture medium or transformant.

According to the present invention, it is possible to remove the introns from a gene sequence and link only the exons allowing for so-called artificial splicing. According to the present invention, it is also possible to express a protein encoded by a giant gene, which could not be affected because the cDNA could not be synthesized by conventional methods. Moreover, a compound produced by the expressed protein can be obtained by culturing a host having the expression vector introduced therein.

By applying the method of the present invention to a sequence which is presumed to be a gene based on genome sequence data but its product has not been isolated or identified, it is possible to synthesize the unknown product encoded by the presumed gene and specify the function of that protein.

Also by applying the present invention to a fungal gene to prepare an expression vector and expressing it in a yeast host system, it is possible to synthesize a fungal protein without denaturing the protein in a heterologous expression system.

BRIEF DESCRIPTION OF THE DRAWINGS

FIG. 1 is a schematic view showing the sequence of exons in a hypothetical PKS gene (CHGG_10128), and the primers for amplifying the exons.

FIG. 5 shows a Western blot and SDS-PAGE results to detect expression of 6-MSA synthase (MSAS).

FIG. 11 is a schematic view showing the sequence of exons in a hypothetical PKS gene (CHGG_00542), and the primers for amplifying each exon.

FIG. 14 shows a Western blot to detect gene expression by an expression vector for a hypothetical PKS gene (CHGG_00542).

FIG. 15 shows the LC-MS spectrum of a solid extracted from a yeast carrying an expression vector for a hypothetical PKS gene (CHGG_00542).

FIG. 16 shows the H-NMR spectrum of Compound 1 (CHGG_00542-1) and Compound 2 (CHGG_00542-2), which were isolated from the culture medium of a yeast carrying an expression vector for a hypothetical PKS gene (CHGG_00542).

PREFERRED EMBODIMENTS OF THE INVENTION

Figure 2:
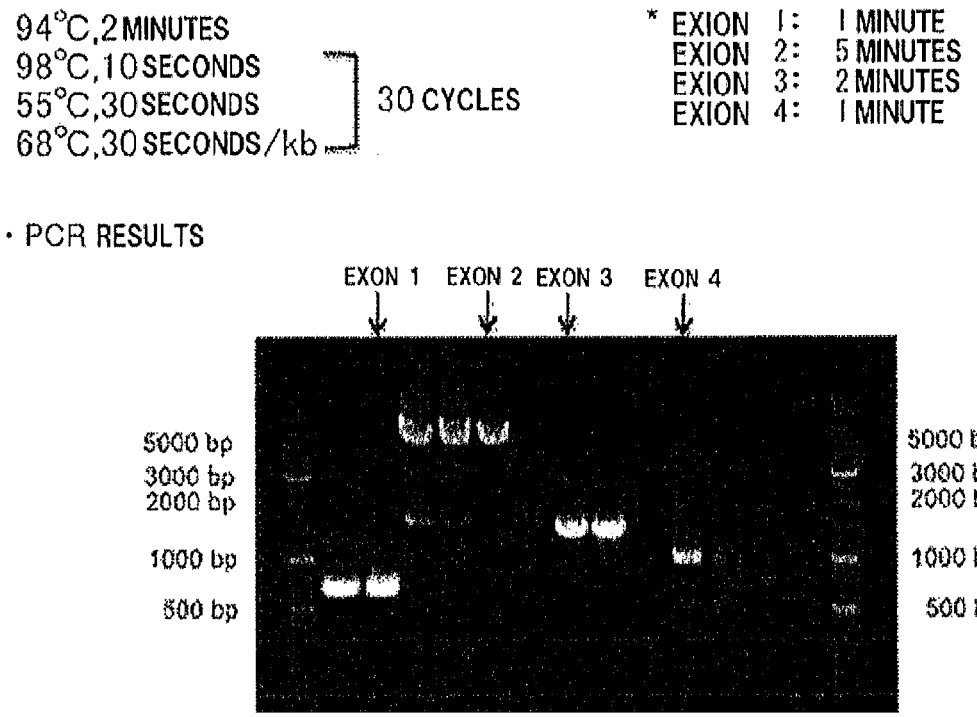
FIG. 2 shows the results of PCR amplification of the exon sequences of a hypothetical PKS gene (CHGG_10128).

The present invention relates to a method for preparing an expression vector comprising linking only exon sequences using gap repair cloning method to remove introns from a eukaryotic gene.

According to the present invention, multiple genes such as a hypothetical gene sequence to be expressed and a gene sequence of an enzyme for synthesizing the presumed substrate for the protein encoded by that gene sequence were introduced into a single vector to prepare an expression vector. Moreover, multiple expression vectors were introduced into the same cell via transformation, and multiple genes were introduced on a chromosome. Such methods allowed genes to be expressed more efficiently than with conventional gap repair cloning method (see Hisao Moriya et al., PLos ONE 2010), and the production yield of the target protein and a compound synthesized by the protein were successfully increased.

By conventional methods known in the art, it has been extremely difficult to express a giant gene with an unknown function that contains many intron sequences, and to elucidate the function of the translated protein, because (i) giant genome genes are difficult to be spliced and expressed heterologously, and (ii) even if a gene is expressed and a protein is obtained, it is difficult to specify the function of the resulting protein with existing techniques. By contrast, with the method of the present invention using a gap repair cloning technique, the inventors have successfully obtained a presumed cDNA sequence from a giant genome gene of unknown function, and have expressed the protein encoded by the sequence. Moreover, by expressing the gene of an enzyme for synthesizing a presumed substrate for the protein together, the inventors successfully obtained a compound synthesized by the protein.

In one aspect of the present invention, it is possible to synthesize cDNA fragments of a giant gene for which full-length cDNA cannot be synthesized with reverse transcriptase, and link the fragments by the gap repair cloning method to obtain a reading frame of the giant gene containing no introns. Particular sequences in a gene are presumed to be either an exon sequence or an intron sequence based on previous findings. However, this is only a presumption, and likely to contain some errors in the case of a giant gene containing many intron sequences. Thus, the reading frame of a giant gene can be obtained more reliably by linking cDNA fragments than by linking presumed exon sequences.

1. DEFINITIONS

A "gene" is a DNA region encoding the information for a protein. The "genome sequence of a presumed gene" is a DNA region which is predicted to encode information for a protein based on previous findings. Such a prediction can be easily obtained using commercial software, and prediction results by NCBI programs, for example, are publicly available (http://www.ncbi.nlm.nih.gov/).

An "exon" or "exon sequence" is a DNA region contained in a gene that will be transcribed into mRNA, or an mRNA region transcribed from that DNA region. An "intron" or "intron sequence" is a DNA region contained in a gene that does not code for protein information, and is not contained in mRNA because it is removed by RNA splicing after transcribed into a primary transcription product. In eukaryotes, a gene is first transcribed as a primary transcription product, and then the introns are removed by RNA splicing and the exons are linked together to form mRNA. In eukaryotic genes, the exons are often separated by introns. Based on previous findings, it is possible to presume whether a given sequence in a gene is an exon sequence or intron sequence, and prediction results from NCBI programs have been published in, for example (http://www.ncbi.nlm.nih.gov/). As used herein, the terms "exon" and "intron" also include sequences that are presumed to be exons and sequences that are presumed to be introns.

As used herein, a "fragment" is a DNA fragment containing a partial sequence of a gene.

As used herein, the "5' terminal part" and "3' terminal part" are polynucleotides comprising continuous sequences of multiple nucleotides extending from the 5' terminus and 3' terminus of a fragment, respectively. The term "multiple" means any length of nucleotides that allows the primers to work effectively, and allows homologous recombination to occur. As used herein, a "restriction enzyme-treated terminal part" is a polynucleotide comprising a continuous sequence of multiple nucleotides extending from an end of the vector that is produced by restriction enzyme treatment, and "multiple" means any length of nucleotides that allows for homologous recombination to occur.

As used herein, a "forward primer" is a primer having a sequence complementary to the 5' end of the sense strand of a DNA sequence to be amplified by PCR, while a "reverse primer" is a primer having a sequence complementary to the 5' end of the antisense strand of a DNA sequence to be amplified by PCR.

As used herein, a "complementary sequence" is a sequence capable of hybridizing with a template sequence under stringent conditions, and does not need to be entirely complementary. Specifically, it is desirable that at least 80%, preferably at least 90%, more preferably 100% of the primer sequence be complementary.

As used herein, a "homologous sequence" is a sequence that is homologous to a degree that allows homologous recombination to occur between fragments to be linked. The greater the degree of homology the better, and at least 99%, more preferably at least 99.9% homology is preferred, or most preferably the two sequences are identical.

As used herein, a "fungus" is a microorganism classified as a fungus, meaning a filamentous fungus. Examples of "fungi" include, but are not limited to, those of the genus *Penicilium*, *Chaetomium* or *Aspergillus*.

A "polyketide synthase (PKS)" is an enzyme involved in biosynthesis of a polyketide compound, where "polyketide compound" is a general term for secondary metabolites produced by actinomycetes, filamentous fungi and plants. A "secondary metabolite" is a natural product that is not contained in all organisms, but is produced by metabolism in the biosynthesis of a substance that is not directly involved in the common life processes of organisms (that is, secondary metabolism). Examples of polyketide compounds include, but are not limited to, antibiotics such as tetracycline and erythromycin and anti-cancer drugs such as daunomycin. A "nonribosomal peptide synthetase (NRPS)" is an enzyme that is involved not in normal peptide translation to synthesize a peptide from an mRNA template, but in a reaction where substrates are transferred between regularly assembled enzymes to polymerize peptides to synthesis a protein.

2. METHOD OF PREPARING EXPRESSION VECTOR

The present invention provides a method of preparing an expression vector by PCR to amplify exons contained in a giant gene containing introns into multiple fragments, and then linking the fragments together with a restriction enzyme-treated vector by the gap repair cloning method. According to the present invention, it is possible to remove the introns from a gene sequence and link only the exons to effect so-called artificial splicing.

Gap repair cloning is a method that utilizes a recombinational repair mechanism found in budding yeasts to build a plasmid construct in a budding yeast or fission yeast. If DNA fragments possess homologous regions, the DNA fragments will be joined via homologous recombination (see for example Hisao Moriya et al., PLos ONE 2010). With the gap repair method it is possible to precisely link DNA fragments from those fragments prepared to contain homologous and specific sequences.

(1-1) Step of Exon Sequence Amplification by PCR (a) Genome Extraction

In the method of the present invention, a genome is first extracted from a eukaryote containing a target gene. Genome extraction can be accomplished by methods well known to those skilled in the art. A commercial kit may also be used.

(b) Primer Design

In the method of the present invention, the exon sequences are amplified to form multiple fragments by PCR. Specifically, when the exons are separated by introns, the individual exons are amplified as individual fragments. When an individual exon is too large to be amplified by PCR, the individual exon is amplified as multiple fragments of a length that can be amplified by PCR.

Figure 3:
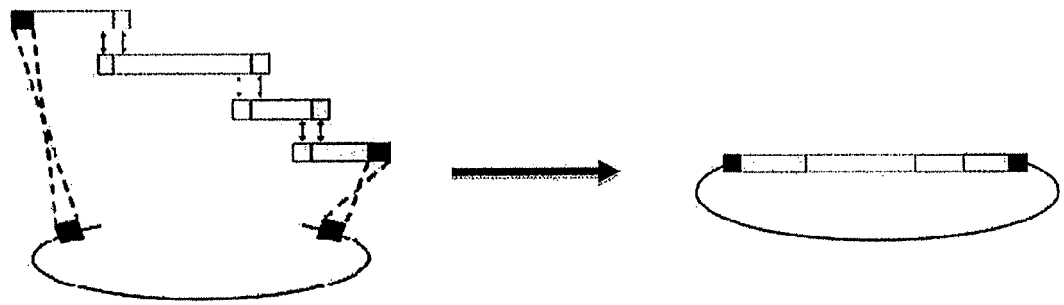
FIG. 3 is a schematic view showing homologous recombination of the exon sequences of a hypothetical PKS gene (CHGG_10128) in a budding yeast.

In gap repair cloning, homologous recombination will occur between fragments having homologous regions, and two fragments are linked to each other (see FIG. 3). In the present invention a linking site of a fragment must have a sequence homologous to the terminal part of a second fragment to be linked, or homologous to a restriction enzyme-treated terminal part of the vector to be linked. Therefore, a primer used in the present invention is designed not only to amplify a fragment by PCR, but also to add to the terminal part of the fragment a sequence homologous to the terminal part of a second fragment to be linked or homologous to a restriction enzyme-treated terminal part of the vector. In other words, the primer must be constructed to have a sequence that serves as a primer for binding to a template strand, and a sequence for adding a sequence that is homologous to the sequence of a fragment to be linked to the end of the fragment.

Primer design is explained in detail below with reference to FIG. 1, where 4 exons (exons 1 to 4 starting from the 5' end) are amplified, linked together and inserted into a restriction enzyme-treated vector.

To amplify exon 1, the primer for the sense strand (exon 1 forward primer) is designed to have a sequence complementary to the 3' terminal part of the sense strand of the restriction enzyme-treated terminal part of the vector (upper case bold in FIG. 1) and a sequence complementary to the sequence of the 5' terminal part of the sense strand of exon 1 (upper case in FIG. 1), in order from the 5' end to the 3' end. The primer for the antisense strand (exon 1 reverse primer) is designed to have a sequence complementary to the 3' terminal part of the antisense strand of exon 2 (lower case italics in FIG. 1) and a sequence complementary to the sequence of the 5' terminal part of the antisense strand of exon 1 (underlined upper case in FIG. 1), in order from the 5' end. PCR using the primers will generate an amplified fragment of the sequence comprising exon 1 with a sequence homologous to the sequence of the 3' terminal part of the restriction enzyme-treated part of the vector added to the 5' end and with a sequence homologous to the 5' terminal part of exon 2 added to the 3' end.

To amplify exon 2, the primer for the sense strand (exon 2 forward primer) is designed to have a sequence complementary to the 3' terminal part of the sense strand of exon 1 (underlined uppercase in FIG. 1) and a sequence complementary to the sequence of the 5' terminal part of the sense strand of exon 2 (lower case italics in FIG. 1), in order from the 5' end to the 3' end. The primer for the antisense strand (exon 2 reverse primer) is designed to have a sequence complementary to the 3' terminal part of the antisense strand of exon 3 (lower case in FIG. 1) and a sequence complementary to the sequence of the 5' terminal part of the antisense strand of exon 2 (underlined uppercase italics in FIG. 1), in order from the 5' end. PCR using the primers will generate an amplified fragment of a sequence comprising exon 2 with a sequence homologous to the sequence of the 3' terminal part of exon 1 added to the 5' end and with a sequence homologous to the 5' terminal part of exon 3 added to the 3' end.

To amplify exon 3, the primer for the sense strand (exon 3 forward primer) is designed to have a sequence complementary to the 3' terminal part of the sense strand of exon 2 (underlined uppercase italics in FIG. 1) and a sequence complementary to the sequence of the 5' terminal part of the sense strand of exon 3 (lower case in FIG. 1), in order from the 5' end to the 3' end. The primer for the antisense strand (exon 3 reverse primer) is designed to have a sequence complementary to the 3' terminal part of the antisense strand of exon 4 (uppercase with broken underline in FIG. 1) and a sequence complementary to the sequence of the 5' terminal part of the antisense strand of exon 3 (double-underlined uppercase in FIG. 1), in order from the 5' end. PCR using the primers will generate an amplified fragment of a sequence comprising exon 3 with a sequence homologous to the sequence of the 3' terminal part of exon 2 added to the 5' end and with a sequence homologous to the 5' terminal part of exon 4 added to the 3' end.

To amplify exon 4, the primer for the sense strand (exon 4 forward primer) is designed to have a sequence complementary to the 3' terminal part of the sense strand of exon 3 (double-underlined upper case in FIG. 1) and a sequence complementary to the sequence of the 5' terminal part of the sense strand of exon 4 (upper case with broken underline in FIG. 1), in order from the 5' end to the 3' end. The primer for the antisense strand (exon 4 reverse primer) is designed to have a sequence complementary to the 3' terminal part of the restriction enzyme-treated terminal part of the vector (underlined uppercase bold in FIG. 1) and a sequence complementary to the sequence of the 5' terminal part of the antisense strand of exon 4 (lower case bold in FIG. 1), in order from the 5' end. PCR using the primers will generate an amplified fragment of a sequence comprising exon 4 with a sequence homologous to the 3' terminal part of exon 3 added to the 5' end and with a sequence homologous to the restriction enzyme-treated terminal part of the vector added to the 3' end.

The exon 1 reverse primer and exon 2 forward primer, the exon 2 reverse primer and the exon 3 forward primer, and the exon 3 reverse primer and exon 4 forward primer consist, respectively, of mutually complementary sequences (complementary sequences are shown in the same font style in FIG. 1).

In the primer sequences, the lengths of the sequence parts that function as primers for binding to the template strands, or in other words the lengths of the sequence parts at the 3' terminal ends of the forward and reverse primer, can be any lengths that allow for the primers to function effectively in PCR. The length of a primer that functions effectively in PCR can be set appropriately by a person skilled in the art and is not particularly limited, but may be 5 to 50 bp or preferably 10 to 40 bp or more preferably 15 to 30 bp for example. The total length of the primer may be any length that allows for homologous recombination to occur in the gap repair cloning method. The length of such a homologous sequence is about 25 bp, or preferably about 50 bp, or more preferably about 75 bp. For example, the total length of a primer used in the present invention is, but not limited to, about 25 bp, or preferably about 50 bp, or more preferably about 75 bp.

(c) Fragment Amplification

The exon sequences are amplified as multiple fragments by PCR using primers designed as described in (b) above, with a genome extracted from a eukaryote as a template. The PCR reaction conditions can be set appropriately by a person skilled in the art. The PCR reaction can also be performed using a commercial kit.

Using primers designed as described in (b) above, it is possible to obtain fragments each comprising an exon having at both ends of the exon the sequence of the terminal part of the vector or a second exon to be linked.

(1-2) cDNA Fragment Synthesis and Amplification Step

(a) mRNA Extraction and Synthesis of cDNA Fragments with Reverse Transcriptase In one embodiment of the present invention, mRNA is first extracted from a eukaryote containing a target gene. mRNA extraction can be performed using methods known to those skilled in the art. A commercial kit may also be used. For example, total RNA is extracted, and mRNA is purified using an oligo-dT column. Next, single-stranded complementary DNA (cDNA) fragments of the resulting mRNA are synthesized with reverse transcriptase. The reverse transcription reaction can be performed by a person skilled in the art using well-known methods. For example, single-stranded cDNA fragments are obtained using oligo-dT primers or oligo-dT adapter primers. Alternatively, oligo-dT primers or oligo-dT adapter primers may be applied to total RNA together with a reverse transcriptase to reverse transcribe only the mRNA to obtain single-stranded cDNA fragments.

(b) Primer Design

As described in (b) of (1-1) above, in order to link fragments via homologous recombination of fragments having homologous regions, the linking sites of the fragments must have sequences homologous to the terminal part of a fragment to be linked or to a restriction enzyme-treated terminal part of the vector to be linked. Thus, primers used in the method of the present invention are designed both to amplify a fragment by PCR, and to add to the terminal parts of the fragment a sequence homologous to a terminal part of a fragment to be linked or to a restriction enzyme-treated terminal part of the vector to be linked. That is, the primer used in the present invention is constructed to have a sequence that functions as a primer for binding to a template strand, and a sequence for adding a sequence to the end of the fragment that is homologous to a sequence of a fragment to be linked.

As in the method described in (b) of (1-1) above, primers used for amplifying cDNA fragments are designed based on the anticipated sequences of the exons and introns, and on the sequences of the restriction enzyme-treated ends of the vector.

(c) Fragment Amplification cDNA fragments are amplified by PCR using primers designed as described in (b) above, with the single-stranded cDNA fragments obtained in (a) above as the template. The PCR reaction conditions can be set appropriately by a person skilled in the art. The PCR reaction can also be performed using a commercial kit.

(2) Restriction Enzyme Treatment of the Vector

In the present invention, the vector is first digested with a restriction enzyme. The restriction enzyme may be any of those well known in the art, and restriction enzyme treatment may be performed by methods well known in the art. The vector may be cleaved in one place or in two or more places by the restriction enzyme.

A vector has a selection marker and replication origin for a budding yeast or fission yeast. Examples of vectors having yeast hosts include YIp vectors, YEp vectors, YRp vectors, YcP vectors and the like, and for example pGPD-2 can be used. Examples of selection markers include auxotrophic reporter genes and genes coding for traceable marker proteins, such as genes coding for green fluorescent protein (GFP), yellow fluorescent protein (YFP) and cyan fluorescent protein (CFP), as well as other reporter genes, such as the LacZ gene and drug resistance genes. The vector may also contain a promoter region, a transcription termination region. The promoter region and transcription termination region are placed within the vector so as to control expression of the target gene and selection marker.

(3) Expression Vector Preparation Step

The fragments amplified by PCR and the restriction enzyme-treated vector are introduced simultaneously to transform a budding yeast or fission yeast. Homologous recombination will occur in the budding yeast or fission yeast between fragments having homologous sequences, and between fragments and restriction enzyme-treated terminal parts of the vector, thereby forming an expression vector comprising linked fragments. In the method of the present invention, fragments are prepared for multiple genes including not only the sequence of the presumed gene to be expressed, but also the gene for an enzyme for synthesizing the presumed substrate of the protein encoded by the gene sequence, and the gene for an enzyme for modification of the protein, and introduced into a single vector.

The following explanation provides an example where exons 1 to 4 amplified in accordance with (b) of (1-1) above and FIG. 1 are linked and incorporated into a restriction enzyme-treated vector (FIG. 3).

In the preliminary PCR amplification step, fragments are formed to comprise exons 1 to 4 having sequences homologous to the vector or to the respective exon to be linked in both ends thereof. Homologous recombination occurs between the sequence of the restriction enzyme-treated 3' terminal part of the vector and a sequence homologous to the restriction enzyme-treated 3' terminal part of the vector, which has been added to the 5' end of exon 1. In the case of exon 1 and exon 2, a sequence comprising the sequence of the 3' terminal part of exon 1 and the sequence of the 5' terminal part of exon 2 is present at both the 3' terminal part of exon 1 and the 5' terminal part of exon 2, thus homologous recombination occurs between these two sequences, thereby linking the 5' end of exon 2 to the 3' end of exon 1. Similarly, in the case of exons 2 and exon 3 and exon 3 and exon 4, the 5' end of exon 3 is linked to the 3' end of exon 2 and the 5' end of exon 4 is linked to the 3' end of exon 3. Because a sequence homologous to the sequence of the restriction enzyme-treated 5' terminal part of the vector is added to the 3' end of exon 4, homologous recombination occurs between this sequence and the sequence of the restriction enzyme-treated 5' terminal part of the vector.

As a result of such homologous recombination, an expression vector can be obtained where the sequences of exons 1 to 4 of the gene are linked in the order that they are naturally encoded in the gene. In other words the expression vector comprises a sequence that represent a predicted cDNA sequence of the gene.

In one aspect of the present invention, an expression vector comprising a sequence of linked cDNA fragments, or in other words a full-length cDNA sequence can be obtained by homologous recombination.

A well-known method, for example electroporation, can be used for introducing the fragments into a budding yeast or fission yeast.

According to the method of the present invention, homologous recombination between the terminal parts of multiple fragments can occur simultaneously, and thus multiple fragments may be incorporated into the vector simultaneously. Moreover, fragments up to about 20 kbp in length can be incorporated by the method of the present invention. Using the method of the present invention, the cDNA sequence of a gene up to about 20 kbp or about 15 kbp or about 10 kbp or about 5 kbp in length can be incorporated into an expression vector.

The expression vector thus prepared may be isolated by selecting a transformant with a selection marker and collecting the expression vector contained in the transformant.

3. EXPRESSION VECTOR FOR PKS GENE FROM *CHAETOMIUM GLOBOSUM*

In one aspect of the present invention, an expression vector for a PKS gene from *Chaetomium globosum* can be prepared in accordance with the method of the section 2 above. A plurality of genes of presumed PKS genes are present in *Chaetomium globosum*, but production of the proteins encoded by the genes as natural products has not been identified, nor have they been artificially synthesized. The introns can be removed from such genes (CHGG_10128, ANID_03386, ANID_07903, CHGG_00046, CHGG_00542, CHGG_04068, CHGG_05286 and CHGG_09586), and only the exon sequences are linked to prepare an expression vector comprising the linked exons. That is, it is possible to prepare expression vectors (SEQ ID NO:14 and SEQ ID NOs:22 to 28) comprising the presumed cDNA sequences of the genes (SEQ ID NO:29 and SEQ ID NOs:15 to 21).

In one aspect of the present invention, cDNA fragments of the PKS genes (CHGG_10128, ANID_03386, ANID_07903, CHGG_00046, CHGG_00542, CHGG_04068, CHGG_05286 and CHGG_09586) can be linked to prepare an expression vector comprising the full-length cDNA sequence.

An expression vector for a PKS gene from *Chaetomium globosum* may also contain either or both of a gene encoding a modifying enzyme with the function of modifying the PKS (npgA gene) and a gene encoding an enzyme that produces maronyl-CoA as a substrate for the PKS (matB gene). These genes may be incorporated into the vector in advance, or they may be prepared as fragments and introduced by homologous recombination together with the PKS gene.

4. TRANSFORMANT HAVING INTRODUCED EXPRESSION VECTOR

An expression vector comprising a sequence of linked exons or a full-length cDNA sequence obtained according to the method of the present invention may be introduced into a host cell to produce a transformant. The host cell may be either *E. coli* or a yeast cell, with yeast being desirable. This is because eukaryotic proteins can be synthesized without being denatured when expressed heterologously in a yeast expression system. Transformation can be accomplished by introducing one or multiple expression vectors into a single cell. Multiple genes may be introduced into the chromosome.

5. PROTEIN PRODUCED BY TRANSFORMANT

One aspect of the present invention provides a protein produced by a transformant having an introduced expression vector.

A protein can be obtained by culturing the transformant of the present invention under conditions that permit expression of the full-length cDNA sequence or sequence of linked exons introduced into the expression vector. The transformant can be cultured in a medium commonly used in the art. The culture methods are well known to those skilled in the art, and the temperature, pH, culture time, and presence or absence of aeration and agitation and the like can be set appropriately by those skilled in the art.

Methods for extracting a protein from a cultured transformant comprise collecting the transformant by known methods from the culture, suspending it in a suitable liquid buffer, disrupting it by ultrasound, lysozyme and/or freeze-drying treatment, and then obtaining a raw extract by centrifugation or filtration. A surfactant, protein denaturant or the like can be added to the buffer as appropriate.

Methods for isolating and purifying the protein from the raw extract include aluminum sulfate precipitation and other salting-out methods, gel filtration, and other well-known methods in the art.

A protein produced by a transformant can also be expressed as a fused protein with a tag, using fusion production methods commonly used in the art of genetic engineering. A known tag may be used including His tag, HA tag, myc tag, FLAG tag or the like. A protein with a tag may be isolated and purified by affinity chromatography.

6. METHOD OF PREPARING COMPOUND PRODUCED BY PROTEIN ENCODED BY GENE OR GENOME SEQUENCE OF PRESUMED GENE CONTAINING INTRON USING EXPRESSION VECTOR

In one aspect of the present invention, it is possible to prepare a compound that is synthesized by a protein produced by a transformant having an introduced expression vector.

The transformant of the present invention is cultured under conditions that permit expression of a full-length cDNA sequence or a sequence of linked exons introduced into an expression vector, to effect expression of the protein encoded by that sequence. The transformant of the present invention can be cultured in a medium that is commonly used in the art. The culture method is known to those skilled in the art, and the temperature, pH, culture time, presence or absence of aeration or agitation and the like can be set appropriately by those skilled in the art. The medium, culture method, culture time and other culture conditions are preferably optimized so as to maximize the amount of the compound that is produced.

When a transformant is cultured, a compound synthesized by the protein encoded by a full-length cDNA sequence or sequence of linked exons introduced into the expression vector will accumulate in the transformed cells or in the culture medium. The compound is isolated from the transformed cells or culture medium. The isolation method can be selected appropriately from methods known in the art according to the physical properties of the compound. For example, when the compound accumulates in the culture medium, the transformed cells can be removed from the culture medium by centrifugation or the like, then the compound can be isolated by solvent extraction or with ion exchange resin, or by adsorption or partition chromatography and gel filtration, either alone or in combination. In the case of a compound that accumulates within the transformed cells, the transformed cells can be collected from the culture medium by centrifugation or the like, suspended in a suitable buffer, and disrupted by ultrasound, lysozyme, and/or freeze-drying treatment or the like, and a raw extract is obtained by centrifugation or filtration. Then the compound can be isolated by solvent extraction or ion exchange resin, or by adsorption or partition chromatography and gel filtration, either alone or in combination. The isolated compound can be further purified by methods known in the art according to its physical properties.

As shown in Example 2, about 1 gram of the compound can be obtained from 1 liter of culture medium by using the expression vector of the present invention. Since a practical level of productivity is about 0.1 gram per 1 liter of culture medium, the productivity accomplished by the invention is quite high in comparison with a practical level of productivity.

In one aspect of the present invention, it is possible to obtain a secondary metabolite by preparing an expression vector containing a biosynthesis gene or the genome sequence of a presumed gene for a secondary fungal metabolite, and culturing a transformant having the expression vector introduced therein. Thus, the method of the present invention makes it possible to obtain unknown secondary metabolites and may offer the potential for the production of useful bioactive substances.

The entire contents of all the patents and reference documents that are explicitly cited in the specification are incorporated herein by reference. Moreover, the contents described in the specification and drawings of Japanese Patent Applications Nos. 2010-181279 and 2011-007312, which are the priority applications, are also incorporated herein by reference.

The present invention is explained in more detail below by means of examples, but these examples do not limit the present invention.

EXAMPLES

Example 1

Preparation of Expression Vectors for PKS Gene From *Chaetomium globosum*, and Gene Expression

1. CHGG_10128

The entire genome sequence of the fungus *Chaetomium globosum* has been identified, and gene regions encoding polyketide synthases (PKS) and the anticipated exon sequences and intron sequences in these regions have been predicted by the NCBI program (available at ncbi/n1 m.nih-.gov). One of the genes (CHGG_10128) that are presumed to code for polyketide synthases (PKS) (SEQ ID NO:1) was selected for further experiments.

(1) Amplification of Exon Sequences by PCR

DNA was extracted from *Chaetomium globosum*. Because CHGG_10128 is presumed to have 3 intron sequences, four exon sequences (excluding the intron sequences) were amplified by PCR. Forward primers were synthesized each comprising, in order from the 5' end to the 3' end, a sequence complementary to the sequence of the 3' terminal part of the sense strand of a fragment to which the amplified fragment is to be joined, or a sequence complementary to the sequence of the 3' terminal part of the sense strand of a restriction enzyme-treated terminal part of the vector, and a sequence complementary to the sequence of the 5' terminal part of the sense strand of the fragment to be amplified. Reverse primers were synthesized each comprising, in order from the 5' terminus to the 3' terminus, a sequence complementary to the sequence of the 3' terminal part of the antisense strand of a fragment to which the amplified fragment is to be joined, or a sequence complementary to the sequence of the 3' terminal part of the antisense strand of a restriction enzyme-treated terminal part of the vector, and a sequence complementary to the sequence of the 5' terminal part of the antisense strand of the fragment to be amplified (FIG. 1).

As shown in FIG. 1, exons are designated as exons 1 to 4 (SEQ ID NOs:10 to 13) from the 5' end. The forward primer for exon 1 is represented by SEQ ID NO:2, the reverse primer of exon 1 by SEQ ID NO:3, the forward primer of exon 2 by SEQ ID NO:4, the reverse primer of exon 2 by SEQ ID NO:5, the forward primer of exon 3 by SEQ ID NO:6, the reverse primer of exon 3 by SEQ ID NO:7, the forward primer of exon 4 by SEQ ID NO:8, and the reverse primer of exon 4 by SEQ ID NO:9.

The PCR react of 2 minutes of denaturing at 94° C., followed by 30 cycles of 10 seconds at 98° C., 30 seconds at 55° C. and 1 minute at 68° C. for exon 1, 10 seconds at 98° C., 30 seconds at 55° C. and 5 minutes at 68° C. for exon 2, 10 seconds at 98° C., 30 seconds at 55° C. and 2 minutes at 68° C. for exon 3, and 10 seconds at 98° C., 30 seconds at 55° C. and 1 minute at 68° C. for exon 4, respectively. KOD-Plus-Neo (Toyobo) was used as the polymerase.

(2) Preparation of Expression Vector by Homologous Recombination

Amplification of exon 1, exon 2, exon 3 and exon 4 was at the expected size by electrophoresis (FIG. 2), and PCR products corresponding to the bands at the expected size were introduced into a budding yeast (*Saccharomyces cerevisiae*) together with a restriction enzyme-treated vector and sequences encoding His and HA tags. Commercially available pRS425 was used as the vector, and SalI and SacI as the restriction enzymes. Homologous recombination was accomplished by recombinase of the yeast to obtain an expression vector (SEQ ID NO:14) comprising exon 1, exon 2, exon 3 and exon 4 (FIG. 3). An expression vector having the sequence of exons 1 to 4 (SEQ ID NO:29) formed by homologous recombination was selected using the marker Leu.

(3) Expression of Target Protein in Yeast

Figure 4:
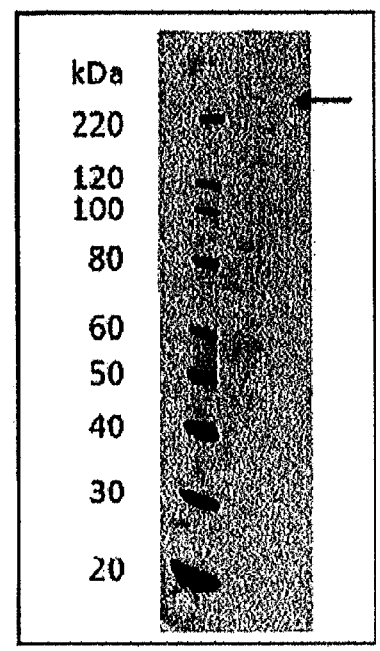
FIG. 4 shows a Western blot to detect gene expression by an expression vector for a hypothetical PKS gene (CHGG_10128).

The resulting expression vector was introduced into a yeast to transform the yeast. The transformant was cultured for 24 hours in a SC/Leu (2% raffinose) culture medium, and galactose was added to a final concentration of n. After 12 hours of culture, the yeast was collected, and a protein was extracted from the yeast. The extracted protein was subjected to Western blotting to confirm gene expression. The molecular weight of the PKS based on the sequence of the linked exons 1 to 4 (SEQ ID NO:29) was 279 kDa, and the molecular weight of the tag peptides is 8 kDa, and thus the product was anticipated to have a molecular weight of 287 kDa. Indeed a band was found at about this size (FIG. 4). In the Western blotting anti-His antibody (Sigma, 4000x) was used as the primary antibody and anti-mouse antibody (Invitrogen, 1x) as the secondary antibody. The product was detected by chemiluminescence from alkali phosphatase.

2. Other Genes

The same procedure as the section 1 above was applied for other genes presumed to code for PKS enzymes (ANID_03386, ANID_07903, CHGG_00046, CHGG_00542, CHGG_04068, CHGG_05286 and CHGG_09586), and expression vectors (SEQ ID NOs:22 to 28 in that order) were prepared each comprising the sequence that was presumed to be the cDNA sequence of the genes (SEQ ID NOs:15 to 21, respectively). The expression vector was introduced into yeast to transform the yeast, and protein expression was confirmed as described in the section 1 above.

Example 2

Production of Compound (6-methylsalicylic acid) in Vivo 6-methylsalicylic acid (6-MSA) has been studied as a typical fungal polyketide, and it is known that its synthesizing enzyme (6-methylsalicylic acid synthase, 6-MSA synthase, MSAS) can also be expressed in *E. coli*. The following experiments were therefore performed on 6-methylsalicylic acid synthase to show that the compound can actually be produced with a transformant having an introduced expression vector prepared by the method of the present invention.

1. Construction of Expression Vector and Expression of MSAS

DNA was extracted from a fungus *Aspergillus terreus*. Because the gene for 6-MSA synthase (SEQ ID NO:30) has 1 intron sequence, two exon sequences were amplified by PCR, excluding the intron sequence. To this end, a forward primer (SEQ ID NO:31) and reverse primer (SEQ ID NO:32) and another forward primer (SEQ ID NO:33) and reverse primer (SEQ ID NO:34) were designed and used so as to add to each fragment a sequence homologous to the end of the fragment to be joined or a sequence homologous to the restriction enzyme-treated terminal part of the vector.

As in Example 1, fragments comprising the amplified exon sequences were introduced into the ORF (open reading frame) of pKW1250 (Leu2d) together with a sequence coding for HA as a tag, to construct an expression vector (SEQ ID NO:35) comprising cDNA of the 6-MSA synthase gene by homologous recombination. In addition, npgA and matB were also incorporated by the gap repair cloning method. The expression vector was selected using a marker Ura (uracil).

The expression vector was introduced into a yeast to transform the yeast, and expression of MSAS (204 kDa) was confirmed. Specifically, the expression vector was first introduced into a yeast to transform the yeast, which was then cultured for 24 hours in SC/Leu (2% raffinose) culture medium, and galactose was added to a final concentration of 2%. After 12 hours of culture, the yeast was collected, crushed with beads, and separated with a nickel column (Ni-NTA resin, Qiagen) to obtain the following samples (FIG. 5): cell-free extract (lane 1), soluble fraction (lane 2), non-adsorbed fraction (lane 3), wash fraction (lane 4), elution fraction (imidazole concentration 100 mM) (lane 5), elution fraction (imidazole concentration 200 mM) (lane 6), elution fraction (imidazole concentration 500 mM) (lane 7). The resulting samples were subjected to SDS-PAGE and Western blotting to confirm gene expression. The gel was CBB stained. In Western blotting, anti-HA antibody (Roche, 1000x) was used as the primary antibody and anti-mouse antibody (Invitrogen, 1x) as the secondary antibody. The product was detected by chemoluminescence from alkali phosphatase. The results are shown in FIG. 5. Maronyl-CoA synthetase (MATE) (57 kDa) and phosphopantetheinyl transferase (SFP) (32 kDa) were also detected as controls. The MSAS production was much lower than those proteins.

Expression of proteins in yeast was carried out according to Jay D. Keasling et al (Nature 2006).

2. 6-MSA Reference

Because MSAS did not work in vitro, 6-MSA was purchased from Santa Cruz Biotechnology Co. (U.S.), and used as a standard for the compound produced by the enzyme reaction. The compound was detected by LC/MS and preparative HPLC to obtain reference data.

Figure 6A:
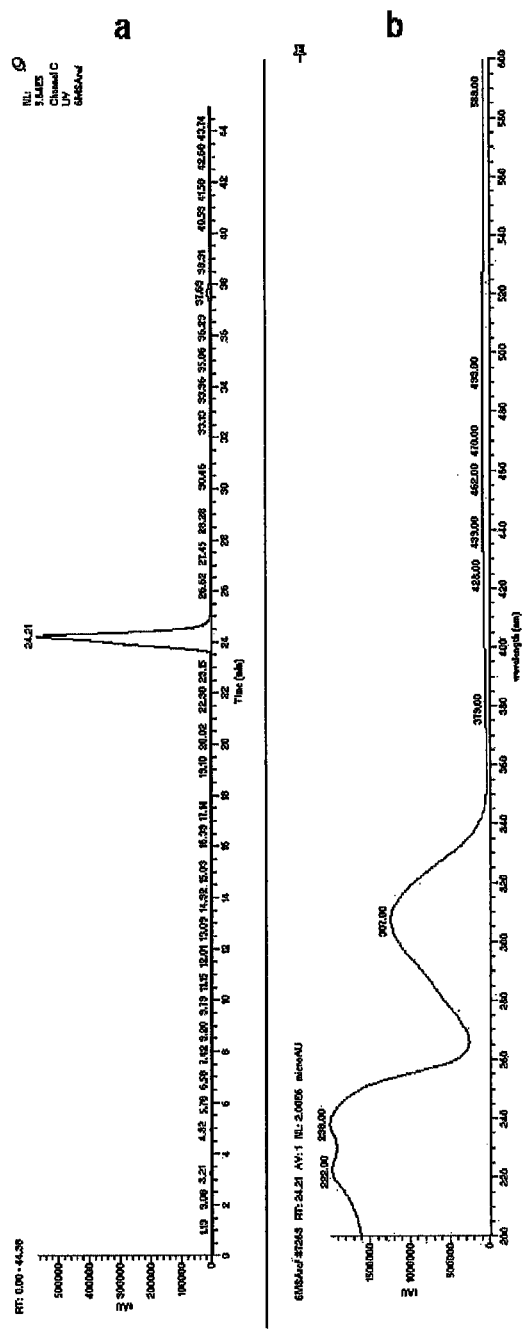
FIG. 6A shows a chromatogram detecting absorption at a wavelength of 254 nm (a) and the ultraviolet absorption spectrum (b) of a standard 6-MSA sample.
Figure 6B:
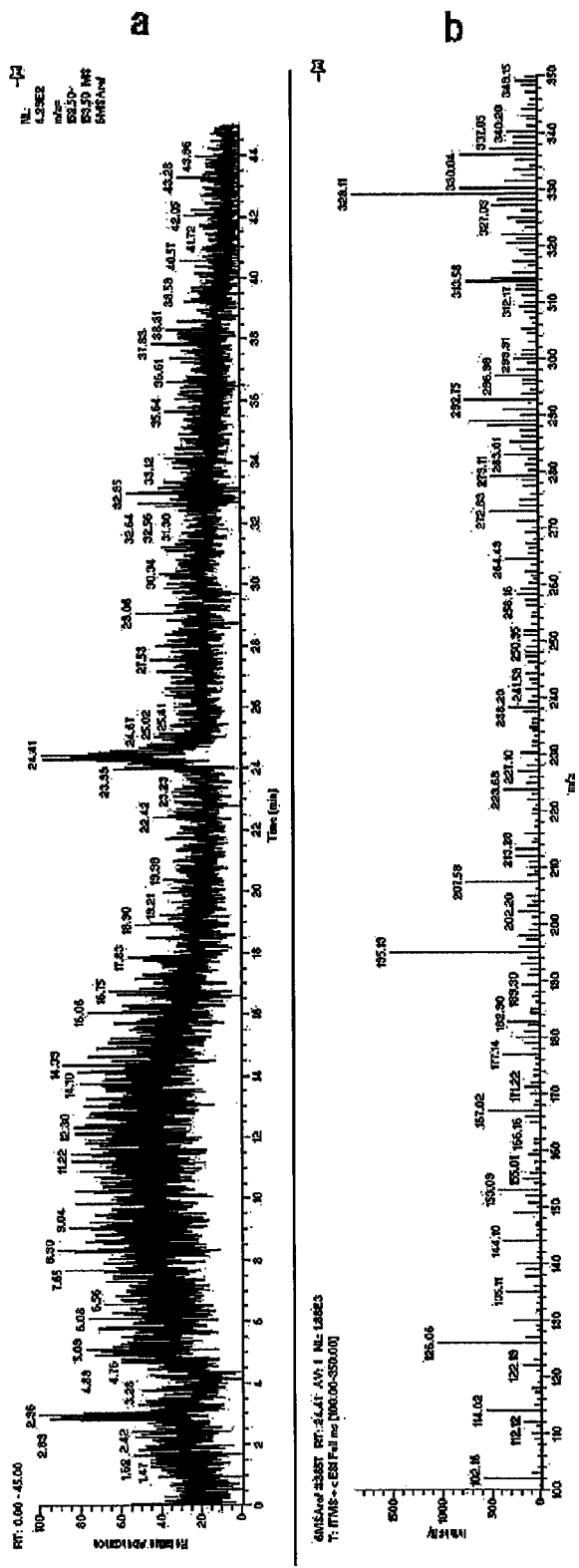
FIG. 6B shows a chromatogram (a) and mass spectrum (b) from mass spectrometry of a standard 6-MSA sample.

In the LC/MS measurement, ionization was detected by the electron ionization method. The results from LC/MS are shown in FIGS. 6A and 6B. In FIG. 6A, a shows a chromatogram detected at an absorption wavelength of 254 nm, and b shows the ultraviolet absorption spectrum of the target compound. In FIG. 6B, a shows a chromatogram from mass spectrometry, and b shows the mass spectrum of the target compound. It can be seen from b of FIG. 6A and b of FIG. 6B that detection of 6-MSA was difficult by MS due to poor ionization, but was easy by UV.

Figure 7:
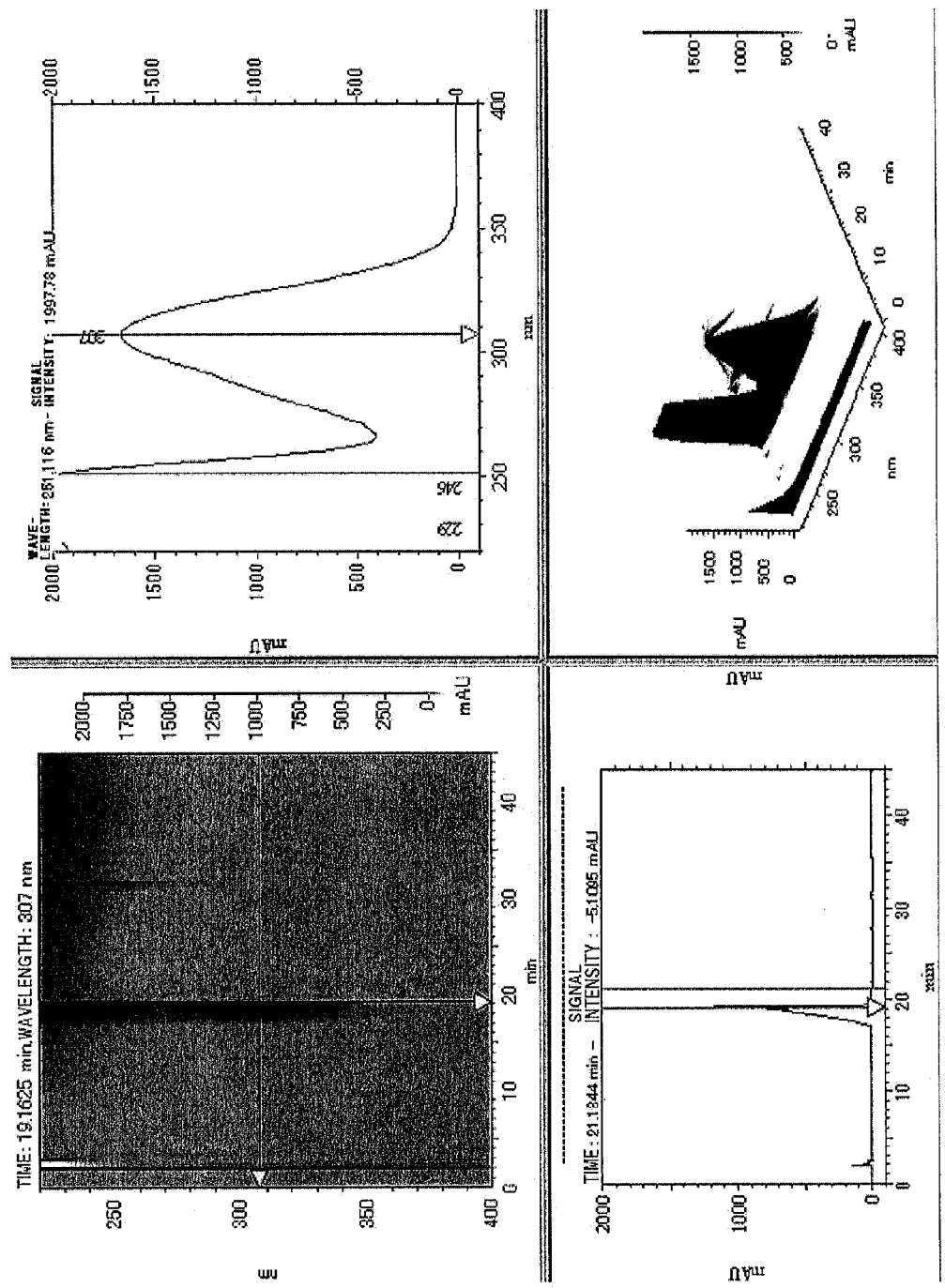
FIG. 7 shows HPLC data for a standard 6-MSA sample.

In the preparative HPLC, 6-MSA was detected using C18 column at a flow rate of 1 mL/min and an absorption wavelength of 254 nm. The results of preparative HPLC are shown in FIG. 7. It can be seen from FIG. 7 that the peak at a retention time of 27.4 minutes corresponds to 6-MSA.

3. In Vivo Production of 6-MSA

The expression vector prepared in the section 1 above was introduced into a yeast to transform the yeast, which was then cultured as follows.

Figure 8A:
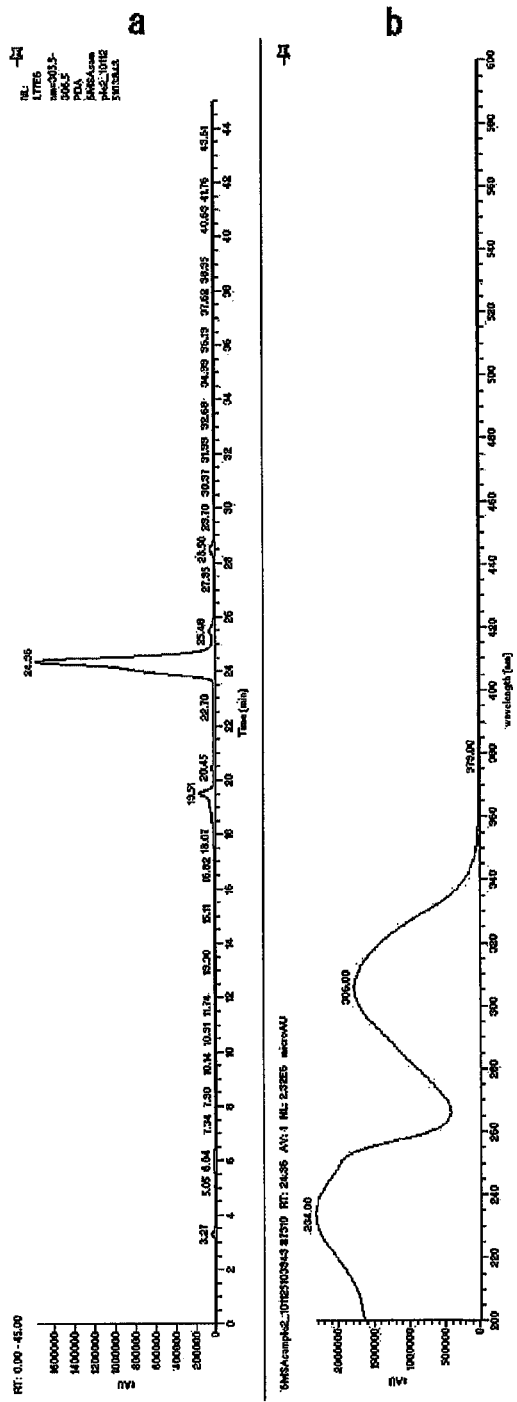
FIG. 8A shows a chromatogram detecting absorption at a wavelength of 254 nm (a) and the ultraviolet absorption spectrum (b) of a yeast extract sample.
Figure 8B:
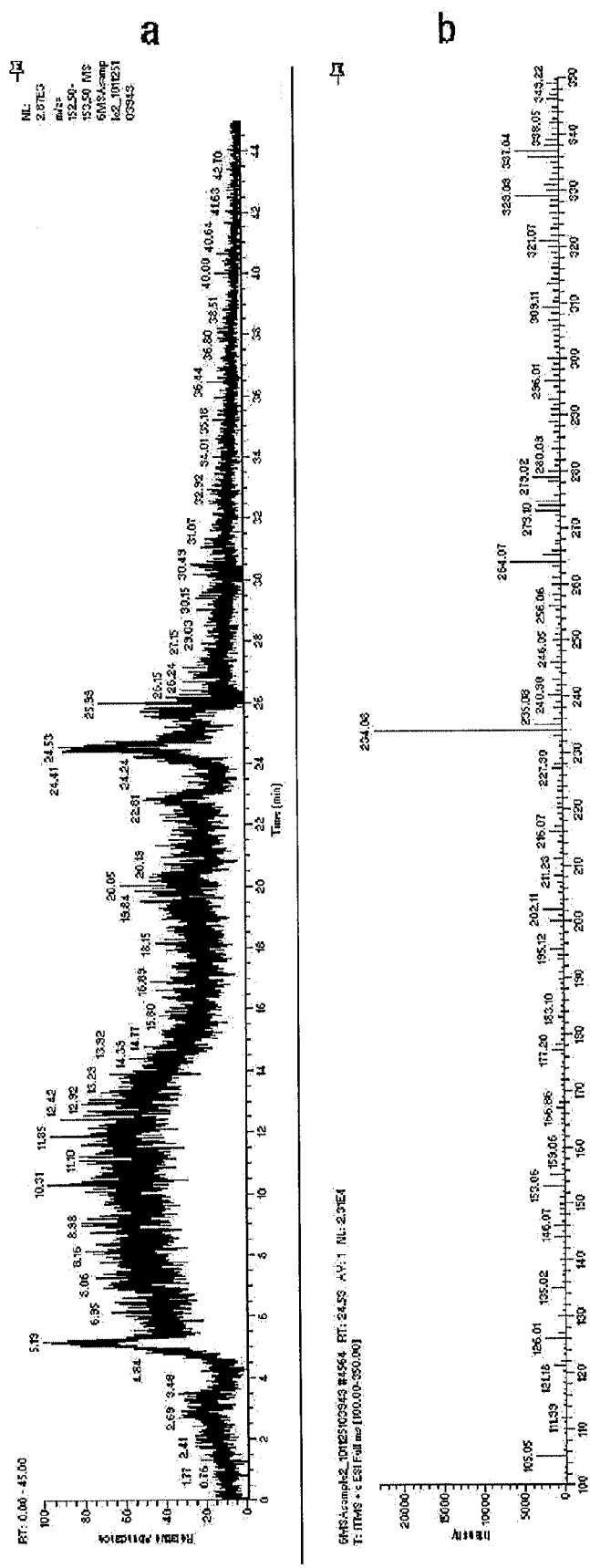
FIG. 8B shows a chromatogram (a) and mass spectrum (b) from mass analysis of a yeast extract sample.
Figure 9:
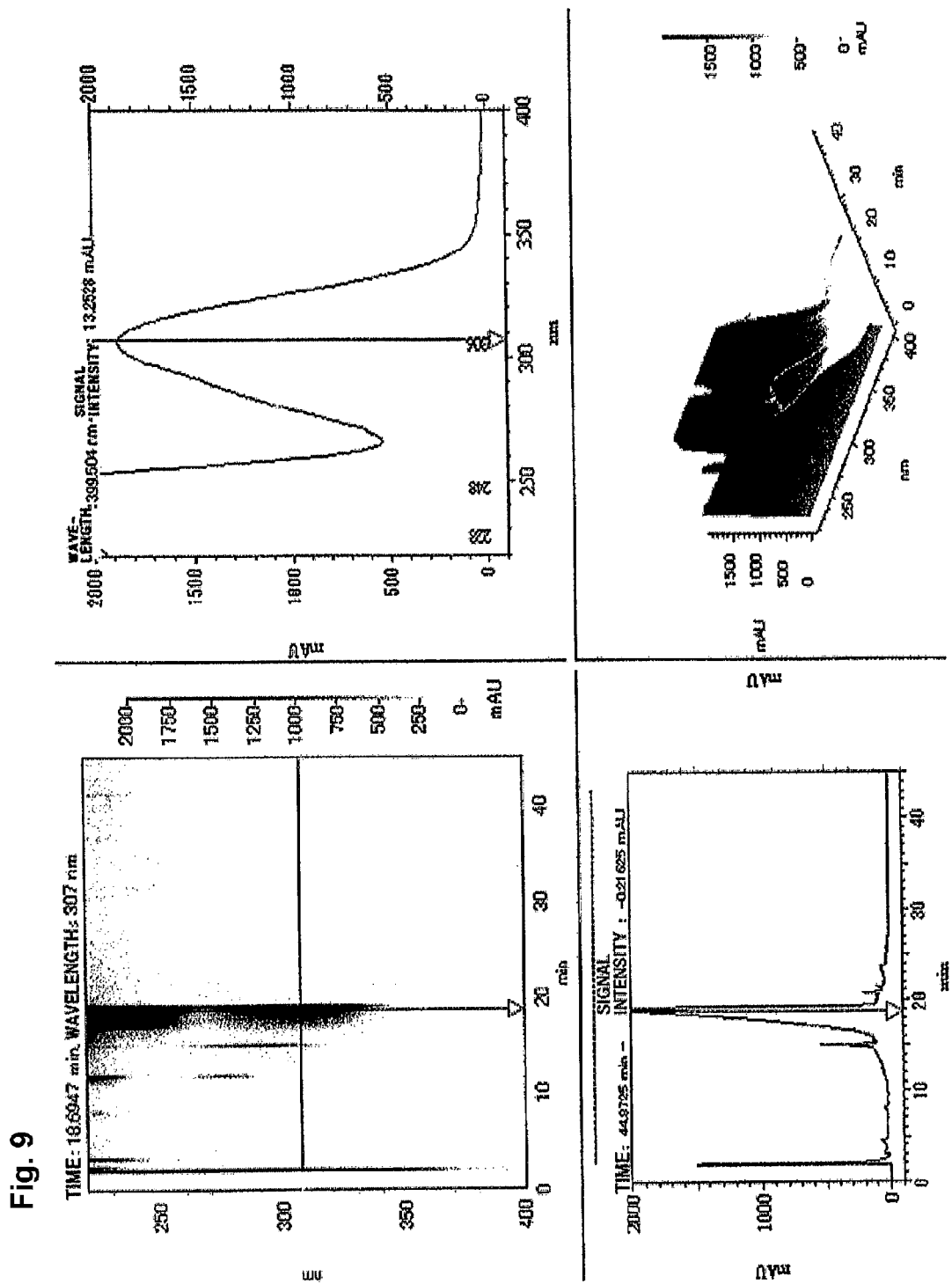
FIG. 9 shows HPLC data for a yeast extract sample.
Figure 10A:
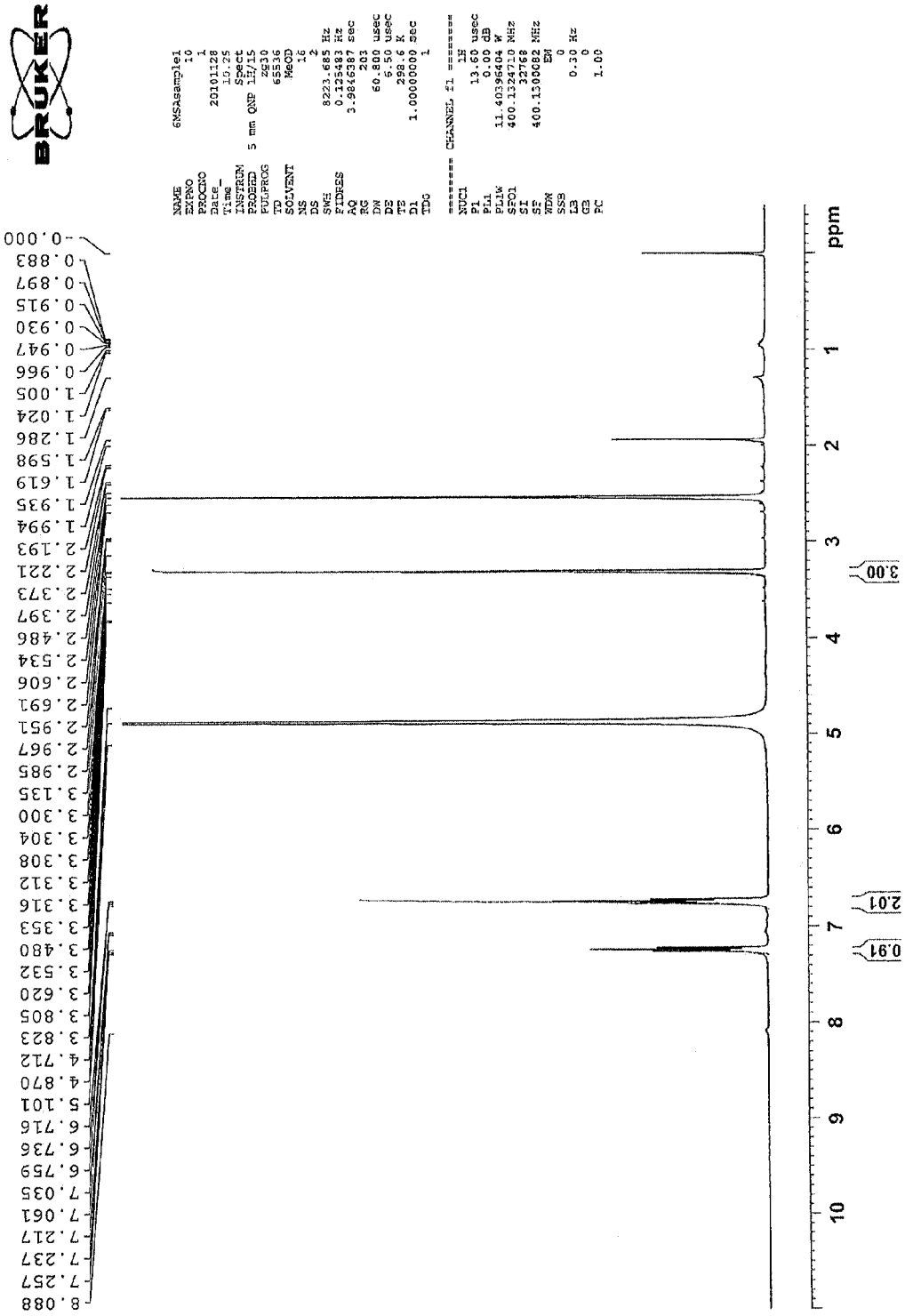
FIG. 10A shows the H-NMR spectrum of a fraction separated by HPLC from a yeast extract sample.
Figure 10B:
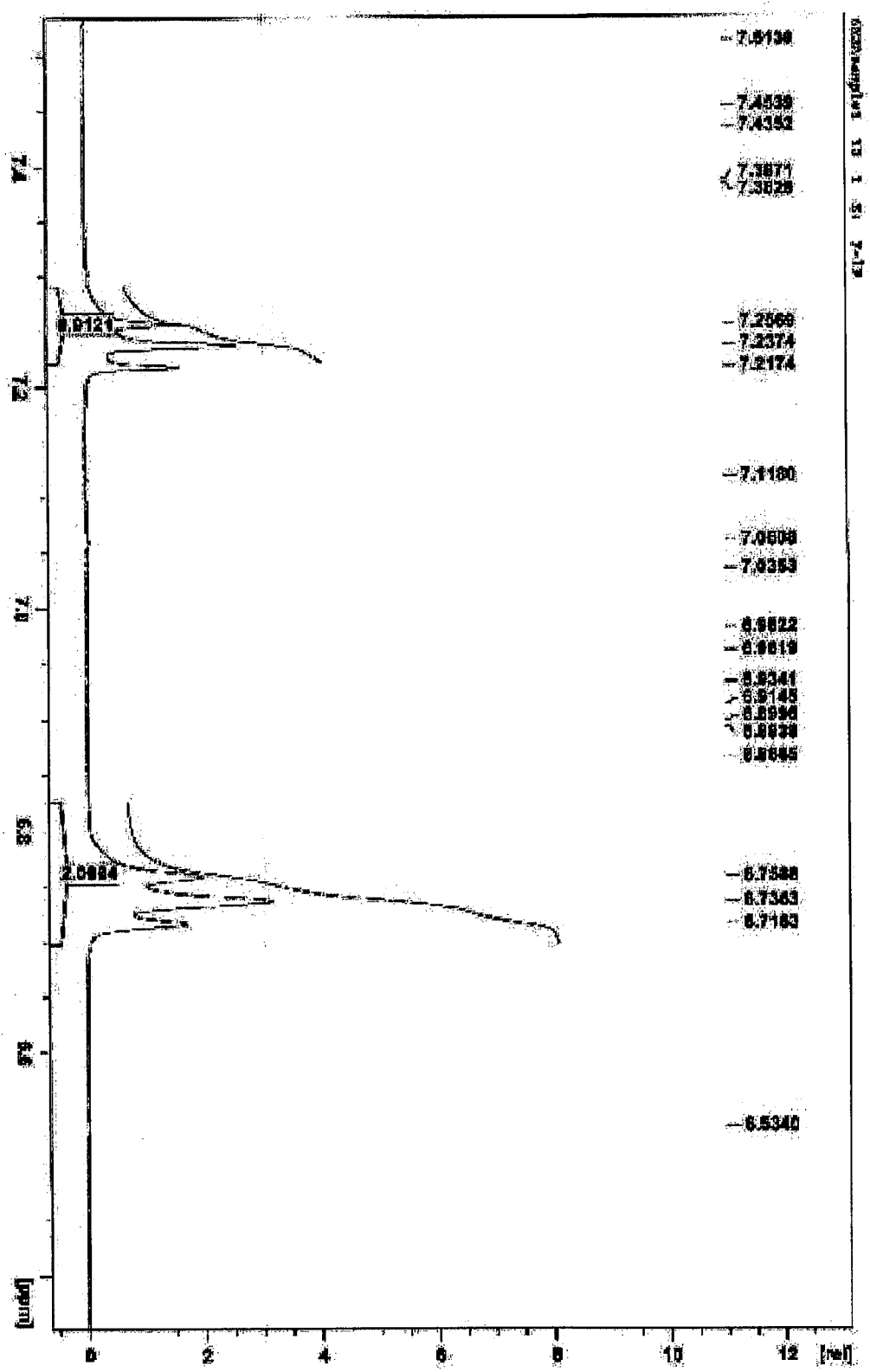
FIG. 10B shows an enlarged view of the H-NMR spectrum shown in FIG. 10A.

1: 48 hours, at 30° C., culture on SC/Ura plate
2: 24 hours, at 30° C., shaking culture in 2 mL SC/Ura
3: 48 hours, at 30° C., shaking culture in 25 mL SC/Leu
4: 12 hours, at 30° C., shaking culture in 1 L YPD
5: Galactose was added to the final concentration of 2%
6: 6 days shaking culture The culture medium was centrifuged and the supernatant was collected, and the pH of the supernatant was adjusted to 1 to 2 with HCl. The supernatant was extracted with an equivalent amount of ethyl acetate, and the target product (6-MSA) was dried to obtain at about 1 g of the target compound per 1 L of culture medium. The resulting solid was dissolved in methanol, analyzed by LC/MS, and separated by HPLC. The measurement conditions were as in the section 2 above. FIG. 8 shows the LC/MS spectrum, and FIG. 9 shows the HPLC spectrum. In FIG. 8A, a shows a chromatogram detected at an absorption wavelength of 254 nm, and b shows the ultraviolet absorption spectrum of the target compound. In FIG. 8B, a shows a chromatogram from mass spectrometry, and b shows the mass spectrum of the target compound. Based on the reference data obtained in the section 2 above, a fraction with a retention time of 27 minutes was separated by HPLC. The separated fraction was dried, dissolved in deuterated methanol (MeOD (4D)), and subjected to NMR spectrum analysis. The results are shown in FIGS. 10A and 10B.

These results showed that the transformed yeast produced 6-MSA, demonstrating that a transformant having an introduced expression vector prepared by the method of the present invention was indeed able to produce a secondary metabolite.

Example 3

Preparation of Expression Vector for PKS Gene (CHGG 00542) from *Chaetomium globosum*, and Gene Expression 1. Construction of CHGG 00542 Gene Expression Vector One of the genes presumed to encode a polyketide synthase (PKS) of *Chaetomium globosum* was selected (CHGG_00542) for further experiments. It has the sequence (SEQ ID NO:36) where 5 adenine residues (residues 492, 3925, 3965, 4529 and 6077) are substituted with guanine.

(1) Amplification of Exon Sequences by PCR

DNA was extracted from *Chaetomium globosum*. Because CHGG_00542 is presumed to have 3 intron sequences, 4 exon sequences excluding the intron sequences were amplified by PCR (exons 1 to 4 in order from the 5' end; SEQ ID NOs:37 to 40). To this end, an exon 1 forward primer (SEQ ID NO:41), and exon 1 reverse primer (SEQ ID NO:42), an exon 2 forward primer (SEQ ID NO:43) and exon 2 reverse primer (SEQ ID NO:44), and an exon 3 forward primer (SEQ ID NO:45) and an exon 3.4 reverse primer (SEQ ID NO:46) were designed and used so as to add to each fragment a sequence homologous to the end of a fragment to be joined or to a restriction enzyme-treated terminal part of the vector (FIG. 11). The exon 3.4 reverse primer was synthesized from a sequence homologous to the sequence of the 3' terminal part of the antisense strand of a restriction enzyme-treated terminal part of the vector, a sequence homologous to the sequence of the antisense strand of exon 4, and a sequence homologous to the sequence of the 5' terminal part of the antisense strand of exon 3, in order from the 5' end to the 3' end (FIG. 11).

The PCR reaction consisted of 2 minutes of denaturing at 94° C., followed by 30 cycles of a reaction of 15 seconds at 94° C., 30 seconds at 55° C. and 30 seconds at 68° C. for exon 1, 15 seconds at 94° C., 30 seconds at 55° C. and 30 seconds at 68° C. for exon 2, and 15 seconds at 94° C., 30 seconds at 55° C. and 6 minutes at 68° C. for exon 3.4, respectively. KOD-Plus (Toyobo) was used as the polymerase.

(2) Preparation of Expression Vector by Homologous Recombination

Figure 12:
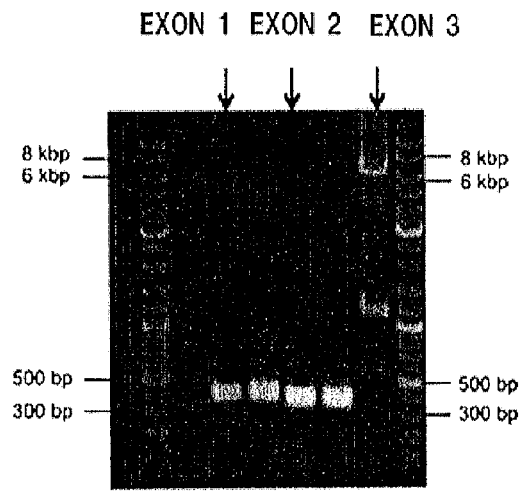
FIG. 12 shows the results of PCR amplification of the exon sequences of a hypothetical PKS gene (CHGG_00542).
Figure 13:
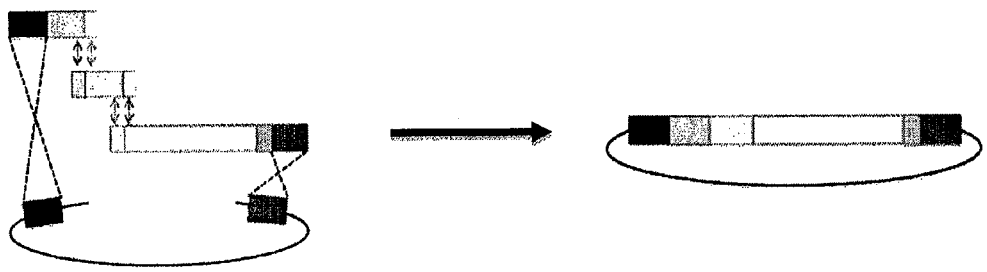
FIG. 13 is a schematic view showing homologous recombination of the exon sequences of a hypothetical PKS gene (CHGG_00542) in a budding yeast.

Amplification of exon 1, exon 2 and exon 3.4 was confirmed by electrophoresis (FIG. 12), and PCR products corresponding to the bands at the expected size were introduced into a budding yeast together with a restriction enzyme-treated vector and sequences coding for His and HA tags. Commercially available pRS425 was used as the vector, and SalI and SacI as the restriction enzymes. Homologous recombination was accomplished by recombinase of the yeast to obtain an expression vector comprising exon 1, exon 2, and exon 3.4 (FIG. 13). An expression vector having the sequence of exons 1 to 4 (SEQ ID NO:47) was selected using the marker Leu. npgA and matB were also incorporated by the gap repair cloning method.

(3) Expression of Target Protein in Yeast

Expression of the target protein in yeast was confirmed by the same method as in Example 1. The molecular weight of the PKS based on the linked sequences of exons 1 to 4 was 239 kDa, and the molecular weight of the tag peptides is 8 kDa, and thus the product was anticipated to have a molecular weight of 247 kDa. Indeed a band was found at about this size (FIG. 14).

2. Enzyme Function Analysis of CHGG_00542 Using in Vivo Synthesis System, and Isolation and Structural Determination of Synthesis Product The yeast culture medium obtained in the section 1 above was centrifuged, the supernatant was collected. The target compound was extracted with an amount of ethyl acetate equivalent to the supernatant and dried. About 0.01 g of solid was obtained from 1 L of culture medium. The resulting solid was dissolved in methanol, analyzed by LC/MS, and separated by HPLC. The measurement conditions were the same as for 6-MSA (2. of Example 2). The LC/MS spectrum is shown in FIG. 15 together with the HPLC spectrum. Two different compounds were separated, which were designated as Compound 1 (CHGG_542-1) and Compound 2 (CHGG_542-2). The separated compounds were dried, dissolved separately in deuterated acetone (acetone (6D)), and subjected to NMR spectrum analysis.

The $^1$HNMR spectrum (FIG. 16) shows that the isolated Compound 1 (CHGG_542-1) is a compound whose chemical structure has already been determined, while the Compound 2 (CHGG_542-2) is a novel compound.

These results showed production of Compound 1 (CHGG 542-1) and Compound 2 (CHGG 542-2) by the transformed yeast, demonstrating that a transformant having an introduced expression vector produced by the method of the present invention was indeed able to produce a novel compound.

INDUSTRIAL APPLICABILITY

The present invention makes it possible to remove the introns from a gene sequence and link only the exons together, suggesting that the present invention permits so-called artificial splicing. According to the invention, it is possible to express unknown biosynthesis gene clusters, thus it may be possible to produce a protein encoded by gene clusters that have not been isolated or structurally determined, and to produce useful bioactive substances that are synthesized by the protein. The present invention may contribute to provide new drugs and agricultural chemicals, or lead compounds thereof.

Applicant submits that the material contained on the compact disc COPY 1 submitted with this application, namely the contents of the file:

PS14-9007US Sequence Listing which was created on Feb. 13, 2013 and is 326 KB in size is hereby incorporated by reference. The content of the file PS14-9007US Sequence Listing is the same as the paper copy submitted with the application.

Applicant hereby incorporates by reference the contents of International Application No. PCT/JP2011/004566 including any biological sequence listing contained therein.

The invention claimed is:

1. A method of preparing a compound produced by a protein encoded by the gene or genome sequence of the presumed gene containing an intron by using an expression vector prepared by a method of preparing an expression vector by linking exon sequences of a eukaryotic gene containing an intron or from the genome sequence of a presumed eukaryotic gene containing an intron to form the expression vector containing the linked sequences, said method comprising the steps of:

(a) amplifying exon sequences from a genome extracted from a eukaryote by PCR to prepare multiple fragments, wherein the forward primer used in the PCR has, in order from the 5' end to the 3' end, a sequence complementary to the sequence of the 3' terminal part of the sense strand of a fragment to which the amplified fragment is to be linked, or a sequence complementary to the sequence of the 3' terminal part of the sense strand of a restriction enzyme-treated terminal part of the vector, and a sequence complementary to the sequence of the 5' terminal part of the sense strand of the fragment to be amplified, and wherein the reverse primer has, in order from the 5' end to the 3' end, a sequence complementary to the sequence of the 3' terminal part of the antisense strand of a fragment to which the amplified fragment is to be linked, or a sequence complementary to the sequence of the 3' terminal part of the antisense strand of a restriction enzyme-treated terminal part of the vector, and a sequence complementary to the sequence of the 5' terminal part of the antisense strand of the fragment to be amplified, whereby a sequence homologous to a terminal part of a fragment to be linked to the fragment to be amplified or a sequence homologous to a restriction enzyme-treated terminal part of the vector are added to the end of the fragment to be amplified; and (b) simultaneously transforming a budding yeast or fission yeast with the fragments obtained in the step (a) and a restriction enzyme-treated vector to obtain the expression vector containing fragments linked to the fragments and fragments linked to the vector that are joined via homologous recombination, wherein the gene or genome sequence of the presumed gene encodes a polyketide synthase gene or nonribosomal peptide synthetase gene, and wherein the linked sequence is a polynucleotide comprising the nucleotide sequence of SEQ ID NOs:15 to 21, 29 or 47.

2. The method according to claim 1, comprising culturing a transformant having an introduced expression vector, and collecting the compound from the culture medium or the transformant.

3. A method of preparing a compound produced by a protein encoded by the gene or genome sequence of the presumed gene containing an intron by using an expression vector prepared by a method of preparing an expression vector comprising a full-length cDNA sequence from a eukaryotic gene containing an intron or of the genome sequence of a presumed eukaryotic gene containing an intron, said method comprising the steps of:

(a) synthesizing cDNA fragments from mRNA extracted from a eukaryote and amplifying the cDNA fragments by PCR, wherein the forward primer used in the PCR has, in order from the 5' end to the 3' end, a sequence complementary to the sequence of the 3' terminal part of the sense strand of a fragment to which the amplified fragment is to be linked, or a sequence complementary to the sequence of the 3' terminal part of the sense strand of a restriction enzyme-treated terminal part of the vector, and a sequence complementary to the sequence of the 5' terminal part of the sense strand of the fragment to be amplified, and wherein the reverse primer has, in order from the 5' end to the 3' end, a sequence complementary to the sequence of the 3' terminal part of the antisense strand of a fragment to which the amplified fragment is to be linked, or a sequence complementary to the sequence of the 3' terminal part of the antisense strand of the restriction enzyme-treated terminal part of the vector, and a sequence complementary to the sequence of the 5' terminal part of the antisense strand of the fragment to be amplified, whereby a sequence homologous to a terminal part of a fragment to be linked to the fragment to be amplified or a sequence homologous to a restriction enzyme-treated terminal part of the vector are added to the end of the fragment to be amplified; and (b) simultaneously transforming a budding yeast or fission yeast with the cDNA fragments obtained in the step (a) and a restriction enzyme-treated vector to obtain the expression vector containing fragments linked to the fragments and fragments linked to the vector that are joined via homologous recombination, wherein the gene or genome sequence of the presumed gene encodes a polyketide synthase gene or nonribosomal peptide synthetase gene, and wherein the linked sequence is a polynucleotide comprising the nucleotide sequence of SEQ ID NOs:15 to 21, 29 or 47.

4. The method according to claim 3, comprising culturing a transformant having an introduced expression vector, and collecting the compound from the culture medium or the transformant.

* * * * *